(12) United States Patent
Addis et al.

(10) Patent No.: US 11,781,138 B2
(45) Date of Patent: Oct. 10, 2023

(54) FN3 DOMAIN-SIRNA CONJUGATES AND USES THEREOF

(71) Applicant: Aro Biotherapeutics Company, Philadelphia, PA (US)

(72) Inventors: Russell C. Addis, Philadelphia, PA (US); Zhanna Druzina, Philadelphia, PA (US); Robert Kolakowski, Philadelphia, PA (US); Swapnil Kulkarni, Philadelphia, PA (US); Steven G. Nadler, Philadelphia, PA (US); Karyn O'Neil, Philadelphia, PA (US); Yao Xin, Philadelphia, PA (US)

(73) Assignee: Aro Biotherapeutics Company, Philadelphia, PA (US)

( * ) Notice: Subject to any disclaimer, the term of this patent is extended or adjusted under 35 U.S.C. 154(b) by 168 days.

(21) Appl. No.: 17/070,337

(22) Filed: Oct. 14, 2020

(65) Prior Publication Data

US 2021/0108201 A1  Apr. 15, 2021

Related U.S. Application Data

(60) Provisional application No. 63/054,896, filed on Jul. 22, 2020, provisional application No. 62/979,557, filed on Feb. 21, 2020, provisional application No. 62/914,725, filed on Oct. 14, 2019.

(51) Int. Cl.
  *C12N 15/113* (2010.01)
  *A61K 47/64* (2017.01)
  *A61K 31/713* (2006.01)
  *C07K 14/78* (2006.01)

(52) U.S. Cl.
  CPC .......... *C12N 15/113* (2013.01); *A61K 31/713* (2013.01); *A61K 47/6435* (2017.08); *C07K 14/78* (2013.01); *C12N 2310/11* (2013.01); *C12N 2320/32* (2013.01)

(58) Field of Classification Search
  CPC .................. C12N 15/113; C12N 2310/14
  See application file for complete search history.

(56) References Cited

U.S. PATENT DOCUMENTS

| | | | |
|---|---|---|---|
| 4,281,061 A | 7/1981 | Zuk et al. | |
| 5,223,409 A | 6/1993 | Ladner et al. | |
| 5,643,763 A | 7/1997 | Dunn et al. | |
| 5,643,768 A | 7/1997 | Kawasaki | |
| 5,658,727 A | 8/1997 | Barbas et al. | |
| 5,691,157 A | 11/1997 | Gong et al. | |
| 5,846,456 A | 12/1998 | Liu | |
| 5,856,456 A | 1/1999 | Whitlow et al. | |
| 6,018,030 A | 1/2000 | Ferrari et al. | |
| 6,162,903 A | 12/2000 | Trowern et al. | |
| 6,172,197 B1 | 1/2001 | McCafferty et al. | |
| 6,355,776 B1 | 3/2002 | Ferrari et al. | |
| 6,462,189 B1 | 10/2002 | Koide | |
| 6,472,147 B1 | 10/2002 | Janda et al. | |
| 6,521,427 B1 | 2/2003 | Evans | |
| 6,582,915 B1 | 6/2003 | Griffiths et al. | |
| 6,670,127 B2 | 12/2003 | Evans | |
| 6,673,901 B2 | 1/2004 | Koide | |
| 6,703,199 B1 | 3/2004 | Koide | |
| 6,818,418 B1 | 11/2004 | Lipovsek et al. | |
| 6,846,655 B1 | 1/2005 | Wagner et al. | |
| 6,969,108 B2 | 11/2005 | Fukumoto et al. | |
| 7,078,490 B2 | 7/2006 | Koide | |
| 7,115,396 B2 | 10/2006 | Lipovsek et al. | |
| 7,119,171 B2 | 10/2006 | Koide | |
| 7,153,661 B2 | 12/2006 | Koide | |
| 7,288,638 B2 | 10/2007 | Jure-Kunkel et al. | |
| 7,427,672 B2 | 9/2008 | Imanishi et al. | |
| 7,709,214 B2 | 5/2010 | Freeman et al. | |
| 7,794,710 B2 | 9/2010 | Chen et al. | |
| 7,842,476 B2 | 11/2010 | McGregor et al. | |
| 7,943,743 B2 | 5/2011 | Korman et al. | |
| 8,217,149 B2 | 7/2012 | Irving et al. | |
| 8,278,419 B2 | 10/2012 | Jacobs et al. | |
| 8,293,482 B2 | 10/2012 | Jacobs et al. | |
| 8,552,154 B2 | 10/2013 | Freeman et al. | |
| 8,569,227 B2 | 10/2013 | Jacobs | |
| 8,741,295 B2 | 6/2014 | Olive | |
| 8,779,108 B2 | 7/2014 | Queva et al. | |
| 8,981,063 B2 | 3/2015 | Chen | |
| 9,156,887 B2 | 10/2015 | Jacobs | |
| 9,175,082 B2 | 11/2015 | Zhou et al. | |
| 9,200,273 B2 | 12/2015 | Diem et al. | |
| 9,212,224 B2 | 12/2015 | Cogswell et al. | |
| 9,326,941 B2 | 5/2016 | Chae et al. | |

(Continued)

FOREIGN PATENT DOCUMENTS

| CN | 102076713 A | 5/2011 |
|---|---|---|
| CN | 103827361 A | 5/2014 |

(Continued)

OTHER PUBLICATIONS

Itoh, et al., "Application of Inverse Substrates to Trypsin-Catalyzed Peptid Synthesis", Bioorganic Chemistry (1996) 24, 0007, pp. 59-68.

Kumaran et al., "Confrmationally driven protease-catalyzed splicing of peptide segments: V8 protease-mediated syntheses of fragments derived from thermolysin and ribonuclease A", Protein Science, (1997) 6: pp. 2233-2241.

Kunkel et al., "Rapid and Efficient Site-Specific Mutagenesis without Phenotypic Selection", Methods In Enzymology, (1987) vol. 154 pp. 367-375.

(Continued)

*Primary Examiner* — Brian Whiteman

(74) *Attorney, Agent, or Firm* — Goodwin Procter LLP

(57) ABSTRACT

The present disclosure relates to compositions, such as siRNA molecules and FN3 domains conjugated to the same, as well as methods of making and using the molecules.

36 Claims, 11 Drawing Sheets

Specification includes a Sequence Listing.

(56) References Cited

U.S. PATENT DOCUMENTS

| | | |
|---|---|---|
| 9,546,368 B2 | 1/2017 | Bennett et al. |
| 9,644,023 B2 | 5/2017 | Torres et al. |
| 9,695,228 B2 | 7/2017 | Mark et al. |
| 9,897,612 B2 | 2/2018 | Diem et al. |
| 10,196,446 B2 | 2/2019 | Goldberg et al. |
| 10,233,448 B2 | 3/2019 | Maier et al. |
| 10,597,438 B2 | 3/2020 | Diem et al. |
| 10,611,823 B2 | 4/2020 | Diem et al. |
| 10,626,165 B2 | 4/2020 | Hawkins et al. |
| 2004/0197332 A1 | 10/2004 | Ullrich et al. |
| 2004/0259781 A1 | 12/2004 | Chiquet-Ehrismann et al. |
| 2005/0004029 A1 | 1/2005 | Garcia |
| 2005/0038229 A1 | 2/2005 | Lipovsek et al. |
| 2005/0255548 A1 | 11/2005 | Lipovsek et al. |
| 2005/0272083 A1 | 12/2005 | Seshagiri |
| 2006/0040278 A1 | 2/2006 | Cojocaru et al. |
| 2006/0246059 A1 | 11/2006 | Lipovsek et al. |
| 2006/0270604 A1 | 11/2006 | Lipovsek et al. |
| 2007/0148126 A1 | 6/2007 | Chen et al. |
| 2007/0160533 A1 | 7/2007 | Chen et al. |
| 2007/0184476 A1 | 8/2007 | Hsieh et al. |
| 2008/0015339 A1 | 1/2008 | Lipovsek et al. |
| 2008/0220049 A1 | 9/2008 | Chen et al. |
| 2008/0241159 A1 | 10/2008 | Gerritsen et al. |
| 2009/0042906 A1 | 2/2009 | Huang et al. |
| 2009/0176654 A1 | 7/2009 | Cappuccilli et al. |
| 2009/0274693 A1 | 11/2009 | Gilmer et al. |
| 2009/0299040 A1 | 12/2009 | Camphausen et al. |
| 2009/0311803 A1 | 12/2009 | Way et al. |
| 2010/0093662 A1 | 4/2010 | Defaye et al. |
| 2010/0136129 A1 | 6/2010 | Agueros Bazo et al. |
| 2010/0144601 A1 | 6/2010 | Jacobs et al. |
| 2010/0179094 A1 | 7/2010 | Emanuel et al. |
| 2010/0203142 A1 | 8/2010 | Zhang et al. |
| 2010/0216708 A1 | 8/2010 | Jacobs et al. |
| 2010/0221248 A1 | 9/2010 | Wittrup et al. |
| 2010/0254989 A1 | 10/2010 | Bossenmaier et al. |
| 2010/0255056 A1 | 10/2010 | Jacobs et al. |
| 2011/0021746 A1 | 1/2011 | Cappuccilli et al. |
| 2011/0038866 A1 | 2/2011 | Hastewell et al. |
| 2011/0053842 A1 | 3/2011 | Camphausen et al. |
| 2011/0081345 A1 | 4/2011 | Moore et al. |
| 2011/0118144 A1 | 5/2011 | Hyun et al. |
| 2011/0124527 A1 | 5/2011 | Cappuccilli et al. |
| 2011/0274623 A1 | 11/2011 | Jacobs |
| 2011/0287009 A1 | 11/2011 | Scheer et al. |
| 2012/0225870 A1 | 9/2012 | Janne et al. |
| 2012/0244164 A1 | 9/2012 | Beste et al. |
| 2012/0263723 A1 | 10/2012 | Davies et al. |
| 2012/0270797 A1 | 10/2012 | Wittrup et al. |
| 2012/0315639 A1 | 12/2012 | Deng et al. |
| 2012/0321666 A1 | 12/2012 | Cooper et al. |
| 2013/0012435 A1 | 1/2013 | Camphausen et al. |
| 2013/0039927 A1 | 2/2013 | Dewhurst et al. |
| 2013/0079243 A1 | 3/2013 | Diem et al. |
| 2013/0123342 A1* | 5/2013 | Brown ................ C07H 21/02 435/375 |
| 2013/0130377 A1 | 5/2013 | Lee et al. |
| 2013/0184212 A1 | 7/2013 | Camphausen et al. |
| 2013/0226834 A1 | 8/2013 | Gannalo, II |
| 2013/0273561 A1 | 10/2013 | Walker et al. |
| 2014/0141000 A1 | 5/2014 | Chiu et al. |
| 2014/0155325 A1 | 6/2014 | Mark et al. |
| 2014/0155326 A1 | 6/2014 | Mark et al. |
| 2014/0255408 A1 | 9/2014 | Chiu et al. |
| 2014/0271467 A1 | 9/2014 | Hackel et al. |
| 2014/0341917 A1 | 11/2014 | Nastri et al. |
| 2014/0349929 A1 | 11/2014 | Camphausen et al. |
| 2014/0371296 A1 | 12/2014 | Bennett et al. |
| 2015/0005364 A1 | 1/2015 | Chae et al. |
| 2015/0104808 A1 | 4/2015 | Goldberg et al. |
| 2015/0118288 A1 | 4/2015 | Lee |
| 2015/0197571 A1 | 7/2015 | Freeman et al. |
| 2015/0203580 A1 | 7/2015 | Papadopoulos et al. |
| 2015/0210756 A1 | 7/2015 | Torres et al. |
| 2015/0252097 A1 | 9/2015 | Camphausen et al. |
| 2015/0274835 A1 | 10/2015 | Marasco et al. |
| 2015/0346208 A1 | 12/2015 | Couto et al. |
| 2015/0355184 A1 | 12/2015 | Pierce et al. |
| 2016/0041182 A1 | 2/2016 | Diem et al. |
| 2016/0303256 A1 | 10/2016 | Liu |
| 2016/0326232 A1 | 11/2016 | Rosa et al. |
| 2016/0355599 A1 | 12/2016 | Sagert et al. |
| 2017/0174748 A1 | 6/2017 | Mitchell et al. |
| 2017/0258948 A1 | 9/2017 | Morin et al. |
| 2017/0281795 A1* | 10/2017 | Geall .................... A61K 47/60 |
| 2017/0348397 A1 | 12/2017 | Diem et al. |
| 2017/0362301 A1 | 12/2017 | Anderson et al. |
| 2019/0127444 A1 | 5/2019 | Brezski et al. |
| 2019/0175651 A1 | 6/2019 | Lee et al. |
| 2019/0184018 A1 | 6/2019 | Manoharan et al. |
| 2019/0184028 A1* | 6/2019 | Dudkin ................ A61K 9/5123 |
| 2019/0202927 A1 | 7/2019 | Sagert et al. |
| 2019/0256575 A1 | 8/2019 | Chen et al. |
| 2019/0263915 A1 | 8/2019 | Goldberg et al. |
| 2019/0330361 A1 | 10/2019 | Chin et al. |

FOREIGN PATENT DOCUMENTS

| | | |
|---|---|---|
| CN | 105907719 A | 8/2016 |
| EP | 0985039 A2 | 3/2000 |
| EP | 1137941 A1 | 10/2001 |
| EP | 1210428 A1 | 6/2002 |
| EP | 1266025 A1 | 12/2002 |
| EP | 2935329 A1 | 10/2015 |
| JP | 2011507543 A | 3/2011 |
| JP | 2011517314 A | 6/2011 |
| JP | 2011520961 A | 7/2011 |
| JP | 2011522517 A | 8/2011 |
| JP | 2012507295 A | 3/2012 |
| JP | 2014530014 A | 11/2014 |
| JP | 2016504291 A | 2/2016 |
| KR | 10-2016-0067966 A | 6/2016 |
| WO | 9638557 A1 | 12/1996 |
| WO | 2001014557 A1 | 3/2001 |
| WO | 0164942 A1 | 9/2001 |
| WO | 0232925 A2 | 4/2002 |
| WO | 03104418 A2 | 12/2003 |
| WO | 2004029224 A2 | 4/2004 |
| WO | 2004058821 A2 | 7/2004 |
| WO | 2005018534 A2 | 3/2005 |
| WO | 2005042708 A2 | 5/2005 |
| WO | 2007000671 A2 | 1/2007 |
| WO | 2007085815 A2 | 8/2007 |
| WO | 2008066752 A2 | 6/2008 |
| WO | 2008079973 A2 | 7/2008 |
| WO | 2008127710 A2 | 10/2008 |
| WO | 2008156642 A1 | 12/2008 |
| WO | 2009023184 A2 | 2/2009 |
| WO | 2009058379 A2 | 5/2009 |
| WO | 2009083804 A2 | 7/2009 |
| WO | 2009085462 A1 | 7/2009 |
| WO | 2009086116 A2 | 7/2009 |
| WO | 2009102421 A2 | 8/2009 |
| WO | 2009111691 A2 | 9/2009 |
| WO | 2009126834 A2 | 10/2009 |
| WO | 2009133208 A1 | 11/2009 |
| WO | 2009142773 A2 | 11/2009 |
| WO | 2010039248 A1 | 4/2010 |
| WO | 2010051274 A2 | 5/2010 |
| WO | 2010051310 A2 | 5/2010 |
| WO | 2010060095 A1 | 5/2010 |
| WO | 2010093627 A3 | 10/2010 |
| WO | 2010115202 A2 | 10/2010 |
| WO | 2010115551 A1 | 10/2010 |
| WO | 2011005133 A1 | 1/2011 |
| WO | 2011110642 A2 | 9/2011 |
| WO | 2011130324 A1 | 10/2011 |
| WO | 2011131746 A1 | 10/2011 |
| WO | 2011137319 A2 | 11/2011 |
| WO | 2011151412 A1 | 12/2011 |
| WO | 2012016245 A2 | 2/2012 |
| WO | 2012162418 A1 | 11/2012 |
| WO | 2013049275 A1 | 4/2013 |

(56) References Cited

FOREIGN PATENT DOCUMENTS

| WO | 2014081944 A2 | 5/2014 |
|---|---|---|
| WO | 2014081954 A1 | 5/2014 |
| WO | 2014100079 A1 | 6/2014 |
| WO | 2014165082 A2 | 10/2014 |
| WO | 2014165093 A2 | 10/2014 |
| WO | 2014189973 A2 | 11/2014 |
| WO | 2014209804 A1 | 12/2014 |
| WO | 2015057545 A2 | 4/2015 |
| WO | 2015061668 A1 | 4/2015 |
| WO | 2015089073 A2 | 6/2015 |
| WO | 2015092393 A2 | 6/2015 |
| WO | 2015109124 A2 | 7/2015 |
| WO | 2015143199 A1 | 9/2015 |
| WO | 2015195163 A1 | 12/2015 |
| WO | 2016000619 A1 | 1/2016 |
| WO | 20160004043 A1 | 1/2016 |
| WO | 2016086021 A1 | 6/2016 |
| WO | 2016086036 | 6/2016 |
| WO | 2016179534 | 11/2016 |
| WO | 2016197071 A1 | 12/2016 |
| WO | 2017011618 A1 | 1/2017 |
| WO | 2017223180 A2 | 12/2017 |
| WO | 2018148501 A1 | 8/2018 |

OTHER PUBLICATIONS

Wattanachaisaereekul, "Production of Polyketides by *Saccharomyces cerevisiae*", Ph.D. Thesis (2007) Center for Microbial Biotechnology, BioCentrum-DTU Technical University of Denmark, pp. 1-187.
Hackel et al., "Use of 64Cu-Labeled Fibronectin Domain with EGFR-Overexpressing Tumor Xenograft: Molecular Imaging1", Radiology (2012) vol. 263:No. 1 pp. 179-188.
Non-Final Office Action dated Aug. 18, 2021 in U.S. Appl. No. 16/801,787.
McCracken, "Non-invasive monitoring of hematopoietic reconstitution and immune cell function through Positron Emission Tomography" University of California, Los Angeles, Dissertaton ProQuest LLC (2014) pp. 1-202.
Natarajan, et al., "A Novel Engineered Anti-CD20 Tracer Enables Early Time PET Imaging in a Humanized Transgenic Mouse Model of B-cell Non-Hodgkins Lymphoma", Clin Cancer Res (2013) 19: pp. 6820-6829.
Non-Final Office Action dated Sep. 24, 2021 in U.S. Appl. No. 16/820,844.
Non-Final Office Action dated Feb. 4, 2022 in U.S. Appl. No. 16/801,787.
Non-Final Office Action dated Feb. 10, 2022 in U.S. Appl. No. 16/218,990.
Olson, William C. et al, "Antibody-drug Conjugates Targeing Prostate-Specific Membrane Antigen," Frontiers in Bioscience (Landmark Edition) 19: pp. 12-33, Jan. 1, 2014.
Gill et al., "Monoclonal Anti-epidermal Growth Factor Receptor Antibodies Which Are Inhibitors of Epidermal Growth racier Binding and Antagonists of Epidermal Growth Factor-stimulated tyrosine Protein Kinase Activity," The Journal Jf Biological Chemistry, vol. 259, No. 12, pp. 7755-7760 (1984).
Goldstein et al., "Biological efficacy of a chimeric antibody to the epidermal growth factor receptor in a human umor xenografl model," Clinical Cancer Research, vol. 1, pp. 1311-1318 (1995).
Grünwald et al., "Developing Inhibitors of the Epidermal Growth Factor Receptor for Cancer Treatment," Journal of tie National Cancer Institute, vol. 95, No. 12, pp. 851-867 (2003).
Hirsch et al, "Combination of EGFR gene copy number and protein expression predicts outcome for advanced non-, mall-cell lung cancer patients treated with gefitnib," Annals of Oncology, vol. 18, pp. 752-760 (2007).
Hynes et al., "ERBB Receptors and Cancer: the Complexity of Targeted Inhibitors," Nature Reviews, vol. 5, pp. 341-356 (2005).

Chimu RA et al., "Expression of c-mel/HGF Receptor in Human Non-small Cell Lung Carcinomas in vitro and in vivo and Its Prognostic Significance," Japan Journal of Cancer Research, vol. 87. pp. 1063-1069 (1996).
Jänne et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, vol. 12, No. 14 Suppl, pp. 4416s-4420s (2006).
Jacobs et al., "FN3 Domain Engineering", Protein Engineering, pp. 145-162, 2012.
Li et al., "Skin toxicities associated with epidermal growth factor receptor inhibitors," Target Oncology, vol. 4, pp. 107-119 (2009).
Linardou et al., "Somatic EGFR mutations and efficacy of tyrosine kinase inhibitors in NSCLC," National Review of :; linical Oncology, vol. 6, pp. 352-366 (2009).
Ma et al., "c-Met: Structure, functions and potential for therapeutic inhibition," Cancer and Metastasis Reviews, vol. 22 pp. 309-325 (2003).
Mendelsohn et al., "Epidermal Growth Factor Receptor Targeting in Cancer," Seminars in Oncology, vol. 33, pp. 369-385 (2006).
Mendelsohn et al., "The EGF receptor family as targets for cancer therapy," Oncogene, vol. 19, pp. 6550-6565 2000).
Määttä et al., "Proteolytic Cleavage and Phosphorylation of a Tumor-associated ErbB4 Isoform Promote Ligand-ndependent Survival and Cancer Cell Growth," Molecular Biology, vol. 17, pp. 67-79 (2006).
NCBI Reference Sequence NP _005219.2, "Epidermal Growth Factor Receptor Isoform a Precursor [*Homo sapiens*]," pp. 1-14 (May 18, 2014).
Panek et al.,"ln Vitro Pharmacological Characterization of PD 166285, a New Nanomolar Potent and Broadly Active Protein Tyrosine Kinase Inhibitor," The Journal of Pharmacology and Experimental Therapeutics, vol. 283, No. 3, pp. 1433-1444 (1997).
Peters et al., "MET: a promising anticancer therapeutic target," Nature Reviews Clinical Oncology, vol. 9, pp. 314-326 (2012).
Prewett et al., "Mouse-Human chimeric Anti-Epidermal Growth Factor Receptor Antibody C225 Inhibits the Growth Jf Human Renal Cell Carcinoma Xenografts in Nude Mice," Clinical Cancer Research, vol. 4, pp. 2957-2966 (1998).
Riel Yet al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, vol. 12, No. 3, pp. g39-844 (2006).
Sakakura et al., "Gains, Losses, and Amplifications of Genomic Materials in Primary Gastric Cancers Analyzed by :; omparative Genomic Hybridization," Genes, Chromosomes & Cancer, vol. 24, pp. 299-305 (1999).
Schmidt et al., "Novel mutations of the MET proto-0ncogene in papillary rental carcinomas," Oncogene, vol. 18, pp. ]343-2350 (1999).
Siegfried et al., "The Clinical Significance of Hepatocyte Growth Factor for Non-Small Cell Lung Cancer," Annals of Thoracic Surgery, vol. 66, pp. 1915-1918 (1998).
Sierra et al., "c-MET as a potential therapeutic target and biomarker in cancer," Therapeutic Advances in Medical :: >ncology, vol. 3, No. 51, pp. 521-535 (2011).
Stamos et al., "Crystal structure of the HGF b-chain in complex with the Serna domain of the Met receptor," The EMBO Journal, vol. 23, pp. 2325-2335 (2004).
Mamluk et al., "Anti-tumor effect of CT-322 as an Adnectin inhibitor of vascular endothelial growth factor receptor-2", mAbs, 2(2), pp. 199-208, 2010.
Klein et al. "Abstract LB-312: Bispecific Centyrin Simultaneously targeting EGFR and c—Met demonstrates improved ô €?'ctivity compared to the mixture of single agents", Cancer Research, 73 (8 Supplement), Abstract LB-312, Apr. 2013.
Jacobs et al., "Fusion to a highly stable consensus albumin binding domain allows for tunable pharmacokinetics", Protein Engineering, Design & Selection, vol. 28, No. 10, pp. 385-393, 2015.
Notice of Allowance dated Mar. 3, 2020 in U.S. Appl. No. 15/840,303.
Makkouk Amani et al: "Rationale for anti-CD137 cancer immunotherapy", European Journal of Cancer, Elsevier, Amster-

(56) References Cited

OTHER PUBLICATIONS dam, NL, vol. 54, Jan. 2, 2016 (Jan. 2, 2016), pp. 112-119, XP029401784, ISSN: 0959-8049, DOI: 10.1016/j.ejca.2015.09.026 *abstractp. 114, right-hand column, paragraph 4-p. 116, right-hand column, paragraph 1table 1*.
Shalom D. Goldberg et al: "Engineering a targeted delivery platform using Centyrins", Protein Engineering, Design and Selection, Oct. 13, 2016 (Oct. 13, 2016), XP055384705, GB ISSN: 1741-0126, DOI: 10.1093/protein/gzw054 *abstractp. 564, left-hand column, paragraph 2-right-hand column, line 3 p. 567, right-hand column, paragraph 2p. 568, right-hand column, paragraph 2-p. 569, left-hand column, paragraph 2table 1**figure 1a*.
Burton Earle Barnett et al: "Disclosures", Blood, vol. 128, No. 22, Dec. 2, 2016 (Dec. 2, 2016), pp. 4557-4557, XP055711182, US ISSN: 0006-4971, doi: 10.1182/blood.V128.22.4557.4557 *abstract*.
Final Office Action dated Jul. 10, 2020 in U.S. Appl. No. 15/637,276.
Zucali, et al., "Role of cMET expression in non-small-cell lung cancer patients treated with eGFR tyrosine kinase inhibitors", Annals of Anocology (2008) 19:: 1605-1612.
Burgess et al., "Possible dissociation of the heparin-binding and mitogenic activities of heparin-binding (acidic fibroblast) growth factor-1 from its receptor-binding activities by site-directed mutagenesis of a single lysine residue" J Cell Biol (1990) 111:pp. 2129-2138.
Lazar et al., "Transforming growth factor alpha: mutation of aspartic acid 47 and leucie 48 results in different biological activities", Mol Cell Biol. (1988) 8: pp. 1247-1252.
Brown et al., "Tolerance of single, but not multiple, amino acid replacements in antibody VH CDR 2: a means of minimizing B cell wastage from somatic hypermutation", J. Immuno. (1996) pp. 3285-3291.
Rudikoff el al., "Single amino acid substitution altering antigen-binding specificity", Proc Natl Acad Sci (1982) 79(6): pp. 1979-1983.
Vajdos et al., "Comprehensive funtional maps of the antigen-binding site of an anti-ErbB2 antibody obtained with shotgun scanning mutagenisis", J. Mol. Biol. (2002) 32(2): pp. 415-428.
Non-Final Office Action dated Jul. 9, 2021 in U.S. Appl. No. 16/821,064.
Rybalov et al., "PSMA, EpCAM, VEGF and GRPR as Imaging Targets in Locally Recurrent Prostate Cancer after Radiotherapy", Int. J. Mol. Sci. (2014) 15, pp. 6046-6061.
Non-Final Office Action dated Feb. 3, 2021 in U.S. Appl. No. 16/218,990.
Final Office Action dated Jul. 21, 2020 in U.S. Appl. No. 16/218,990.
Lejon et al., "Structural basis for the binding of naproxen to human serum albumin in the presence of fatty acids and the GA module", Acta Cryst. (2008) F pp. 64-69.
Lee et al., "A Glu-ruea-Lys Ligand-conjugated Lipid nanoparticle/siRNA System Inhibits Androgen Receptor Expression In Vivo", Molecular Therapy-Nucleic Acids (2016) 5, e348: pp. 1-11.
Pace, "Determination and Analysis of Urea and Guanidine Hydrochloride Denaturation Curves", Methods in Enzymology (1986) vol. 131, pp. 266-280.
Chen et al., "Cell-Surface Display of Heterologous Proteins: From High-Throughput Screening to Environmental Applications", Biotechnology and Bioengineering, (2002) vol. 79, No. 5, pp. 496-503.
Mattheakis et al., "An in vitro polysome display system for identifying ligands from very large peptide libraries", Proc. Natl. Acad. Sci. (1994) Vo . . . 91, pp. 9022-9026.
Hoogenboom et al., "Natural and designer binding sites made by phage display technology" Immunology Today (2000) vol. 21, No. 8, pp. 371-378.
Smith, "Filamentous fusion phage: novel expression vectors that display cloned antigens on the virion surface.", Association of Science (1985) vol. 228, pp. 1315(3).
Capellas, "Enzymatic Condensation of Cholecystokinin CCK-8 (4-6) and CCK-8 (7-8) Peptide Fragments in Organic Media", Biotechnology and Bioengineering (1997) vol. 56, No. 4, pp. 456-463.
Alfthan et al., "Properties of a single-chain antibody containing different linker peptides," Protein Engineering, vol. B, No. 7, pp. 725-731 (1995).
Birtalan et al., "The Intrinsic Contributions of Tyrosine, Serine, Glycine and Arginine to the Affinity and Specificity of Antibodies," Journal of Molecular Biology, vol. 377, pp. 1518-1528 (2008).
Bork et al., "Proposed acquisition of an animal protein domain by bacteria," Proceedings of the National Academy of Science, USA, vol. 89, pp. 8990-8994 (1992).
Hallewell et al., "Genetically Engineered Polymers of Human CuZN Superoxide Dismutase," The Journal of Biological Chemistry, vol. 264, No. 9, pp. 5260-5268 (1989).
Hanes et al, "In vitro selection and evolution of functional proteins by using ribosome display," Proceedings of the National Academy of Sciences USA, vol. 94, pp. 4937-4942 (1997).
Jacobs et al., "Design of novel FN3 domains with high stability by a consensus sequence approach," Protein Engineering, Design & Selection, vol. 25, No. 3, pp. 107-117 (2012).
Diem et al., "Selection of high-affinity Centyrin FN3 domains from a simply library diversified at a combination of strand and loop positions." Protein Engin Design (2014) Selection 27(10): 419-429.
Tannock and Hill. The Basic Science of Oncology. 1998. New York: McGraw-Hill;; pp. 357-358.
Song et al. Cancer stem cells—an old idea that's new again: implications for the diagnosis and treatment of breast cancer. Expert Opin Biol Ther 7:4):431-438, 2007.
Binz et al., "High-affinity binders selected from designed ankyrin repeat protein libraries," Nature Biotechnology, vol. e2, No. 5, pp. 575-582 (May 2004).
Garon et al., "Pembrolizumab for the Treatment of Non-Small-Cell Lung Cancer," The New England Journal of Medicine, vol. 372, No. 21, pp. 2018-2028 (May 21, 2015).
Koide et al., "High-affinity single-domain binding proteins with a binary-code interface," PNAS, vol. 104, No. 16, pp. 6632-6637(Apr. 17, 2017).
Lepenies et al., "The Role of Negative Costimulators Dunng Parasitic Infections," Endocrine, Metabolic & Immune Disorders—Drug Targets, vol. 8, pp. 279-288 (2008).
McLaughlin et al., "Quantitative Assessmenet of the Heterogeneity of PD-L 1 Expression in Non-small Cell Lung Cancer (NSCLC)," JAMA Oncol., vol. 2, No. 1, pp. 46-54, (Jan. 2016).
Meinke et al., "Cellulose-Binding Polypeptides from Cellulomonas fimi: Endoglucanase D (CenD), a Family A b-1,4-Glucanase," Journal of Bacterology, vol. 175, No. 7, pp. 1910-1918 (1993).
Odegrip et al., "CIS display: In vitro selection of peptides from libraries of protein-DNA complexes," Proceedings of he National Academy of Science USA, vol. 101, No. 9, pp. 2806-2810 (2004).
Olson et al., "Design, expression, and stability of a diverse protein library based on the human fibronectin type III ô €,?omain," Protein Science, vol. 16, pp. 476-484 (2007).
Roberts et al., "RNA-peptide fusions for the in vitro selection of peptides and proteins," Proceedings of the National Academy of Science USA, vol. 94, pp. 12297-12302 (1997).
Robinson et al., "Covalent Attachment of Arc Repressor Subunits by a Peptide Linker Enhances Affinity for Operator DNA," Biochemistry, vol. 35, pp. 109-116 (1996).
Strohl, William R., "Optimization of Fe-mediated effector functions of monoclonal antibodies," Current Opinion in Biotechnology, vol. 20, pp. 685-691 (2009).
Tie et al., "Safety and efficacy of nivolumab in the treatment of cancers: A meta-analysis of 27 prospective clinical rials," International Journal of Cancer, vol. 140, pp. 948-958, (2017).
Wang et al., "VISTA, a novel mouse Ig superfamily ligand that negatively regulates T cell responses," Journal of Experimental Medicine, vol. 208, No. 3, pp. 577-592 (Mar. 14, 2011).
Watanabe et al., "Gene Cloning of Chitinase A1 from Bacillus circulans WL-12 Revealed Its Evolutionary Relationship to Serratia Chitinase and to the Type III Homology Units of Fibronectin," Journal of Biological Chemistry, vol. 265, pp. 15659-15665 (1990).
Cooper et al., "4-1 BB (CD 137) controls the clonal expansion and survival of COB T cells in vivo but does not t: ontribute the development of cytotoxicity", Eur. J_ Immunol., vol. 32, pp. 521-529, 2002.

(56) References Cited

OTHER PUBLICATIONS

Gramaglia et al., "Co-stimulation of antigen-specific CD4 T cells by 4-1BB ligand," Eur. J. Immunol., vol. 30, pp. ô €?"92-402 (2000).

DeBenedette et al., "Role of 4-1BB Ligand in Costimulation of T Lymphocyte Growth and its Upregulation on M12 B rymphomas by cAMP," J_ Exp_ Med., vol. 181, pp. 985-992 (1995).

Langstein et al., "CD137 Induces Proliferation and Endomitosis in Monocytes," Blood, vol. 94, No. 9, pp. 3161-3168 1999).

Langstein et al., "CD137 (ILA/4-1 BB), a Member of the TNF Receptor Family, Induces Monocyte Activation via Bidirectional Signaling," The Journal of Immunology, vol. 160, pp. 2488-2494 (1998).

Lee et al., "4-1BB Promotes the Survival of COB+ T Lymphocytes by Increasing Expression of Bcl-xL and Bfl-11," The Journal of Immunol., vol. 169, pp. 4882-4888 (2002).

Michel et al., "A soluble form of CD137 (ILA/4-1BB), a member of the TNF receptor family, is released by activated ymphocytes and is detectable in sera of patients with rheumatoid arthritis," Eur. J_ Immunol., vol. 28, pp. 290-295 1998).

Michel et al., "CD137-induced apoptosis is independent of CD95," Immunology, vol. 98, pp. 42-46 (1999).

Schwarz et al., "ILA, a Member of the Human Nerve Growth FactorfTumor Necrosis Factor Receptor Family, Regulates T-Lymphocyte Proliferation and Survival," Blood, vol. 87, No. 7, pp. 2839-2845 (Apr. 1, 1996).

Shuford et al., "4-18B Costimulatory Signals Preferentially Induce COB+ T Cell Proliferation and Lead to the amplification In Vivo of Cytotoxic T Cell Responses," J_ Exp_ Med., vol. 186, No. 1, pp. 47-55 (Jul. 7, 1997).

Takahashi et al., "Cutting Edge: 4-1 BB Is a Bona Fide COB T Cell Survival Signal," J Immunol., vol. 162, pp. 0037-5040 (1999).

Alderson et al., "Molecular and Biological Characterization of Human 4-1 BB and its Ligand", Eur. J_ Immunol., vol. N, pp. 2219-2227, 1994.

Hurtado et al., "Potential role of 4-1 BB in T cell Activation Comparison with the Costimulatory Molecule CD28", Journal of Immunology, vol. 155, pp. 3360-3367, 1995.

Hurtado et al., "Signals through 4-1BB are Costimulatory to previously activated splenic T cells and inhibit activation-induced cell death", Journal of Immunology, vol. 158, pp. 2600-2609, 1997.

Maus et al., Ex vivo expansion of polyclonal and antigen-specific cytotoxic T lymphocytes by artificial APCs Expressing ligands for the T-cell receptor, CD28 and 4-1BB Nature Biotechnology, vol. 20, pp. 143-148, Feb. 2002.

Michel et al., "Expression of soluble CD137 correlates with activation-induced cell death of lymphocytes", Cytokine, vol. 12, No. 6, pp. 742-746, 2000.

Zhou et al., Characterization of human homologue of 4-1 BB and its ligand, Immunology Letters, vol. 45, pp. p7-73, 1995.

Pauly et al., CD137 is expressed by follicular dendritic cells and costimulates B lymphocyte activation in germinal t; enters, Journal of Leukocyte Biology, vol. 72, pp. 35-42, Jul. 2002.

Langstein et al., Identification of CD137 as a potent monocyte survival factor, Journal of Leukocyte Biology, vol. 65, pp. 829-833, Jun. 1999.

Kwon et al., cDNA sequences of two inducible T-cell genes, Proc. Natl. Acad. Sci., vol. 86, pp. 1963-1967, Mar. 1989.

Lehmann et al., Engineering proteins for thermostability the use of sequence alignments versus rational design and directed evolution, Current Opinion in Biotechnology, vol. 12, pp. 371-375 (2001).

Chiba et al., Amyloid Fibril Formation in the Context of Full-length Protein Effects of Praline mutations on the Amyloid fibril formation of b2-Microglobulin, Journal of Biological Chemistry, vol. 278, No. 47, pp. 47016-47024, Nov. 2003.

Goldberg et al., "Engineering a Targeted Delivery Platform using Centyrins" Protein Engineering, Design & selection, vol. 29, No. 12, pp. 563-572, 2016.

Strand et al., "Site-Specific Radioiodination of HER2-Targeting Affibody Molecules using 4-Iodophenethylmaleimide Decreases Renal Uptake of Radioactivity"; Chemitry Open, vol. 4, pp. 174-182, 2015.

Hylarides et al., "Preparation and in Vivo Evaluation of an N-9p-[1251]1odophenethyl) maleimide—Antibody Conjugate" Bioconjugate Chem., vol. 2, pp. 435-440, 1991.

Lohse et al., Fluorescein-Conjugated Lysine monomers for Solid Phase Synthesis of Fluorescent Peptides and PNA Pligomers Bioconjugate Chem, vol. 8, pp. 503-509, 1997 .pdf.

Binz, et al., "Engineered proteins as specific binding reagents," Current Opinion in Biotechnology, 16: 459-469 (2005).

Skerra, et al., "Engineered protein scaffolds for molecular recognition," Journal of Molecular Recognition, 13: 167-187 (2000).

Koide, et al., "The Fibronectin Type III Domain as a Scaffold for Novel Binding Proteins," Journal of Molecular Biology, 284: 1141-1151 (1998).

Karatan, et al., "Molecular Recognition Properties of FN3 Mono bodies that Bind the Src SH3 Domain," Chemistry & Biology, 11: 835-844 (2004).

Parker, et al., "Antibody mimics based on human fibronectin type three domain engineered for thermostability and high-affinity binding to vascular endothelial growth factor receptor two," Protein Engineering, Design & Selection, 18(9):435-444 (2005).

Siggers et al. Conformational dynamics in loop swap mutants of homologous fibronectin type III domains. Biophys J. Oct. 1, 2007 ;93(7):2447-56.

Skolnick et al. From genes to protein structure and function: novel applications of computational approaches in the genomic era. Trends Biotechnol. 18(1 ):34-9, 2000.

Attwood TK. Genomics. The Babel of bioinformatics. Science. 290(5491 ):471-473, 2000.

Miller et al Ligand binding to proteins: the binding landscape model. Protein Sci. Oct. 1997;6(10):2166-79.

Kuntz. Structure-based strategies for drug design and discovery. Science. 1992 257(5073):1078-1082.

Koivunen et al. Identification of Receptor Ligands with Phage Display Peptide Libraries J Nucl Med; 40:883-888, 1999.

Reiss et al. Inhibition of platelet aggregation by grafting RGD and KGD sequences on the structural scaffold of small disulfide-rich proteins. Platelets 17(3):153-157, 2006.

Helms et al. Destabilizing loop swaps in the CDRs of an immunoglobulin VL domain. Protein Science 4:2073-2081, 1995.

Bass, et al., "Hormone Phage: An Enrichment Method for Variant Proteins with Altered Binding Properties," Proteins: Structure, Function, and Genetics, 8: 309-314 (1990).

Clarke, et al., "Folding and Stability of a Fibronectin Type III Domain of Human Tenascin," Journal of Molecular Biology, 270: 771-778 (1997).

Dehouck, et al., "Fast and accurate predictions of protein stability changes upon mutations using statistical potentials and neural networks: PoPMuSiC-2.0," Bioinformatics, 25(19): 2537-2543 (2009).

Dineen, et al., "The Adnectin CT-322 is a novel VEGF receptor 2 inhibitor that decreases tumor burden in an orthotopic mouse model of pancreatic cancer," BMC Cancer, 8: 352-361 (2008).

Dutta, et al., "High-affinity fragment complementation of a fibronectin type III domain and its application to stability enhancement," Protein Science, 14: 2838-2848 (2005).

Garrard, et al., "Selection of an anti-IGF-1 Fab from a Fab phage library created by mutagenesis of multiple CDR loops," Gene, 128: 103-109 (1993).

Getmanova, et al., "Antagonists to Human and Mouse Vascular Endothelial Growth Factor Receptor 2 Generated by Directed Protein Evolution In Vitro," Chemistry & Biology, 13: 549-556 (2006).

Hackel, et al., "Stability and CDR Composition Biases Enrich Binder Functionality Landscapes," Journal of Molecular Biology, 401: 84-96 (2010).

Hackel, et al., "Picomolar Affinity Fibronectin Domains Engineered Utilizing Loop Length Diversity, Recursive Mutagenesis, and Loop Shuffling," Journal of Molecular Biology, 381: 1238-1252 (2008).

(56) References Cited

OTHER PUBLICATIONS

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2002).
Koide, et al., Teaching an Old Scaffold New Tricks: Monobodies Constructed Using Alternative Surfaces of the FN3 Scaffold, Journal of Molecular Biology, 415: 393-405 (2012).
Lipovsek, et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology, 368: 1024-1041 (2007).
C.N. Pace, "Determination and Analysis of Urea and Guanidine Hydrochloride Denaturation Curves," Methods in Enzymology, 131: 266-280 (1986).
Steiner, et al., "Efficient Selection of DARPins with Sub-nonomolar Affinities using SRP Phage Display," Journal of Molecular Biology, 382: 1211-1227 (2008).
Xu, et al., "Directed Evolution of High-Affinity Antibody Mimics Using mRNA Display," Chemistry & Biology, 9: 933-942 (2002).
Cota, et al., "Two Proteins with the Same Structure Respond very Differently to Mutation: The Role of Plasticity in Protein Stability", Journal of Molecular Biology, 302, 713-725 (2000).
Hamill et al., "The Effect of Boundary Selection on the Stability and Folding of the Third Fibronectin Type III Domain from Human Tenascin", Biochemistry, 37: 8071-8079 (1998).
Garcia-Ibilcieta, et al., "Simple method for production of randomized human tenth fibronectin domain III libraries for use in combinatorial screening procedures," Bio Technologies, 44: 559-562 (2008).
Van den Burg et al., "Selection of mutations for increased protein stability", Curr. Opin. Biotech. 13:333-337 (2002).
SwissProt Accession No. P00533.2, "Epidermal Growth Factor Receptor," pp. 1-49 (Jun. 11, 2014).
Turke et al., "Preexistence and Clonal Selection of MET Amplification in EGFR Mutant NSCLC," Cancer Cell, vol. 17, pp. 77-88 (2010).
Ullrich et al., "Human epidermal growth factor receptor cDNA sequence and aberrant expression of the amplified Jene in A431 epidermoid carcinoma cells," Nature, vol. 309, pp. 418-425 (1984).
Zhang et al., "Complete disulfide bond assignment of a recombinant immunoglobulin G4 monoclonal antibody," Analytical Biochemistry, vol. 311, pp. 1-9 (2002).
Adjei et al., "Early Clinical Development of ARQ197, a Selective, Non-ADP-Competitive Inhibitor Targeting MET Tyrosine Kinase for the Treatment of Advanced Cancers," The Oncologist, vol. 16, pp. 788-799 (2011).
Basel GA et al., "Critical Update and Emerging Trends in Epidermal Growth Factor Receptor Targeting in Cancer," Journal of Clinical Oncology, vol. 23, No. 11, pp. 2445-2459 (2005).
Batley et al., "Inhibition of FGF-1 Receptor Tyrosine Kinase Activity By PD 161570, a New Protein-Tyrosine Kinase nhibitor," Life Sciences, vol. 62, No. 20, pp. 143-150 (1998).
Bean et al., "MET amplification occurs with or without T790M mutations in EGFR mutant lung tumors with acquired esistance to gefilinib or erlotinib," Proceedings of the National Academy of Science, vol. 104, No. 52, pp. 0932-20937 (2007).
Cappuzzo et al., "Epidermal Growth Factor Receptor Gene and Protein and Gefilinib Sensitivity in Non-small-Cell ung Cancer," Journal of the National Cancer Institute, vol. 97, pp. 643-655 (2005).
Christensen et al., "c-Met as a target for human cancer and characterization of inhibitors for therapeutic ntervention," Cancer Letters, vol. 225, pp. 1-26 (2005).
Cooper et al., "Molecular cloning of a new transforming gene from a chemically transformed human cell line," Nature, vol. 311, pp. 29-33 (1984).
DeRoock et al., "Effects of KRAS, BRAF, NRAS, and PIK3CA mutations on the efficacy of cetuximab plus chemotherapy in chemotherapy-refractory metastatic colorectal cancer: a retrospective consortium analysis," Lancet Oncology, vol. 11, pp. 753-762 (2010).
Downward et al., "Autophosphorylation sites on the epidermal growth factor receptor," Nature, vol. 311, pp. 183-485 ( 1984).
Engelman et al., "MET Amplification Leads to Gefitinib Resistance in Lung Cancer by Activating ERBB3 Signaling," Science, vol. 316, pp. 1039-1043 (2007).
Ferguson, Kathryn M., "Structure-Based View of Epidermal Growth Factor Receptor Regulation," Annual Review of Biophysics, vol. 37, pp. 535-373 (2008).
International Search Report and Written Opinion from PCT/US2022/024846 dated Sep. 12, 2022.
Tang et al., "Anti-Transferrin Receptor-Modified Amphotericin B-Loaded PLA-PEG Nanoparticles Cure Candidal Meningitis and Reduce Durg Toxicity," Oct. 5, 2015, International Journal of Medicine, 2015:10, pp. 6227-6241.
MorphoSys AG, "Slonomics", published at https://www.morphosys.com/science/drug-development-capabilities/slonomics on Apr. 15, 2017 (archived at http://web.archive.org/web/20170415114844/https://www.morphosys.com/science/drug-development-capabilities/slonomics).
NCBI GenBank, NCBI Reference Sequence: NP_002151.2, "Tenascin isoform 1 precursor [*Homo sapiens*]", available at https://www.ncbi.nlm.nih.gov/protein/np_002151 (accessed Mar. 30, 2023).
NCBI GenBank, NCBI Reference Sequence: NP_001120972.1, "Hepatocyte growth factor receptor isoform a preproprotein [*Homo sapiens*]", available at https://www.ncbi.nlm.nih.gov/protein/np_001120972.1 (accessed Mar. 30, 2023).
UniProt, UniProtKB Accession No. P10039, "TNC—Tenascin—*Gallus gallus* (Chicken) | UniProtKB | UniProt", available at https://www.uniprot.org/uniprotkb/P10039/entry (accessed Mar. 30, 2023).

\* cited by examiner

AB14 is SEQ ID NO: 393 linked to siRNA AB03

AB14 is SEQ ID NO: 393 linked to siRNA AB03

FN3 DOMAIN-SIRNA CONJUGATES AND USES THEREOF

CROSS-REFERENCE TO RELATED APPLICATIONS

The present application claims priority to U.S. Provisional Application No. 62/914,725, filed Oct. 14, 2019, U.S. Provisional Application No. 62/979,557, filed Feb. 21, 2020, and U.S. Provisional Application No. 63/054,896, filed Jul. 22, 2020, each of which is hereby incorporated by reference in its entirety.

This application is also related to U.S. Provisional Application No. 62/914,654, filed Oct. 14, 2019, U.S. Provisional Application No. 62/914,643, filed Oct. 14, 2019, U.S. Provisional Application No. 62/949,020, filed Dec. 17, 2019, U.S. application Ser. No. 17/070,020, filed Oct. 14, 2020, and PCT Application No. PCT/US20/55465, filed Oct. 14, 2020, each of which is hereby incorporated by reference in its entirety.

FIELD

The present embodiments relate to siRNA molecules that can be conjugated fibronectin type III domains (FN3) and methods of making and using the molecules.

SEQUENCE LISTING

This application contains a Sequence Listing which has been submitted in ASCII format via EFS-Web and is hereby incorporated by reference in its entirety. The ASCII text file was created on Dec. 15, 2020, it is named 145965_02301_SeqList_15_Dec_2020_ST25.TXT, and it is 473 kilobytes in size.

BACKGROUND

Therapeutic nucleic acids include, e.g., small interfering RNA (siRNA), micro RNA (miRNA), antisense oligonucleotides, ribozymes, plasmids, immune stimulating nucleic acids, antisense, antagomir, antimir, microRNA mimic, supermir, U1 adaptor, and aptamer. In the case of siRNA or miRNA, these nucleic acids can down-regulate intracellular levels of specific proteins through a process termed RNA interference (RNAi). The therapeutic applications of RNAi are extremely broad, since siRNA and miRNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by siRNA constructs are, first, their susceptibility to nuclease digestion in plasma and, second, their limited ability to gain access to the intracellular compartment where they can bind the protein RISC when administered systemically as the free siRNA or miRNA. Certain delivery systems, such as lipid nanoparticles formed from cationic lipids with other lipid components, such as cholesterol and PEG lipids, and oligonucleotides (such as siRNA) have been used to facilitate the cellular uptake of the oligonucleotides. However, these have not been shown to be successful in efficiently and effectively delivering siRNA to its intended target.

There remains a need for compositions and methods for delivering siRNA to its intended cellular target. The present embodiments fulfills these needs as well as others.

SUMMARY

In some embodiments, siRNA conjugated to FN3 domains that bind CD71 protein are provided.

In some embodiments, siRNA conjugated to FN3 domains that bind EPCAM protein are provided.

In some embodiments, siRNA conjugated to FN3 domains that bind EGFR protein are provided.

In some embodiments, FN3 domains are provided that comprise the amino acid sequence of any FN3 domain provided herein. In some embodiments, the FN3 domains bind to CD71, EPCAM, or EGFR. In some embodiments, the FN3 domains specifically bind to CD71, EPCAM, or EGFR.

In some embodiments, the composition comprises two FN3 domains connected by a linker, such as a flexible linker. In some embodiments, the two FN3 domains bind to different targets. In some embodiments, a first FN3 domain binds to one of CD71, EPCAM, or EGFR. In some embodiments, a second FN3 domain binds to one of CD71, EPCAM, or EGFR that is not the same as first FN3 domain.

In some embodiments, oligonucleotides, such as dsRNA or siRNA molecules are provided herein. In some embodiments, the oligonucleotides have the sequences as provided herein, with or without the modifications provided herein. In some embodiments, the oligonucleotides are provided in a composition, such as a pharmaceutical composition. In some embodiments, the oligonucleotides are conjugated to a polypeptide.

In some embodiments, composition comprising one or more FN3 domains conjugated to a siRNA molecule are provided.

In some embodiments, a composition having a formula of $(X1)_n$-$(X2)_q$-$(X3)_y$-L-X4, wherein X1 is a first FN3 domain; X2 is second FN3 domain; X3 is a third FN3 domain or half-life extender molecule; L is a linker; and X4 is a nucleic acid molecule, wherein n, q, and y are each independently 0 or 1, are provided.

In some embodiments, a composition having a formula of C—$(X1)_n$-$(X2)_q$-$(X3)_y$-L-X4, wherein C is a polymer; X1 is a first FN3 domain; X2 is second FN3 domain; X3 is a third FN3 domain or half-life extender molecule; L is a linker; and X4 is a nucleic acid molecule, wherein n, q, and y are each independently 0 or 1, are provided.

In some embodiments, a composition having a formula of $(X1)_n$-$(X2)_q$-$(X3)_y$-L-X4-C, wherein X1 is a first FN3 domain; X2 is second FN3 domain; X3 is a third FN3 domain or half-life extender molecule; L is a linker; X4 is a nucleic acid molecule; and C is a polymer, wherein n, q, and y are each independently 0 or 1, are provided.

In some embodiments, a composition having a formula of X4-L-$(X1)_n$-$(X2)_q$-$(X3)_y$, wherein X1 is a first FN3 domain; X2 is second FN3 domain; X3 is a third FN3 domain or half-life extender molecule; L is a linker; and X4 is a nucleic acid molecule, wherein n, q, and y are each independently 0 or 1, are provided.

In some embodiments, a composition having a formula of C—X4-L-$(X1)_n$-$(X2)_q$-$(X3)_y$, wherein C is a polymer; X1 is a first FN3 domain; X2 is second FN3 domain; X3 is a third FN3 domain or half-life extender molecule; L is a linker; and X4 is a nucleic acid molecule, wherein n, q, and y are each independently 0 or 1, are provided.

In some embodiments, a composition having a formula of X4-L-$(X1)_n$-$(X2)_q$-$(X3)_y$-C, wherein X1 is a first FN3 domain; X2 is second FN3 domain; X3 is a third FN3 domain or half-life extender molecule; L is a linker; X4 is a nucleic acid molecule; and C is a polymer, wherein n, q, and y are each independently 0 or 1, are provided.

In some embodiments, pharmaceutical compositions comprising one or more of the compositions provided herein are provided.

In some embodiments, methods of treating cancer in a subject in need thereof, the method comprising administering to the subject a composition provided herein are provided.

In some embodiments, a use of a composition as provided herein or of any of in the preparation of a pharmaceutical composition or medicament for treating cancer are provided.

In some embodiments, methods of reducing the expression of a target gene in a cell, the method comprising contacting the cell with a composition as provided herein are provided.

In some embodiments, isolated polynucleotides encoding the FN3 domains described herein are provided.

In some embodiments, a vector comprising the polynucleotides described herein are provided.

In some embodiments, a host cell comprising the vectors described herein are provided.

In some embodiments, methods of producing the FN3 domains are provided. In some embodiments, the method comprises culturing a host cell comprising a vector encoding or expressing the FN3 domain. In some embodiments, the method further comprises purifying the FN3 domain. In some embodiments, the FN3 domain binds CD71, EPCAM, or EGFR.

In some embodiments, pharmaceutical compositions comprising a FN3 domain that binds to CD71, EPCAM, or EGFR linked to a nucleic acid molecule and a pharmaceutically acceptable carrier are provided. In some embodiments, the composition does not comprise (e.g. is free of) a compound or protein that binds to ASGPR.

In some embodiments, kits comprising one or more of the FN3 domains with or without the nucleic acid molecules are provided.

DETAILED DESCRIPTION OF THE DISCLOSURE

Figure 1:
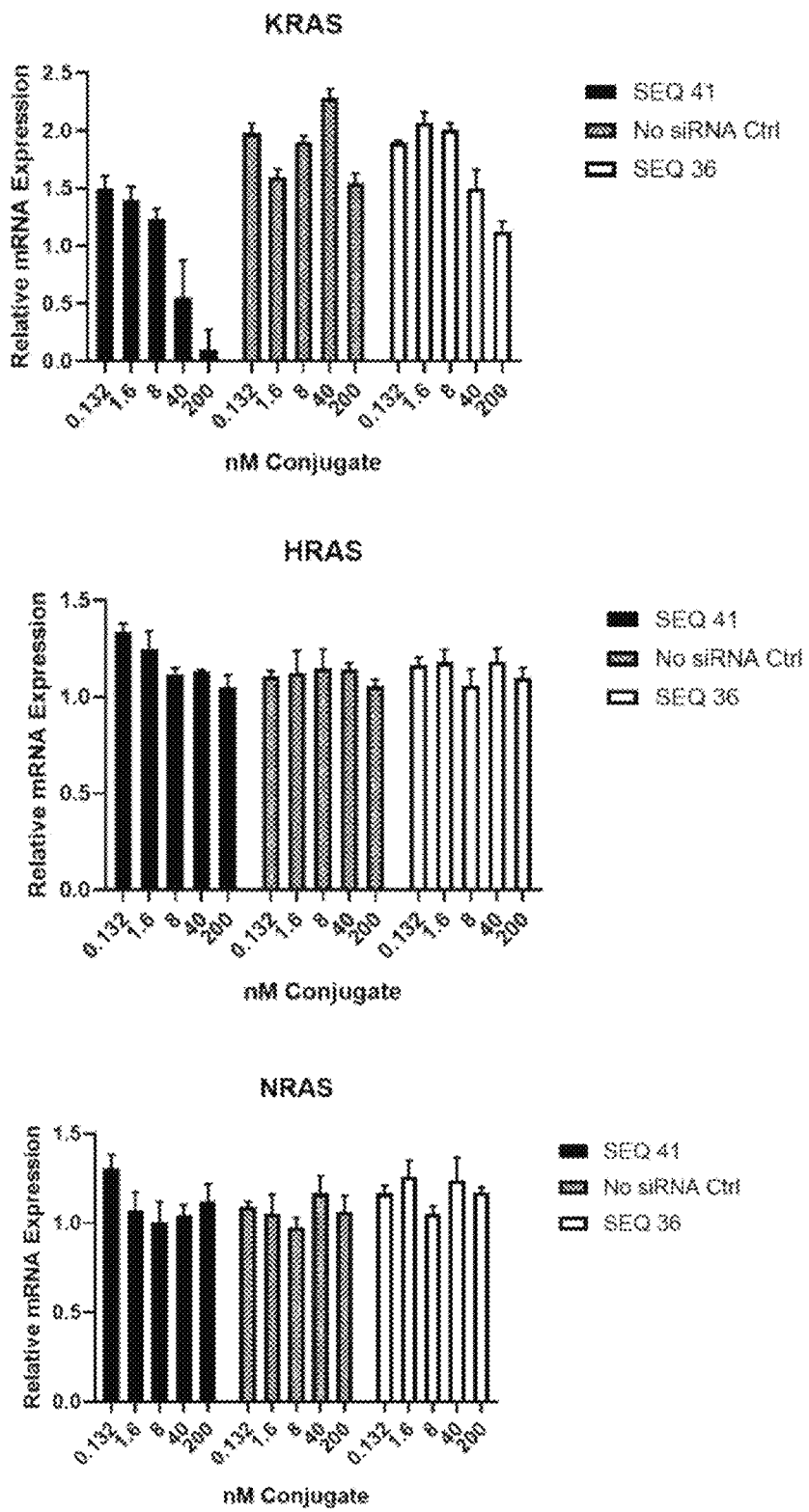
FIG. 1 illustrates the knock-down of KRAS with a FN3-siRNA conjugate.

As used in this specification and the appended claims, the singular forms "a," "an," and "the" include plural referents unless the content clearly dictates otherwise. Thus, for example, reference to "a cell" includes a combination of two or more cells, and the like.

"Fibronectin type III (FN3) domain" (FN3 domain) refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the $3^{rd}$ FN3 domain of tenascin (TN3), or the $10^{th}$ FN3 domain of fibronectin (FN10).

The term "capture agent" refers to substances that bind to a particular type of cells and enable the isolation of that cell from other cells. Exemplary capture agents are magnetic beads, ferrofluids, encapsulating reagents, molecules that bind the particular cell type and the like.

"Sample" refers to a collection of similar fluids, cells, or tissues isolated from a subject, as well as fluids, cells, or tissues present within a subject. Exemplary samples are tissue biopsies, fine needle aspirations, surgically resected tissue, organ cultures, cell cultures and biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium and lavage fluids and the like.

"Substituting" or "substituted" or "mutating" or "mutated" refers to altering, deleting of inserting one or more amino acids or nucleotides in a polypeptide or polynucleotide sequence to generate a variant of that sequence.

"Variant" refers to a polypeptide or a polynucleotide that differs from a reference polypeptide or a reference polynucleotide by one or more modifications for example, substitutions, insertions or deletions.

"Specifically binds" or "specific binding" refers to the ability of a FN3 domain to bind to its target, such as CD71, with a dissociation constant ($K_D$) of about $1 \times 10^{-6}$ M or less, for example about $1 \times 10^{-7}$ M or less, about $1 \times 10^{-8}$ M or less, about $1 \times 10^{-9}$ M or less, about $1 \times 10^{-10}$ M or less, about $1 \times 10^{-11}$ M or less, about $1 \times 10^{-12}$ M or less, or about $1 \times 10^{-13}$ M or less. Alternatively, "specific binding" refers to the ability of a FN3 domain to bind to its target (e.g. CD71) at least 5-fold above a negative control in standard ELISA assay. In some embodiments, a negative control is an FN3 domain that does not bind CD71. In some embodiment, an FN3 domain that specifically binds CD71 may have cross-reactivity to other related antigens, for example to the same predetermined antigen from other species (homologs), such as *Macaca Fascicularis* (cynomolgus monkey, cyno) or *Pan troglodytes* (chimpanzee).

"Library" refers to a collection of variants. The library may be composed of polypeptide or polynucleotide variants.

"Stability" refers to the ability of a molecule to maintain a folded state under physiological conditions such that it retains at least one of its normal functional activities, for example, binding to a predetermined antigen such as CD71.

"CD71" refers to human CD71 protein having the amino acid sequence of SEQ ID NOs: 2 or 3. In some embodiments, SEQ ID NO: 2 is full length human CD71 protein. In some embodiments, SEQ ID NO: 3 is the extracellular domain of human CD71.

"Tencon" refers to the synthetic fibronectin type III (FN3) domain having the sequence shown in SEQ ID NO:1

(SPPKDLVVTEVTEETVNLAWDNEMRVTEYLVVYTPTHEGGLEMQFRVPGDQTSTIIQE LEPGVEYFIRVFAILENKKSIPVSARVAT) and described in U.S. Pat. Publ. No. 2010/0216708.

A "cancer cell" or a "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

"Vector" refers to a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than about 50 amino acids may be referred to as "peptides".

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Subject" includes any human or nonhuman animal. "Nonhuman animal" includes all vertebrates, e g, mammals and non-mammals, such as nonhuman primates, sheep, dogs, cats, horses, cows chickens, amphibians, reptiles, etc. Except when noted, the terms "patient" or "subject" are used interchangeably.

"Isolated" refers to a homogenous population of molecules (such as synthetic polynucleotides or a polypeptide such as FN3 domains) which have been substantially separated and/or purified away from other components of the system the molecules are produced in, such as a recombinant cell, as well as a protein that has been subjected to at least one purification or isolation step. "Isolated FN3 domain" refers to an FN3 domain that is substantially free of other cellular material and/or chemicals and encompasses FN3 domains that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

In some embodiments, a composition comprising a polypeptide, such as a polypeptide comprising a FN3 domain, linked to a nucleic acid molecule are provided. The nucleic acid molecule can be, for example, a siRNA molecule.

Accordingly, in some embodiments, the siRNA is a double-stranded RNAi (dsRNA) agent capable of inhibiting the expression of a target gene. The dsRNA agent comprises a sense strand and an antisense strand. In some embodiments, each strand of the dsRNA agent can range from 12-40 nucleotides in length. For example, each strand can be from 14-40 nucleotides in length, 17-37 nucleotides in length, 25-37 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

In some embodiments, the sense strand and antisense strand typically form a duplex dsRNA. The duplex region of a dsRNA agent may be from 12-40 nucleotide pairs in length. For example, the duplex region can be from 14-40 nucleotide pairs in length, 17-30 nucleotide pairs in length, 25-35 nucleotides in length, 27-35 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotide pairs in length.

In some embodiments, the dsRNA comprises one or more overhang regions and/or capping groups of dsRNA agent at the 3'-end, or 5'-end or both ends of a strand. The overhang can be 1-10 nucleotides in length, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

In some embodiments, the nucleotides in the overhang region of the dsRNA agent can each independently be a modified or unmodified nucleotide including, but not limited to 2'-sugar modified, such as, 2-F 2'-Omethyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be other sequence.

The 5'- or 3'-overhangs at the sense strand, antisense strand or both strands of the dsRNA agent may be phosphorylated. In some embodiments, the overhang region contains two nucleotides having a phosphorothioate between the two nucleotides, where the two nucleotides can be the same or different. In one embodiment, the overhang is present at the 3'-end of the sense strand, antisense strand or both strands. In one embodiment, this 3'-overhang is present in the antisense strand. In one embodiment, this 3'-overhang is present in the sense strand.

The dsRNA agent may comprise only a single overhang, which can strengthen the interference activity of the dsRNA, without affecting its overall stability. For example, the single-stranded overhang is located at the 3'-terminal end of the sense strand or, alternatively, at the 3'-terminal end of the antisense strand. The dsRNA may also have a blunt end, located at the 5'-end of the antisense strand (or the 3'-end of the sense strand) or vice versa. Generally, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand favor the guide strand loading into RISC process. For example the single overhang comprises at least two, three, four, five, six, seven, eight, nine, or ten nucleotides in length.

In some embodiments, the dsRNA agent may also have two blunt ends, at both ends of the dsRNA duplex.

In some embodiments, every nucleotide in the sense strand and antisense strand of the dsRNA agent may be modified. Each nucleotide may be modified with the same or different modification which can include one or more alteration of one or both of the non-linking phosphate oxygens and/or one or more of the linking phosphate oxygens; alteration of a constituent of the ribose sugar, e.g., of the 2 hydroxyl on the ribose sugar; wholesale replacement of the phosphate moiety with "dephospho" linkers; modification or replacement of a naturally occurring base; and replacement or modification of the ribose-phosphate backbone.

In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In one embodiment, each residue of the sense strand and antisense strand is independently modified with 2'-O-methyl or 2'-fluoro.

In some embodiments, at least two different modifications are typically present on the sense strand and antisense strand. Those two modifications may be the 2'-deoxy, 2'-O-methyl or 2'-fluoro modifications, acyclic nucleotides or others.

In one embodiment, the sense strand and antisense strand each comprises two differently modified nucleotides selected from 2'-fluoro, 2'-O-methyl or 2'-deoxy.

The dsRNA agent may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA agent comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. In some embodiments, these terminal three nucleotides may be at the 3'-end of the antisense strand.

In some embodiments, the dsRNA composition is linked by a modified base or nucleoside analogue as described in U.S. Pat. No. 7,427,672, which is incorporated herein by reference. In some embodiments, the modified base or nucleoside analogue is referred to as the linker or L in formulas described herein.

In some embodiments, the modified base or nucleoside analogue has the structure as shown in Chemical Formula I and a salt thereof.

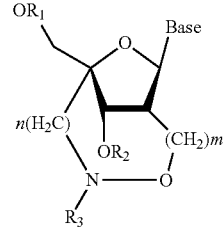

(Chemical Formula I)

where Base represents an aromatic heterocyclic group or aromatic hydrocarbon ring group optionally having a substituent, $R_1$ and $R_2$ are identical or different, and each represent a hydrogen atom, a protective group for a hydroxyl group for nucleic acid synthesis, an alkyl group, an alkenyl group, a cycloalkyl group, an aryl group, an aralkyl group, an acyl group, a sulfonyl group, a silyl group, a phosphate group, a phosphate group protected with a protective group for nucleic acid synthesis, or —$P(R_4)R_5$ where $R_4$ and $R_5$ are identical or different, and each represent a hydroxyl group, a hydroxyl group protected with a protective group for nucleic acid synthesis, a mercapto group, a mercapto group protected with a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted by an alky group having 1 to 5 carbon atoms, $R_3$ represents a hydrogen atom, an alkyl group, an alkenyl group, a cycloalkyl group, an aryl group, an aralkyl group, an acyl group, a sulfonyl group, or a functional molecule unit substituent, and m denotes an integer of 0 to 2, and n denotes an integer of 1 to 3.

In some embodiments, the modified base or nucleoside analogue has the structure as shown in Chemical Formula I and salts thereof, wherein $R_1$ is a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, or a silyl group.

In some embodiments, the modified base or nucleoside analogue has the structure as shown in Chemical Formula I and salts thereof, wherein $R_1$ is a hydrogen atom, an acetyl group, a benzoyl group, a methanesulfonyl group, a p-toluenesulfonyl group, a benzyl group, a p-methoxybenzyl group, a trityl group, a dimethoxytrityl group, a monomethoxytrityl group, or a tert-butyldiphenylsilyl group.

In some embodiments, the modified base or nucleoside analogue has the structure as shown in Chemical Formula I and salts thereof, wherein $R_2$ is a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, a silyl group, a phosphoroamidite group, a phosphonyl group, a phosphate group, or a phosphate group protected with a protective group for nucleic acid synthesis.

In some embodiments, the modified base or nucleoside analogue has the structure as shown in Chemical Formula I and salts thereof, wherein $R_2$ is a hydrogen atom, an acetyl group, a benzoyl group, a methanesulfonyl group, a p-toluenesulfonyl group, a benzyl group, a p-methoxybenzyl group, a tert-butyldiphenylsilyl group, —P(OC$_2$H$_4$CN)(N(i-Pr)$_2$), —P(OCH$_3$)(N(i-Pr)$_2$), a phosphonyl group, or a 2-chlorophenyl- or 4-chlorophenylphosphate group.

In some embodiments, the modified base or nucleoside analogue has the structure as shown in Chemical Formula I and salts thereof, wherein $R_3$ is a hydrogen atom, a phenoxyacetyl group, an alkyl group having 1 to 5 carbon atoms, an alkenyl group having 1 to 5 carbon atoms, an aryl group having 6 to 14 carbon atoms, a methyl group substituted by one to three aryl groups, a lower aliphatic or aromatic sulfonyl group such as a methanesulfonyl group or a p-toluenesulfonyl group, an aliphatic acyl group having 1 to 5 carbon atoms such as an acetyl group, or an aromatic acyl group such as a benzoyl group.

In some embodiments, the modified base or nucleoside analogue has the structure as shown in Chemical Formula I and salts thereof, wherein the functional molecule unit substituent as $R_3$ is a fluorescent or chemiluminescent labeling molecule, a nucleic acid incision activity functional group, or an intracellular or nuclear transfer signal peptide.

In some embodiments, the modified base or nucleoside analogue has the structure as shown in Chemical Formula I and salts thereof, wherein Base is a purin-9-yl group, a 2-oxopyrimidin-1-yl group, or a purin-9-yl group or a 2-oxopyrimidin-1-yl group having a substituent selected from the following a group: a group: A hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom.

In some embodiments, the modified base or nucleoside analogue has the structure as shown in Chemical Formula I and salts thereof, wherein Base is 6-aminopurin-9-yl (i.e., adeninyl), 6-aminopurin-9-yl having the amino group protected with a protective group for nucleic acid synthesis, 2,6-diaminopurin-9-yl, 2-amino-6-chloropurin-9-yl, 2-amino-6-chloropurin-9-yl having the amino group protected with a protective group for nucleic acid synthesis, 2-amino-6-fluoropurin-9-yl, 2-amino-6-fluoropurin-9-yl having the amino group protected with a protective group for nucleic acid synthesis, 2-amino-6-bromopurin-9-yl, 2-amino-6-bromopurin-9-yl having the amino group protected with a protective group for nucleic acid synthesis, 2-amino-6-hydroxypurin-9-yl (i.e., guaninyl), 2-amino-6-hydroxypurin-9-yl having the amino group protected with a protective group for nucleic acid synthesis, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl, 6-mercaptopurin-9-yl, 2-oxo-4-amino-1,2-dihydropyrimidin-1-yl (i.e., cytosinyl), 2-oxo-4-amino-1,2-dihydropyrimidin-1-yl having the amino group protected with a protective group for nucleic acid synthesis, 2-oxo-4-amino-5-fluoro-1,2-dihydropyrimidin-1-yl, 2-oxo-4-amino-5-fluoro-1,2-dihydropyrimidin-1-yl having the amino group protected with a protective group for nucleic acid synthesis, 4-amino-2-oxo-5-chloro-1,2-dihydropyrimidin-1-yl, 2-oxo-4-methoxy-1,2-dihydropyrimidin-1-yl, 2-oxo-4-mercapto-1,2-dihydropyrimidin-1-yl, 2-oxo-4-hydroxy-1,2-dihydropyrimidin-1-yl (i.e., uracinyl), 2-oxo-4-hydroxy-5-methyl-1,2-dihydropyrimidin-1-yl (i.e., thyminyl), 4-amino-5-methyl-2-oxo-1,2-dihydropyrimidin-1-yl (i.e., 5-methylcytosinyl), or 4-amino-5-methyl-2-oxo-1,2-dihydropyrimidin-1-yl having the amino group protected with a protective group for nucleic acid synthesis.

In some embodiments, the modified base or nucleoside analogue has the structure as shown in Chemical Formula I and salts thereof, wherein m is 0, and n is 1.

In some embodiments, the modified base or nucleoside analogue is a DNA oligonucleotide or RNA oligonucleotide analogue, containing one or two or more of one or more types of unit structures of nucleoside analogues having the structure as shown in Chemical Formula II, or a pharmacologically acceptable salt thereof, provided that a form of linking between respective nucleosides in the oligonucleotide analogue may contain one or two or more phosphorothioate bonds [—OP(O)(S$^-$)O—] aside from a phosphodiester bond [—OP(O$_2$$^-$)O—] identical with that in a natural nucleic acid, and if two or more of one or more types of these structures are contained, Base may be identical or different between these structures:

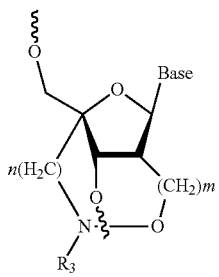

(Chemical Formula II)

where Base represents an aromatic heterocyclic group or aromatic hydrocarbon ring group optionally having a substituent, $R_3$ represents a hydrogen atom, an alkyl group, an alkenyl group, a cycloalkyl group, an aryl group, an aralkyl group, an acyl group, a sulfonyl group, a silyl group, or a functional molecule unit substituent, and m denotes an integer of 0 to 2, and n denotes an integer of 1 to 3.

In some embodiments, the oligonucleotide analogue or the pharmacologically acceptable salt thereof has the structure as shown in Chemical Formula II, wherein $R_1$ is a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, or a silyl group.

In some embodiments, the oligonucleotide analogue or the pharmacologically acceptable salt thereof has the structure as shown in Chemical Formula II, wherein $R_1$ is a hydrogen atom, an acetyl group, a benzoyl group, a methanesulfonyl group, a p-toluenesulfonyl group, a benzyl group, a p-methoxybenzyl group, a trityl group, a dimethoxytrityl group, a monomethoxytrityl group, or a tert-butyldiphenylsilyl group.

In some embodiments, the oligonucleotide analogue or the pharmacologically acceptable salt thereof has the structure as shown in Chemical Formula II, wherein $R_2$ is a hydrogen atom, an aliphatic acyl group, an aromatic acyl group, an aliphatic or aromatic sulfonyl group, a methyl group substituted by one to three aryl groups, a methyl group substituted by one to three aryl groups having an aryl ring substituted by a lower alkyl, lower alkoxy, halogen, or cyano group, a silyl group, a phosphoroamidite group, a phosphonyl group, a phosphate group, or a phosphate group protected with a protective group for nucleic acid synthesis.

In some embodiments, the oligonucleotide analogue or the pharmacologically acceptable salt thereof has the structure as shown in Chemical Formula II, wherein $R_2$ is a hydrogen atom, an acetyl group, a benzoyl group, a benzyl group, a p-methoxybenzyl group, a methanesulfonyl group, a p-toluenesulfonyl group, a tert-butyldiphenylsilyl group, —P(OC$_2$H$_4$CN)(N(i-Pr)$_2$), —P(OCH$_3$)(N(i-Pr)$_2$), a phosphonyl group, or a 2-chlorophenyl- or 4-chlorophenylphosphate group.

In some embodiments, the oligonucleotide analogue or the pharmacologically acceptable salt thereof has the structure as shown in Chemical Formula II, wherein $R_3$ is a hydrogen atom, a phenoxyacetyl group, an alkyl group having 1 to 5 carbon atoms, an alkenyl group having 1 to 5 carbon atoms, an aryl group having 6 to 14 carbon atoms, a methyl group substituted by one to three aryl groups, a lower aliphatic or aromatic sulfonyl group such as a methanesulfonyl group or a p-toluenesulfonyl group, an aliphatic acyl group having 1 to 5 carbon atoms such as an acetyl group, or an aromatic acyl group such as a benzoyl group.

In some embodiments, the oligonucleotide analogue or the pharmacologically acceptable salt thereof has the structure as shown in Chemical Formula II, wherein the functional molecule unit substituent as $R_3$ is a fluorescent or chemiluminescent labeling molecule, a nucleic acid incision activity functional group, or an intracellular or nuclear transfer signal peptide.

In some embodiments, the oligonucleotide analogue or the pharmacologically acceptable salt thereof has the structure as shown in Chemical Formula II, wherein Base is a purin-9-yl group, a 2-oxopyrimidin-1-yl group, or a purin-9-yl group or a 2-oxopyrimidin-1-yl group having a substituent selected from the following a group: a group: A hydroxyl group, a hydroxyl group protected with a protective group for nucleic acid synthesis, an alkoxy group having 1 to 5 carbon atoms, a mercapto group, a mercapto group protected with a protective group for nucleic acid synthesis, an alkylthio group having 1 to 5 carbon atoms, an amino group, an amino group protected with a protective group for nucleic acid synthesis, an amino group substituted by an alkyl group having 1 to 5 carbon atoms, an alkyl group having 1 to 5 carbon atoms, and a halogen atom.

In some embodiments, the oligonucleotide analogue or the pharmacologically acceptable salt thereof has the structure as shown in Chemical Formula II, wherein Base is 6-aminopurin-9-yl (i.e. adeninyl), 6-aminopurin-9-yl having the amino group protected with a protective group for nucleic acid synthesis, 2,6-diaminopurin-9-yl, 2-amino-6-chloropurin-9-yl, 2-amino-6-chloropurin-9-yl having the amino group protected with a protective group for nucleic acid synthesis, 2-amino-6-fluoropurin-9-yl, 2-amino-6-fluoropurin-9-yl having the amino group protected with a protective group for nucleic acid synthesis, 2-amino-6-bromopurin-9-yl, 2-amino-6-bromopurin-9-yl having the amino group protected with a protective group for nucleic acid synthesis, 2-amino-6-hydroxypurin-9-yl (i.e., guaninyl), 2-amino-6-hydroxypurin-9-yl having the amino group protected with a protective group for nucleic acid synthesis, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl, 6-mercaptopurin-9-yl, 2-oxo-4-amino-1,2-dihydropyrimidin-1-yl (i.e., cytosinyl), 2-oxo-4-amino-1,2-dihydropyrimidin-1-yl having the amino group protected with a protective group for nucleic acid synthesis, 2-oxo-4-amino-5-fluoro-1,2-dihydropyrimidin-1-yl, 2-oxo-4-amino-5-fluoro-1,2-dihydropyrimidin-1-yl group having the amino group protected with a protective group for nucleic acid synthesis, 4-amino-2-oxo-5-chloro-1,2-dihydropyrimidin-1-yl, 2-oxo-4-methoxy-1,2-dihydropyrimidin-1-yl, 2-oxo-4-mercapto-1,2-dihydropyrimidin-1-yl, 2-oxo-4-hydroxy-1,2-dihydropyrimidin-1-yl (i.e., uracinyl), 2-oxo-4-hydroxy-5-methyl-1,2-dihydropyrimidin-1-yl (i.e., thyminyl), 4-amino-5-methyl-2-oxo-1,2-dihydropyrimidin-1-yl (i.e., 5-methylcytosinyl), or 4-amino-5-methyl-2-oxo-1,2-dihydropyrimidin-1-yl having the amino group protected with a protective group for nucleic acid synthesis.

In some embodiments, the oligonucleotide analogue or the pharmacologically acceptable salt thereof has the structure as shown in Chemical Formula II, wherein m is 0, and n is 1.

In some embodiments, compositions described herein further comprises a polymer (polymer moiety C). In some instances, the polymer is a natural or synthetic polymer, consisting of long chains of branched or unbranched monomers, and/or cross-linked network of monomers in two or three dimensions In some instances, the polymer includes a polysaccharide, lignin, rubber, or polyalkylen oxide (e.g., polyethylene glycol). In some instances, the at least one polymer includes, but is not limited to, alpha-, omega-dihydroxylpolyethyleneglycol, biodegradable lactone-based polymer, e.g. polyacrylic acid, polylactide acid (PLA), poly (glycolic acid) (PGA), polypropylene, polystyrene, polyolefin, polyamide, polycyanoacrylate, polyimide, polyethylenterephthalat (PET, PETG), polyethylene terephthalate (PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer comprises polyalkylene oxide. In some instances, the polymer comprises PEG. In some instances, the polymer comprises polyethylene imide (PEI) or hydroxy ethyl starch (HES).

In some instances, C is a PEG moiety. In some instances, the PEG moiety is conjugated at the 5' terminus of the nucleic acid molecule while the binding moiety is conjugated at the 3' terminus of the nucleic acid molecule. In some instances, the PEG moiety is conjugated at the 3' terminus of the nucleic acid molecule while the binding moiety is conjugated at the 5' terminus of the nucleic acid molecule. In some instances, the PEG moiety is conjugated to an internal site of the nucleic acid molecule. In some instances, the PEG moiety, the binding moiety, or a combination thereof, are conjugated to an internal site of the nucleic acid molecule. In some instances, the conjugation is a direct conjugation. In some instances, the conjugation is via native ligation.

In some embodiments, the polyalkylene oxide (e.g., PEG) is a polydispers or monodispers compound. In some instances, polydispers material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some embodiments, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some embodiments, the polyalkylene oxide (e.g., PEG) is a discrete PEG, in which the discrete PEG is a polymeric PEG comprising more than one repeating ethylene oxide units. In some instances, a discrete PEG (dPEG) comprises from 2 to 60, from 2 to 50, or from 2 to 48 repeating ethylene oxide units. In some instances, a dPEG comprises about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some instances, a dPEG comprises about 2 or more repeating ethylene oxide units. In some instances, a dPEG comprises about 3 or more repeating ethylene oxide units. In some instances, a dPEG comprises about 4 or more repeating ethylene oxide units. In some instances, a dPEG comprises about 5 or more repeating ethylene oxide units. In some instances, a dPEG comprises about 6 or more repeating ethylene oxide units. In some instances, a dPEG comprises about 7 or more repeating ethylene oxide units. In some instances, a dPEG comprises about 8 or more repeating ethylene oxide units. In some instances, a dPEG comprises about 9 or more repeating ethylene oxide units. In some instances, a dPEG comprises about 10 or more repeating ethylene oxide units. In some instances, a dPEG comprises about 11 or more repeating ethylene oxide units. In some instances, a dPEG comprises about 12 or more repeating ethylene oxide units. In some instances, a dPEG comprises about 13 or more repeating ethylene oxide units. In some instances, a dPEG comprises about 14 or more repeating ethylene oxide units. In some instances, a dPEG comprises about 15 or more repeating ethylene oxide units. In some instances, a dPEG comprises about 16 or more repeating ethylene oxide units. In some instances, a dPEG comprises about 17 or more repeating ethylene oxide units. In some instances, a dPEG comprises about 18 or more repeating ethylene oxide units. In some instances, a dPEG comprises about 19 or more repeating ethylene oxide units. In some instances, a dPEG comprises about 20 or more repeating ethylene oxide units. In some instances, a dPEG comprises about 22 or more repeating ethylene oxide units. In some instances, a dPEG comprises about 24 or more repeating ethylene oxide units. In some instances, a dPEG comprises about 26 or more repeating ethylene oxide units. In some instances, a dPEG comprises about 28 or more repeating ethylene oxide units. In some instances, a dPEG comprises about 30 or more repeating ethylene oxide units. In some instances, a dPEG comprises about 35 or more repeating ethylene oxide units. In some instances, a dPEG comprises about 40 or more repeating ethylene oxide units. In some instances, a dPEG comprises about 42 or more repeating ethylene oxide units. In some instances, a dPEG comprises about 48 or more repeating ethylene oxide units. In some instances, a dPEG comprises about 50 or more repeating ethylene oxide units. In some cases, a dPEG is synthesized as a single molecular weight compound from pure (e.g., about 95%, 98%, 99%, or 99.5%) staring material in a step-wise fashion. In some cases, a dPEG has a specific molecular weight, rather than an average molecular weight. In some cases, a dPEG described herein is a dPEG from Quanta Biodesign, LMD.

In some embodiments, the dsRNA agent comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In some embodiments, the dsRNA agent can comprise a phosphorus-containing group at the 5'-end of the sense strand or antisense strand. The 5'-end phosphorus-containing group can be 5'-end phosphate (5'-P), 5'-end phosphorothioate (5'-PS), 5'-end phosphorodithioate (5'-PS$_2$), 5'-end vinylphosphonate (5'-VP), 5'-end methylphosphonate (MePhos), or 5'-deoxy-5'-C-malonyl. When the 5'-end phosphorus-containing group is 5'-end vinylphosphonate (5'-VP), the 5'-VP can be either 5'-E-VP isomer, such as trans-vinylphosphate or cis-vinylphosphate, or mixtures thereof. Representative structures of these modifications can be found in, for example, U.S. Pat. No. 10,233,448, which is hereby incorporated by reference in its entirety.

In some embodiments, the dsRNA agents are 5' phosphorylated or include a phosphoryl analog at the 5' prime terminus. 5'-phosphate modifications include those which are compatible with RISC mediated gene silencing. Suitable modifications include: 5'-monophosphate ((HO$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g. RP(OH)(O)—O-5'-, 5'-alkenylphosphonates (i.e. vinyl, substituted vinyl), (OH)$_2$(O)P-5'-CH2-), 5'-alkyletherphosphonates (R=alkylether=methoxymethyl (MeOCH2-), ethoxymethyl, etc., e.g. RP(OH)(O)—O-5'-). In some embodiments, the modification can in placed in the antisense strand of a dsRNA agent.

In some embodiments, the antisense strand of the dsRNA agent is 100% complementary to a target RNA to hybridize thereto and inhibits its expression through RNA interference. The target RNA can be any RNA expressed in a cell. In another embodiment, the antisense strand of the dsRNA agent is at least 99%, at least 98%, at least 97%, at least 96%, 95%, at least 90%, at least 85%, at least 80%, at least 75%, at least 70%, at least 65%, at least 60%, at least 55%, or at least 50% complementary to a target RNA. In some embodiments, the target RNA is KRAS RNA. In some embodiments, the target RNA is NRAS or HRAS. In some embodiments, the siRNA targets KRAS but does not significantly target NRAS or HRAS. In some embodiments, the siRNA molecule is a siRNA that reduces the expression of KRAS and does not significantly reduce the expression of HRAS and NRAS. In some embodiments, the siRNA molecule is a siRNA that reduces the expression of KRAS and does not reduce the expression of HRAS and NRAS by more than 50% in an assay described herein at a concentration of no more than 200 nm as described herein.

The siRNA can be targeted against any gene or RNA (e.g. mRNA) transcript of interest. In some embodiments, the KRAS transcript that is targeted can have a substitution that would encode a G12C, G12V, G12S and G12D mutation in the KRAS protein. Accordingly, in some embodiments, the siRNA targets a KRAS transcript that encodes for a KRAS mutant protein comprising a G12C, G12V, G12S and/or G12D mutation (substitution).

Other modifications and patterns of modifications can be found in, for example, U.S. Pat. No. 10,233,448, which is hereby incorporated by reference.

In some embodiments the siRNA is linked to a protein, such as a FN3 domain The siRNA can be linked to multiple FN3 domains that bind to the same target protein or different target proteins.

In some embodiments, compositions are provided herein having a formula of $(X1)_n$-$(X2)_q$-$(X3)_y$-L-X4, wherein X1 is a first FN3 domain, X2 is second FN3 domain, X3 is a third FN3 domain or half-life extender molecule, L is a linker, and X4 is a nucleic acid molecule, such as, but not limited to a siRNA molecule, wherein n, q, and y are each independently 0 or 1. In some embodiments, X1, X2, and X3 bind to different target proteins. In some embodiments, y is 0. In some embodiments, n is 1, q is 0, and y is 0. In some embodiments, n is 1, q is 1, and y is 0. In some embodiments, n is 1, q is 1, and y is 1. In some embodiments, the third FN3 domain increases the half-life of the molecule as a whole as compared to a molecule without X3. In some embodiments, the half-life extending moiety is a FN3 domain that binds to albumin Examples of such FN3 domains include, but are not limited to, those described in U.S. Patent Application Publication No. 20170348397 and U.S. Pat. No. 9,156,887, which is hereby incorporated by reference in its entirety. The FN3 domains may incorporate other subunits for example via covalent interaction. In some embodiments, the FN3 domains further comprise a half-life extending moiety. Exemplary half-life extending moieties are albumin, albumin variants, albumin-binding proteins and/or domains, transferrin and fragments and analogues thereof, and Fc regions Amino acid sequences of the human Fc regions are well known, and include IgG1, IgG2, IgG3, IgG4, IgM, IgA and IgE Fc regions. In some embodiments, the FN3 domains may incorporate a second FN3 domain that binds to a molecule that extends the half-life of the entire molecule, such as, but not limited to, any of the half-life extending moieties described herein. In some embodiments, the second FN3 domain binds to albumin, albumin variants, albumin-binding proteins and/or domains, and fragments and analogues thereof.

In some embodiments, compositions are provided herein having a formula of (X1)-(X2)-L-(X4), wherein X1 is a first FN3 domain, X2 is second FN3 domain, L is a linker, and X4 is a nucleic acid molecule. In some embodiments, X4 is a siRNA molecule. In some embodiments, X1 is a FN3 domain that binds to one of CD71, EGFR, or EpCAM. In some embodiments, X2 is a FN3 domain that binds to one of CD71, EGFR, or EpCAM. In some embodiments X1 and X2 do not bind to the same target protein. In some embodiments, X1 and X2 bind to the same target protein, but at different binding sites on the protein. In some embodiments, X1 and X2 bind to the same target protein. In some embodiments, X1 and X2 are FN3 domains that bind to CD71. In some embodiments, X1 and X2 are FN3 domains that bind to EpCAM. In some embodiments, X1 is a FN3 domain that binds to CD71 and X2 is a FN3 domain that binds to EpCAM. In some embodiments, X1 is a FN3 domain that binds to EpCAM and X2 is a FN3 domain that binds to CD71. In some embodiments, any of the FN3 domains listed above or herein can be replaced or substituted with a FN3 domain that binds to EGFR. Non-limiting examples of EGFR FN3 binding domains are provided herein and can also be found in U.S. Pat. No. 9,695,228, which is hereby incorporated by reference in its entirety. In some embodiments, the composition does not comprise (e.g. is free of) a compound or protein that binds to ASGPR.

In some embodiments, compositions or complexes are provided having a formula of $A_1$-$B_1$, wherein $A_1$ has a formula of C-$L_1$-$X_S$ and $B_1$ has a formula of $X_{AS}$-$L_2$-$F_1$, wherein:

C is a polymer, such as PEG;
$L_1$ and $L_2$ are each, independently, a linker;
$X_S$ is a 5' to 3' oligonucleotide sense strand of a double stranded siRNA molecule;
$X_{AS}$ is a 3' to 5' oligonucleotide antisense strand of a double stranded siRNA molecule;
$F_1$ is a polypeptide comprising at least one FN3 domain;
wherein $X_S$ and $X_{AS}$ form a double stranded oligonucleotide molecule to form the composition/complex.

In some embodiments, the sense strand is a sense strand as provided for herein.

In some embodiments, the antisense strand is an antisense strand as provided for herein.

In some embodiments, the sense and antisense strand form a double stranded siRNA molecule that targets RAS, such as KRAS. In some embodiments, the double stranded oligonucleotide is about 21-23 nucleotides base pairs in length.

In some embodiments, C is a natural or synthetic polymer, consisting of long chains of branched or unbranched monomers, and/or cross-linked network of monomers in two or three dimensions In some instances, the polymer includes a polysaccharide, lignin, rubber, or polyalkylen oxide, which can be for example, polyethylene glycol. In some instances, the at least one polymer includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylenterephthalat (PET, PETG), polyethylene terephthalate (PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer comprises polyalkylene oxide. In some instances, the polymer comprises PEG. In some instances, the polymer comprises polyethylene imide (PEI) or hydroxy ethyl starch (HES).

In some embodiments, the polyalkylene oxide (e.g., PEG) is a polydispers or monodispers compound. In some instances, polydispers material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some embodiments, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some embodiments, the polyalkylene oxide (e.g., PEG) is a discrete PEG, in which the discrete PEG is a polymeric PEG comprising more than one repeating ethylene oxide units. In some instances, a discrete PEG (dPEG) comprises from 2 to 60, from 2 to 50, or from 2 to 48 repeating ethylene oxide units. In some instances, a dPEG comprises about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some instances, a dPEG comprises about 2 or more repeating ethylene oxide units. In some instances, a dPEG comprises about 3 or more repeating ethylene oxide units. In some instances, a dPEG comprises about 4 or more repeating ethylene oxide units. In some instances, a dPEG comprises about 5 or more repeating ethylene oxide units. In some instances, a dPEG comprises about 6 or more repeating ethylene oxide units. In some instances, a dPEG comprises about 7 or more repeating ethylene oxide units. In some instances, a dPEG comprises about 8 or more repeating ethylene oxide units. In some instances, a dPEG comprises about 9 or more repeating ethylene oxide units. In some instances, a dPEG comprises about 10 or more repeating ethylene oxide units. In some instances, a dPEG comprises about 11 or more repeating ethylene oxide units. In some instances, a dPEG comprises about 12 or more repeating ethylene oxide units. In some instances, a dPEG comprises about 13 or more repeating ethylene oxide units. In some instances, a dPEG comprises about 14 or more repeating ethylene oxide units. In some instances, a dPEG comprises about 15 or more repeating ethylene oxide units. In some instances, a dPEG comprises about 16 or more repeating ethylene oxide units. In some instances, a dPEG comprises about 17 or more repeating ethylene oxide units. In some instances, a dPEG comprises about 18 or more repeating ethylene oxide units. In some instances, a dPEG comprises about 19 or more repeating ethylene oxide units. In some instances, a dPEG comprises about 20 or more repeating ethylene oxide units. In some instances, a dPEG comprises about 22 or more repeating ethylene oxide units. In some instances, a dPEG comprises about 24 or more repeating ethylene oxide units. In some instances, a dPEG comprises about 26 or more repeating ethylene oxide units. In some instances, a dPEG comprises about 28 or more repeating ethylene oxide units. In some instances, a dPEG comprises about 30 or more repeating ethylene oxide units. In some instances, a dPEG comprises about 35 or more repeating ethylene oxide units. In some instances, a dPEG comprises about 40 or more repeating ethylene oxide units. In some instances, a dPEG comprises about 42 or more repeating ethylene oxide units. In some instances, a dPEG comprises about 48 or more repeating ethylene oxide units. In some instances, a dPEG comprises about 50 or more repeating ethylene oxide units. In some cases, a dPEG is synthesized as a single molecular weight compound from pure (e.g., about 95%, 98%, 99%, or 99.5%) staring material in a step-wise fashion. In some cases, a dPEG has a specific molecular weight, rather than an average molecular weight. In some cases, a dPEG described herein is a dPEG from Quanta Biodesign, LMD.

In some embodiments, $L_1$ is any linker that can be used to link the polymer C to the sense strand $X_S$. In some embodiments, $L_1$ has a formula of:

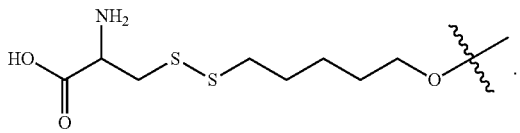 [SMILES: *OCCCCCSSCC(N)C(=O)O]

In some embodiments, $L_2$ is any linker that can be used to link the polypeptide of $F_1$ to the antisense strand $X_{AS}$. In some embodiments, $L_2$ has a formula of in the complex of:

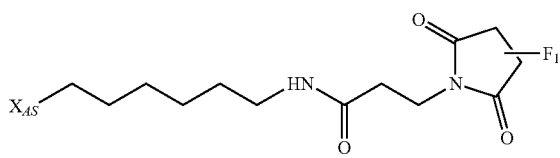

wherein $X_{AS}$ and $F_1$ are as defined above. In some embodiments, the linker is covalently attached to F1 through a cysteine residue present on F1, which can be illustrated as follows:

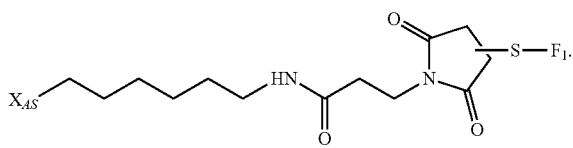

In some embodiments, A1-B1 has a formula of:

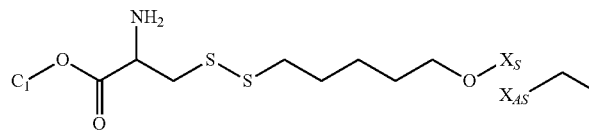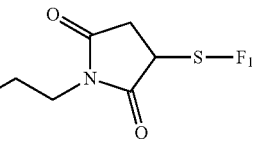

wherein $C_1$ is the polymer C, such as PEG as provided for herein, $X_S$ is a 5' to 3' oligonucleotide sense strand of a double stranded siRNA molecule; $X_{AS}$ is a 3' to 5' oligonucleotide antisense strand of a double stranded siRNA molecule; and $F_1$ is a polypeptide comprising at least one FN3 domain, wherein $X_S$ and $X_{AS}$ form a double stranded siRNA molecule.

In some embodiments, $F_1$ comprises polypeptide having a formula of $(X_1)_n$-$(X_2)_q$-$(X_3)_y$, wherein $X_1$ is a first FN3 domain; $X_2$ is second FN3 domain; $X_3$ is a third FN3 domain or half-life extender molecule; wherein n, q, and y are each independently 0 or 1, provided that at least one of n, q, and y is 1. In some embodiments, n, q, and y are each 1. In some embodiments, n and q are 1 and y is 0. In some embodiments n and y are 1 and q is 0.

In some embodiment $X_1$ is a CD71 FN3 binding domain, such as one provided herein. In some embodiments, $X_2$ is a CD71 FN3 binding domain. In some embodiments, X1 and $X_2$ are different CD71 FN3 binding domains In some embodiments, the binding domains are the same. In some embodiments, $X_3$ is a FN3 domain that binds to human serum albumin In some embodiments, $X_3$ is a Fc domain without effector function that extends the half-life of a protein. In some embodiments, $X_1$ is a first CD71 binding domain, $X_2$ is a second CD71 binding domain, and $X_3$ is a FN3 albumin binding domain. In some embodiments, $X_2$ is an EPCAM binding domain instead of a second CD71 binding domain. In some embodiments, X1 is an EPCAM binding FN3 domain, X2 is a CD71 FN3 binding domain, and X3 is an albumin FN3 binding domain. Examples of such polypeptides are provided herein and below. In some embodiments, compositions are provided herein having a formula of C—$(X1)_n$-$(X2)_q$-$(X3)_y$-L-X4, wherein C is a polymer; X1 is a first FN3 domain; X2 is second FN3 domain; X3 is a third FN3 domain or half-life extender molecule; L is a linker; and X4 is a nucleic acid molecule, wherein n, q, and y are each independently 0 or 1.

In some embodiments, compositions are provided herein having a formula of $(X1)_n$-$(X2)_q$-$(X3)_y$-L-X4-C, wherein X1 is a first FN3 domain; X2 is second FN3 domain; X3 is a third FN3 domain or half-life extender molecule; L is a linker; X4 is a nucleic acid molecule; and C is a polymer, wherein n, q, and y are each independently 0 or 1.

In some embodiments, compositions are provided herein having a formula of X4-L-$(X1)_n$-$(X2)_q$-$(X3)_y$, wherein X1 is a first FN3 domain; X2 is second FN3 domain; X3 is a third FN3 domain or half-life extender molecule; L is a linker; and X4 is a nucleic acid molecule, wherein n, q, and y are each independently 0 or 1.

In some embodiments, compositions are provided herein having a formula of C—X4-L-$(X1)_n$-$(X2)_q$-$(X3)_y$, wherein C is a polymer; X1 is a first FN3 domain; X2 is second FN3 domain; X3 is a third FN3 domain or half-life extender molecule; L is a linker; and X4 is a nucleic acid molecule, wherein n, q, and y are each independently 0 or 1.

In some embodiments, compositions are provided herein having a formula of X4-L-$(X1)_n$-$(X2)_q$-$(X3)_y$-C, wherein X1 is a first FN3 domain; X2 is second FN3 domain; X3 is a third FN3 domain or half-life extender molecule; L is a linker; X4 is a nucleic acid molecule; and C is a polymer, wherein n, q, and y are each independently 0 or 1.

In some embodiments, the siRNA molecule comprises a sequence pair from Table 1.

Table 1

| | siRNA Sense and Anti-sense sequences | | | |
|---|---|---|---|---|
| siRNA Pair | SEQ ID NO | Sense Strand 5'-3' | SEQ ID NO | Anti-sense strand 5'-3' |
| A | 10 | cscsUfgucUf CfUfugGfaua uUfca(invdT) | 11 | UfsGfsaauauc caagaGfacagg susu |
| B | 12 | CsasGfcuaAf UfUfcaGfaau cAfua(invdT) | 13 | UfsAfsugauuc ugaauUfagcug susu |

TABLE 1-continued siRNA Sense and Anti-sense sequences

| siRNA Pair | SEQ ID NO | Sense Strand 5'-3' | SEQ ID NO | Anti-sense strand 5'-3' |
|---|---|---|---|---|
| C | 14 | GsasAfuuaGfCfufguAfucguCfaa (invdT) | 15 | UfsUfsgacgauacagcUfaauuscusu |
| D | 16 | CfscsUfgUfcUfCfUfuGfgauAfuUfcAf (invdT) | 17 | usGfsaAfuAfUfCfcAfagaGfaCfaGfgsUfsu |
| E | 18 | csAfsgCfuAfaUfUfcfaGfaauCfuAfuAf (invdt) | 19 | usAfsuGfaUfUfCfuGfaauUfaGfcUfgsUfsu |
| F | 20 | GfsasAfuUfaGfCfUfgUfaucGfuCfaAf (invdt) | 21 | usUfsgAfcGfAfUfacaGfcUfaAfuUfcsUfsu |
| G | 22 | CfscsUfgUfcUfcUfuGfgAfuAfuUfcAf (invdT) | 23 | usGfsaAfuAfuCfcAfagaGfaCfaGfgsUfsu |
| H | 24 | csAfsgCfuAfaUfUfcfaGfaAfuCfaUfa (invdt) | 25 | UfsasUfgAfuUfcUfgAfaUfuAfgCfgsUfsu |
| I | 26 | gsAfsaUfuAfgCfuGfuAfuCfgUfcAfa (invdt) | 27 | UfsusGfaCffaUfaCfaGfeUfaAfuUfcsUfsu |
| J | 28 | cscsUfgucUfCfUfugGfauauUfca (invdt) | 29 | UfsGfsaauaucaagaGfacagsusu |
| K | 30 | CsasGfcuaAfUfUfcaGfaaucAfua (invdt) | 31 | UfsAfsugauucugaauUfagcugsusu |
| L | 32 | gsasAfuuaGfCfUfguAfucguCfaa (invdt) | 33 | UfsUfsgacgauacagcUfaauuscsusu |
| M | 34 | CsasGfcuaAfUfUfcaGfaaucAfua (invdT) | 35 | UfsAfsugauucugaauUfagcugsusu |
| N | 36 | asusAfuaaAfCfUfugUfgguaGfua | 37 | UfsAfscuaccacaaguUfuauaususu |
| O | 38 | usasAfacuUfGfUfggUfagugGfga | 39 | UfsCfscaacuaccacaAfguuuasusu |
| P | 40 | csasAfgagUfGfCfcuUfgacgAfua | 41 | UfsAfsucgucaaggcaCfucuugsusu |
| Q | 42 | gscsCfuugAfCfGfauAfcagcUfaa | 43 | UfsUfsagcuguaucguCfaaggcsusu |
| R | 44 | usgsAfcgaUfAfCfagCfuaauUfca | 45 | UfsGfsaauuagcuguaUfcgucasusu |
| S | 46 | csgsAfuacAfGfCfuaAfuucaGfaa | 47 | UfsUfscugaauuagcuGfuaucgsusu |
| T | 48 | gsusGfgacGfAfAfuaUfgauCfaa (invdT) | 49 | UfsUfsggaucauauucGfuccacsusu |
| U | 50 | gsgsAfcgaAfUfAfugAfucaAfca (invdT) | 51 | UfsGfsuuggaucauauUfcgucsusu |
| V | 52 | gsasCfgaaUfAfUfgaUfccaaCfaa (invdT) | 53 | UfsUfsguuggaucauaUfcgucsusu |
| W | 54 | ascsGfaauAfUfGfaucfaaCfaAfaa | 55 | UfsUfsuguuggaucauAfuucgususu |
| X | 56 | csgsAfauaUfGfAfucCfaacaAfua (invdT) | 57 | UfsAfsuuguugauucaUfauucgsusu |
| Y | 58 | asasUfaugAfUfCfcaAfcaauAfga (invdT) | 59 | UfsCfsuauugUfggauCfauauususu |
| Z | 60 | gsasUfccaAfCfAfauAfgaggAfua (invdT) | 61 | UfsAfsuccucuauuguUfggaucsu |
| AA | 62 | cscsAfacaAfUfAfgaGfgauuCfca (invdT) | 63 | UfsGfsgaauccucuauUfguuggsusu |
| BB | 64 | csusAfcagGfAfAfgcAfaguaGfua (invdT) | 65 | UfsAfscuacuugcuucCfguagsusu |
| CC | 66 | ascsAfggaAfGfCfaaGfuaguAfaa (invdT) | 67 | UfsUfsuacuacugcuUfccugusu |
| DD | 68 | gsusAfauuGfAfUfggAfgaaaCfca (invdT) | 69 | UfsGfsguuucuccaucAfauuacsu |
| EE | 70 | csusUfggaUfAfUfucUfcgaCfaa (invdT) | 71 | UfsGfsugucgagaauaUfccaagsu |
| FF | 72 | csasGfcagGfUfCfaaGfaggaGfua (invdT) | 73 | UfsAfsccucuugaccCfugcugsu |
| GG | 74 | gscsAfaugAfGfGfgaCfcaguAfc | 75 | UfsGfsuacugucccuCfauugesu |
| HH | 76 | csasAfugaGfGfGfacCfaguaCfaa | 77 | UfsUfsguacuggucccUfcauugsu |
| II | 78 | ususUfgugUfAfUfuuGfccauAfaa | 79 | UfsUfsuauggcaauaCfacaaasu |
| JJ | 80 | ususGfccaUfAfAfauAfauaCfuaa | 81 | UfsUfsaguauuauuuAfggcaasu |
| KK | 82 | usgsCfcauAfAfAfuaAfuacuAfaa | 83 | UfsUfsuaguauuauuuAfuggcasu |

Table 1-continued siRNA Sense and Anti-sense sequences

| siRNA Pair | SEQ ID NO | Sense Strand 5'-3' | SEQ ID NO | Anti-sense strand 5'-3' |
|---|---|---|---|---|
| LL | 84 | cscsAfuaaAfUfAfauAfcuaaAfua(invdT) | 85 | UfsAfsuuuaguauuauUfuauggsusu |
| MM | 86 | csasUfaaaUfAfAfuaCfuaaaUfca(invdT) | 87 | UfsGfsauuuaguauuaUfuuaugsusu |
| NN | 88 | asusAfaauAfAfUfacUfaaauCfaa(invdT) | 89 | UfsUfsgauuuaguauuAfuuuausu |
| OO | 90 | gsasAfgauAfUfUfcaCfcauuAfua | 91 | UfsAfsuaauggugaauAfucuucsu |
| PP | 92 | asgsAfuauUfCfAfccAfuuauAfga(invdT) | 93 | UfsCfsuauaauggugaAfuaucusu |
| QQ | 94 | asusAfuucAfCfCfauUfauagAfga(invdT) | 95 | UfsCfsucuauaagguGfaauausu |
| RR | 96 | asgsAfacaAfAfUfuaAfaagaGfua(invdT) | 97 | UfsAfscucuuuaauUfgcuucsusu |
| SS | 98 | gsasCfucuGfAfAfgaUfguacCfua(invdT) | 99 | UfsAfsgguacaucuucAfgagucsusu |
| TT | 100 | csusGfaagAfUfGfuaCfcuauGfga | 101 | UfsCfscauaggacauCfuucagsusu |
| UU | 102 | asgsAfacaGfUfAfgaCfacaaAfaa(invdT) | 103 | UfsUfsuuuguucuacUfguucusu |
| VV | 104 | csasGfgacUfUfAfgcAfagaaGfua(invdT) | 105 | UfsAfscucuuugcuaaGfuccugsusu |
| WW | 106 | gsusUfgauGfAfUfgcCfuucuAfua(invdT) | 107 | UfsAfsuagaaggcaucAfucaacsusu |
| XX | 108 | asusGfaugCfCfUfucUfaucAfua(invdT) | 109 | UfsAfsuguauagaaggCfaucausu |
| YY | 110 | usgsAfugcCfUfUfcuAfuacAfua(invdT) | 111 | UfsAfsauguauagaagGfcaucasusu |
| ZZ | 112 | gsasUfgccUfUfCfuaUfacauUfaa(invdT) | 113 | UfsUfsaauguauagaaGfgcaucsusu |
| AAA | 114 | asusGfccuUfCfUfauAfcauUfga(invdT) | 115 | UfsCfsuaauguauagaAfggcausu |
| BBB | 116 | csusUfcuaUfAfCfauUfaguuCfga(invdT) | 117 | UfsCfsgaacuauguaUfagaagsusu |
| CCC | 118 | UscsUfauaCfAfUfuaGfuucgAfga(invdT) | 119 | UfsCfsucgaacuaaugUfauagasu |
| DDD | 120 | UsasUfacaUfUfAfguUfcgagAfaa(invdT) | 121 | UfsUfsucucgaacuaaUfguatasusu |
| EEE | 122 | AsusAfcauUfAfGfuuCfgagaAfaa(invdT) | 123 | UfsUfsuucucgaacuaAfuguatsusu |
| FFF | 124 | UsasCfauuAfGfUfucGfagaaAfua(invdT) | 125 | UfsAfsuuucucgaacuAfauguasusu |
| GGG | 126 | UsusAfguuCfGfAfgaAfauucGfaa(invdT) | 127 | UfsUfscgaauuucucgAfacuaasusu |
| HHH | 128 | AsgsUfucgAfGfAfaaUfucgaAfaa(invdT) | 129 | UfsUfsuucgaauuucuCfgaacususu |
| III | 130 | AsgsAfaauUfCfGfaaAfacauAfaa(invdT) | 131 | UfsUfsuauguuucgaAfuuucususu |
| JJJ | 132 | GsasAfauuCfGfAfaaAfcauAfaa(invdT) | 133 | UfsUfsuauguuucgaAfuuucsusu |
| KKK | 134 | AsasAfuucGfAfAfaaCfauaAfga(invdT) | 135 | UfsCfsuuuauguuuuCfgaauuusu |
| LLL | 136 | AsasUfucgAfAfAfacAfuaaAfgaa(invdT) | 137 | UfsUfscuuuauguuuuCfgaauusu |
| MMM | 138 | AsusGfagcAfAfAfgaUfgguaAfaa(invdT) | 139 | UfsUfsuuaccaucuuuGfcucausu |
| NNN | 140 | AsgsCfaaaGfAfUfggUfaaaAfga(invdT) | 141 | UfsCfsuuuuuaccaucUfuugcusussu |
| OOO | 142 | AsusUfucuGfUfCfuuGfggguUfua(invdT) | 143 | UfsAfsaaccccaagacAfgaaausu |
| PPP | 144 | GsgsGfuuuUfUfGfguGfcaugCfaa(invdT) | 145 | UfsUfsgcaugcaccaaAfaaccsusu |
| QQQ | 146 | CsgsCfacaAfGfGfcaCfuggGfuaa(invdT) | 147 | UfsUfsacccagugccUfgugcgsusu |
| RRR | 148 | GscsAfcaaGfGfCfacUfgggUfua(invdT) | 149 | UfsAfsucccagugccUfugugcsusu |
| SSS | 150 | csUfsCfUfuGfgauAfuUfcAf(invdT) | 151 | usGfsasAfsusAfUfCfcAfagaGfaCfaGfgsUfsu |
| TTT | 152 | AfsasUfUfCfaGfaauCfuAfuAf(invdt) | 153 | usAfsusGfsasUfUfCfuGfaauUfaGfcUfgsUfsu |

Table 1-continued siRNA Sense and Anti-sense sequences

| siRNA Pair | SEQ ID NO | Sense Strand 5'-3' | SEQ ID NO | Anti-sense strand 5'-3' |
|---|---|---|---|---|
| UUU | 154 | AfsasUfUfCfaGfaauCfuAfuAf(invdt) | 155 | usAfsusGfsasUfUfCfuGfaauUfaGfcUfgsUfsu |
| VVV | 156 | csUfscUfuGfgAfuAfuUfcAf(invdT) | 157 | usGfsaAfsusAfsuCfcAfaGfaGfaCfaGfgsUfsu- |
| WWW | 158 | AfsasUfuCfaGfaAfuCfaUfa(invdt) | 159 | UfsasUfsgsAfsuUfcUfgAfaUfuAfgCfgsUfsu |
| XXX | 160 | AfsgsCfuGfuAfuCfgUfcAfa(invdt) | 161 | UfsusGfsasCfsaUfaCfaGfcUfaAfuUfcsUfsu |
| YYY | 162 | csUfsCfufugGfauauUfca(invdt)- | 163 | UfsGfsasasusauccaagaGfacaggsusu |
| ZZZ | 164 | asAfsUfUfcaGfaaucAfua(invdt) | 165 | UfsAfsusgsasuucugaauUfagcugsusu |
| AAAA | 166 | asGfsCfUfguAfucguCfaa(invdt) | 167 | UfsUfsgsascsgauacagcUfaauucsusu |
| BBBB | 168 | CfscsUfgUfcUfCfUfuGfgauAfgUfcAf(invdT)- | 169 | usGfsaAfuAfUfCfcAfagaGfaCfaGfgsUfsu |
| CCCC | 170 | csAfsgCfuAfaUfUfCfaGfaauCfgAfuAf(invdt)- | 171 | usAfsuGfaUfUfCfuGfaauUfaGfcUfgsUfsu- |
| DDDD | 172 | GfsasAfuUfaGfUfgUfau cGfgCfaAf(invdt) | 173 | usUfsgAfcGfAfUfacaGfcUfaAfuUfcsUfsu- |
| EEEE | 174 | CfscsUfgUfcUfcUfuGfgAfuAfgUfcAf(invdT)- | 175 | usGfsaAfuAfuCfcAfaGfaGfaCfaGfgsUfsu |
| FFFF | 176 | csAfsgCfuAfaUfuCfaGfaAfgCfaUfa(invdt) | 177 | UfsasUfgAfuUfcUfgAfaUfaUfaAfgCfgsUfsu |
| GGGG | 178 | gsAfsaUfuAfgCfuGfuAfuCfgUfcAfa(invdt) | 179 | UfsusGfaCfaUfaCfaGfcUfaAfuUfcsUfsu |
| HHHH | 180 | cscsUfgucUfCfUfugGfauagUfca(invdt) | 181 | UfsGfsaauauccaagaGfacaggsu |
| IIII | 182 | csasGfcuaAfUfUfcaGfaagcAfua(invdt) | 183 | UfsAfsugauucugaauUfagcugsusu |
| JJJJ | 184 | gsasAfuuaGfCfUfguAfucggCfaa(invdt) | 185 | UfsUfsgacgauacagcUfaauucsusu |
| KKKK | 212 | CcsAcsrGrCrUrArArUrUrCrArGrArArUrCrAsTcsAc | 213 | (vinyl-p)sAfsuGfaUfUfCfuGfaauUfaGfcUfgUfsasUf |
| LLLL | 214 | CfsasGfcUfaAfUfUfcAfgaaUfcAfua | 215 | (vinyl-p)-sAfsuGfaUfUfCfuGfaauUfaGfcUfgUfsasUf |
| MMMM | 216 | csasrGrCrUrArArUrUrCrArGrArArUrCrAsusa | 217 | (vinyl-p)sAfsuGfaUfUfCfuGfaauUfaGfcUfgUfsasUf |

Abbreviations Key: n = 2'-O-methyl residues, Nf = 2'-F residues, rN = unmodified residue, Nc = 2',4'-BNAnc (2'-O,4'-C-aminomethylene bridged nucleic acid), s = phosphorothioate, (invdt) = inverted Dt, vinyl-p: (E)-vinylphosphonate, (n/N = anynucleotide)

As described herein, in some embodiments, the nucleic acid molecules can be modified to include a linker at the 5' end of the of the sense strand of the dsRNA. In some embodiments, the nucleic acid molecules can be modified to include a vinyl phosphonate at the 5' end of the of the anti-sense strand of the dsRNA. In some embodiments, the nucleic acid molecules can be modified to include a linker at the 3' end of the of the sense strand of the dsRNA. In some embodiments, the nucleic acid molecules can be modified to include a vinyl phosphonate at the 3' end of the of the anti-sense strand of the dsRNA. The linker can be used to link the dsRNA to the FN3 domain. The linker can covalently attach, for example, to a cysteine residue on the FN3 domain that is there naturally or that has been substituted as described herein, and for example, in U.S. Pat. No. 10,196,446, which is hereby incorporated by reference in its entirety. Non-limiting examples of such modified strands of the dsRNA are illustrated in Table 2.

TABLE 2

Pairs with Linker and/or vinyl phosphonate

| | SEQ ID NO | Sense 5'-3' | SEQ ID NO | Antisense 5'-3' | Linker |
|---|---|---|---|---|---|
| AB01 | 186 | L-cscsUfgucUfCfUfugGfauauUfca(invdT) | 187 | (vinyl-p)-UfsGfsaauauccaagaGfacaggsusu | mal-NH—(CH$_2$)$_6$— |
| AB02 | 188 | L-csasGfcuaAfUfUfcaGfaaucAfua(invdT) | 189 | (vinyl-p)-UfsAfsugauucugaauUfagcugsusu | mal-NH—(CH$_2$)$_6$— |
| AB03 | 190 | CfsasGfcUfaAfUfUfcAfgaaUfcAfua-L | 191 | (vinyl-p)-sAfsuGfaUfUfCfuGfaauUfaGfcUfgUfsasUf | mal-C$_2$H$_4$C(O)NH—(CH$_2$)$_6$— |
| AB04 | 192 | CfsasGfcUfaAfuUfcAfgAfaUfcAfua-L | 193 | (vinyl-p)-sAfsuGfaUfuCfuGfaAfuUfaGfcUfgUfsasUf | mal-C$_2$H$_4$C(O)NH—(CH$_2$)$_6$— |
| AB05 | 194 | (L)cscsUfgucUfCfUfugGfauauUfca(invdT) | 195 | (vinu)sGfsaauauccaagaGfacaggsusu | mal-C$_2$H$_4$C(O)NH—(CH$_2$)$_6$— |
| AB06 | 196 | (L)csasGfcuaAfUfUfcaGfaaucAfua | 197 | (vinu)sAfsugauucugaauUfagcugsusu | mal-C$_2$H$_4$C(O)NH—(CH$_2$)$_6$— |
| AB07 | 198 | (L)cscsUfgUfcUfcUfuGfgAfuAfuUfcAf(invdT) | 199 | (vinu)sGfsaAfuAfuCfcAfaGfaGfaCfaggsusu | mal-C$_2$H$_4$C(O)NH—(CH$_2$)$_6$— |
| AB08 | 200 | cscsUfgucUfCfUfugGfauauUfca(L) | 201 | (vinu)sGfsaauauccaagaGfacaggsusu | mal-C$_2$H$_4$C(O)NH—(CH$_2$)$_6$— |
| AB09 | 202 | (L)cscsUfgucUfCfUfugGfauauUfca(invdT) | 203 | (vinu)sGfsaauauccaagaGfacaggsusu | (Mal-(PEG)$_{12}$NH(CH$_2$)$_6$) |
| AB10 | 204 | CfscsUfgUfcUfCfUfuGfgauAfuUfcAf(L)- | 205 | (vinu)sGfsaAfuAfUfCfcAfagaGfaCfaGfgsUfsu | mal-C2H4C(O)NH—(CH2)6— |
| AB11 | 206 | CfsasGfcUfaAfUfUfcAfgaaUfcAfuAf(L)- | 207 | vinu)sAfsuGfaUfUfCfuGfaaufaGfcfgsUfsu- | mal-C$_2$H$_4$C(O)NH—(CH$_2$)$_6$— |
| AB12 | 208 | usUfsgAfcGfaUfaCfAfGfcUfaauUfcAfuAf(L) | 209 | vinu)sGfsaAfuUfAfGfcfguaUfcGfuCfaAfsgsGf | mal-C$_2$H$_4$C(O)NH—(CH$_2$)$_6$— |
| AB13 | 210 | (vinu)CfsasGfcUfaAfUfUfcAfgaaUfcAfua | 211 | AfsuGfaUfUfCfuGfaauUfaGfcUfgUfsasUf-L | mal-C$_2$H$_4$C(O)NH—(CH$_2$)$_6$— |
| AB14 | 218 | C$_C$sA$_C$srGrCrUrArArUrUrCrArGrArArUrCrArAsT$_C$sA$_C$ | 219 | (vinyl-p)sAfsuGfaUfUfCfuGfaauUfaGfcUfgUfsasUf | |
| AB15 | 220 | X-CfsasGfcUfaAfUfUfcAfgaaUfcAfua-L | 221 | (vinyl-p)-sAfsuGfaUfUfCfuGfaauUfaGfcUfgUfsasUf | mal-C$_2$H$_4$C(O)(NH)—(CH$_2$)$_6$ |
| AB16 | 222 | csasrGrCrUrArArUrUrCrArGrArArUrCrAsusa-(L) | 223 | (vinyl-p)sAfsuGfaUfUfCfuGfaauUfaGfcUfgUfsasUf | mal-C$_2$H$_4$C(O)(NH)—(CH$_2$)$_6$ |

Abbreviations Key: n = 2'-O-methyl residues, Nf = 2'-F residues, rN = unmodified residue, N$_C$ = 2',4'-BNA$^{NC}$ (2'-O,4'-C-aminomethylene bridged nucleic acid), s = phosphorothioate, (invdt) = inverted Dt, Vinu = vinylphosphonate, vinyl-p = (E)-vinylphosphonate, (L) is a linker, and

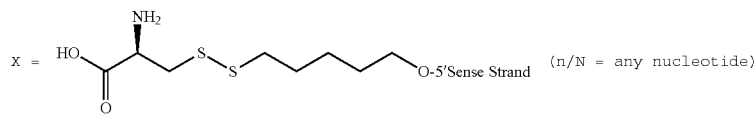

(n/N = any nucleotide)

Structure of the linkers (L) are as follows:
mal-$C_2H_4C(O)(NH)$-$(CH_2)_6$— is
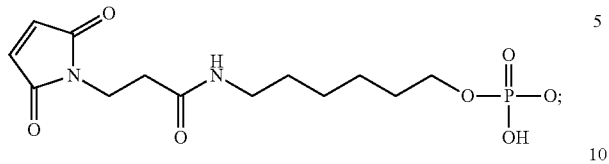
(Mal-$(PEG)_{12}$)(NH)$CH_2$)$_6$) is
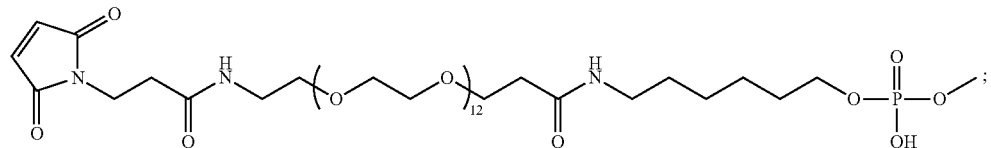
and
Mal-NH—$(CH_2)_6$—, which can also be referred to as aminohexyl linker-$(CH_2)_6$—, is
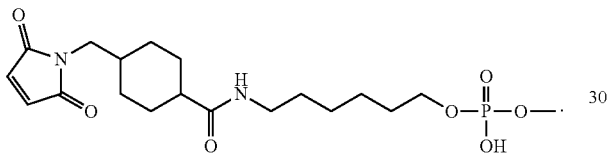
When connected to the siRNA, the structures, L-(X4) can be represented by the following formulas:
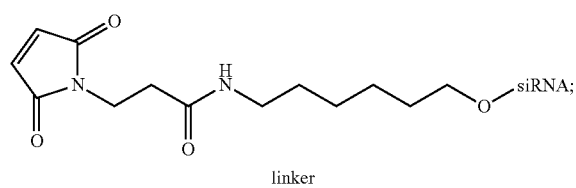
linker
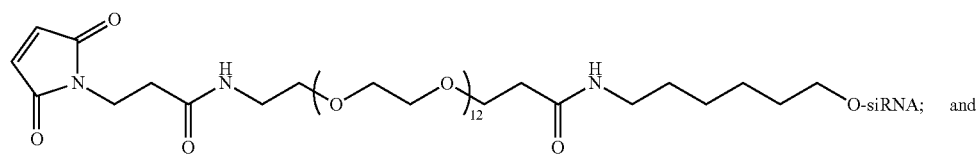
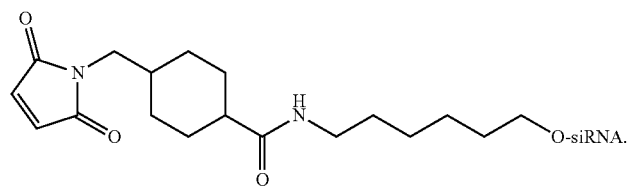

Although certain siRNA sequences are illustrated herein with certain modified nucleobases, the sequences without such modifications are also provided herein. That is, the sequence can comprise the sequences illustrated in the tables provided herein without any modifications. The unmodified siRNA sequences can still comprise, in some embodiments, a linker at the 5' end of the of the sense strand of the dsRNA. In some embodiments, the nucleic acid molecules can be modified to include a vinyl phosphonate at the 5' end of the of the anti-sense strand of the dsRNA. In some embodiments, the nucleic acid molecules can be modified to include a linker at the 3' end of the of the sense strand of the dsRNA. In some embodiments, the nucleic acid molecules can be modified to include a vinyl phosphonate at the 3' end of the of the anti-sense strand of the dsRNA. The linker can be as provided herein.

In some embodiments, the FN3 proteins comprise a polypeptide comprising a polypeptide that binds CD71 are provided. In some embodiments, the polypeptide comprises a FN3 domain that binds to CD71. In some embodiments, the polypeptide comprises a sequence of SEQ ID NOs: 300, 301, 302, 303, 304, 305, 306, 307, 308, 309, 310, 311, 312, 313, 314, 315, 316, 317, 318, 319, 320, 321, 322, 323, 324, 325, 326, 327, or 328 are provided. In some embodiments, the polypeptide that binds CD71 comprises a sequence of SEQ ID NOs: 300, 301, 302, 303, 304, 305, 306, 307, 308, 309, 310, 311, 312, 313, 314, 315, 316, 317, 318, 319, 320, 321, 322, 323, 324, 325, 326, 327, or 328. The sequence of CD71 protein that the polypeptides can bind to can be, for example, SEQ ID Nos: 2 or 3. In some embodiments, the FN3 domain that binds to CD71 specifically binds to CD71.

In some embodiments, the FN3 domain that binds CD71 is based on Tencon sequence of SEQ ID NO:1 or Tencon 27 sequence of SEQ ID NO:4 (LPAPKNLVVSRVTED-SARLSWTAPDAAFDSFLIQYQESEKVGEAIVLTVPGS-ERSYDLT GLKPGTEYTVSIYGVKGGHRSNPL-SAIFTT), optionally having substitutions at residues positions 11, 14, 17, 37, 46, 73, or 86 (residue numbering corresponding to SEQ ID NO:4).

In some embodiments, an isolated FN3 domain that binds CD71 comprises the amino acid sequence of SEQ ID NOs: 300, 301, 302, 303, 304, 305, 306, 307, 308, 309, 310, 311, 312, 313, 314, 315, 316, or 317.

In some embodiments, an isolated FN3 domain that binds CD71 comprises the amino acid sequence of SEQ ID NOs: 318, 319, 320, 321, 322, 323, 324, 325, 326, 327, or 328.

In some embodiments, an isolated FN3 domain that binds CD71 comprises the amino acid sequence of SEQ ID NOs: 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, or 623.

In some embodiments, an isolated FN3 domain that binds CD71 comprises the amino acid sequence of SEQ ID NO:300.

In some embodiments, an isolated FN3 domain that binds CD71 comprises the amino acid sequence of SEQ ID NO:301.

In some embodiments, an isolated FN3 domain that binds CD71 comprises the amino acid sequence of SEQ ID NO:302.

In some embodiments, an isolated FN3 domain that binds CD71 comprises the amino acid sequence of SEQ ID NO:303.

In some embodiments, an isolated FN3 domain that binds CD71 comprises the amino acid sequence of SEQ ID NO:304.

In some embodiments, an isolated FN3 domain that binds CD71 comprises the amino acid sequence of SEQ ID NO:305.

In some embodiments, an isolated FN3 domain that binds CD71 comprises the amino acid sequence of SEQ ID NO:306.

In some embodiments, an isolated FN3 domain that binds CD71 comprises the amino acid sequence of SEQ ID NO:307.

In some embodiments, an isolated FN3 domain that binds CD71 comprises the amino acid sequence of SEQ ID NO:308.

In some embodiments, an isolated FN3 domain that binds CD71 comprises the amino acid sequence of SEQ ID NO:309.

In some embodiments, an isolated FN3 domain that binds CD71 comprises the amino acid sequence of SEQ ID NO:310.

In some embodiments, an isolated FN3 domain that binds CD71 comprises the amino acid sequence of SEQ ID NO:311.

In some embodiments, an isolated FN3 domain that binds CD71 comprises the amino acid sequence of SEQ ID NO:312.

In some embodiments, an isolated FN3 domain that binds CD71 comprises the amino acid sequence of SEQ ID NO:313.

In some embodiments, an isolated FN3 domain that binds CD71 comprises the amino acid sequence of SEQ ID NO:314.

In some embodiments, an isolated FN3 domain that binds CD71 comprises the amino acid sequence of SEQ ID NO:315.

In some embodiments, an isolated FN3 domain that binds CD71 comprises the amino acid sequence of SEQ ID NO:316.

In some embodiments, an isolated FN3 domain that binds CD71 comprises the amino acid sequence of SEQ ID NO:317.

In some embodiments, an isolated FN3 domain that binds CD71 comprises the amino acid sequence of SEQ ID NO:318.

In some embodiments, an isolated FN3 domain that binds CD71 comprises the amino acid sequence of SEQ ID NO:319.

In some embodiments, an isolated FN3 domain that binds CD71 comprises the amino acid sequence of SEQ ID NO:320.

In some embodiments, an isolated FN3 domain that binds CD71 comprises the amino acid sequence of SEQ ID NO:321.

In some embodiments, an isolated FN3 domain that binds CD71 comprises the amino acid sequence of SEQ ID NO:322.

In some embodiments, an isolated FN3 domain that binds CD71 comprises the amino acid sequence of SEQ ID NO:323.

In some embodiments, an isolated FN3 domain that binds CD71 comprises the amino acid sequence of SEQ ID NO:324.

In some embodiments, an isolated FN3 domain that binds CD71 comprises the amino acid sequence of SEQ ID NO:325.

In some embodiments, an isolated FN3 domain that binds CD71 comprises the amino acid sequence of SEQ ID NO:326.

In some embodiments, an isolated FN3 domain that binds CD71 comprises the amino acid sequence of SEQ ID NO:327.

In some embodiments, an isolated FN3 domain that binds CD71 comprises the amino acid sequence of SEQ ID NO:328.

In some embodiments, an isolated FN3 domain that binds CD71 comprises the amino acid sequence of SEQ ID NO: 395. In some embodiments, an isolated FN3 domain that binds CD71 comprises the amino acid sequence of SEQ ID NO: 396. In some embodiments, an isolated FN3 domain that binds CD71 comprises the amino acid sequence of SEQ ID NO: 397. In some embodiments, an isolated FN3 domain that binds CD71 comprises the amino acid sequence of SEQ ID NO: 398. In some embodiments, an isolated FN3 domain that binds CD71 comprises the amino acid sequence of SEQ ID NO: 399. In some embodiments, an isolated FN3 domain that binds CD71 comprises the amino acid sequence of SEQ ID NO: 400. In some embodiments, an isolated FN3 domain that binds CD71 comprises the amino acid sequence of SEQ ID NO: 401. In some embodiments, an isolated FN3 domain that binds CD71 comprises the amino acid sequence of SEQ ID NO: 402. In some embodiments, an isolated FN3 domain that binds CD71 comprises the amino acid sequence of SEQ ID NO: 403. In some embodiments, an isolated FN3 domain that binds CD71 comprises the amino acid sequence of SEQ ID NO: 404. In some embodiments, an isolated FN3 domain that binds CD71 comprises the amino acid sequence of SEQ ID NO: 405. In some embodiments, an isolated FN3 domain that binds CD71 comprises the amino acid sequence of SEQ ID NO: 406. In some embodiments, an isolated FN3 domain that binds CD71 comprises the amino acid sequence of SEQ ID NO: 407. In some embodiments, an isolated FN3 domain that binds CD71 comprises the amino acid sequence of SEQ ID NO: 408. In some embodiments, an isolated FN3 domain that binds CD71 comprises the amino acid sequence of SEQ ID NO: 409. In some embodiments, an isolated FN3 domain that binds CD71 comprises the amino acid sequence of SEQ ID NO: 410. In some embodiments, an isolated FN3 domain that binds CD71 comprises the amino acid sequence of SEQ ID NO: 411. In some embodiments, an isolated FN3 domain that binds CD71 comprises the amino acid sequence of SEQ ID NO: 412. In some embodiments, an isolated FN3 domain that binds CD71 comprises the amino acid sequence of SEQ ID NO: 413. In some embodiments, an isolated FN3 domain that binds CD71 comprises the amino acid sequence of SEQ ID NO: 414. In some embodiments, an isolated FN3 domain that binds CD71 comprises the amino acid sequence of SEQ ID NO: 415. In some embodiments, an isolated FN3 domain that binds CD71 comprises the amino acid sequence of SEQ ID NO: 416. In some embodiments, an isolated FN3 domain that binds CD71 comprises the amino acid sequence of SEQ ID NO: 417. In some embodiments, an isolated FN3 domain that binds CD71 comprises the amino acid sequence of SEQ ID NO: 418. In some embodiments, an isolated FN3 domain that binds CD71 comprises the amino acid sequence of SEQ ID NO: 419. In some embodiments, an isolated FN3 domain that binds CD71 comprises the amino acid sequence of SEQ ID NO: 420. In some embodiments, an isolated FN3 domain that binds CD71 comprises the amino acid sequence of SEQ ID NO: 421. In some embodiments, an isolated FN3 domain that binds CD71 comprises the amino acid sequence of SEQ ID NO: 422. In some embodiments, an isolated FN3 domain that binds CD71 comprises the amino acid sequence of SEQ ID NO: 423. In some embodiments, an isolated FN3 domain that binds CD71 comprises the amino acid sequence of SEQ ID NO: 424. In some embodiments, an isolated FN3 domain that binds CD71 comprises the amino acid sequence of SEQ ID NO: 425. In some embodiments, an isolated FN3 domain that binds CD71 comprises the amino acid sequence of SEQ ID NO: 426. In some embodiments, an isolated FN3 domain that binds CD71 comprises the amino acid sequence of SEQ ID NO: 427. In some embodiments, an isolated FN3 domain that binds CD71 comprises the amino acid sequence of SEQ ID NO: 428. In some embodiments, an isolated FN3 domain that binds CD71 comprises the amino acid sequence of SEQ ID NO: 429. In some embodiments, an isolated FN3 domain that binds CD71 comprises the amino acid sequence of SEQ ID NO: 430. In some embodiments, an isolated FN3 domain that binds CD71 comprises the amino acid sequence of SEQ ID NO: 431. In some embodiments, an isolated FN3 domain that binds CD71 comprises the amino acid sequence of SEQ ID NO: 432. In some embodiments, an isolated FN3 domain that binds CD71 comprises the amino acid sequence of SEQ ID NO: 433. In some embodiments, an isolated FN3 domain that binds CD71 comprises the amino acid sequence of SEQ ID NO: 434. In some embodiments, an isolated FN3 domain that binds CD71 comprises the amino acid sequence of SEQ ID NO: 435. In some embodiments, an isolated FN3 domain that binds CD71 comprises the amino acid sequence of SEQ ID NO: 436. In some embodiments, an isolated FN3 domain that binds CD71 comprises the amino acid sequence of SEQ ID NO: 437. In some embodiments, an isolated FN3 domain that binds CD71 comprises the amino acid sequence of SEQ ID NO: 438. In some embodiments, an isolated FN3 domain that binds CD71 comprises the amino acid sequence of SEQ ID NO: 439. In some embodiments, an isolated FN3 domain that binds CD71 comprises the amino acid sequence of SEQ ID NO: 440. In some embodiments, an isolated FN3 domain that binds CD71 comprises the amino acid sequence of SEQ ID NO: 441. In some embodiments, an isolated FN3 domain that binds CD71 comprises the amino acid sequence of SEQ ID NO: 442. In some embodiments, an isolated FN3 domain that binds CD71 comprises the amino acid sequence of SEQ ID NO: 443. In some embodiments, an isolated FN3 domain that binds CD71 comprises the amino acid sequence of SEQ ID NO: 444. In some embodiments, an isolated FN3 domain that binds CD71 comprises the amino acid sequence of SEQ ID NO: 445. In some embodiments, an isolated FN3 domain that binds CD71 comprises the amino acid sequence of SEQ ID NO: 446. In some embodiments, an isolated FN3 domain that binds CD71 comprises the amino acid sequence of SEQ ID NO: 447. In some embodiments, an isolated FN3 domain that binds CD71 comprises the amino acid sequence of SEQ ID NO: 448. In some embodiments, an isolated FN3 domain that binds CD71 comprises the amino acid sequence of SEQ ID NO: 449. In some embodiments, an isolated FN3 domain that binds CD71 comprises the amino acid sequence of SEQ ID NO: 450. In some embodiments, an isolated FN3 domain that binds CD71 comprises the amino acid sequence of SEQ ID NO: 451. In some embodiments, an isolated FN3 domain that binds CD71 comprises the amino acid sequence of SEQ ID NO: 452. In some embodiments, an isolated FN3 domain that binds CD71 comprises the amino acid sequence of SEQ ID NO: 453. In some embodiments, an isolated FN3 domain that binds CD71 comprises the amino acid sequence of SEQ ID NO: 454. In some embodiments, an isolated FN3 domain that binds CD71 comprises the amino acid sequence of SEQ ID NO: 455. In some embodiments, an isolated FN3 domain that binds CD71 comprises the amino acid sequence of SEQ ID NO: 456. In some embodiments, an isolated FN3 domain that binds CD71 comprises the amino acid sequence of SEQ ID NO: 457. In some embodiments, an isolated FN3 domain that binds CD71 comprises the amino acid sequence of SEQ ID NO: 458. In some embodiments, an isolated FN3 domain that binds CD71 comprises the amino acid sequence of SEQ ID NO: 459. In some embodiments, an isolated FN3 domain that binds CD71 comprises the amino acid sequence of SEQ ID NO: 460. In some embodiments, an isolated FN3 domain that binds CD71 comprises the amino acid sequence of SEQ ID NO: 461. In some embodiments, an isolated FN3 domain that binds CD71 comprises the amino acid sequence of SEQ ID NO: 462. In some embodiments, an isolated FN3 domain that binds CD71 comprises the amino acid sequence of SEQ ID NO: 463. In some embodiments, an isolated FN3 domain that binds CD71 comprises the amino acid sequence of SEQ ID NO: 464. In some embodiments, an isolated FN3 domain that binds CD71 comprises the amino acid sequence of SEQ ID NO: 465. In some embodiments, an isolated FN3 domain that binds CD71 comprises the amino acid sequence of SEQ ID NO: 466. In some embodiments, an isolated FN3 domain that binds CD71 comprises the amino acid sequence of SEQ ID NO: 467. In some embodiments, an isolated FN3 domain that binds CD71 comprises the amino acid sequence of SEQ ID NO: 468. In some embodiments, an isolated FN3 domain that binds CD71 comprises the amino acid sequence of SEQ ID NO: 469. In some embodiments, an isolated FN3 domain that binds CD71 comprises the amino acid sequence of SEQ ID NO: 470. In some embodiments, an isolated FN3 domain that binds CD71 comprises the amino acid sequence of SEQ ID NO: 471. In some embodiments, an isolated FN3 domain that binds CD71 comprises the amino acid sequence of SEQ ID NO: 472. In some embodiments, an isolated FN3 domain that binds CD71 comprises the amino acid sequence of SEQ ID NO: 473. In some embodiments, an isolated FN3 domain that binds CD71 comprises the amino acid sequence of SEQ ID NO: 474. In some embodiments, an isolated FN3 domain that binds CD71 comprises the amino acid sequence of SEQ ID NO: 475. In some embodiments, an isolated FN3 domain that binds CD71 comprises the amino acid sequence of SEQ ID NO: 476. In some embodiments, an isolated FN3 domain that binds CD71 comprises the amino acid sequence of SEQ ID NO: 477. In some embodiments, an isolated FN3 domain that binds CD71 comprises the amino acid sequence of SEQ ID NO: 478. In some embodiments, an isolated FN3 domain that binds CD71 comprises the amino acid sequence of SEQ ID NO: 479. In some embodiments, an isolated FN3 domain that binds CD71 comprises the amino acid sequence of SEQ ID NO: 480. In some embodiments, an isolated FN3 domain that binds CD71 comprises the amino acid sequence of SEQ ID NO: 481. In some embodiments, an isolated FN3 domain that binds CD71 comprises the amino acid sequence of SEQ ID NO: 482. In some embodiments, an isolated FN3 domain that binds CD71 comprises the amino acid sequence of SEQ ID NO: 483. In some embodiments, an isolated FN3 domain that binds CD71 comprises the amino acid sequence of SEQ ID NO: 484. In some embodiments, an isolated FN3 domain that binds CD71 comprises the amino acid sequence of SEQ ID NO: 485. In some embodiments, an isolated FN3 domain that binds CD71 comprises the amino acid sequence of SEQ ID NO: 486. In some embodiments, an isolated FN3 domain that binds CD71 comprises the amino acid sequence of SEQ ID NO: 487. In some embodiments, an isolated FN3 domain that binds CD71 comprises the amino acid sequence of SEQ ID NO: 488. In some embodiments, an isolated FN3 domain that binds CD71 comprises the amino acid sequence of SEQ ID NO: 489. In some embodiments, an isolated FN3 domain that binds CD71 comprises the amino acid sequence of SEQ ID NO: 490. In some embodiments, an isolated FN3 domain that binds CD71 comprises the amino acid sequence of SEQ ID NO: 491. In some embodiments, an isolated FN3 domain that binds CD71 comprises the amino acid sequence of SEQ ID NO: 492. In some embodiments, an isolated FN3 domain that binds CD71 comprises the amino acid sequence of SEQ ID NO: 493. In some embodiments, an isolated FN3 domain that binds CD71 comprises the amino acid sequence of SEQ ID NO: 494. In some embodiments, an isolated FN3 domain that binds CD71 comprises the amino acid sequence of SEQ ID NO: 495. In some embodiments, an isolated FN3 domain that binds CD71 comprises the amino acid sequence of SEQ ID NO: 496. In some embodiments, an isolated FN3 domain that binds CD71 comprises the amino acid sequence of SEQ ID NO: 497. In some embodiments, an isolated FN3 domain that binds CD71 comprises the amino acid sequence of SEQ ID NO: 498. In some embodiments, an isolated FN3 domain that binds CD71 comprises the amino acid sequence of SEQ ID NO: 499. In some embodiments, an isolated FN3 domain that binds CD71 comprises the amino acid sequence of SEQ ID NO: 500. In some embodiments, an isolated FN3 domain that binds CD71 comprises the amino acid sequence of SEQ ID NO: 501. In some embodiments, an isolated FN3 domain that binds CD71 comprises the amino acid sequence of SEQ ID NO: 502. In some embodiments, an isolated FN3 domain that binds CD71 comprises the amino acid sequence of SEQ ID NO: 503. In some embodiments, an isolated FN3 domain that binds CD71 comprises the amino acid sequence of SEQ ID NO: 504. In some embodiments, an isolated FN3 domain that binds CD71 comprises the amino acid sequence of SEQ ID NO: 505. In some embodiments, an isolated FN3 domain that binds CD71 comprises the amino acid sequence of SEQ ID NO: 506. In some embodiments, an isolated FN3 domain that binds CD71 comprises the amino acid sequence of SEQ ID NO: 507. In some embodiments, an isolated FN3 domain that binds CD71 comprises the amino acid sequence of SEQ ID NO: 508. In some embodiments, an isolated FN3 domain that binds CD71 comprises the amino acid sequence of SEQ ID NO: 509. In some embodiments, an isolated FN3 domain that binds CD71 comprises the amino acid sequence of SEQ ID NO: 510. In some embodiments, an isolated FN3 domain that binds CD71 comprises the amino acid sequence of SEQ ID NO: 511. In some embodiments, an isolated FN3 domain that binds CD71 comprises the amino acid sequence of SEQ ID NO: 512. In some embodiments, an isolated FN3 domain that binds CD71 comprises the amino acid sequence of SEQ ID NO: 513. In some embodiments, an isolated FN3 domain that binds CD71 comprises the amino acid sequence of SEQ ID NO: 514. In some embodiments, an isolated FN3 domain that binds CD71 comprises the amino acid sequence of SEQ ID NO: 515. In some embodiments, an isolated FN3 domain that binds CD71 comprises the amino acid sequence of SEQ ID NO: 516. In some embodiments, an isolated FN3 domain that binds CD71 comprises the amino acid sequence of SEQ ID NO: 517. In some embodiments, an isolated FN3 domain that binds CD71 comprises the amino acid sequence of SEQ ID NO: 518. In some embodiments, an isolated FN3 domain that binds CD71 comprises the amino acid sequence of SEQ ID NO: 519. In some embodiments, an isolated FN3 domain that binds CD71 comprises the amino acid sequence of SEQ ID NO: 520. In some embodiments, an isolated FN3 domain that binds CD71 comprises the amino acid sequence of SEQ ID NO: 521. In some embodiments, an isolated FN3 domain that binds CD71 comprises the amino acid sequence of SEQ ID NO: 522. In some embodiments, an isolated FN3 domain that binds CD71 comprises the amino acid sequence of SEQ ID NO: 523. In some embodiments, an isolated FN3 domain that binds CD71 comprises the amino acid sequence of SEQ ID NO: 524. In some embodiments, an isolated FN3 domain that binds CD71 comprises the amino acid sequence of SEQ ID NO: 525. In some embodiments, an isolated FN3 domain that binds CD71 comprises the amino acid sequence of SEQ ID NO: 526. In some embodiments, an isolated FN3 domain that binds CD71 comprises the amino acid sequence of SEQ ID NO: 527. In some embodiments, an isolated FN3 domain that binds CD71 comprises the amino acid sequence of SEQ ID NO: 528. In some embodiments, an isolated FN3 domain that binds CD71 comprises the amino acid sequence of SEQ ID NO: 529. In some embodiments, an isolated FN3 domain that binds CD71 comprises the amino acid sequence of SEQ ID NO: 530. In some embodiments, an isolated FN3 domain that binds CD71 comprises the amino acid sequence of SEQ ID NO: 531. In some embodiments, an isolated FN3 domain that binds CD71 comprises the amino acid sequence of SEQ ID NO: 532. In some embodiments, an isolated FN3 domain that binds CD71 comprises the amino acid sequence of SEQ ID NO: 533. In some embodiments, an isolated FN3 domain that binds CD71 comprises the amino acid sequence of SEQ ID NO: 534. In some embodiments, an isolated FN3 domain that binds CD71 comprises the amino acid sequence of SEQ ID NO: 535. In some embodiments, an isolated FN3 domain that binds CD71 comprises the amino acid sequence of SEQ ID NO: 536. In some embodiments, an isolated FN3 domain that binds CD71 comprises the amino acid sequence of SEQ ID NO: 537. In some embodiments, an isolated FN3 domain that binds CD71 comprises the amino acid sequence of SEQ ID NO: 538. In some embodiments, an isolated FN3 domain that binds CD71 comprises the amino acid sequence of SEQ ID NO: 539. In some embodiments, an isolated FN3 domain that binds CD71 comprises the amino acid sequence of SEQ ID NO: 540. In some embodiments, an isolated FN3 domain that binds CD71 comprises the amino acid sequence of SEQ ID NO: 541. In some embodiments, an isolated FN3 domain that binds CD71 comprises the amino acid sequence of SEQ ID NO: 542. In some embodiments, an isolated FN3 domain that binds CD71 comprises the amino acid sequence of SEQ ID NO: 543. In some embodiments, an isolated FN3 domain that binds CD71 comprises the amino acid sequence of SEQ ID NO: 544. In some embodiments, an isolated FN3 domain that binds CD71 comprises the amino acid sequence of SEQ ID NO: 545. In some embodiments, an isolated FN3 domain that binds CD71 comprises the amino acid sequence of SEQ ID NO: 546. In some embodiments, an isolated FN3 domain that binds CD71 comprises the amino acid sequence of SEQ ID NO: 547. In some embodiments, an isolated FN3 domain that binds CD71 comprises the amino acid sequence of SEQ ID NO: 548. In some embodiments, an isolated FN3 domain that binds CD71 comprises the amino acid sequence of SEQ ID NO: 549. In some embodiments, an isolated FN3 domain that binds CD71 comprises the amino acid sequence of SEQ ID NO: 550. In some embodiments, an isolated FN3 domain that binds CD71 comprises the amino acid sequence of SEQ ID NO: 551. In some embodiments, an isolated FN3 domain that binds CD71 comprises the amino acid sequence of SEQ ID NO: 552. In some embodiments, an isolated FN3 domain that binds CD71 comprises the amino acid sequence of SEQ ID NO: 553. In some embodiments, an isolated FN3 domain that binds CD71 comprises the amino acid sequence of SEQ ID NO: 554. In some embodiments, an isolated FN3 domain that binds CD71 comprises the amino acid sequence of SEQ ID NO: 555. In some embodiments, an isolated FN3 domain that binds CD71 comprises the amino acid sequence of SEQ ID NO: 556. In some embodiments, an isolated FN3 domain that binds CD71 comprises the amino acid sequence of SEQ ID NO: 557. In some embodiments, an isolated FN3 domain that binds CD71 comprises the amino acid sequence of SEQ ID NO: 558. In some embodiments, an isolated FN3 domain that binds CD71 comprises the amino acid sequence of SEQ ID NO: 559. In some embodiments, an isolated FN3 domain that binds CD71 comprises the amino acid sequence of SEQ ID NO: 560. In some embodiments, an isolated FN3 domain that binds CD71 comprises the amino acid sequence of SEQ ID NO: 561. In some embodiments, an isolated FN3 domain that binds CD71 comprises the amino acid sequence of SEQ ID NO: 562. In some embodiments, an isolated FN3 domain that binds CD71 comprises the amino acid sequence of SEQ ID NO: 563. In some embodiments, an isolated FN3 domain that binds CD71 comprises the amino acid sequence of SEQ ID NO: 564. In some embodiments, an isolated FN3 domain that binds CD71 comprises the amino acid sequence of SEQ ID NO: 565. In some embodiments, an isolated FN3 domain that binds CD71 comprises the amino acid sequence of SEQ ID NO: 566. In some embodiments, an isolated FN3 domain that binds CD71 comprises the amino acid sequence of SEQ ID NO: 567. In some embodiments, an isolated FN3 domain that binds CD71 comprises the amino acid sequence of SEQ ID NO: 568. In some embodiments, an isolated FN3 domain that binds CD71 comprises the amino acid sequence of SEQ ID NO: 569. In some embodiments, an isolated FN3 domain that binds CD71 comprises the amino acid sequence of SEQ ID NO: 570. In some embodiments, an isolated FN3 domain that binds CD71 comprises the amino acid sequence of SEQ ID NO: 571. In some embodiments, an isolated FN3 domain that binds CD71 comprises the amino acid sequence of SEQ ID NO: 572. In some embodiments, an isolated FN3 domain that binds CD71 comprises the amino acid sequence of SEQ ID NO: 573. In some embodiments, an isolated FN3 domain that binds CD71 comprises the amino acid sequence of SEQ ID NO: 574. In some embodiments, an isolated FN3 domain that binds CD71 comprises the amino acid sequence of SEQ ID NO: 575. In some embodiments, an isolated FN3 domain that binds CD71 comprises the amino acid sequence of SEQ ID NO: 576. In some embodiments, an isolated FN3 domain that binds CD71 comprises the amino acid sequence of SEQ ID NO: 577. In some embodiments, an isolated FN3 domain that binds CD71 comprises the amino acid sequence of SEQ ID NO: 578. In some embodiments, an isolated FN3 domain that binds CD71 comprises the amino acid sequence of SEQ ID NO: 579. In some embodiments, an isolated FN3 domain that binds CD71 comprises the amino acid sequence of SEQ ID NO: 580. In some embodiments, an isolated FN3 domain that binds CD71 comprises the amino acid sequence of SEQ ID NO: 581. In some embodiments, an isolated FN3 domain that binds CD71 comprises the amino acid sequence of SEQ ID NO: 582. In some embodiments, an isolated FN3 domain that binds CD71 comprises the amino acid sequence of SEQ ID NO: 583. In some embodiments, an isolated FN3 domain that binds CD71 comprises the amino acid sequence of SEQ ID NO: 584. In some embodiments, an isolated FN3 domain that binds CD71 comprises the amino acid sequence of SEQ ID NO: 585. In some embodiments, an isolated FN3 domain that binds CD71 comprises the amino acid sequence of SEQ ID NO: 586. In some embodiments, an isolated FN3 domain that binds CD71 comprises the amino acid sequence of SEQ ID NO: 587. In some embodiments, an isolated FN3 domain that binds CD71 comprises the amino acid sequence of SEQ ID NO: 588. In some embodiments, an isolated FN3 domain that binds CD71 comprises the amino acid sequence of SEQ ID NO: 589. In some embodiments, an isolated FN3 domain that binds CD71 comprises the amino acid sequence of SEQ ID NO: 590. In some embodiments, an isolated FN3 domain that binds CD71 comprises the amino acid sequence of SEQ ID NO: 591. In some embodiments, an isolated FN3 domain that binds CD71 comprises the amino acid sequence of SEQ ID NO: 592. In some embodiments, an isolated FN3 domain that binds CD71 comprises the amino acid sequence of SEQ ID NO: 593. In some embodiments, an isolated FN3 domain that binds CD71 comprises the amino acid sequence of SEQ ID NO: 594. In some embodiments, an isolated FN3 domain that binds CD71 comprises the amino acid sequence of SEQ ID NO: 595. In some embodiments, an isolated FN3 domain that binds CD71 comprises the amino acid sequence of SEQ ID NO: 596. In some embodiments, an isolated FN3 domain that binds CD71 comprises the amino acid sequence of SEQ ID NO: 597. In some embodiments, an isolated FN3 domain that binds CD71 comprises the amino acid sequence of SEQ ID NO: 598. In some embodiments, an isolated FN3 domain that binds CD71 comprises the amino acid sequence of SEQ ID NO: 599. In some embodiments, an isolated FN3 domain that binds CD71 comprises the amino acid sequence of SEQ ID NO: 600. In some embodiments, an isolated FN3 domain that binds CD71 comprises the amino acid sequence of SEQ ID NO: 601. In some embodiments, an isolated FN3 domain that binds CD71 comprises the amino acid sequence of SEQ ID NO: 602. In some embodiments, an isolated FN3 domain that binds CD71 comprises the amino acid sequence of SEQ ID NO: 603. In some embodiments, an isolated FN3 domain that binds CD71 comprises the amino acid sequence of SEQ ID NO: 604. In some embodiments, an isolated FN3 domain that binds CD71 comprises the amino acid sequence of SEQ ID NO: 605. In some embodiments, an isolated FN3 domain that binds CD71 comprises the amino acid sequence of SEQ ID NO: 606. In some embodiments, an isolated FN3 domain that binds CD71 comprises the amino acid sequence of SEQ ID NO: 607. In some embodiments, an isolated FN3 domain that binds CD71 comprises the amino acid sequence of SEQ ID NO: 608. In some embodiments, an isolated FN3 domain that binds CD71 comprises the amino acid sequence of SEQ ID NO: 609. In some embodiments, an isolated FN3 domain that binds CD71 comprises the amino acid sequence of SEQ ID NO: 610. In some embodiments, an isolated FN3 domain that binds CD71 comprises the amino acid sequence of SEQ ID NO: 611. In some embodiments, an isolated FN3 domain that binds CD71 comprises the amino acid sequence of SEQ ID NO: 612. In some embodiments, an isolated FN3 domain that binds CD71 comprises the amino acid sequence of SEQ ID NO: 613. In some embodiments, an isolated FN3 domain that binds CD71 comprises the amino acid sequence of SEQ ID NO: 614. In some embodiments, an isolated FN3 domain that binds CD71 comprises the amino acid sequence of SEQ ID NO: 615. In some embodiments, an isolated FN3 domain that binds CD71 comprises the amino acid sequence of SEQ ID NO: 616. In some embodiments, an isolated FN3 domain that binds CD71 comprises the amino acid sequence of SEQ ID NO: 617. In some embodiments, an isolated FN3 domain that binds CD71 comprises the amino acid sequence of SEQ ID NO: 618. In some embodiments, an isolated FN3 domain that binds CD71 comprises the amino acid sequence of SEQ ID NO: 619. In some embodiments, an isolated FN3 domain that binds CD71 comprises the amino acid sequence of SEQ ID NO: 620. In some embodiments, an isolated FN3 domain that binds CD71 comprises the amino acid sequence of SEQ ID NO: 621. In some embodiments, an isolated FN3 domain that binds CD71 comprises the amino acid sequence of SEQ ID NO: 622. In some embodiments, an isolated FN3 domain that binds CD71 comprises the amino acid sequence of SEQ ID NO: 623.

In some embodiments, the isolated FN3 domain that binds CD71 comprises an initiator methionine (Met) linked to the N-terminus of the molecule.

In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 300-317. In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 318-328. In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 395-623. Percent identity can be determined using the default parameters to align two sequences using BlastP available through the NCBI website. The sequences of the FN3 domains that bind to CD71 can be found, for example, in Table 3.

TABLE 3

CD71-binding FN3 domain sequences

| SEQ ID | Amino Acid sequence of FN3 domains that bind to CD71 |
|---|---|
| 300 | MLPAPKNLVVSRVTEDSARLSWTAPDAAFDSFTIQYEELTTVGEAIYLR VPGSERSYDLTGLKPGTEYVVWIEGVKGGLRSNPLGAAFTT |
| 301 | MLPAPKNLVVSRVTEDSARLSWTAPDAAFDSFAITYIEWWDVGEAIGL KVPGSERSYDLTGLKPGTEYRVHIQGVKGGNNSYPLDALFTT |

TABLE 3-continued

CD71-binding FN3 domain sequences

| SEQ ID | Amino Acid sequence of FN3 domains that bind to CD71 |
|---|---|
| 302 | MLPAPKNLVVSRVTEDSARLSWTAPDAAFDSFEIAYFEAIWNGEAIYLTVPGSERSYDLTGLKPGTEYQVEIRGVKGGPTSRPLFAWFTT |
| 303 | MLPAPKNLVVSRVTEDSARLSWTAPDAAFDSFTITYIEWWENGEAIALSVPGSERSYDLTGLKPGTEYQVGIAGVKGGYKSYPLWALFTT |
| 304 | MLPAPKNLVVSRVTEDSARLSWTAPDAAFDSFHIIYTEEEKEGEAIYLRVPGSERSYDLTGLKPGTEYLVEIEGVKGGKRSVPLNASFTT |
| 305 | MLPAPKNLVVSRVTEDSARLSWTAPDAAFDSFHIAYEESHTTGEAIFLRVPGSERSYDLTGLKPGTEYSVSIEGVKGGHYSPPLTAKFTT |
| 306 | MLPAPKNLVVSRVTEDSARLSWTAPDAAFDSFDIDYREWWTLGEAIVLTVPGSERSYDLTGLKPGTEYYVNIQGVKGGLRSYPLSAIFTT |
| 307 | MLPAPKNLVVSRVTEDSARLSWTAPDAAFDSFVIEYWEYVGHGEAIVLTVPGSERSYDLTGLKPGTEYSVGIYGVKGGSLSRPLSAIFTT |
|

TABLE 3-continued

CD71-binding FN3 domain sequences

| SEQ ID | Amino Acid sequence of FN3 domains that bind to CD71 |
|---|---|
| 327 | MLPAPKNLVVSRVTEDSARLSWTAPDAAFDSFTIWYAEAIGHGEAIVLTVPGSERSYDLTGLKPGTEYWVDIWGVKGGQQSKPLSAIFTT |
| 328 | MLPAPKNLVVSRVTEDSARLSWRVESRTFDSFLIQYQESEKVGEAIVLTVPGSERSYDLTGLKPGTEYTVSIYGVVWDTRDNPISNPLSAIFTT |
| 3 | MLPAPKNLVVSRVTEDSARLSWTAPDAAFDSFPILYLELNHHGEEIVLTVPGSERSYDLTGLKPGTEYWVYIFGVKGGMYSAPLSAIFTTG TABLE 3-continued

| CD71-binding FN3 domain sequences | |
|---|---|
| SEQ ID | Amino Acid sequence of FN3 domains that bind to CD71 |
| 417 | MLLAPKNLVVSRVTEDSARLSWTAPDAAFDSFAIEYFEYTGEGEAIVLT VPGSERSYDLTGLKPGTEYYVGIYGVKGGYLSRPLSAIFTT |
| 418 | MLPAPKNLVVSHVTEDSARLSWTAPDAAFDSFDIEYYELVGSGEAIVLT VPGSERSYDLTGLKPGTEYYVAIYGVKGGYLSRPLSAIFTT |
| 419 | MLPAPKNLVVSRVTEDSARLSWTAPDAAFDSFGIAYYERSGAGEAIVLT VPGSERSYDLTGLKPGTEYMVYINGVKGGFVSSPLSAIFTT |
| 420 | MLPAPKNLVVSRVTEDSARLSWTAPDAAFDSFTIAYEEHGLVGEAIYLR VPGSERSYDLTGLKPGTEYHVGIMGVKGGVFSSPLSAIFTT |
| 421 | MLPAPKNLVVSRVTEDSARLSWTAPDAAFDSFFIQYTESHWVGEAIVLT VPGSERSYDLTGLKPGTEYAVPIEGVKGGDSSTPLSAIFTT |
| 422 | MLPAPKNLVVSRVTEDSARLSWTAPDAAFDSFTIIYGEVNPYGEAIVLT VPGSERSYDLTGLKPGTEYDVFIEGVKGGHLSWPLSAIFTT |
| 423 | MLPAPKNLVVSRVTEDSARLSWTAPDAAFDSFHIAYEELVTEGEAIYLR VPGSERSYDLTGLKPGTEYLVDIEGVKGGHLSSPLSAIFTT |
| 424 | MLPAPKNLVVSRVTEDSARLSWTAPDAAFDSFFIHYHEWWEAGEAIVL TVPGSERSYDLTGLKPGTEYLVDIPGVKGGDLSVPLSAIFTT |
| 425 | MLPAPKNLVVSRVTEDSARLSWTAPDAAFDSFWIYYYESVGTGEAIVLT VPGSERSYDLTGLKPGTEYFVDISGVKVGTYSLPLSAIFTT |
| 426 | MLPAPKNLVVSRVTEDSARLSWTAPDAAFDSFFIAYFEFANPGEAIVLT VPGSERSYDLTGLKPGTEYKVVIQGVKGGTPSEPLSAISTT |
| 427 | MLPAPKNLVVSRVTEDSARLSWTAPDAAFDSFDIHYKEHSWWGEAIVL TVPGSERSYDLTGLKPGTEYIVPIPGVKGGGISRPLSAIFTT |
| 428 | MLPAPKNLVVSRVTEDSARLSWTAPDAAFDSFAIEYWEAVGSGEAIVLT VPGSERSYDLTGLKPGTEYHVYIYGVKGGYLSLPLSAIFTT |
| 429 | MLPAPKNLVVSRVTEDSARLSWTAPDAAFDSFFIGYLEPQPPGEAIVLTV PGSERSYDLTGLKPGTEYNVTIQGVKGGFPSMPLSAIFTTT |
| 430 | MLPAPKNLVVSRVTEDSARLSWTAPDAAFDSFSIAYSEVRYDGEAIVLT VPGSERSYDLTGLKPGTEYVVPIGGVKGGGSSSPLSAIFTT |
| 431 | MLPAPKNLVVSRVTEDSARLSWTAPDAAFDSFTIPYGEAFNPGEAIVLT VPGSERSYDLTGLKPGTEYDVFIEGVKGGTLSWPLSAIFTT |
| 432 | MLPAPKNLVVSRVTEDSARLSWTAPDAAFDSFRILYGEVDPWGEAIVLT VPGSERSYDLTGLKPGTEYDVWIEGVKGGKLSWPLSAIFTT |
| 433 | MLPAPKNLVVSRVTEDSARLSWTAPDAAFDSFHIEYEETPQKGEAIFLR VPGSERSYDLTGLKPGTEYVVNIRGVKGGDLSSPLGALFTT |
| 434 | MLPAPKNLVVSRVTEDSARLSWTAPDAAFDSFRIEYIEWWVGGEAIVLT VPGSERSYDLTGLKPGTEYWVDIKGVKGGKRSYPLSAIFTT |
| 435 | MLPAPKNLVVSRVTEDSARLSWTAPDAAFDSFSIDYPEFPVRGEAIVLT VPGSERSYDLTGPKPGTEYNVTIQGVKGGFPSMPLSAIFTT |
| 436 | MLPAPKNLVVSRVTEDSARLSWTAPDAAFDSFQIPYWEQSLGGEAIVLT VPGSERSYDLTGLKPGTEYEVWIEGVKGGDLSFPLSAISTT |
| 437 | MLPAPKNLVVSRVTEDSARLSWTAPDAAFDSFVIPYEEYLYTGEAIVLT VPGSERSYDLTGLKPGTEYDVWIEGVKGGLTSWPLSAIFTT |
| 438 | MLPAPKNLVVSRVTEDSARLSWTAPDAAFDSFSIDYPEFPVRGEAIVLT VPGSERSYDLTGLKPGTEYAVTIWGVKGGFTSQPLSAIFTT |
| 439 | MLPAPKNLVVSRVTEDSARLSWTAPDAAFDSFVIEYFEFVGEGEAIVLT VPGSERSYDLTGLKPGTEYDVGIYGVKGGSLSSPLSAIFTT |
| 440 | MLPAPKNLVVSRVTEDSARLSWTAPDAAFDSFSIDYLELGESGEAIVLT VPGSERSYDLTGLKPGTEYWVYIFGVKGGYPSAPLSAIFTT |
| 441 | MLPAPKNLVVSRVTEDSARLSWTAPDAAFDSFPIPYGESPPSGEAIVLTV PGSERSYDLTGLKPGTEYVVIIRGVKGGGRSGPLSAISTT |

TABLE 3-continued

CD71-binding FN3 domain sequences

| SEQ ID | Amino Acid sequence of FN3 domains that bind to CD71 |
|---|---|
| 442 | MLPAPKNLVVSRVTEDSARLSWTAPDAAFDSFIINYIEIVQYGEAIVLTV<br>PGSERSYDLTGLKPGTEYPESIWGVKGGGASSPLSAIFTT |
| 443 | MLPAPKNLVVSRVTEDSARLSWTAPDAAFDSFDIEYYEAVGAGEAIVLT<br>VPGSERSYDLTGLKPGTEYTVGIYGVKGGWLSKPLSVIFTT |
| 444 | MLPAPKNLVVSRVTEDSARLSWTAPDAAFDSFHIPYVEAEVPGEAIQLH<br>VPGSERSYDLTGLKPGTEYYVEIWGVKGGFYSPPLIAEFTT |
| 445 | MLPAPKNLVVSRVTEDSARLSWTAPDAAFDSFSIDYYEGKGYGEAIVLT<br>VPGSERSYDLTGLKPGTEYQVLISGVKGGKYSLPLSAIFTT |
| 446 | MLPAPKNLVVSRVTEDSARLSWTAPDAAFDSFTIVYAEVTYDGEAIVLT<br>VPGSERSYDLTGLKPGTEYDVFIEGVKGGELSWPLSAIFTT |
| 447 | MLPAPKNLVVSRVTEDSARLSWTAPDAAFDSFPIVYGEAWVTGEAIVLT<br>VPGSERSYDLTGLKPGTEYDVWIEGVKGGELSWPLSAIFTT |
| 448 | MLPAPKNLVVSRVTEDSARLSWTAPDAAFDSFWIDYYERKYVGEAIVL<br>TVPGSERSYDLTGLKPGTEYEVTIYGVKGGWYSDPLSAIFTT |
| 449 | MLPAPKNLVVSRVTEDSARLSWTAPDAAFDSFPISYYEMSGLGEAIVLT<br>VPGSERSYDLTGLKPGTEYMVYIFGVKGGLNSLPLSAIFTT |
| 450 | MLPAPKNLVVSRVTEDSARLSWTAPDAAFDSFIYYIESYPAGEAIVLTV<br>PGSERSYDLTGLKPGTEYWMGIDGVKGGRWSTPLSAIFTT |
| 451 | MLPAPKNLVVSRVTEDSARLSWTAPDAAFDSFEIEYDEPSVAGEAIVLT<br>VPGSERSYDLTGLKPGTEYRVFIWGVKGGNQSWPLSAIFTT |
| 452 | MLPAPKNLVVSRVTEDSARLSWTAPDAAFDSFFIKYIEWWADGEAIVLT<br>VPGSERSYDLTGLKPGTEYLVEIYGVKGGRQSYPLSAIFTT |
| 453 | MLPAPKNLVVSRVTEDSARLSWTAPDAAFDSFDISYWESGKYGEAIVLT<br>VPGSESSYDLTGLKPGTEYLVDIFGVKGGYPSEPLSAIFTT |
| 454 | MLPAPKNLVVSRVTEDSARLSWTAPDAAFDSFWISYEESDTEGEAIYLR<br>VPGSERSYDLTGLKPGTEYNVTIQGVKGGFPSMPLSAIFTT |
| 455 | MLPAPKNLVVSRVTEDSARLSWTAPDAAFDSFVIEYFEQFNLGEAIVLT<br>VPGSERSYDLTGLKPGTEYLVGIYGVKGGWLSHPLSAIFTT |
| 456 | MLPAPKNLVVSRVTKDSARLSWTAPDAAFDSFHIAYEEATTYGEAIFLR<br>VPGSERSYDLTGLKPGTEYEVKIHGVKGGADSKPLVAPFTT |
| 457 | MLPAPKNLVVSRVTEDSARLSWTAPDAAFDSFHIAYEEADSEGEAIYLR<br>VPGSERSYDLTGLKPGTEYSVNIQGVKGGIVSFPLHAEFTT |
| 458 | MLPAPKNLVVSRVTEDSARLSWTAPDAAFDSFIIPYAEVRPDGEAIVLTV<br>PGSERSYDLTGLKPGTEYSVLIHGVKGGKLSLPLSAIFTT |
| 459 | MLPAPKNLVVSRVTEDSARLSWTAPDAAFDSFFIPYAEPSPTGEAIVLTV<br>PGSERSYDLTGLKPGTEYDVWIEGVKGGTLSWPLSAIFTT |
| 460 | MLPAPKNLVVSRVTEDSARLSWTAPDAAFDSFYIAYAEPRPDGEAIVLT<br>VPGSERSYDLTGLKPGTEYSVLIHGVKGGLLSSPLSAIFTT |
| 461 | MLPAPKNLVVSRVTEDSARLSWTAPDAAFDSFFIGYLEPQPPGEAIVLTV<br>PGSERSYDLTGLKPGTEYSVLIHGVKGGRNSDPLSAISTT |
| 462 | MLPAPKNLVVSRVTEDSARLSWTAPDAAFDSFHIEYEEQYSTGEAIYLR<br>VPGSERSYDLTGLKPGTEYHVDIEGVKGGRRSFPLNAFFTT |
| 463 | MLPAPKNLVVSRVTEDSARLSWTAPDAAFDSFIIPYAEVRPDGEAIVLTV<br>PGSERSYDLTGLKPGTEYSVLIHGVKGGKLSEPLSAIFTT |
| 464 | MLPAPKNLVVSRVTEDSARLSWTAPDAAFDSFPIAYAEPSPTGEAIVLTV<br>PGSERSYDLTGLKPGTEYSVLIHGVKGGHLSDPLSAIFTT |
| 465 | MLPAPKNLVVSRVTEDSARLSWTAPDAAFDSFFIPYAEPSPTGEAIVLTV<br>PGSERSYDLTGLKPGTEYGVVILGVKGGYGSDPLSAIFTT |

TABLE 3-continued

CD71-binding FN3 domain sequences

| SEQ ID | Amino Acid sequence of FN3 domains that bind to CD71 |
|---|---|
| 466 | MLPAPKNLVVSRVTEDSARLSWTAPDAAFDSFFIGYLEPQPPGEAIVLTV<br>PGSERSYDLTGLKPGTEYNVTIQGVKGGFPSSPLSAIFTT |
| 467 | MLPAPKNLVVSRVTEDSARLSWTAPDAALDSFRIAYTEYFVGGEAIVLT<br>VPGSERSYDLTGLKPGTEYGVGIYGVKGGAGSSPLSAIFTT |
| 468 | MLPAPKNLVVSRVTEDSARLSWTAPDAAFDSFFIPYAEPRPDGEAIVLT<br>VPGSERSYDLTGLKPGTEYSVLIHGVKGGLLSSPLSAIFTT |
| 469 | MLPAPKNLVVSRVTEDSARLSWTAPDAAFDSFPITYRERSQYGEAIVLT<br>VPGSERSYDLTGLKPGTEYVVPIEGVKGGRGSKPLSAIFTT |
| 470 | MLPAPKNLVVSRVTEDSARLSWTAPDAAFDSFAIEYFENLGIGEAIVLTV<br>PGSERSYDLTGLKPGTEYVVNIYGVKGGWLSSPLSAIFTT |
| 471 | MLPAPKNLVVSRVTEDSARLSWTAPDAAFDSFAIEYYEYVGNGEAIVLT<br>VPGSERSYDLTGLKPGTEYQVGIYGVKGGYYSRPLSAIFTT |
| 472 | MLPAPKNLVVSRVTEDSARLSWTAPDAAFDSFIIDYLELDDYGEAIVLT<br>VPGSERSYDLTGLKPGTEYPVYIYGVKGGLPSTPLSAIFTT |
| 473 | MLPAPKNLVVSRVTEDSARLSWTAPDAAFDSFLIPYAETSPSGEAIVLTV<br>PGSERSYDLTGLKPGTEYSVLIHGVKGGRNSDPLSAIFTT |
| 474 | MLPAPKNLVVSRVTEDSARLSWTAPDAAFDSFNIAYGEWRQHGEAIVL<br>TVPGSERSYDLTGLKPGTEYDVFIDGVKGGNLSWPLSAIFTT |
| 475 | MLPAPKNLVVSRVTEDSARLSWTAPDAAFDSFTIRYWEELPTGEAIVLT<br>VPGSERSYDLTGLKPGTEYTVEIFGVKGGYLSRPLSAISTT |
| 476 | MLPAPKNLVVSRVTEDSARLSWTAPDAAFDSFHIAYEEATTYGEAIFLR<br>VPGSERSYDLTGLKPGTEYDVWIEGVKGGTISGPLSAIFTT |
| 477 | MLPAPKNLVVSRVTEDSARLSWTAPDAAFDSFPIAYAEPRPDGEAIVLT<br>VPGSERSYDLTGLKPGTEYFVDIFGVKGGTLSRPLSAIFTT |
| 478 | MLPAPKNLVVSRVTEDSARLSWTAPDAAFDSFLIPYAETSPSGEAIVLTV<br>PGSERSYDLTGLKPGTEYSVLIHGVKGGHLSDPLSAIFTT |
| 479 | MLPARKNLVVSRVTEDSARLSWTAPDAAFDSFFIPYAEPSPTGEAIVLTV<br>PGSERSYDLTGLKPGTEYSVLIHGVKGGHLSDPLSAISTT |
| 480 | MLPAPKNLVVSRVTEDSARLSWTAPDAAFDSFTILYNEIQNVGEAIVLT<br>VPGSERSYDLTGLKPGTEYDVWIEGVKGGELSWPLSAIFTT |
| 481 | MLPAPKNLVVSRVTEDSARLSWTAPDAAFDSFFIGYLEPQPPGEAIVLTV<br>PGSERSYDLTGLKPGTEYNVTIQGVKGGTPSEPLSAIFTT |
| 482 | MLPAPKNLVVSRVTEDSARLSWTTPDAAFDSFFIGYLEPYPPGEAIVLTV<br>PGSERSYDLTGLKPGTEYVVSIQGVKGGKPSDPLSAIFTT |
| 483 | MLPAPKNLVVSRVTEDSARLSWTAPDAAFDSFFIGYLEPQPPGEAIVLTV<br>PGSERSYDLTGLKPGTEYNVTIQGVKGGFPSVPLSAIFTT |
| 484 | MLPAPKNLVVSRVTEDSARLSWTAPDAAFDSFFIGYPEYPATGEAIVLT<br>VPGSERSYDLTGLKPGTEYFVDINGVKGGSLSYPLSAIFTT |
| 485 | MLPAPKNLVVSRVTEDSARLSWTAPDAAFDSFAIRYLEWWDVGEAIVL<br>TVPGSERSYDLTGLKPGTEYLVEIKGVKGGKFSYPLSAIFTT |
| 486 | MLPAPKNLVVSRVTEDSARLSWTAPDAAFDSFPIEYDEWWALGEAITLI<br>VPASERSYDLTGLKPGTEYVVKIHGVKGGQRSYPLIAFFTT |
| 487 | MLPAPKNLVVSRVTEDSARLSWTAPDAAFDSFTIHYRELYVQAIVLTVP<br>GSERSYDLTGLKPGTEYLVMIPGVKGGPTSVPLSAIFTT |
| 488 | MLPAPKNLVVSRVTEDSARLSWTAPDAAFDSFFIGYLEPQPPGEAIVLTV<br>PGSERSYDLTGLKPGTEYKVVIQGVKGGTPSEPLSAIFTT |
| 489 | MLPAPKNLVVSRVTEDSARLSWTAPDAAFDSFFIGYLEPQPPGEAIVLTV<br>PGSERSYDLTGLKPGTEYSVVIQGVKGGFPSDPLSAIFTT |
| 490 | MLPAPKNLVVSRVTEDSARLSWTAPDAAFDSFPIAYAEPRPDGEAIVLT<br>VPGSERSYDLTGLKPGTEYSVGIHGVKGGHDSSPLSAIFTT |

TABLE 3-continued

CD71-binding FN3 domain sequences

| SEQ ID | Amino Acid sequence of FN3 domains that bind to CD71 |
|---|---|
| 491 | MLPAPKNLVVSRVTEDSARLSWTAPDAAFDSFFIGYLEPQPPGEAIVLTV<br>PGSERSYDLTGLKPGTEYNVTIQGVKGGRASGPLSAIFTT |
| 492 | MLPAPKNLVVSRVTEDSARLSWTAPDAAFDSFDIAYAEPIPRGEAIVLTV<br>PGSERSYDLTGLKPGTEYSVLIHGVKGGRRSVPLSAIFTT |
| 493 | MLPAPKNLVVSRVTEDSARLSWTAPDAAFDSFYIAYAEPRPDGEAIVLT<br>VPGSERSYDLTGLKPGTEYPVPIPGVKGGPGSSPLSAIFTT |
| 494 | MLPAPKNLVVSRVTEDSARLSWTAPDAAFDSFEISYYEMRGYGEAIVLT<br>VPGSERSYDLTGLKPGTEYSVLIHGVEGGDYSSPLSAISTT |
| 495 | MLPAPKNLVVSHVTEDSARLSWTAPDAAFDSFPIAYAEPRPDGEAIVLT<br>VPGSERSYDLTGLKPGTEYSVLIHGVKGGLLSSPLSAIFTT |
| 496 | MLPAPKNLVVSRVTEDSARLSWTAPDAAFDSFFIGYLEPYPPGEAIVLTV<br>PGSERSYDLTGLKPGTEYVVSIQGVKGGTPSQPLSAIFTT |
| 497 | MLPAPKNLVVSRVTEDSARLSWTAPDAAFDSFLIPYAETSPSGEAIVLTV<br>PGSERSYDLTGLKPGTEYSVLIHGVKGGRPSNPLVAAFTT |
| 498 | MLPAPKNLVVSRITEDSARLSWTAPDAAFDSFGIGYYEHKRFGEAIQLS<br>VPGSERSYDLTGLKPGTEYEVDIEGVKGGVLSWPLFAEFTT |
| 499 | MLPAPKNLVVSRVTEDSARLSWTAPDAAFDSFEIDYDELAIYGEAIVLT<br>VPGSERSYDLTGLKPGTEYGVMIIGVKGGLPSDPLSAIFTT |
| 500 | MLPAPKNLVVSRVTEDSARLSWTAPDAAFDSFFIGYLESAEAIVLTVPGS<br>ERSYDLTGLKPGTEYLVTIQGVKGGIASDPLSAIFTT |
| 501 | MLPAPKNLVVSRVTEDSARLSWTAPDAAFDFVIEYFEFVGYGEAIVLT<br>VPGSERSYDLTGLKPGTEYSVGIYGVKGGKLSPPLSAIFTT |
| 502 | MLPAPKNLVVSRVTEDSARLSWTAPDAAFDSFLIPYAETSPSGEAIVLTV<br>PGSERSYDLTGLKPGTEYSVLIHGVKGGKLSLPLSAIFTT |
| 503 | MLPAPKNLVVSRVTEDSARLSWTAPDAAFDSFHEWVYFGEAIVLTVPG<br>SERSYDLTGLKPGTEYFVDIWGVKGGTVSKPLSAIFTT |
| 504 | MLPAPKNLVVSRVTEDSARLSWTAPDAAFDSFFIGYPEYPATGEAITLFV<br>PGSERSYDLTGLKPGTEYNVVIQGVKGGRPSNPLVVAFTT |
| 505 | MLPAPENLVVSRVTEDSARLSWTAPDAAFDSFEITYEENWRRGEAIVLT<br>VPGSERSYDLTGPKPGTEYIVIIQGVKGGAESWPLSAIFTT |
| 506 | MLPAPKNLVVSRVTEDSARLSWTALDAAFDSFFIGYLEPQPPGEAIVLT<br>VPGSERSYDLTGLKPGTEYNVTIQGVKGGFPSMPLSAIFTT |
| 507 | MLPAPKNLVVSRVTEDSARLSWTAPDAAFDSFTIWYAEAVGNGEAIVL<br>TVPGSERSYDLTGLKPGTEYWVDIWGVKGGEFSSPLSAIFTT |
| 508 | MLPAPKNLVVSRVTEDSARLSWTAPDAAFDSFEIDYDELAIYGEAIVLT<br>VPGSERSYDLTGLKPGTEYRVFIYGVKGGWTSWPLSTIFTT |
| 509 | MLPAPKNLVVSRVTEDSARLSWTAPDAAFDSFPIEYDEIPFWGEAIVLTV<br>PGSERSYDLTGLKPGTEYRVWIHGVKGGNSSWPLSAIFTT |
| 510 | MLPAPKNLVVSRVTEDSARLSWTAPDAAFDSFNIHYVEWWVLGEAIVL<br>TVPGSERSYDLTGLKPGTEYPVYIYGVKGGPKSIPLSAIFTT |
| 511 | MLPAPKNLVVSRVTEDSARLSWTAPDAAFDSFKIDYLEINDNGEAIVLT<br>VPGSERSYDLTGLKPGTEYPVYIWGVKGGYPSSPLSAIFTT |
| 512 | MLPAPKNLVVSRVTEDSARLSWTAPDAAFDSFLIAYNEDRKFGEAIVLT<br>VPGSERSYDLTGLKPGTEYDVWIEGVKGGSLSFPLSAIFTT |
| 513 | MLPAPKNLVVSRVTEDSARLSWTAPDAAFDSFGIRYFEWWDLGEAIVL<br>TVPGSERSYDPTGLKPGTEYNVTIQGVKGGFPSMPLSAIFTT |
| 514 | MLPAPKNLVVSRVTEDSARLSWTAPDAAFDSFYIEYYEWMHTGEAIVL<br>TVPGSERSYDLTGLKPGTEYSVYIYGVKGGYPSSPLSAIFTT |
| 515 | MLPAPKNLVVSRVTEDSARLSWTAPDAAFDSFNIDYWETWVIGEAIVLT<br>VPGSERSYDLTGLKPGTEYEVIIPGVKGGTISPPLSAIFTT |

TABLE 3-continued

CD71-binding FN3 domain sequences

| SEQ ID | Amino Acid sequence of FN3 domains that bind to CD71 |
|---|---|
| 516 | MLPAPKNLVVSRVTEDSARLSWTAPDAAFDSFYIDYLELTYSGEAIVLTVPGSERSYDLTGLKPGTEYYVYIYGVKGGYPSSPLSAIFTT |
| 517 | MLPAPKNLVVSRVTEDSARLSWTAPDAALDSFRIEYYESYGHGEAIVLTVPGSERSYDLTGLKPGTEYDVGIYGVKGGYYSRPLSAIFTT |
| 518 | MLPAPKNLVVSRVTEDSARLPWTAPDAAFDSFWISYYESVGYGEAIVLTVPGSERSYDLTGLKPGTEYYVDISGVKGGVYSLPLSAIFTT |
| 519 | MLPAPKNLVVSRVTEDSARLSWTAPDAAFDSFDIDYDEPAWNGEAIVLTVPGSERSYDLTGLKPGTEYRVFIYGVKGGNTSWPLSAIFTT |
| 520 | MLPAPKNLVVSRVTEDSARLSWTAPDAAFDSFDIEYDELWKNGEAIVLTVPGSERSYDLTGLKPGTEYRVFIYGVKGGYGSFPLSAIFTT |
| 521 | MLPAPKNLVVSRVTEDSARLSWTAPDAAFDSFFIGYLEPQPPGEAIVLTVPGSERSYDLTGLKPGTEYNVTIQGVKGGTPSEPLSAISTT |
| 522 | MLPAPKNLVVSRVTEDSARLSWTAPDAAFDSFGIVYREPYVGGEAIVLTVPGSERSYDLTGLKPGTEYGVPIPGVKGGYDSGPLSAIFTT |
| 523 | MLPAPKNLVVSRVTEDSARLSWTAPDAAFDSFTIPYIEYVWWGEAIVLTVQGSERSYDLTGLKPGTEYPVTIGGVKGGSRSHPLHAHFTT |
| 524 | MLPAPKNLVVSRVTEDSARLSWTAPDAAFDSFSIVYGERFVNGEAIVLTVPGSERSYDLTGLKPGTEYHVYIDGVKGGDLSWPLSAIFTT |
| 525 | MLPAPKNLVVSRVTEDSARLSWTAPDAAFDSFWINYYEAQPDGEAIVLTVPGSERSYDLTGLKPGTEYDVEIAGVKGGTASLPLSAIFTT |
| 526 | MLPAPKNLVVSRVTEDSARLSWTAPDAAFDSFIIEYWEQIGVGEAIVLTVPGSERSYDLTGLKPGTEYWVGIYGVKGGLLSSPLSAIFTT |
| 527 | MLPAPKNLVVSRVTEDSARLSWTAPDAAFDSFWIYYWEIERAGEAIRLDVPGSERSYDLTGLKPGTEYRVDIWGVKGGPTSGPLRATFTT |
| 528 | MLPAPKNLVVSRVTEDSARLSWTAPDAAFDSFAIPYGERQELGEAIVLTVPGSERSYDLTGLKPGTEYFVVIQGVKGGQPSYPLSAIFTT |
| 529 | MLPAPKNLVVSRVTEDSARLSWTAPDAAFDSFLIPYAETSPTGEAIVLTVPGSERSYDLTGLKPGTEYSVLIHGVKGGYPSSPLSAIFTT |
| 530 | MLPAPKNLVVSRVTEDSARLSWTAPDAAFDSFPIAYAEPTPSGEAIVLTVPGSERSYDLTGLKPGTEYSVLIHGVKGGGLSLPLSAIFTT |
| 531 | MLPAPKNLVVSRVTEDSARLSWTAPDAAFDSFIIEYWEWYFAGEAIVLTVPGSERSYDLTGLKPGTEYTVWITGVKGGTWSEPLSAIFTT |
| 532 | MLPAPKNLVVSRVTEDSARLSWTAPDAAFDSFTILYYEMVGEGEAIVLTVPGSERSYDLTGPKPGTEYWVDIYGVKGGGWSRPLSAIFTT |
| 533 | MLPAPKNLVVSRVTEDSARLSWTAPDAAFDSFHIDYLELTYAGEAIVLTVPGSERSYDLTGLKPGTEYYVTIYGVKGGYPSSPLSAIFTT |
| 534 | MLPAPKNLVVSRVTEDSARLSWTAPDAAFDSFHIIYEEDGTEGEAIYLRVPGSERSYDLTGLKPGTEYEVDIEGVKGGVLSWPLFAEFTT |
| 535 | MLPAPKNLVVSRVTEDSARLSWTAPDAAFDSFHISYQEVVAEGEAIYLRVPGSERSYDLTGLKPGTEYYVLIHGVKGGYESKPLDASFTT |
| 536 | MLPAPKNLVVSRVTEDSARLSWTAPDAAFDSFYIEYFEWTGSGEAIVLTVPGSERSYDLTGLKPGTEYNVAIYGVKGGAVSYPLSAIFTT |
| 537 | MLPAPKNLVVSRVTEDSARLSWTAPDAAFDSFTIWYAEALGDGEAIVLTVPGSERSYDLTGLKPGTEYFVDIPGVKGGTRSSPLSAISTT |
| 538 | MLLAPKNLVVSRVTEDSARLSWTAPDAAFDSFRYLEQGLYGEAIVLTVPGSERSYDLTGLKPGTEYWVEIIGVKGGEYSTPLSAIFTT |
| 539 | MLPAPKNLVVSRVTEDSARLSWTAPDAAFDSFKIEYFEYVGYGEAIVLTVPGSERSYDLTGLKPGTEYYVAIYGVKGGWYSRPLSAIFTT |
| 540 | MLPAPKNLVVSRVTEDSARLSWTAPDAAFDSFHIIYEEVLTEGEAIYLRVPGSERSYDLTGLKPGTEYGVTIKGVKGGAYSIPLIATFTT |

TABLE 3-continued

CD71-binding FN3 domain sequences

| SEQ ID | Amino Acid sequence of FN3 domains that bind to CD71 |
|---|---|
| 541 | MLPAPKNLVVSRVTEDSARLSWTAPDAAFDSFRIRYLEWWNIGEAIVLT VPGSERSYDLTGLKPGTEYHVDIWGVKGGYSSYPLSAIFTT |
| 542 | MLPAPKNLVVSRVTEDSARLSWTAPDAAFDSFEIYYVEWSEAGEAIVLT VPGSERSYDLTGLKPGTEYRVEIRGVKGGSWSSPLSAIFTT |
| 543 | MLPAPKNLVVSRVTEDSARLSWTAPDAAFDSFSIHYDEDWRRGEAIVLT VPGSERSYDLTGLKPGTEYLVEIPGVKGGKASYPLSAIFTT |
| 544 | MLPAPKNLVVSRVTEDSARLSWTAPDAAFDSFQIRYPKRWISGEAIVLT VPGSERSYDLTGLKPGTEYEVVIRGVKGGEYSWPLSAIFTT |
| 545 | MLPAPKNLVVSRVTEDSARLSWTAPDAAFDSFEIPYIETVALGEAIVLTV PGSERSYDLTGLKPGTEYYVEIYGVKGGSYSYPLSAISTT |
| 546 | MLPAPKNLVVSRVTEDSARLSWTAPDAAFDSFTIAYDETLNLGEAIVLT VPGSERSYDLTGLKPGTEYIVGIFGVKGGTHSWPLSAIFTT |
| 547 | MLPAPKNLVVSRVTEDSARLSWTAPDAAFDSFYIVYAEPIPNGEAIVLT VPGSERSYDLTGLKPGTEYSVLIHGVKGGRNSDPLSAIFTT |
| 548 | MLPAPKNLVVSRVTEDSARLSWTAPDAAFDSFYITYWETWDYGEAIVL TVPGSERSYDLTGLKPGTEYKVPITGVKGGGPSVPLSAIFTT |
| 549 | MLPAPKNLVVSRVTEDSARLSWTAPDAAFDSFSINYREWWSDGEAIYL PVPGSERSYDLTGLKPGTEYAVYIQGVKGGSRSFPLHAWFTT |
| 550 | MLPAPKNLVVSRVTEDSARLSWTAPDAAFDSFWIEYYEELGSGEAIVLT VPGSERSYDLTGLKPGTEYRVYIYGVKGGYPSSPLSAIFTT |
| 551 | MLPAPKNLVVSRVTEDSARLSWTAPDAAFDSFTILYGEMGTTGEAIVLT VPGSERSYDLTGLKPGTEYDVFIEGVKGGELSWPLSAIFTT |
| 552 | MLPAPKNLVVSRVTEDSARLSWTAPDAAFDSFKIFYQEFGGEAIVLTVP GSERSYDLTGLKPGTEYWVDIYGVKGGYTSSPLSAIFTT |
| 553 | MLPAPKNLVVSRVTEDSARLSWTAPDAAFDSFAITYYEGRWRGEAIVL TVPGSERSYDLTGLKPGTEYGVPIRGVKGGTGSLPLSAIFTT |
| 554 | MLPAPKNLVVSRVTEDSARLSWTAPDAAFDSFRIKYLEWWLGGEAIVL TVPGSERSYDLTGLKPGTEYWVDIQGVKGGVLSWPLSAIFTT |
| 555 | MLPAPKNLVVSRVTEDSARLSWTAPDAAFDSFNIYYYEWFVSGEAIVLT VPGSERSYDLTGLKPGTEYFVDIDGVKGGYRSRPLSAIFTT |
| 556 | MLPAPKNLVVSRVTEDSARLSWTAPDAAFDSFPIKYLEWWSWGEAIVL TVPGSERSYDLTGLKPGTEYRVPISGVKGGGMSGPLSAIFTT |
| 557 | MLPAPKNLVVSRVTEDSARLSWTAPDAAFDSFAIPYYEWVNHGEAIVL TVPGSERSYDLTGLKPGTEYPVGIDGVKGGGPSWPLSAIFTT |
| 558 | MLPAPKNLVVSRVTEDSARLSWTAPDAAFDSFHIDYSEFHLRGEAIVLT VPGSERSYDLTGLKPGTEYLGIFGVKGGEQSGPLSAIFTT |
| 559 | MLPAPKNLVVSRITEDSARLSWTAPDAAFDSFGIAYNEGDHYGEAIVLT VPGSERSYDLTGLKPGTEYSVWIEGVKGGNLSYPLSAIFTT |
| 560 | MLPAPKNLVVSRVTEDSARLSWTAPDAAFDSFTIAYNEQNHYGEAIVLT VPGSERSYDLTGLKPGTEYGVWIEGVKGGTLSWPLSAIFTT |
| 561 | MLPAPKNLVVSRVTEDSARLSWTAPDAAFDSFYIEWTYKGEAIVLTVPG SERSYDLTGLKPGTEYFVGIPGVKGGKSSYPLSAIFTTNPKGDTP |
| 562 | MGSLPAPKNLVVSRVTEDSARLSWTAPDAAFDSFAIPYAEPSPTGEAIVL TVPGSERSYDLTGLKPGTEYPVWIQGVKGGSPSAPLSAEFTT |
| 563 | MLPAPKNLVVSRVTEDSARLSWTAPDAAFDSFSIDYFESVGFGEAIVLT VPGSERSYDLTGLKPGTEYDVQITGVKGGPHSLPLSAIFTT |
| 564 | MLPAPKNLVVSRVTEDSARLSWTAPDAAFDSFFIGYLEPYPPGEAIVLTV PGSERSYDLTGLKPGTEYAVEIAGVKGGLLSSPLSAISTT |
| 565 | MLPAPKNLVVSRVTEDSARLSWTAPDAAFDSFFIGYLEPQPPGEAIVLTV PGSERSYDLTGLKPGTEYNVTIQGVKGGFPSMPLSAIVTT |

TABLE 3-continued

CD71-binding FN3 domain sequences

| SEQ ID | Amino Acid sequence of FN3 domains that bind to CD71 |
|---|---|
| 566 | MLPAPKNLVVSRVTEDSARLSWTAPDAAFDSFDIGYTEYGGYGEAIVLTVPGSERSYDLTGLKPGTEYWVLIQGVKGGGSSVPLSAIFTT |
| 567 | MLPAPKNLVVSRVTEDSARLSWTAPDAAFDSFTIEYWETIGGGEAIVLTVPGSERSYDLTGLKPGTEYYVGIYGVKGGWWSRPLSAIFTT |
| 568 | MLPAPKNLVVSRVTEDSARLSWTAPDAAFDSFFIPYAEPSPTGEAIVLTVPGSERSYDLTGLKPGTEYSVLIHGVKGGHLSDPLSAISTT |
| 569 | MLPAPKNLVVSRVTEDSARLSWTAPDAAFDSFDIEYYELIGRGEAIVLTVPGSERSYDLTGLKPGTEYWVGIYGVKGGWLSRPLSAIFTT |
| 570 | MLPAPKNLVVSRVTEDSARLSWTAPDAAFDSFHIVYHEPRPSGEAIVLTVPGSERSYDLTGLKPGTEYEVGIVGVKGGDLSVPLSAIFTT |
| 571 | MLPAPKNLVVSRVTEDSARLSWTAPDAAFDSFHIVYHEPRPSGEAIVLTVPGSERSYDLTGLKPGTEYEVGIVSVKGGDLSVPLSAIFTT |
| 572 | MLPAPKNLVVSRVTEDSARLSWTAPDAAFDSFFIPYAEPSPTGEAIVLTVPGSERSYDLTGLKPGTEYDVWIEGVKGGVLSWPLSAIFTT |
| 573 | MLPAPKNLVVSRVTEDSARLSWTAPDAAFDSFTIEYFEFVDAGEAIVLTVPGSERSYDLTGLKPGTEYWVEIWGVKGGSWSKPLSAIFTT |
| 574 | MLPAPKNLVVSRVTEDSARLSWTAPDAAFDSFNISYYEYFVHGEAIVLTVPGSERSYDLTGLKPGTEYYVIDGVKGGDPSEPLSAIFTT |
| 575 | MLPAPKNLVVSRVTEDSARLSWTAPDAAFDSFTIVYGEWGVPGEAIVLTVPGSERSYDLTGLKPGTEYDVWIEGVKGGDLSWPLSAIVTT |
| 576 | MLPAPKNLVVSRVTEDSARLSWTAPDAAFDSFAIEYFEYTGEGEAIVLTVPGSERSYDLTGLKPGTEYYVGIYGVKGGYLSRPLSAIFTT |
| 577 | MLPAPKNLVVSRVTEDSARLSWTAPDAAFDSFFIGYLEPQPPGEAIVLTVPGSERSYDLTGLKPGTEYNVTIQGVKGGFPSMPLSAISTT |
| 578 | MLPAPKNLVVSRVTEDSARLSWTAPDAAFDSFRIKYQEWWVEGEAIVLTVPGSERSYDLTGLKPGTEYVVQIAGVKGGLSSYPLSAIFTT |
| 579 | MLPAPKNLVVSRVTEDSARLSWTAPDAAFDSFWIYYIETSHQGEAIVLTVPGSERSYDLTGLKPGTEYFVLIKGVKGGYDSVPLSAIFTT |
| 580 | MLPAPKNLVVSRVTEDSARLSWTAPDAAFDSFMIRYQEGTRWGEAIVLTVPGSERSYDLTGLKPGTEYIVMIAGVKGGQISLPLSAIFTT |
| 581 | MLPAPKNLVVSRVTEDSARLSWTAPDAAFDSFPIVYSEIHVIGEAIVLTVPGSERSYDLTGLKPGTEYDVWIEGVKGGHLSEPLSAIFTT |
| 582 | MLPAPKNLVVSRVTEDSARLSWTAPDAAFDSFTIVYGEAGAFGEAIVLTVPGSERSYDLTGLKPGTEYDVLIEGVKGGNLSWPLSAIFTT |
| 583 | MLPAPKNLVVSRVTEDSARLSWTAPDAAFDSFHINYAEVYTKGEAILLTVPGSERSYDLTGLKPGTEYEVYIPGVKGGPFSRPLNAQFTT |
| 584 | MLPAPKNLVVSRVTEDSARLSWTAPDAAFDSFLIRYQEWQRWGEAIVLTVPGSERSYDLTGLKPGTEYTVHIAGVKGGMLSLPLSAIFTT |
| 585 | MLPAPKNLVVSRVTEDSARLSWTAPDAAFDSFYIPYAETRDDGEAIVLTVPGSERSYDLTGLKPGTEYSVLIHGVKGGDLSSPLSAIFTT |
| 586 | MLPAPKNLVVSRVTEDSARLSWTAPDAAFDSFGIPYAESTPTGEAIVLTVPGSERSYDLTGLKPGTEYSVLIHGVKGGHLSDPLSAIFTT |
| 587 | MLPAPKNLVVSRVTEDSARLSWTAPDAAFDSFTIFKDGEAIVLTVPGSERSYDLTGLKPGTEYYVYIYGVKGGYPSKPLSAIFTT |
| 588 | MLPAPKNLVVSRVTEDSVRLSWTAPDAAFDSFAISYEEWWVHGEAIVLTVPGSERSYDLTGLKPGTEYSVVIPGVKGGLYSWTLSAISTT |
| 589 | MLPAPKNLVVSRVTEDSARLSWTAPDAAFDSFLIAYAEVTLHGEAIVLTVPGSERSYDLTGLKPGTEYSVLIHGVKGGRNSDPLSAIFTT |
| 590 | MLPAPKNLVVSRVTEDSARLSWTAPDAAFDSFRIDYLELTSLGEAIVLTVPGSERSYDLTGLKPGTEYPVPILGVKGGLSSWPLSAIFTT |

TABLE 3-continued

CD71-binding FN3 domain sequences

| SEQ ID | Amino Acid sequence of FN3 domains that bind to CD71 |
|---|---|
| 591 | MLPAPKNLVVSRVTEDSARLSWTAPDAAFDSFWINYYEGIGEGEAIVLT<br>VPGSERSYDLTGLKPGTEYYVDISGVKGGSYSLPLSAIFTT |
| 592 | MLPAPKNLVVSRVTEDSARLSWTAPDAAFDSFPIAYAEPRPDGEAIVLT<br>VPGSERSYDLTGLKPGTEYSVLIHGVKGGHLSDPLSAIFTT |
| 593 | MLPAPKNLVVSRVTEDSARLSWTAPDAAFDSFSIEYYESVGLGEAIVLT<br>VPGSERSYDLTGLKPGTEYDVSIYGVKGGYLSRPLSAIFTT |
| 594 | MLPAPKNLVVRXVTEDSARLSWTAPDAAFDSFEIEYDEPYRGGEAIVLT<br>VPGSERSYDLTSLKPGTEYPVSIGGVKGGITSDPLSAIFTT |
| 595 | MLPAPKNLVVSRVTEDSARLSWTAPDAAFDSFYIDYDEIHDWGEAIVLT<br>VPGSERSYDLTGLKPGTEYAVQIGGVKGGSFSWTLSAIFTT |
| 596 | MLPAPKNLVVSRVTEDSARLSWTAPDAAFDSFAIVYHEPRPDGEAIVLT<br>VPGSERSYDLTGLKPGTEYEVVILGVKGGVHSYPLSAIFTT |
| 597 | MLPAPKNLVVSRVTEDSARLSWTAPDAAFDSFPIAYAEPRPDGEAIVLT<br>VPGSERSYDLTGLKPGTEYSVLIHGVKGGLLSSPLSAIFTT |
| 598 | MLPAPKNLVVSRVTEDSARLSWTAPDAAFDSFFIGYLEPQPPGEAIVLTV<br>PGSERSYDLTGLKPGTEYNVTIQGVKGGFPSMPLSAIFTT |
| 599 | MLPAPKNLVVSRVTEDSARLSWTAPDAAFDSFLIPYAETSPSGEAIVLTV<br>PGSERSYDLTGLKPGTEYSVLIHGVKGGDYSSPLSAIFTT |
| 600 | MLPAPKNLVVSRVTEDSARLSWTAPDAAFDSFNIYYPEFPVRGEAIVLT<br>VPGSERSYDLTGLKPGTEYVVSIWGVKGGTQSWPLSAIFTT |
| 601 | MLPAPKNLVVSRVTEDSARLSWTAPDAAFDSFTIEYHESGPVGEAIVLT<br>VPGSERSYDLTGLKPGTEYMVWIFGVKGGFVSRPLSAIFTT |
| 602 | MLPAPKNLVVSRVTEDSARLSWTAPDAAFDSFLIPYAETSPSGEAIVLTV<br>PGSERSYDLTGLKPGTEYSVLIHGVKGGDYSSPLSAISTT |
| 603 | MLPAPKNLVVSRVTEDSARLSWTAPDAAFDSFAIPYYEDTNDGEAIVLT<br>VPGSERSYDLTGLKPGTEYWVSIQGVKGGTVSGPLSAIFTT |
| 604 | MLPAPKNLVVSRVTEDSARLSWTAPDAAFDSFFYLEQAWGGEAIVLTV<br>PGSERSYDLTGLKPGTEYWVEITGVKGGYASSPLSAIFTT |
| 605 | MLPAPKNLVVSRVTEDSARLSWTAPDAAFDSFHIEYEEPETEGEAIYLH<br>VPGSERSYDLTGLKPGTEYKVLIRGVKGGSYSIPLQAPFTT |
| 606 | MLPAPKNLVVSRVTEDSARLSWTAPDAAFDSFDIAYWELTPSGEAIELL<br>VPGSERSYDLTGLKPGTEYRVDIIGVKGGFISEPLGATFTT |
| 607 | MLPAPKNLVVSRVTEDSARLSWTAPDAAFDSFTIEYWEFTGSGEAIVLT<br>VPGSERSYDLTGLKPGTEYDVSIYGVKGGWLSYPLSAIFTT |
| 608 | MLPAPKNLVVSRVTEDSARLSWTAPDAAFDSFSIIYSEWNVTGEAIVLT<br>VPGSERSYDLTGLKPGTEYDVWIEGVKGGGMSKPLSAISTT |
| 609 | MLPAPKNLVVSRVTEDSARLSWTAPDAAFDSFFIGYLEPIPSGEAIVLTV<br>PGSERSYDLTGLKPGTEYPVVIQGVKGGHPSQPLSAIFTT |
| 610 | MLPAPKNLVVSRVTEDSARLSWTAPDAAFDSFFIGYLEPQPPGEAIILTV<br>PGSERSYDLTGLKPGTEYNVTIQGVKGGFPSMPLSAIFTT |
| 611 | MLPAPKNLVVSRVTEDSARLSWTAPDAAFDSFLIPYAETSPSGEAITLFV<br>PGSERSYDLTGLKPGTEYNVVIQGVKGGRPSNPLVAASTT |
| 612 | MLPAPKNLVVSRVTEDSARLSWTAPDAAFDSFPIAYAEPRPDGEAIVLT<br>VPGSERSYDLTGLKPGTEYSVLIHGVKGGLLSSPLSAISTT |
| 613 | MLPAPKNLVVSRVTEDSARLSWTAPDAAFDSFLIEYWESVGYGEAIVLT<br>VPGSERSYDLTGLKPGTEYWVGIYGVKGGYYSRPLSAIFTT |
| 614 | MLPAPKNLVVSRVTEDSARLSWTAPDAAFDSFFIGYLEPQPPGEAIVLTV<br>PGSERSYDLTGLKPGTEYNVTIHGVKGGTPSMPLSAIFTT |
| 615 | MLPAPKNLVVSRVTEDSARLSWTAPDAAFDSFEIEYDEPYRGGEAIVLT<br>VPGSERSYDLTSLKPGTEYPVSIGGVKGGITSDPLSAIFTT |

TABLE 3-continued

CD71-binding FN3 domain sequences

| SEQ ID | Amino Acid sequence of FN3 domains that bind to CD71 |
|---|---|
| 616 | MLPAPKNLVVSRVTEDSARLSWTAPDAAFDSFDIYYPEYYDRGEAIVLT<br>VPGSERSYDLTGLKPGTEYTVYIDGVKGGGGSGPLSAIFTT |
| 617 | MLPAPKNLVVSRVTEDSARLSWTAPDAAFDSFFIAYFEFANPGEAIVLT<br>VPGSERSYDLTGLKPGTEYKVVIQGVKGGTPSEPLSAIFTT |
| 618 | MLPAPKNLVVSRVTEDSARLSWTAPDAAFDSFIITYWEHVGDGEAIVLT<br>VPGSERSYDLTGLKPGTEYFVEIYGVKGGYLSKPLSAIFTT |
| 619 | MLPAPKNLVVSRVTEDSARLSWTAPDAAFDSFEIDYDEPFVYGEAIVLT<br>VPGSERSYDLTGLKPGTEYRVFIFGVKGGNGSWPLSAIFTT |
| 620 | MLPAPKNLVVSRVTEDSARLSWTAPDAAFDSFYIEYFETQGYGEAIVLT<br>VPGSERSYDLTGLKPGTEYYVAIYGVKGGYLSRPLSAIFTT |
| 621 | MLPAPKNLVVSRVTEDSARLSWTAPDAAFDSFPITYSEPAHYGEAIVLT<br>VPGSERSYDLTGLKPGTEYHVGIMGVKGGVFSSPLSAIFTT |
| 622 | MLPAPKNLVVSEVTEDSARLSWQGVARAFDSFLITYREQIFAGEVIVLT<br>VPGSERSYDLTGLKPGTEYPVWIQGVKGGSPSAPLSAISTT |
| 623 | MLPAPKNLVVSRVTEDSARLSWTAPDAAFDSFIIDYLELDQEGEAIVLT<br>VPGSERSYDLTGLKPGTEYAVYIFGVKGGYPSTPLSAIFTT |

As provided herein, in some embodiments, the FN3 domain that binds to CD71 binds to SEQ ID NO: 2 (human mature CD71) or SEQ ID NO: 5 (human mature CD71 extracellular domain), sequence of each provided below:

```
2   MTKEYQDLQHLDNEESDHHQLRKGPPPPQPLLQRLCSGPRLLLLSLGL
    SLLLLVVVCVIGSQNSQLQEELRGLRETFSNFTASTEAQVKGLSTQGG
    NVGRKMKSLESQLEKQQKDLSEDHSSLLLHVKQFVSDLRSLSCQMAAL
    QGNGSERTCCPVNWVEHERSCYWFSRSGKAWADADNYCRLEDAHLVVV
    TSWEEQKFVQHHIGPVNTWMGLHDQNGPWKWVDGTDYETGFKNWRPEQ
    PDDWYGHGLGGGEDCAHFTDDGRWNDDVCQRPYRWVCETELDKASQEP
    PLL

5   QNSQLQEELRGLRETFSNFTASTEAQVKGLSTQGGNVGRKMKSLESQL
    EKQQKDLSEDHSSLLLHVKQFVSDLRSLSCQMAALQGNGSERTCCPVN
    WVEHERSCYWFSRSGKAWADADNYCRLEDAHLVVVTSWEEQKFVQHHI
    GPVNTWMGLHDQNGPWKWVDGTDYETGFKNWRPEQPDDWYGHGLGGGE
    DCAHFTDDGRWNDDVCQRPYRWVCETELDKASQEPPLL
```

In some embodiments, the FN3 domain that binds to EpCAM comprises a polypeptide comprising an amino acid sequence of SEQ ID NOs: 329, 330, 331, 332, 333, 334, or 335 are provided.

In some embodiments, fibronectin type III (FN3) domains that bind or specifically bind human EpCAM protein (SEQ ID NO: 336) are provided. As provided herein, these FN3 domains can bind to the EpCAM protein. Also provided, even if not explicitly stated is that the domains can also specifically bind to the EpCAM protein. Thus, for example, a FN3 domain that binds to EpCAM would also encompass a FN3 domain protein that specifically binds to EpCAM. In some embodiments, an isolated FN3 domain that binds or specifically binds EpCAM is provided.

In some embodiments, the FN3 domain may bind EpCAM at least 5-fold above the signal obtained for a negative control in a standard ELISA assay.

In some embodiments, the FN3 domain that binds or specifically binds EpCAM comprises an initiator methionine (Met) linked to the N-terminus of the molecule. In some embodiments, the FN3 domain that binds or specifically binds EpCAM comprises a cysteine (Cys) linked to a C-terminus of the FN3 domain. The addition of the N-terminal Met and/or the C-terminal Cys may facilitate expression and/or conjugation of half-life extending molecules.

In some embodiments, the FN3 domain that binds EpCAM is based on Tencon sequence of SEQ ID NO:1 or Tencon 27 sequence of SEQ ID NO:4, optionally having substitutions at residues positions 11, 14, 17, 37, 46, 73, or 86 (residue numbering corresponding to SEQ ID NO:4).

In some embodiments, an isolated FN3 domain that binds EpCAM comprises the amino acid sequence of SEQ ID NOs:329, 330, 331, 332, 333, 334, or 335.

In some embodiments, an isolated FN3 domain that binds EpCAM comprises the amino acid sequence of SEQ ID NO:329.

In some embodiments, an isolated FN3 domain that binds EpCAM comprises the amino acid sequence of SEQ ID NO:330.

In some embodiments, an isolated FN3 domain that binds EpCAM comprises the amino acid sequence of SEQ ID NO:331.

In some embodiments, an isolated FN3 domain that binds EpCAM comprises the amino acid sequence of SEQ ID NO:332.

In some embodiments, an isolated FN3 domain that binds EpCAM comprises the amino acid sequence of SEQ ID NO:333.

In some embodiments, an isolated FN3 domain that binds EpCAM comprises the amino acid sequence of SEQ ID NO:334.

In some embodiments, an isolated FN3 domain that binds EpCAM comprises the amino acid sequence of SEQ ID NO:335.

In some embodiments, the isolated FN3 domain that binds EpCAM comprises an initiator methionine (Met) linked to the N-terminus of the molecule.

In some embodiments, the isolated FN3 domain that binds EpCAM comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 329-335. Percent identity can be determined using the default parameters to align two sequences using BlastP available through the NCBI website.

The sequences of FN3 domains that can bind to EpCAM are provided in Table 4.

TABLE 4

EpCAM-binding FN3 domain sequences

| SEQ ID NO: | Amino Acid sequences of FN3 domains that bind to EpCAM |
|---|---|
| 329 | MLPAPKNLVVSRVTEDSARLSWTAPDAAFDSFSISYRERS AWGEAIALVVPGSERSYDLTGLKPGIEYIVGIIGVKGGLRS NPLRADFTT |
| 330 | MLPAPKNLVVSRVTEDSARLSWTAPYAAFDSFAISYRERS REGEVIALTVPGSERSYDLTGLKPGTEYIVGILGVKGGRRS KPLRAQFTT |
| 331 | MLPAPKNLVVSRVTEDSARLSWEGYRNNAHFDSFLIQYQ ESEKVGEAIVLTVPGSERSYDLTGLKPGTEYTVSIYGVVAA VPRNYYSNPLSAIFTT |
| 332 | MLPAPKNLVVSRVTEDSARLSWTAPDAAFDSFYIRYYEGS GYGEAIVLTVPGSERSYDLTGLKPGTEYYVYIGGVKGGSP SSPLSAIFTTG |
| 333 | MLPAPKNLVVSRVTEDSARLSWTAPDAAFDSFKIGYWEW RKYGEAIELNVPGSERSYDLTGLKPGTEYRVLIYGVKGGA GSHPLRALFTT |
| 334 | MLPAPKNLVVSRVTEDSARLSWTAPDAAFDSFSISYRERS AWGEAIALVVPGSERSYDLTGLKPGIEYIVGIIGVKGGLRS NPLRADFTTGGGGSGGGGSGGGGSGGGGSLPAPKNLVVS RVTEDSARLSWTAPDAAFDSFHIEYWEQSIVGEAIVLTVPG SERSYDLTGLKPGTEYRVWIYGVKGGNDSWPLSAIFTT |
| 335 | MLPAPKNLVVSRVTEDSARLSWTAPYAAFDSFAISYRERS REGEVIALTVPGSERSYDLTGLKPGTEYIVGILGVKGGRRS KPLRAQFTTGGGGSGGGGSGGGGSGGGGSLPAPKNLVVS RVTEDSARLSWTAPDAAFDSFHIEYWEQSIVGEAIVLTVPG SERSYDLTGLKPGTEYRVWIYGVKGGNDSWPLSAIFTT |

In some embodiments, the sequences provided herein, including those that bind to EpCAM or CD71, does not comprise the initial methionine. The methionine, for example, can be removed when the FN3 domain is linked to another domain, such as a linker or other FN3 domain.

The sequence of EpCAM is as follows:

| SEQ ID NO: 336 | QEECVCENYKLAVNCFVNNNRQCQCTSVGAQNTVICSKL AAKCLVMKAEMNGSKLGRRAKPEGALQNNDGLYDPDCD ESGLFKAKQCNGTSMCWCVNTAGVRRTDKDTEITCSERV RTYWIIIELKHKAREKPYDSKSLRTALQKEITTRYQLDPKFI TSILYENNVITIDLVQNSSQKTQNDVDIADVAYYFEKDVK GESLFHSKKMDLTVNGEQLDLDPGQTLIYYVDEKAPEFSM QGLK |

In some embodiments, the FN3 domain that binds to EGFR comprises a polypeptide comprising an amino acid sequence of SEQ ID NOs: 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, or 368 are provided.

As provided herein, these FN3 domains can bind to the EGFR protein. Also provided, even if not explicitly stated is that the domains can also specifically bind to the EGFR protein. Thus, for example, a FN3 domain that binds to EGFR would also encompass a FN3 domain protein that specifically binds to EGFR. In some embodiments, an FN3 domain that binds or specifically binds EGFR is provided.

In some embodiments, the FN3 domain may bind EGFR at least 5-fold above the signal obtained for a negative control in a standard ELISA assay.

In some embodiments, the FN3 domain that binds or specifically binds EGFR comprises an initiator methionine (Met) linked to the N-terminus of the molecule. In some embodiments, the FN3 domain that binds or specifically binds EGFR comprises a cysteine (Cys) linked to a C-terminus of the FN3 domain The addition of the N-terminal Met and/or the C-terminal Cys may facilitate expression and/or conjugation of half-life extending molecules.

In some embodiments, the FN3 domain that binds EGFR comprises the amino acid sequence of SEQ ID NOs: 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, or 368.

In some embodiments, the isolated FN3 domain that binds EGFR comprises an initiator methionine (Met) linked to the N-terminus of the molecule.

In some embodiments, the isolated FN3 domain that binds EGFR comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, or 368. Percent identity can be determined using the default parameters to align two sequences using BlastP available through the NCBI website. The sequences of the FN3 peptides that bind to EGFR can be, for example, found in Table 5.

TABLE 5

EGFR-binding FN3 domain sequences

| SEQ ID NO: | EGFR Binding FN3 Domains (Sequences) |
|---|---|
| 337 | LPAPKNLVVSEVTEDSLRLSWADPHGFYDSFLIQYQESEKVGEAI NLTVPGSERSYDLTGLKPGTEYTVSIYGVHNVYKDTNMRGLPLS AEFTT |
| 338 | LPAPKNLVVSEVTEDSLRLSWTYDRDGYDSFLIQYQESEKVGEAI NLTVPGSERSYDLTGLKPGTEYTVSIYGVHNVYKDTNMRGLPLS AEFTT |
| 339 | LPAPKNLAASEVTEDSLRLSWGYNGDHPDSFLIQYQESEKVGEAI NLTVPGSERSYDLTGLKPGTEYTVSIYGVHNVYKDTNMRGLPLS AEFTT |
| 340 | LPAPKNLVVSEVTEDSLRLSWDDPRGFYESFLIQYQESEKVGEAI NLTVPGSERSYDLTGLKPGTEYTVSIYGVHNVYKDTNMRGLPLS AEFTT |
| 341 | LPAPKNLVVSEVTEDSLRLSWTWPYADLDSFLIQYQESEKVGEAI NLTVPGSERSYDLTGLKPGTEYTVSIYGVHNVYKDTNMRGLPLS AEFTT |
| 342 | LPAPKNLVVSEVTEDSLRLSWGYNGDHPDSFLIQYQESEKVGEAI NLTVPGSERSYDLTGLKPGTEYTVSIYGVHNVYKDTNMRGLPLS AEFTT |
| 343 | LPAPKNLVVSEVTEDSLRLSWDYDLGVYFDSFLIQYQESEKVGE AINLTVPGSERSYDLTGLKPGTEYTVSIYGVHNVYKDTNMRGLP LSAEFTT |

TABLE 5-continued

EGFR-binding FN3 domain sequences

| SEQ ID NO: | EGFR Binding FN3 Domains (Sequences) |
|---|---|
| 344 | LPAPKNLVVSEVTEDSLRLSWDDPWAFYESFLIQYQESEKVGEAINLTVPGSERSYDLTGLKPGTEYTVSIYGVHNVYKDTNMRGLPLSAEFTT |
| 345 | LPAPKNLVVSEVTEDSLRLSWTAPDAAFDSFLIQYQESEKVGEAINLTVPGSERSYDLTGLKPGTEYTVSIYGVLGSYVFEHDVMLPLSAEFTT |
| 346 | LPAPKNLVVSEVTEDSARLSWDDPWAFYESFLIQYQESEKVGEAIVLTVPGSERSYDLTGLKPGTEYTVSIYGVHNVYKDTNMRGLPLSAIFTT |
| 347 | LPAPKNLVVSEVTEDSARLSWTAPDAAFDSFLIQYQESEKVGEAIVLTVPGSERSYDLTGLKPGTEYTVSIYGVLGSYVFEHDVMLPLSAIFTT |
| 348 | LPAPKNLVVSEVTEDSLRLSWTWPYADLDSFLIQYQESEKVGEAINLTVPGSERSYDLTGLKPGTEYTVSIYGVHNVYKDTNMRGLPLSAEFTT |
| 349 | LPAPKNLVVSEVTEDSARLSWADPHGFYDSFLIQYQESEKVGEAIVLTVPGSERSYDLTGLKPGTEYTVSIYGVHNVYKDTNMRGLPLSAIFTT |
| 350 | LPAPKNLVVSEVTEDSARLSWDDPWAFYESFLIQYQESEKVGEAIVLTVPGSERSYDLTGLKPGTEYTVSIYGVHNVYKDTNIRGLPLSAIFTT |
| 351 | LPAPKNLVVSEVTEDSARLSWDDPHAFYESFLIQYQESEKVGEAIVLTVPGSERSYDLTGLKPGTEYTVSIYGVHNVYKDTNIRGLPLSAIFTT |
| 352 | LPAPKNLVVSEVTEDSARLSWADPHGFYDSFLIQYQESEKVGEAIVLTVPGSERSYDLTGLKPGTEYTVSIYGVHNVYKDTNIRGLPLSAIFTT |
| 353 | MLPAPKNLVVSEVTEDSLRLSWADPHGFYDSFLIQYQESEKVGEAINLTVPGSERSYDLTGLKPGTEYTVSIYGVHNVYKDTNMRGLPLSAEFTT |
| 354 | MLPAPKNLVVSEVTEDSLRLSWTYDRDGYDSFLIQYQESEKVGEAINLTVPGSERSYDLTGLKPGTEYTVSIYGVHNVYKDTNMRGLPLSAEFTT |
| 355 | MLPAPKNLVVSEVTEDSLRLSWGYNGDHFDSFLIQYQESEKVGEAINLTVPGSERSYDLTGLKPGTEYTVSIYGVHNVYKDTNMRGLPLSAEFTT |
| 356 | MLPAPKNLVVSEVTEDSLRLSWDDPRGFYESFLIQYQESEKVGEAINLTVPGSERSYDLTGLKPGTEYTVSIYGVHNVYKDTNMRGLPLSAEFTT |
| 357 | MLPAPKNLVVSEVTEDSLRLSWTWPYADLDSFLIQYQESEKVGEAINLTVPGSERSYDLTGLKPGTEYTVSIYGVHNVYKDTNMRGLPLSAEFTT |
| 358 | MLPAPKNLVVSEVTEDSLRLSWGYNGDHFDSFLIQYQESEKVGEAINLTVPGSERSYDLTGLKPGTEYTVSIYGVHNVYKDTNMRGLPLSAEFTT |
| 359 | MLPAPKNLVVSEVTEDSLRLSWDYDLGVYFDSFLIQYQESEKVGEAINLTVPGSERSYDLTGLKPGTEYTVSIYGVHNVYKDTNMRGLPLSAEFTT |
| 360 | MLPAPKNLVVSEVTEDSLRLSWDDPWAFYESFLIQYQESEKVGEAINLTVPGSERSYDLTGLKPGTEYTVSIYGVHNVYKDTNMRGLPLSAEFTT |
| 361 | MLPAPKNLVVSEVTEDSLRLSWTAPDAAFDSFLIQYQESEKVGEAINLTVPGSERSYDLTGLKPGTEYTVSIYGVLGSYVFEHDVMLPLSAEFTT |
| 362 | MLPAPKNLVVSEVTEDSARLSWDDPWAFYESFLIQYQESEKVGEAIVLTVPGSERSYDLTGLKPGTEYTVSIYGVHNVYKDTNMRGLPLSAIFTT |
| 363 | MLPAPKNLVVSEVTEDSARLSWTAPDAAFDSFLIQYQESEKVGEAIVLTVPGSERSYDLTGLKPGTEYTVSIYGVLGSYVFEHDVMLPLSAIFTT |
| 364 | MLPAPKNLVVSEVTEDSLRLSWTWPYADLDSFLIQYQESEKVGEAINLTVPGSERSYDLTGLKPGTEYTVSIYGVHNVYKDTNMRGLPLS AEFTT |
| 365 | MLPAPKNLVVSEVTEDSARLSWADPHGFYDSFLIQYQESEKVGEAIVLTVPGSERSYDLTGLKPGTEYTVSIYGVHNVYKDTNMRGLPLSAIFTT |
| 366 | MLPAPKNLVVSEVTEDSARLSWDDPWAFYESFLIQYQESEKVGEAIVLTVPGSERSYDLTGLKPGTEYTVSIYGVHNVYKDTNIRGLPLSAIFTT |
| 367 | MLPAPKNLVVSEVTEDSARLSWDDPHAFYESFLIQYQESEKVGEAIVLTVPGSERSYDLTGLKPGTEYTVSIYGVHNVYKDTNIRGLPLSAIFTT |
| 368 | MLPAPKNLVVSEVTEDSARLSWADPHGFYDSFLIQYQESEKVGEAIVLTVPGSERSYDLTGLKPGTEYTVSIYGVHNVYKDTNIRGLPLSAIFTT |

In some embodiments, the FN3 domain comprises two FN3 domains connected by a linker. The linker can be a flexible linker. The linker can be a short peptide sequence, such as those described herein. For example, the linker can be a G/S or G/A linker and the like. As provided herein, the linker can be, for example, (GS)$_2$, (SEQ ID NO:369), (GGGS)$_2$ (SEQ ID NO:370), (GGGGS)$_5$ (SEQ ID NO:371), (AP)$_2$ (SEQ ID NO:372), (AP)$_5$ (SEQ ID NO:373), (SEQ ID NO:374), (AP)$_{20}$ (SEQ ID NO:375) and A(EAAAK)$_5$AAA (SEQ ID NO:376). These are non-limiting examples and other linkers can also be used. The number of GGGGS or GGGGA repeats can also be 1, 2, 3, 4, or 5. In some embodiments, the linker comprises one or more GGGGS repeats and one or more GGGGA repeats.

In some embodiments, the FN3 domains may bind CD71, EpCAM, or EGFR, as applicable, with a dissociation constant ($K_D$) of less than about $1 \times 10^{-7}$ M, for example less than about $1 \times 10^{-8}$ M, less than about $1 \times 10^{-9}$ M, less than about $1 \times 10^{-10}$ M, less than about $1 \times 10^{-11}$ M, less than about $1 \times 10^{-12}$ M, or less than about $1 \times 10^{-13}$ M as determined by surface plasmon resonance or the Kinexa method, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are made with standardized solutions of protein scaffold and antigen, and a standardized buffer, such as the buffers described herein.

In some embodiments, the FN3 domain may bind to its target protein at least 5-fold above the signal obtained for a negative control in a standard ELISA assay.

In some embodiments, the FN3 domain that binds or specifically binds its target protein comprises an initiator methionine (Met) linked to the N-terminus of the molecule. In some embodiments, the FN3 domain that binds or specifically binds to its target protein comprises a cysteine (Cys) linked to a C-terminus of the FN3 domain The addition of the N-terminal Met and/or the C-terminal Cys may facilitate expression and/or conjugation of half-life extending molecules.

The FN3 domain can also contain cysteine substitutions, such as those that are described in U.S. Pat. No. 10,196,446, which is hereby incorporated by reference in its entirety. Briefly, in some embodiments, the polypeptide comprising an FN3 domain can have an FN3 domain that has a residue substituted with a cysteine, which can be referred to as a cysteine engineered fibronectin type III (FN3) domain In some embodiments, the FN3 domain comprises at least one cysteine substitution at a position selected from the group consisting of residues 6, 8, 10, 11, 14, 15, 16, 20, 30, 34, 38, 40, 41, 45, 47, 48, 53, 54, 59, 60, 62, 64, 70, 88, 89, 90, 91, and 93 of the FN3 domain based on SEQ ID NO: 1 (LPAPKNLVVSEVTEDSLRLSWTAPDAAF-DSFLIQYQESEKVGEAINLTVPGSERSYDLTG LKPGTEYTVSIYGVKGGHRSNPLSAEFTT, SEQ ID NO: 624) of U.S. Pat. No. 10,196,446, which is hereby incorporated by reference in its entirety, and the equivalent positions in related FN3 domains. A cysteine substitution at a position in the domain or protein comprises a replacement of the existing amino acid residue with a cysteine residue. Other examples of cysteine modifications can be found in, for example, U.S. Patent Application Publication No. 20170362301, which is hereby incorporated by reference in its entirety. The alignment of the sequences can be performed using BlastP using the default parameters at, for example, the NCBI website.

In some embodiments, the FN3 domain that binds to the target protein is internalized into a cell. In some embodiments, internalization of the FN3 domain may facilitate delivery of a detectable label or therapeutic into a cell. In some embodiments, internalization of the FN3 domain may facilitate delivery of a cytotoxic agent into a cell. The cytotoxic agent can act as a therapeutic agent. In some embodiments, internalization of the FN3 domain may facilitate the delivery of any detectable label, therapeutic, and/or cytotoxic agent disclosed herein into a cell. In some embodiments, the cell is a tumor cell. In some embodiments, the cell is a liver cell or a lung cell. In some embodiments, the therapeutic is a siRNA molecule as provided for herein.

As provided herein, the different FN3 domains that are linked to the siRNA molecule can also be conjugated or linked to another FN3 domain that binds to a different target. This would enable the molecule to be multi-specific (e.g. bi-specific, tri-specific, etc.), such that it binds to a first target and another, for example, target. In some embodiments, the first FN3 binding domain is linked to another FN3 domain that binds to an antigen expressed by a tumor cell (tumor antigen).

In some embodiments, FN3 domains can be linked together by a linker to form a bivalent FN3 domain The linker can be a flexible linker. In some embodiments, the linker is a G/S linker. In some embodiments the linker has 1, 2, 3, or 4 G/S repeats. A G/S repeat unit is four glycines followed by a serine, e.g. GGGGS. Other examples of linkers are provided herein and can also be used.

Without being bound to any particular theory, in some embodiments, the FN3 domains that are linked to the nucleic acid molecule may be used in the targeted delivery of the therapeutic agent to cells that express the binding partner of the one or more FN3 domains (e.g. tumor cells), and lead intracellular accumulation of the nucleic acid molecule therein. This can allow the siRNA molecule to properly interact with the cell machinery to inhibit the expression of the target gene and also avoid, in some embodiments, toxicity that may arise with untargeted administration of the same siRNA molecule.

The FN3 domain described herein that bind to their specific target protein may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include $(GS)_2$, (SEQ ID NO:369), $(GGGS)_2$ (SEQ ID NO:370), $(GGGGS)_5$ (SEQ ID NO:371), $(AP)_2$ (SEQ ID NO:372), $(AP)_5$ (SEQ ID NO:373), $(AP)_{10}$ (SEQ ID NO:374), $(AP)_{20}$ (SEQ ID NO:375) and $A(EAAAK)_5AAA$ (SEQ ID NO:376). The dimers and multimers may be linked to each other in a N- to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456). The linkers described in this paragraph may be also be used to link the domains provided in the formula provided herein and above.

Half-Life Extending Moieties

The FN3 domains may also, in some embodiments, incorporate other subunits for example via covalent interaction. In some embodiments, the FN3 domains that further comprise a half-life extending moiety. Exemplary half-life extending moieties are albumin, albumin variants, albumin-binding proteins and/or domains, transferrin and fragments and analogues thereof, and Fc regions Amino acid sequences of the human Fc regions are well known, and include IgG1, IgG2, IgG3, IgG4, IgM, IgA and IgE Fc regions. In some embodiments, the FN3 domains that specifically bind CD22 may incorporate a second FN3 domain that binds to a molecule that extends the half-life of the entire molecule, such as, but not limited to, any of the half-life extending moieties described herein. In some embodiments, the second FN3 domain binds to albumin, albumin variants, albumin-binding proteins and/or domains, and fragments and analogues thereof.

All or a portion of an antibody constant region may be attached to the FN3 domain to impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and may be further modified by modifying residues in the Fc responsible for these activities (for review; see Strohl, *Curr Opin Biotechnol.* 20, 685-691, 2009).

Additional moieties may be incorporated into the FN3 domains such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques.

Alternatively, well known chemical coupling methods may be used to attach the moieties to recombinantly produced molecules disclosed herein.

A pegyl moiety may for example be added to the FN3 domain t by incorporating a cysteine residue to the C-terminus of the molecule, or engineering cysteines into residue positions that face away from the binding face of the molecule, and attaching a pegyl group to the cysteine using well known methods.

FN3 domains incorporating additional moieties may be compared for functionality by several well-known assays. For example, altered properties due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules disclosed herein in in vivo models.

The compositions provided herein can be prepared by preparing the FN3 proteins and the nucleic acid molecules and linking them together. The techniques for linking the proteins to a nucleic acid molecule are known and any method can be used. For example, in some embodiments, the nucleic acid molecule is modified with a linker, such as the linker provided herein, and then the protein is mixed with the nucleic acid molecule comprising the linker to form the composition. For example, in some embodiments, a FN3 domains is conjugated to a siRNA a cysteine using thiol-maleimide chemistry. In some embodiments, a cysteine-containing FN3 domain can be reduced in, for example, phosphate buffered saline (or any other appropriate buffer) with a reducing agent (e.g. tris(2-carboxyethyl) phosphine (TCEP)) to yield a free thiol. Then, in some embodiments, the free thiol containing FN3 domain was mixed with a maleimide linked-modified siRNA duplex and incubated under conditions to form the linked complex. In some embodiments, the mixture is incubated for 0-5 hr, or about 1, 2, 3, 4 or 5 hr at RT. The reaction can be, for example, quenched with N-ethyl maleimide. In some embodiments, the conjugates can be purified using affinity chromatography and ion exchange. Other methods can also be used and this is simply one non-limiting embodiment.

Methods of making FN3 proteins are known and any method can be used to produce the protein. Examples are provided in the references incorporated by reference herein.

Kits

In some embodiments, a kit comprising the compositions described herein are provided.

The kit may be used for therapeutic uses and as a diagnostic kit.

In some embodiments, the kit comprises the FN3 domain conjugated to the nucleic acid molecule.

Uses of the Conjugates FN3 Domains

The compositions provided for herein may be used to diagnose, monitor, modulate, treat, alleviate, help prevent the incidence of, or reduce the symptoms of human disease or specific pathologies in cells, tissues, organs, fluid, or, generally, a host.

In some embodiments, a method of treating a subject having cancer is provided, the method comprising administering to the subject a composition provided for herein.

In some embodiments, the subject has a solid tumor.

In some embodiments, the solid tumor is a melanoma.

In some embodiments, the solid tumor is a lung cancer. In some embodiments, the solid tumor is a non-small cell lung cancer (NSCLC). In some embodiments, the solid tumor is a squamous non-small cell lung cancer (NSCLC). In some embodiments, the solid tumor is a non-squamous NSCLC.

In some embodiments, the solid tumor is a lung adenocarcinoma.

In some embodiments, the solid tumor is a renal cell carcinoma (RCC).

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer. In some embodiments, the solid tumor is castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is pancreatic cancer.

In some embodiments, the solid tumor is a thyroid cancer.

In some embodiments, the solid tumor is a squamous cell carcinoma of the head and neck.

In some embodiments, the solid tumor is a carcinomas of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

In some embodiments, the solid tumor is a genitourinary cancer.

In some embodiments, the solid tumor is an endometriosis.

In some embodiments, the solid tumor is a cervical cancer.

In some embodiments, the solid tumor is a metastatic lesion of the cancer.

In some embodiments, the subject has a hematological malignancy.

In some embodiments, the hematological malignancy is a lymphoma, a myeloma or a leukemia. In some embodiments, the hematological malignancy is a B cell lymphoma. In some embodiments, the hematological malignancy is Burkitt's lymphoma. In some embodiments, the hematological malignancy is Hodgkin's lymphoma. In some embodiments, the hematological malignancy is a non-Hodgkin's lymphoma.

In some embodiments, the hematological malignancy is a myelodysplastic syndrome.

In some embodiments, the hematological malignancy is an acute myeloid leukemia (AML). In some embodiments, the hematological malignancy is a chronic myeloid leukemia (CML). In some embodiments, the hematological malignancy is a chronic myelomoncytic leukemia (CMML).

In some embodiments, the hematological malignancy is a multiple myeloma (MM).

In some embodiments, the hematological malignancy is a plasmacytoma.

In some embodiments, methods of treating cancer in a subject in need thereof are provided. In some embodiments, the methods comprise administering to the subject any composition provided herein. In some embodiments, a use of a composition as provided herein are provided in the preparation of a pharmaceutical composition or medicament for treating cancer. In some embodiments, the composition can be used for treating cancer.

In some embodiments, methods of reducing the expression of a target gene in a cell are provided. In some embodiments, the methods comprise contacting the cell with a composition a composition as provided herein. In some embodiments, the cell is contacted ex-vivo. In some embodiments, the cell is contacted in-vivo. In some embodiments, the target gene is KRAS. The target gene, however, can be any target gene as the evidence provided herein demonstrates that siRNA molecules can be delivered efficiently when conjugated to a FN3 domain.

In some embodiments, methods of delivering a siRNA molecule to a cell in a subject are provided. In some embodiments, the methods comprise administering to the subject a pharmaceutical composition comprising a composition as provided for herein. In some embodiments, the cell is a CD71 positive cell. In some embodiments, the cell is an EpCAM positive cell. In some embodiments, the cell is an EGFR positive cell. In some embodiments, the cell is a CD71 positive cell and an EpCAM positive cell. In some embodiments, the cell is also positive for EGFR. The term "positive cell" in reference to a protein refers to a cell that expresses the protein. In some embodiments, the protein is expressed on the cell surface. In some embodiments, the cell is a muscle cell, a brain cell, or a cell inside the blood brain barrier. In some embodiments, the siRNA downregulates the expression of a target gene in the cell. In some embodiments, the target gene is KRAS. In some embodiments, the KRAS has a mutation. In some embodiments, the mutation in KRAS is a G12C, G12V, G12S or G12D mutation.

In some embodiments, the compositions provided herein may be used to diagnose, monitor, modulate, treat, alleviate, help prevent the incidence of, or reduce the symptoms of human disease or specific pathologies in cells, tissues, organs, fluid, or, generally, a host, also exhibit the property of being able to cross the blood brain barrier. The blood-brain barrier (BBB) prevents most macromolecules (e.g., DNA, RNA, and polypeptides) and many small molecules from entering the brain. The BBB is principally composed of specialized endothelial cells with highly restrictive tight junctions, consequently, passage of substances, small and large, from the blood into the central nervous system is controlled by the BBB. This structure makes treatment and management of patients with neurological diseases and disorders (e.g., brain cancer) difficult as many therapeutic agents cannot be delivered across the BBB with desirable efficiency. Additional conditions that involve disruptions of the BBB include: stroke, diabetes, seizures, hypertensive encephalopathy, acquired immunodeficiency syndrome, traumatic brain injuries, multiple sclerosis, Parkinson's disease (PD) and Alzheimer disease. This ability is especially useful for treating brain cancers including for example: astrocytoma, medulloblastoma, glioma, ependymoma, germinoma (pinealoma), glioblastoma multiform, oligodendroglioma, schwannoma, retinoblastoma, and congenital tumors; or a cancer of the spinal cord, e.g., neurofibroma, meningioma, glioma, and sarcoma. In certain embodiments, the compositions provided for herein can be used to deliver a therapeutic or cytotoxic agent, for example, across the blood brain barrier. In certain embodiments, the compositions provided for herein can be used to deliver a therapeutic or cytotoxic agent, for example, across the blood brain barrier.

In some embodiments, the compositions or pharmaceutical compositions provided herein may be administered alone or in combination with other therapeutics, that is, simultaneously or sequentially. In some embodiments, the other or additional therapeutics are other anti-tumor agent or therapeutics. Different tumor types and stages of tumors can require the use of various auxiliary compounds useful for treatment of cancer. For example, the compositions provided herein can be used in combination with various chemotherapeutics such as taxol, tyrosine kinase inhibitors, leucovorin, fluorouracil, irinotecan, phosphatase inhibitors, MEK inhibitors, among others. The composition may also be used in combination with drugs which modulate the immune response to the tumor such as anti-PD-1 or anti-CTLA-4, among others. Additional treatments can be agents that modulate the immune system, such antibodies that target PD-1 or PD-L1.

"Treat" or "treatment" refers to the therapeutic treatment and prophylactic measures, wherein the object is to prevent or slow down (lessen) an undesired physiological change or disorder, such as the development or spread of cancer. In some embodiments, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the compositions provided herein may vary according to factors such as the disease state, age, sex, and weight of the individual. Exemplary indicators of an effective amount is improved well-being of the patient, decrease or shrinkage of the size of a tumor, arrested or slowed growth of a tumor, and/or absence of metastasis of cancer cells to other locations in the body.

Administration/Pharmaceutical Compositions

In some embodiments, pharmaceutical compositions of the compositions provided herein and a pharmaceutically acceptable carrier, are provided. For therapeutic use, the compositions may be prepared as pharmaceutical compositions containing an effective amount of the domain or molecule as an active ingredient in a pharmaceutically acceptable carrier. "Carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules disclosed herein in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the compositions disclosed herein may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracelebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

EXAMPLES

The following examples are illustrative of the embodiments disclosed herein. These examples are provided for the purpose of illustration only and the embodiments should in no way be construed as being limited to these examples, but rather should be construed to encompass any and all variations which become evidence as a result of the teaching provided herein. Those of skill in the art will readily recognize a variety of non-critical parameters that could be changed or modified to yield essentially similar results.

Example 1: The siRNA sequence pairs, provided in Table 6, were made according to routine synthetic methods. The oligonucleotides were ordered from Axolabs GmbH, and Bio-Synthesis Inc. The oligonucleotides were confirmed by routine techniques.

TABLE 6 siRNA Sense and Anti-sense Sequence Pairs

| siRNA Pair | SEQ ID NO | Sense Strand 5'-3 | SEQ ID NO | Anti-sense strand 5'-3' |
|---|---|---|---|---|
| A | 10 | cscsUfgucUfCfUfugGfauauUfca(invdT) | 11 | UfsGfsaauauccaagaGfacaggsusu |
| B | 12 | CsasGfcuaAfUfUfcaGfaaucAfua(invdT) | 13 | UfsAfsugauucugaauUfagcugsusu |
| C | 14 | GsasAfuuaGfCfufguAfucguCfaa(invdT) | 15 | UfsUfsgacgauacagcUfaauucsusu |
| D | 16 | CfscsUfgUfcUfCfUfuGfgauAfuUfcAf(invdT) | 17 | usGfsaAfuAfUfCfcAfagaGfaCfaGfgsUfsu |
| E | 18 | csAfsgCfuAfaUfUfCfaGfaauCfuAfuAf(invdt) | 19 | usAfsuGfaUfUfCfuGfaauUfaGfcUfgsUfsu |
| F | 20 | GfsasAfuUfaGfCfUfgUfaucGfuCfaAf(invdt) | 21 | usUfsgAfcGfAfUfacaGfcUfaAfuUfcsUfsu |
| G | 22 | CfscsUfgUfcUfcUfuGfgAfuAfuUfcAf(invdT) | 23 | usGfsaAfuAfuCfcAfaGfaGfaCfaGfgsUfsu |
| H | 24 | csAfsgCfuAfaUfuCfaGfaAfuCfaUfa(invdt) | 25 | UfsasUfgAfuUfcUfgAfaUfuAfgCfgsUfsu |
| I | 26 | gsAfsaUfuAfgCfuGfuAfuCfgUfcAfa(invdt) | 27 | UfsusGfaCfaUfaCfaGfcUfaAfuUfcsUfsu |
| J | 28 | cscsUfgucUfCfUfugGfauauUfca(invdt) | 29 | UfsGfsaauauccaagaGfacaggsusu |
| K | 30 | csasGfcuaAfUfUfcaGfaaucAfua(invdt) | 31 | UfsAfsugauucugaauUfagcugsusu |
| L | 32 | gsasAfuuaGfCfUfguAfucguCfaa(invdt) | 33 | UfsUfsgacgauacagcUfaauucsusu |
| M | 34 | csasGfcuaAfUfUfcaGfaaucAfua(invdT) | 35 | UfsAfsugauucugaauUfagcugsusu |

TABLE 6-continued siRNA Sense and Anti-sense Sequence Pairs

| siRNA Pair | SEQ ID NO | Sense Strand 5'-3 | SEQ ID NO | Anti-sense strand 5'-3' |
|---|---|---|---|---|
| N | 36 | asusAfuaaAfCfUfugUfgguaGfua(invdT) | 37 | UfsAfscuaccacaaguUfuauaususu |
| O | 38 | usasAfacuUfGfUfggUfaguuGfga(invdT) | 39 | UfsCfscaacuaccacaAfguuuasusu |
| P | 40 | csasAfgagUfGfCfcuUfgacgAfua(invdT) | 41 | UfsAfsucgucaaggcaCfucuugsusu |
| Q | 42 | gscsCfuugAfCfGfauAfcagcUfaa(invdT) | 43 | UfsUfsagcuguaucguCfaaggcsusu |
| R | 44 | usgsAfcgaUfAfCfagCfuaauUfca(invdT) | 45 | UfsGfsaauuagcuguaUfcgucasusu |
| S | 46 | csgsAfuacAfGfCfuaAfuucaGfaa(invdT) | 47 | UfsUfscugaauu agcuGfu au cgsusu |
| T | 48 | gsusGfgacGfAfAfuaUfgaucCfaa(invdT) | 49 | UfsUfsggaucauauucGfuccacsusu |
| U | 50 | gsgsAfcgaAfUfAfugaAfuccaAfca(invdT) | 51 | UfsGfsuuggaucauauUfcguccsusu |
| V | 52 | gsasCfgaaUfAfUfgaUfccaaCfaa(invdT) | 53 | UfsUfsguuggaucauaUfucgucsusu |
| W | 54 | ascsGfaauAfUfGfauCfcaacAfaa(invdT) | 55 | UfsUfsuguuggaucauAfuucgususu |
| X | 56 | csgsAfauaUfGfAfucCfaacaAfua(invdT) | 57 | UfsAfsuuguuggaucaUfaucgususu |
| Y | 58 | asasUfaugAfUfCfcaAfcaauAfga(invdT) | 59 | UfsCfsuauuguuggauCfauauususu |
| Z | 60 | gsasUfccaAfCfAfauAfgaggAfua(invdT) | 61 | UfsAfsuccucuauuguUfggaucsusu |
| AA | 62 | cscsAfacaAfUfAfgaGfgauuCfca(invdT) | 63 | UfsGfsgaauccucuauUfguuggsusu |
| BB | 64 | csusAfcagGfAfAfgcAfaguaGfua(invdT) | 65 | UfsAfscuacuugcuucCfuguagsusu |
| CC | 66 | ascsAfggaAfGfCfaaGfuaguAfaa(invdT) | 67 | UfsUfsuacuacuugcuUfccugususu |
| DD | 68 | gsusAfauuGfAfUfggAfgaaaCfca(invdT) | 69 | UfsGfsguuucccaucAfauuacsusu |
| EE | 70 | csusUfggaUfAfUfucUfcgacAfca(invdT) | 71 | UfsGfsugucgagaauaUfccaagsusu |
| FF | 72 | csasGfcagGfUfCfaaGfaggaGfua(invdT) | 73 | UfsAfscuccucuugacCfugcugsusu |
| GG | 74 | gscsAfaugAfGfGfgaCfcaguAfca(invdT) | 75 | UfsGfsuacuggucccuCfauugcsusu |
| HH | 76 | csasAfugaGfGfGfacCfaguaCfaa(invdT) | 77 | UfsUfsguacuggucccUfcauugsusu |
| II | 78 | ususUfgugUfAfUfuuGfccauAfaa(invdT) | 79 | UfsUfsuauggcaaauaCfacaaasusu |
| JJ | 80 | ususGfccaUfAfAfauAfauacUfaa(invdT) | 81 | UfsUfsaguauuauuuaUfggcaasusu |
| KK | 82 | usgsCfcauAfAfAfuaAfuacuAfaa(invdT) | 83 | UfsUfsuaguauuauuuAfugcasusu |
| LL | 84 | cscsAfuaaAfUfAfauAfcuaaAfua(invdT) | 85 | UfsAfsuuuaguauuauUfuauggsusu |

TABLE 6-continued siRNA Sense and Anti-sense Sequence Pairs

| siRNA Pair | SEQ ID NO | Sense Strand 5'-3 | SEQ ID NO | Anti-sense strand 5'-3' |
|---|---|---|---|---|
| MM | 86 | csasUfaaaUfAfAfuaCfuaaaUfca(invdT) | 87 | UfsGfsauuuaguauuaUfuuaugsusu |
| NN | 88 | asusAfaauAfAfUfacUfaaauCfaa(invdT) | 89 | UfsUfsgauuuaguauuAfuuuaususu |
| OO | 90 | gsasAfgauAfUfUfcaCfcauuAfua(invdT) | 91 | UfsAfsuaauggugaauAfucuucsusu |
| PP | 92 | asgsAfuauUfCfAfccAfuuauAfga(invdT) | 93 | UfsCfsuauaauggugaAfuaucususu |
| QQ | 94 | asusAfuucAfCfCfauUfauagAfga(invdT) | 95 | UfsCfsucuauaaugguGfaauaususu |
| RR | 96 | asgsAfacaAfAfUfuaAfaagaGfua(invdT) | 97 | UfsAfscucuuuuaauuUfguucususu |
| SS | 98 | gsasCfucuGfAfAfgaUfguacCfua(invdT) | 99 | UfsAfsgguacaucuucAfgagucsusu |
| TT | 100 | csusGfaagAfUfGfuaCfcuauGfga(invdT) | 101 | UfsCfscauagguacauCfuucagsusu |
| UU | 102 | asgsAfacaGfUfAfgaCfacaaAfaa(invdT) | 103 | UfsUfsuuugugucuacUfguucususu |
| VV | 104 | csasGfgacUfUfAfgcAfagaaGfua(invdT) | 105 | UfsAfscuucuugcuaaGfuccugsusu |
| WW | 106 | gsusUfgauGfAfUfgcCfuucuAfua(invdT) | 107 | UfsAfsuagaaggcaucAfucaacsusu |
| XX | 108 | asusGfaugCfCfUfucUfauacAfua(invdT) | 109 | UfsAfsuguauagaaggCfaucaususu |
| YY | 110 | usgsAfugcCfUfUfcuAfuacaUfua(invdT) | 111 | UfsAfsauguauagaagGfcaucasusu |
| ZZ | 112 | gsasUfgccUfUfCfuaUfacauUfaa(invdT) | 113 | UfsUfsaauguauagaaGfgcaucsusu |
| AAA | 114 | asusGfccuUfCfUfauAfcauuAfga(invdT) | 115 | UfsCfsuaauguauagaAfggcaususu |
| BBB | 116 | csusUfcuaUfAfCfauUfaguuCfga(invdT) | 117 | UfsCfsgaacuaauguaUfagaagsusu |
| CCC | 118 | UscsUfauaCfAfUfuaGfuucgAfga (invdT) | 119 | UfsCfsucgaacuaaugUfauagasusu |
| DDD | 120 | UsasUfacaUfUfAfguUfcgagAfaa(invdT) | 121 | UfsUfsucucgaacuaaUfguauasusu |
| EEE | 122 | AsusAfcauUfAfGfuuCfgagaAfaa(invdT) | 123 | UfsUfsuucucgaacuaAfuguaususu |
| FFF | 124 | UsasCfauuAfGfUfucGfagaaAfua(invdT) | 125 | UfsAfsuuucucgaacuAfauguasusu |
| GGG | 126 | UsusAfguuCfGfAfgaAfauucGfaa(invdT) | 127 | UfsUfscgaauuucucgAfacuaasusu |
| HHH | 128 | AsgsUfucgAfGfAfaaUfucgaAfaa(invdT) | 129 | UfsUfsuucgaauuucuCfgaacususu |
| III | 130 | AsgsAfaauUfCfGfaaAfacauAfaa(invdT) | 131 | UfsUfsuauguuucgaAfuuucususu |
| JJJ | 132 | GsasAfauuCfGfAfaaAfcauaAfaa(invdT) | 133 | UfsUfsuuauguuucgAfauuucsusu |
| KKK | 134 | AsasAfuucGfAfAfaaCfauaaAfga(invdT) | 135 | UfsCfsuuuauguuucGfaauuususu |

TABLE 6-continued siRNA Sense and Anti-sense Sequence Pairs

| siRNA Pair | SEQ ID NO | Sense Strand 5'-3 | SEQ ID NO | Anti-sense strand 5'-3' |
|---|---|---|---|---|
| LLL | 136 | AsasUfucgAfAfAfacAfuaaaGfaa(invdT) | 137 | UfsUfscuuuauguuuuCfgaauususu |
| MMM | 138 | AsusGfagcAfAfAfgaUfgguaAfaa(invdT) | 139 | UfsUfsuuaccaucuuuGfcucaususu |
| NNN | 140 | AsgsCfaaaGfAfUfggUfaaaaAfga(invdT) | 141 | UfsCfsuuuuuaccaucUfuugcususu |
| OOO | 142 | AsusUfucuGfUfCfuuGfgggu Ufua(invdT) | 143 | UfsAfsaaccccaagacAfgaaaususu |
| PPP | 144 | GsgsGfuuuUfUfGfguGfcaugCfaa(invdT) | 145 | UfsUfsgcaugcaccaaAfaacccsusu |
| QQQ | 146 | CsgsCfacaAfGfGfcaCfugggUfaa(invdT) | 147 | UfsUfsacccagugccuUfgugcgsusu |
| RRR | 148 | GscsAfcaaGfGfCfacUfggguAfua(invdT) | 149 | UfsAfsuacccagugccUfugugcsusu |
| SSS | 150 | csUfsCfUfuGfgauAfuUfcAf(invdT) | 151 | usGfsasAfsusAfUfCfcAfagaGfaCfaGfgsUfsu |
| TTT | 152 | AfsasUfUfCfaGfaauCfuAfUfAf(invdt) | 153 | usAfsusGfsasUfUfCfuGfaauUfaGfcUfgsUfsu |
| UUU | 154 | AfsasUfUfCfaGfaauCfuAfUfAf(invdt) | 155 | usAfsusGfsasUfUfCfuGfaauUfaGfcUfgsUfsu |
| VVV | 156 | csUfscUfuGfgAfuAfuUfcAf(invdT) | 157 | usGfsaAfsusAfsuCfcAfaGfaGfaCfaGfgsUfsu- |
| WWW | 158 | AfsasUfuCfaGfaAfuCfaUfa(invdt) | 159 | UfsasUfsgsAfsuUfcUfgAfaUfuAfgCfgsUfsu |
| XXX | 160 | AfsgsCfuGfuAfuCfgUfcAfa(invdt) | 161 | UfsusGfsasCfsaUfaCfaGfcUfaAfuUfcsUfsu |
| YYY | 162 | csUfsCfUfugGfauauUfca(invdt)- | 163 | UfsGfsasasasusauccaagaGfacaggsusu |
| ZZZ | 164 | asAfsUfUfcaGfaaucAfua(invdt) | 165 | UfsAfsusgs asuucugaauUfagcugsusu |
| AAAA | 166 | asGfsCfUfguAfucguCfaa(invdt) | 167 | UfsUfsgsascsgauacagcUfaauucsusu |
| BBBB | 168 | CfscsUfgUfcUfCfUfuGfgauAfgUfcAf(invdT)- | 169 | usGfsaAfuAfUfCfcAfagaGfaCfaGfgsUfsu |
| CCCC | 170 | csAfsgCfuAfaUfUfCfaGfaauCfgAfuAf(invdt)- | 171 | usAfsuGfaUfUfCfuGfaauUfaGfcUfgsUfsu- |
| DDDD | 172 | GfsasAfuUfaGfUfgUfaucGfgCfaAf(invdt) | 173 | usUfsgAfcGfAfUfacaGfcUfaAfuUfcsUfsu- |
| EEEE | 174 | CfscsUfgUfcUfCfUfuGfgAfUfAfgUfcAf(invdT)- | 175 | usGfsaAfuAfuCfcAfaGfaGfaCfaGfgsUfsu |
| FFFF | 176 | csAfsgCfuAfaUfCfaGfaAfgCfaUfa(invdt) | 177 | UfsasUfgAfuUfcUfgAfaUfuAfgCfgsUfsu |
| GGGG | 178 | gsAfsaUfAfgCfuGfuAfuCfgUfcAfa(invdt) | 179 | UfsusGfaCfaUfaCfaGfcUfaAfuUfcsUfsu |
| HHHH | 180 | cscsUfgucUfCfUfugGfauagUfca(invdt) | 181 | UfsGfsaauauccaagaGfacaggsusu |
| IIII | 182 | csasGfcuaAfUfUfcaGfaagcAfua(invdt) | 183 | UfsAfsugauucugaauUfagcugsusu |
| JJJJ | 184 | gsasAfuuaGfCfUfguAfucggCfaa(invdt) | 185 | UfsUfsgacgauacagcUfaauucsusu |

TABLE 6-continued siRNA Sense and Anti-sense Sequence Pairs

| siRNA Pair | SEQ ID NO | Sense Strand 5'-3 | SEQ ID NO | Anti-sense strand 5'-3' |
|---|---|---|---|---|
| KKKK | 212 | CcsAcsrGrCrUrArArUrUrCrA rGrArArU rCrAsT$_C$sA$_C$ | 213 | (vinyl-p)sAfsuGfaUfUfCfuGfaa uUfaGfcUf gUfsasUf |
| LLLL | 214 | CfsasGfcUfaAfUfUfcAfgaaUf cAfua | 215 | (vinyl-p)-sAfsuGfaUfUfCfuGfaauU faGfcUfgUfsasUf |
| MMMM | 216 | csasrGrCrUrArArUrUrCrArGr ArArUrCrAsusa | 217 | (vinyl-p)sAfsuGfaUfUfCfuGfaa uUfaGfcUfgUfsasUf |

Abbreviations Key:
n = 2'-O-methyl residues,
Nf = 2'-F residues,
rN = unmodified residue,
N$_C$ = 2',4'-BNA$^{NC}$ (2'-O,4'-C-aminomethylene bridged nucleic acid),
s = phosphorothioate,
(invdt) = inverted Dt,
vinyl-p: (E)-vinylphosphonate,
(n/N = any nucleotide)

Certain siRNAs were evaluated in a HEK-293 rLUC-KRAS reporter assay at 24 hours. siRNAs were delivered by lipofection. EnduRen luciferase substrate was used to generate the luminescent signal. Briefly, a synthetic lentiviral expression vector was constructed so that the DNA sequence encoding the human KRAS open reading frame was fused to the DNA sequence encoding *Renilla* luciferase. This results in a fusion mRNA from which the luciferase protein can be translated. Candidate siRNA sequences targeting the KRAS open reading frame are evaluated for their ability to induce RNAi in the luciferase-KRAS fusion mRNA. Luciferase signal is quantified using EnduRen live cell luciferase substrate (Promega). Stable cell lines expressing the luciferase reporter in HEK-293 and H358 cells were used to assess candidate siRNAs (Table 7), siRNAs attached to linker sequences (Table 8) and FN3-siRNA conjugates (Table 10).

TABLE 7

Results of siRNA Knockdown of Luciferase

| siRNA Pair | SEQ ID NO Sense Strand | SEQ ID NO Antisense strand | Percent knockdown of luciferase signal at 10 pM |
|---|---|---|---|
| N | 36 | 37 | >30 |
| O | 38 | 39 | <30 |
| P | 40 | 41 | >30 |
| Q | 42 | 43 | <30 |
| R | 44 | 45 | <30 |
| S | 46 | 47 | >30 |
| M | 34 | 35 | >30 |
| T | 48 | 49 | >30 |
| U | 50 | 51 | >30 |
| V | 52 | 53 | >30 |
| W | 54 | 55 | <30 |
| X | 56 | 57 | >30 |
| Y | 58 | 59 | <30 |
| Z | 60 | 61 | <30 |
| AA | 62 | 63 | >30 |
| BB | 64 | 65 | >30 |
| CC | 66 | 67 | >30 |
| DD | 68 | 69 | <30 |
| EE | 70 | 71 | <30 |
| FF | 72 | 73 | <30 |

TABLE 7-continued

Results of siRNA Knockdown of Luciferase

| siRNA Pair | SEQ ID NO Sense Strand | SEQ ID NO Antisense strand | Percent knockdown of luciferase signal at 10 pM |
|---|---|---|---|
| GG | 74 | 75 | <30 |
| HH | 76 | 77 | <30 |
| II | 78 | 79 | <30 |
| JJ | 80 | 81 | >30 |
| KK | 82 | 83 | >30 |
| LL | 84 | 85 | >30 |
| MM | 86 | 87 | >30 |
| NN | 88 | 89 | <30 |
| OO | 90 | 91 | >30 |
| PP | 92 | 93 | >30 |
| QQ | 94 | 95 | <30 |
| RR | 96 | 97 | <30 |
| SS | 98 | 99 | <30 |
| TT | 100 | 101 | <30 |
| UU | 102 | 103 | >30 |
| VV | 104 | 105 | <30 |
| WW | 106 | 107 | <30 |
| XX | 108 | 109 | <30 |
| YY | 110 | 111 | <30 |
| ZZ | 112 | 113 | <30 |
| AAA | 114 | 115 | <30 |
| BBB | 116 | 117 | <30 |
| CCC | 118 | 119 | <30 |
| DDD | 120 | 121 | <30 |
| EEE | 122 | 123 | <30 |
| FFF | 124 | 125 | <30 |
| GGG | 126 | 127 | <30 |
| HHH | 128 | 129 | <30 |
| III | 130 | 131 | <30 |
| JJJ | 132 | 133 | <30 |
| KKK | 134 | 135 | <30 |
| LLL | 136 | 137 | <30 |
| MMM | 138 | 139 | <30 |
| NNN | 140 | 141 | <30 |
| SSS | 150 | 151 | <30 |
| TTT | 152 | 153 | >30 |
| UUU | 154 | 155 | <30 |
| VVV | 156 | 157 | <30 |
| WWW | 158 | 159 | >30 |
| XXX | 160 | 161 | <30 |
| YYY | 162 | 163 | >30 |

TABLE 7-continued

Results of siRNA Knockdown of Luciferase

| siRNA Pair | SEQ ID NO Sense Strand | SEQ ID NO Antisense strand | Percent knockdown of luciferase signal at 10 pM |
|---|---|---|---|
| ZZZ | 164 | 165 | <30 |
| AAAA | 166 | 167 | >30 |
| BBBB | 168 | 169 | <30 |
| CCCC | 170 | 171 | >30 |
| DDDD | 172 | 173 | >30 |
| EEEE | 174 | 175 | <30 |
| FFFF | 176 | 177 | >30 |
| GGGG | 178 | 179 | >30 |
| HHHH | 180 | 181 | >30 |
| IIII | 182 | 183 | >30 |
| JJJJ | 184 | 185 | >30 | siRNA linker and vinyl phosphonates were generated according to known methods. The siRNA linker and modified strands made are provided in Table 8.

TABLE 8

Pairs with Linker and/or Vinyl Phophonate

| | SEQ ID NO | Sense 5-3 | SEQ ID NO | Antisense 5-3 | Linker |
|---|---|---|---|---|---|
| AB01 | 186 | L-cscsUfgucUfCfUfugGfauauUfca(invdT) | 187 | (vinyl-p)-UfsGfsaauauccaagaGfacaggsusu | mal-NH—(CH2)6— |
| AB02 | 188 | L-csasGfcuaAfUfUfcaGfaaucAfua(invdT) | 189 | (vinyl-p)-UfsAfsugauucgaauUfagcugsusu | mal-NH—(CH2)6— |
| AB03 | 190 | CfsasGfcUfaAfUfUfcAfgaaUfcAfua-L | 191 | (vinyl-p)-sAfsuGfaUfUfCfuGfaauUfaGfcUfgUfsasUf | mal-C2H4CONH—(CH2)6— |
| AB04 | 192 | CfsasGfcUfaAfuUfcAfgAfaUfcAfua-L | 193 | (vinyl-p)-sAfsuGfaUfuCfuGfaAfuUfaGfcUfgUfsasUf | mal-C2H4CONH—(CH2)6— |
| AB05 | 194 | (L)cscsUfgucUfCfUfugGfauauUfca(invdT) | 195 | (vinu)sGfsaauauccaagaGfacaggsusu | mal-C2H4CONH—(CH2)6— |
| AB06 | 196 | (L)csasGfcuaAfUfUfcaGfaaucAfua | 197 | (vinu)sAfsugauucugaauUfagcugsusu | mal-C2H4CONH—(CH2)6— |
| AB07 | 198 | (L)cscsUfgUfcUfcUfuGfgAfuAfuUfcAf(invdT) | 199 | (vinu)sGfsaAfuAfuCfcAfaGfaGfaCfaggsusu | mal-C2H4CONH—(CH2)6— |
| AB08 | 200 | cscsUfgucUfCfUfugGfauauUfca(L) | 201 | (vinu)sGfsaauauccaagaGfacaggsusu | mal-C2H4CONH—(CH2)6— |
| AB09 | 202 | (L)cscsUfgucUfCfUfugGfauauUfca(invdT) | 203 | (vinu)sGfsaauauccaagaGfacaggsusu | (Mal-PEG12)(NHC6) |
| AB10 | 204 | CfscsUfgUfcUfCfUfuGfgauAfuUfcAf(L)- | 205 | (vinu)sGfsaAfuAfuCfcAfagaGfaCfaGfgsUfsu | Propyl_linker |
| AB11 | 206 | CfsasGfcUfaAfUfUfcAfgaaUfcAfuAf(L)- | 207 | vinu)sAfsuGfaUfUfCfuGfaaufaGfcfgsUfsu- | Propyl_linker |
| AB12 | 208 | usUfsgAfcGfaUfaCfAfGfcUfaauUfcAfuAf(L) | 209 | vinu)sGfsaAfuUfAfGfcfguaUfcGfuCfaAfsgsGf | Propyl_linker |
| AB13 | 210 | (vinu)CfsasGfcUfaAfUfUfcAfgaaUfcAfua | 211 | AfsuGfaUfUfCfuGfaauUfaGfcUfgUfsasUf-L | (Amc6-Glen)[BMPS-Mal] |
| AB14 | 218 | C$_C$A$_C$srGrCrUrArArUrUrCrArGrArArU rCrAsT$_C$sA$_C$ | 219 | (vinyl-p)sAfsuGfaUfUfCfuGfaauUfaGfcUfgUfsasUf | |
| AB15 | 220 | X-CfsasGfcUfaAfUfUfcAfgaaUfcAfua-L | 221 | (vinyl-p)-sAfsuGfaUfUfCfuGfaauUfaGfcUfgUfsasUf | mal-C$_2$H$_4$C(O)(NH)—(CH$_2$)$_6$ |

TABLE 8-continued

Pairs with Linker and/or Vinyl Phophosphonate

| SEQ ID NO | Sense 5-3 | SEQ ID NO | Antisense 5-3 | Linker |
|---|---|---|---|---|
| AB16 | 222 | csasrGrCrUrArArUrUr CrArGrArArUrCrAsusa-(L) | 223 | (vinyl-p)sAfsuGfaUfUfCf uGfaauUfaGfcUfg UfsasUf | mal-$C_2H_4C(O)(NH)-(CH_2)_6$ |

Abbreviations Key: n = 2'-O-methyl residues, Nf = 2'-F residues, rN = unmodified residue, $N_C$ = 2',4'-BNA$^{NC}$ (2'-O,4'-C-aminomethylene bridged nucleic acid), s = phosphorothioate, (invdt) = inverted Dt, Vinu = vinylphosphonate, vinyl-p = (E)-vinylphosphonate, (L) is a linker, and X = 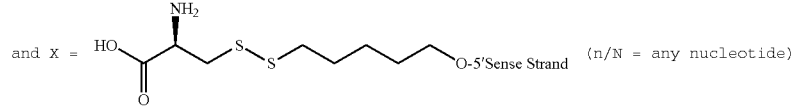  (n/N = any nucleotide)

The sequences with the linkers and/or vinyl phosphonate modified sequences were then evaluated in HEK-293 rLUC-KRAS reporter assay at 24 hours as described above. NAC-quenched linkers were delivered to cells by lipofection. EnduRen luciferase substrate was used to generate the luminescent signal. EC50s and Emax were calculated using Graphpad Prism software. Results provided in Table 9.

TABLE 9 siRNA linker and vinyl phosphonates Results

| siRNA Pair Identifier | EC50 (pM) | Emax (%) |
|---|---|---|
| AB03 | 66.98 | 72.37 |
| AB05 | 94.6 | 80.92 |
| AB06 | 217.2 | 69.69 |
| AB07 | 377.9 | 79.96 |
| AB08 | 157.2 | 79.56 |
| AB09 | 137.5 | 77.42 |
| AB10 | 263.7 | 73.61 |
| AB11 | 125 | 73.75 |
| AB12 | 167 | 62.97 |

FN3-siRNA Conjugates are active. FN3-siRNA conjugates are prepared in H358 KRAS-luciferase reporter line. H358 cells expressing the *Renilla* luciferase-KRAS reporter were treated with FN3-siRNA conjugates for 72 hours. The luciferase assay is described above. EnduRen luciferase substrate was used to generate the luminescent signal. EC50s and Emax were calculated using Graphpad Prism software. FN3 domains were conjugated to siRNA via unique cysteines using thiol-maleimide chemistry. Cysteine-containing FN3 domains in PBS were reduced with tris(2-carboxyethyl) phosphine (TCEP) to yield free thiol. Free thiol containing the FN3 domain was mixed with maleimide linked-modified siRNA duplex, incubated for 2 hr incubation at RT and quenched with N-ethyl maleimide. Conjugates were purified using affinity chromatography and ion exchange. FN3-siRNA conjugate homogeneity was confirmed by SDS-PAGE, analytical SEC and liquid chromatography/mass spectrometry (LC/MS). Results provided in Table 10.

TABLE 10

FN3-siRNA Conjugate Results

| FN3 Domain SEQ ID | FN3-siRNA Conjugate | H358-rLuc-KRAS EC50 (nM) | H358-rLuc-KRAS Emax (%) |
|---|---|---|---|
| 377 | EGFR-KRAS siRNA (AB03) | 0.13 | 77.3 |
| 378 | CD71-KRAS (AB03) | 3.51 | 88.4 |
| 379 | EPCAM12/H9-KRAS siRNA (AB03) | 0.12 | 88.0 |
| 380 | TENCON (Control)-KRAS siRNA (AB03) | 9.20 | 90.5 |
| 381 | CD71/CD71 (CD71_32)-KRAS siRNA (AB03) | 0.059 | 91.9 |
| 382 | CD71/CD71/ABD-KRAS siRNA (AB03) | 0.41 | 92.6 |
| 383 | EPCAM/EPCAM/ABD-KRAS siRNA (AB03) | 0.32 | 77.0 |
| 384 | EPCAM/CD71/ABD-KRAS siRNA (AB03)v1 | 0.20 | 88.8 |
| 385 | EPCAM/CD71/ABD-KRAS siRNA (AB03)v2 | 0.12 | 89.7 |
| 386 | EPCAM/EPCAM_ABDcon KRAS siRNA (AB03) | N.D. | N.D. |
| 387 | EPCAM/EPCAM/ABD-KRAS siRNA (AB03) | N.D. | N.D. |
| 388 | EpCAM/CD71/ABD_V2_KRAS siRNA (AB03) | N.D. | N.D. |
| 389 | CD71/EpCAM/ABD_KRAS siRNA (AB03) | N.D. | N.D. |
| 390 | EpCAM_CD71_ABD | N.D. | N.D. |
| 391 | EpCAM/EpCAM/CD71/ABD_KRAS siRNA (AB03) | N.D. | N.D. |
| 392 | EPCAM/CD71/EPCAM-KRAS siRNA (AB03) | N.D. | N.D. |

Sequences of FN3 Domains referenced in the table above that were conjugated to the siRNA or as shown as controls are provided in Table 11.

TABLE 11

Sequences of FN3 domains

| SEQ ID | SEQUENCE |
|---|---|
| 377 | MLPAPKNLVVSEVTEDSARLSWDDPWAFYESFLIQYQESEKVGEAIVLTV PGSERSYDLTGLKPGTEYTVSIYGVHNVYKDTNIRGLPLSAIFTT |

TABLE 11-continued

Sequences of FN3 domains

| SEQ ID | SEQUENCE |
|---|---|
| 378 | MLPAPKNLVVSRVTEDSARLSWTAPDAAFDSFTIWYAEAIGHGEAIVLTV PGSERSYDLTGLKPGTEYWVDIWGVKGGQQSKPLSAIFTT |
| 379 | MLPAPKNLVVSRVTEDSARLSWTAPYAAFDSFAISYRERSREGEVIALTVP GSERSYDLTGLKPGTEYIVGILGVKGGRRSKPLRAQFTTGGGGSGGGGSG GGGSGGGGSLPAPKNLVVSRVTEDSARLSWTAPDAAFDSPHIEYWEQSIV GEAIVLTVPGSERSYDLTGLKPGTEYRVWIYGVKGGNDSWPLSAIFTT |
| 380 | MLPAPKNLVVSEVTEDSARLSWTAPDAAFDSFLIQYQESEKVGEAIVLTVP GSERSYDLTGLKPGTEYTVSIYGVKGGHRSNPLSAIFTT |
| 381 | MLPAPKNLVVSRVTEDSARLSWTAPDAAFDSFTIWYAEAIGHGEAIVLTV PGSERSYDLTGLKPGTEYWVDIWGVKGGQQSKPLSAIFTTGGGGSGGGGS GGGGSGGGGSLPAPKNLVVSRVTEDSARLSWTAPDAAFDSFTIWYAEAIG HGEAIVLTVPGSERSYDLTGLKPGTEYWVDIWGVKGGQQSKPLSAIFTT |
| 382 | MLPAPKNLVVSRVTEDSARLSWTAPDAAFDSFTIWYAEAIGHGEAIVLTV PGSERSYDLTGLKPGTEYWVDIWGVKGGQQSKPLSAIFTTGGGGSGGGGS GGGGSGGGGSLPAPKNLVVSRVTEDSARLSWTAPDAAFDSFTIWYAEAIG HGEAIVLTVPGSERSYDLTGLKPGTEYWVDIWGVKGGQQSKPLSAIFTTA PAPAPAPAPTIDEWLLKEAKEKAIEELKKAGITSDYYFDLINKAKTVEGVN ALKDEILKA |
| 383 | MLPAPKNLVVSRVTEDSARLSWTAPYAAFDSFAISYRERSREGEVIALTVP GSERSYDLTGLKPGTEYIVGILGVKGGRRSKPLRAQFTTGGGGSGGGGSG GGGSGGGGSLPAPKNLVVSRVTEDSARLSWTAPYAAFDSFAISYRERSRE GEVIALTVPGSERSYDLTGLKPGTEYIVGILGVKGGRRSKPLRAQFTTAPA PAPAPAPTIDEWLLKEAKEKAIEELKKAGITSDYYFDLINKAKTVEGVNAL KDEILKA |
| 384 | MLPAPKNLVVSRVTEDSARLSWTAPYAAFDSFAISYRERSREGEVIALTVP GSERSYDLTGLKPGTEYIVGILGVKGGRRSKPLRAQFTTGGGGSGGGGSG GGGSGGGGSLPAPKNLVVSRVTEDSARLSWTAPDAAFDSFTIWYAEAIGH GEAIVLTVPGSERSYDLTGLKPGTEYWVDIWGVKGGQQSKPLSAIFTTAP APAPAPAPTIDEWLLKEAKEKAIEELKKAGITSDYYFDLINKAKTVEGVNA LKDEILKA |
| 385 | MLPAPKNLVVSRVTEDSARLSWTAPYAAFDSFAISYRERSREGEVIALTVP GSERSYDLTGLKPGTEYIVGILGVKGGRRSKPLRAQFTTAPAPAPAPAPLP APKNLVVSRVTEDSARLSWTAPDAAFDSFTIWYAEAIGHGEAIVLTVPGSE RSYDLTGLKPGTEYWVDIWGVKGGQQSKPLSAIFTTAPAPAPAPAPTIDE WLLKEAKEKAIEELKKAGITSDYYFDLINKAKTVEGVNALKDEILKA |
| 386 | MLPAPKNLVVSRVTEDSARLSWTAPYAAFDSFAISYRERSREGEVIALTVP GSERSYDLTGLKPGTEYIVGILGVKGGRRSKPLRAQFTTGGGGSGGGGSG GGGSGGGGSLPAPKNLVVSRVTEDSARLSWTAPDAAFDSFSISYRERSAW GEAIALVVPGSERSYDLTGLKPGIEYIVGIIGVKGGLRSNPLRADFTTAPAP APAPAPTIDEWLLKEAKEKAIEELKKAGITSDYYFDLINKAKTVEGVNALK DEILKA |
| 387 | MLPAPKNLVVSRVTEDSARLSWTAPDAAFDSFSISYRERSAWGEAIALVV PGSERSYDLTGLKPGIEYIVGIIGVKGGLRSNPLRADFTTGGGGSGGGGSG GGGSGGGGSLPAPKNLVVSRVTEDSARLSWTAPYAAFDSFAISYRERSRE GEVIALTVPGSERSYDLTGLKPGTEYIVGILGVKGGRRSKPLRAQFTTAPA PAPAPAPTIDEWLLKEAKEKAIEELKKAGITSDYYFDLINKAKTVEGVNAL KDEILKA |
| 388 | MLPAPKNLVVSRVTEDSARLSWTAPYAAFDSFAISYRERSREGEVIALTVP GSERSYDLTGLKPGTEYIVGILGVKGGRRSKPLRAQFTTGGGGSGGGGSG GGGSGGGGSLPAPKNLVISRVTEDSARLSWTAPDAAFDSFFIYYIESYPAG EAIVLTVPGSERSYDLTGLKPGTEYWVGIDGVKGGRWSTPLSAIFTTAPAP APAPAPTIDEWLLKEAKEKAIEELKKAGITSDYYFDLINKAKTVEGVNALK DEILKA |
| 389 | MLPAPKNLVVSRVTEDSARLSWTAPDAAFDSFAIYYLESYPEGEAIVLTVP GSERSYDLTGLKPGTEYWVGIDGVKGGTWSSPLSAIFTTGGGGSGGGGSG GGGSGGGGSLPAPKNLVVSRVTEDSARLSWTAPYAAFDSFAISYRERSRE GEVIALTVPGSERSYDLTGLKPGTEYIVGILGVKGGRRSKPLRAQFTTAPA PAPAPAPTIDEWLLKEAKEKAIEELKKAGITSDYYFDLINKAKTVEGVNAL KDEILKA |

TABLE 11-continued

Sequences of FN3 domains

| SEQ ID | SEQUENCE |
|---|---|
| 390 | MLPAPKNLVVSRVTEDSARLSWTAPYAAFDSFAISYRERSREGEVIALTVP GSERSYDLTGLKPGTEYIVGILGVKGGRRSKPLRAQFTTGGGGSGGGGSG GGGSGGGGSLPAPKNLVVSRVTEDSARLSWTAPDAAFDSFAIYYLESYPE GEAIVLTVPGSERSYDLTGLKPGTEYWVGIDGVKGGTWSSPLSAIFTTAPA PAPAPAPTIDEWLLKEAKEKAIEELKKAGITSDYYFDLINKAKTVEGVNAL KDEILKA |
| 391 | MLPAPKNLVVSRVTEDSARLSWTAPYAAFDSFAISYRERSREGEVIALTVP GSERSYDLTGLKPGTEYIVGILGVKGGRRSKPLRAQFTTGGGGSGGGGSG GGGSGGGGSLPAPKNLVVSRVTEDSARLSWTAPDAAFDSFSISYRERSAW GEAIALVVPGSERSYDLTGLKPGIEYIVGIIGVKGGLRSNPLRADFTTGGGG SGGGGSGGGGSGGGGSLPAPKNLVISRVTEDSARLSWTAPDAAFDSFFIYY IESYPAGEAIVLTVPGSERSYDLTGLKPGTEYWVGIDGVKGGRWSTPLSAI FTTAPAPAPAPTIDEWLLKEAKEKAIEELKKAGITSDYYFDLINKAKTV EGVNALKDEILKA |
| 392 | MLPAPKNLVVSRVTEDSARLSWTAPYAAFDSFAISYRERSREGEVIALTVP GSERSYDLTGLKPGTEYIVGILGVKGGRRSKPLRAQFTTAPAPAPAPAPLP APKNLVVSRVTEDSARLSWTAPDAAFDSFTIWYAEAIGHGEAIVLTVPGSE RSYDLTGLKPGTEYWVDIWGVKGGQQSKPLSAIFTTAPAPAPAPAPLPAP KNLVVSRVTEDSARLSWTAPYAAFDSFAISYRERSREGEVIALTVPGSERS YDLTGLKPGTEYIVGILGVKGGRRSKPLRAQFTT |
| 393 | MLPAPKNLVVSRVTEDSARLSWTAPDAAFDSFAIYYLESYPEGEAIVLTVP GSERSYDLTGLKPGTEYWVGIDGVKGGTWSSPLSAIFTTGGGGSGGGGSG GGGSGGGGSLPAPKNLVVSRVTEDSARLSWTAPYAAFDSFAISYRERSRE GEVIALTVPGSERSYDLTGLKPGTEYIVGILGVKGGRRSKPLRAQFTTGGG GSGGGGSGGGGSGGGGSLPAPKNLVASRVTEDSARLSWTAPDAAFDSFNI AYWEPGIGGEAIWLRVPGSERSYDLTGLKPGTEYKVWIHGVKGGASSPPL IARFTTGGHHHHHHC |

SEQ ID NO: 388 was also made N-ethyl maleimide reacted with the C-terminus, which is done to keep the FN3 domain in a monomeric form. The structure can be represented by the following formula:

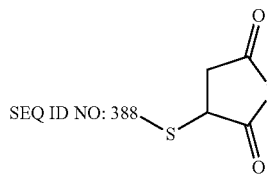

Example 2. FN3-siRNA conjugate (SEQ ID NO:385) specifically lowers endogenous KRAS mRNA. A431 cells (wild-type KRAS, non-KRAS dependent) were treated with the FN3-siRNA (SEQ ID NO: 385 linked to AB03) conjugates for 96 hours. cDNA from the cells was generated and quantitative RT-PCR was performed using Taqman primer/probe assays specific for KRAS, HRAS, and NRAS. Ubiquitin C (UBC) was the endogenous control. The delta-delta Ct method was used to quantify expression of each gene in cells that were treated with FN3-siRNA conjugates. SEQ 41 showed dose-dependent, specific knockdown of KRAS. The corresponding FN3 construct alone (No siRNA Ctrl) did not produce knockdown of KRAS. The non-targeting FN3 control (Tencon) conjugated to the KRAS siRNA did not produce significant knockdown of KRAS. This is illustrated in FIG. 1. The data is also illustrated in tabular form in Table 12.

TABLE 12

Results of FN3-siRNA conjugates

| nM Conjugate | SEQ ID NO: 385 | No siRNA Ctrl | (AB03) |
|---|---|---|---|
| | Relative KRAS mRNA levels | | |
| 0.132 | 1.502 | 1.976 | 1.894 |
| 1.6 | 1.399 | 1.595 | 2.068 |
| 8 | 1.231 | 1.906 | 2.008 |
| 40 | 0.554 | 2.289 | 1.504 |
| 200 | 0.105 | 1.544 | 1.13 |
| | Relative HRAS mRNA levels | | |
| 0.132 | 1.335883 | 1.107742 | 1.167772 |
| 1.6 | 1.246747 | 1.126604 | 1.181024 |
| 8 | 1.119824 | 1.147848 | 1.0595 |
| 40 | 1.131173 | 1.14322 | 1.182572 |
| 200 | 1.048989 | 1.056286 | 1.099616 |
| | Relative NRAS mRNA levels | | |
| 0.132 | 1.3048 | 1.089474 | 1.164604 |
| 1.6 | 1.068661 | 1.052238 | 1.258119 |
| 8 | 1.000139 | 0.974874 | 1.051284 |
| 40 | 1.043022 | 1.164602 | 1.239046 |
| 200 | 1.121631 | 1.062723 | 1.17195 |

Quantitative polymerase chain reaction (qPCR) for quantification of gene knockdown. Quantitative reverse transcription polymerase chain reactions (RT-PCR) were performed on cellular samples in order to directly measure knockdown of endogenous KRAS mRNA. After treatment with FN3-siRNA conjugates, A431 cells are lysed and cDNA is generated using Cells-to-Ct kits (ThermoFisher). cDNAs were quantitated using TaqMan gene expression assays specific for KRAS, HRAS, NRAS, or an endogenous control (ubiquitin C).

Figure 2:
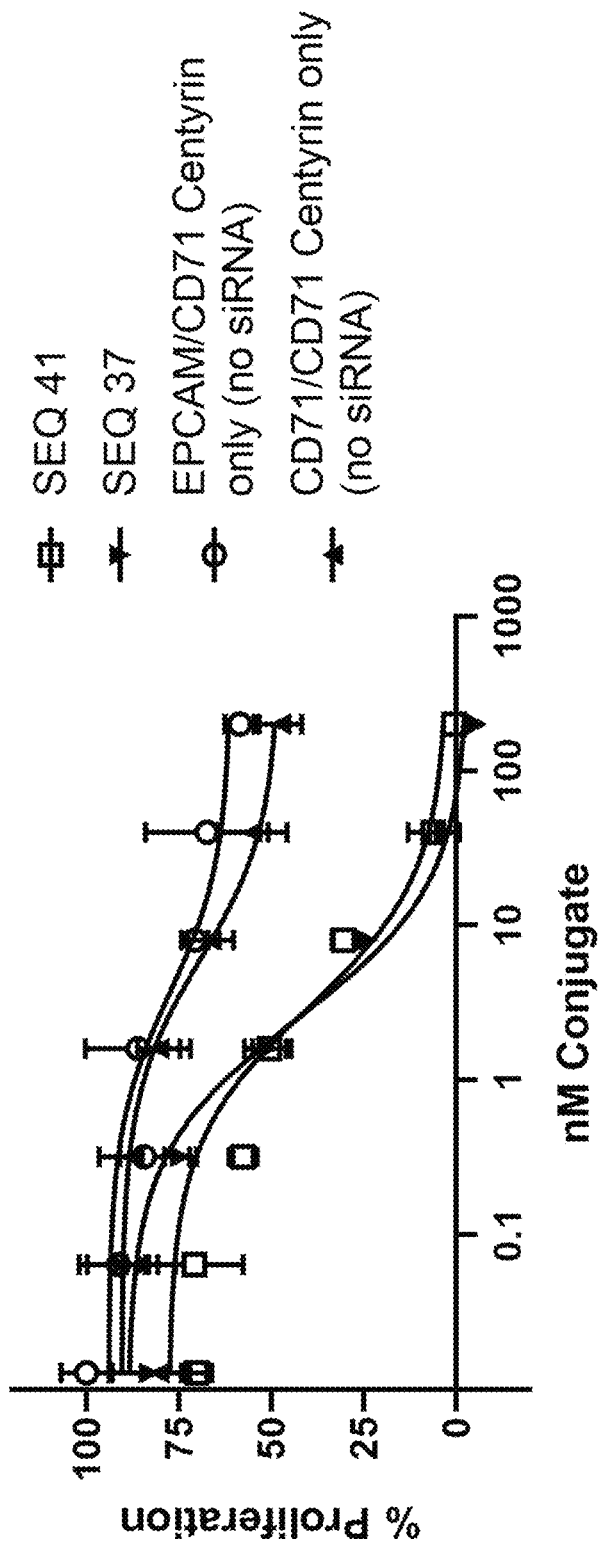
FIG. 2 illustrates the inhibition of cellular proliferation of a FN3-siRNA conjugate.

Example 3. FN3-siRNA conjugates reduce proliferation of KRAS dependent cells. SEQ ID 385 and SEQ ID 381 conjugated to (AB03) reduce proliferation in KRAS-dependent H358 cells in vitro. H358 grown in 3D spheroid conditions were treated with FN3 constructs with or without a conjugated KRAS siRNA. Both the EPCAM/CD71 and CD71/CD71 FN3 domains without the siRNA showed ~25-40% inhibition of proliferation after 7 days of treatment while FN3-KRAS conjugates inhibited proliferation up to 100%. The data is illustrated in FIG. 2.

3-dimensional proliferation assay. Cells are grown as 3-dimensional spheroids using 3D Spheroid Microplates (Corning). These plates favor the formation of 3-D spheroids of tumor cells, a format that is known to support KRAS-driven cell growth. Cell proliferation is measured using CellTiterGlo-3D assays (Promega), which use cellular ATP levels as an indicator of cell number. Following treatment with FN3-siRNA conjugates, H358 spheroids are lysed with CellTiterGlo-3D reagent and quantified using a plate reader to measure luminescence. Percent inhibition of proliferation is calculated by comparing the ATP signal present at the end of the conjugate treatment to the ATP signal present in the starting number of cells immediately prior to treatment (FIG. 2).

Figure 3:
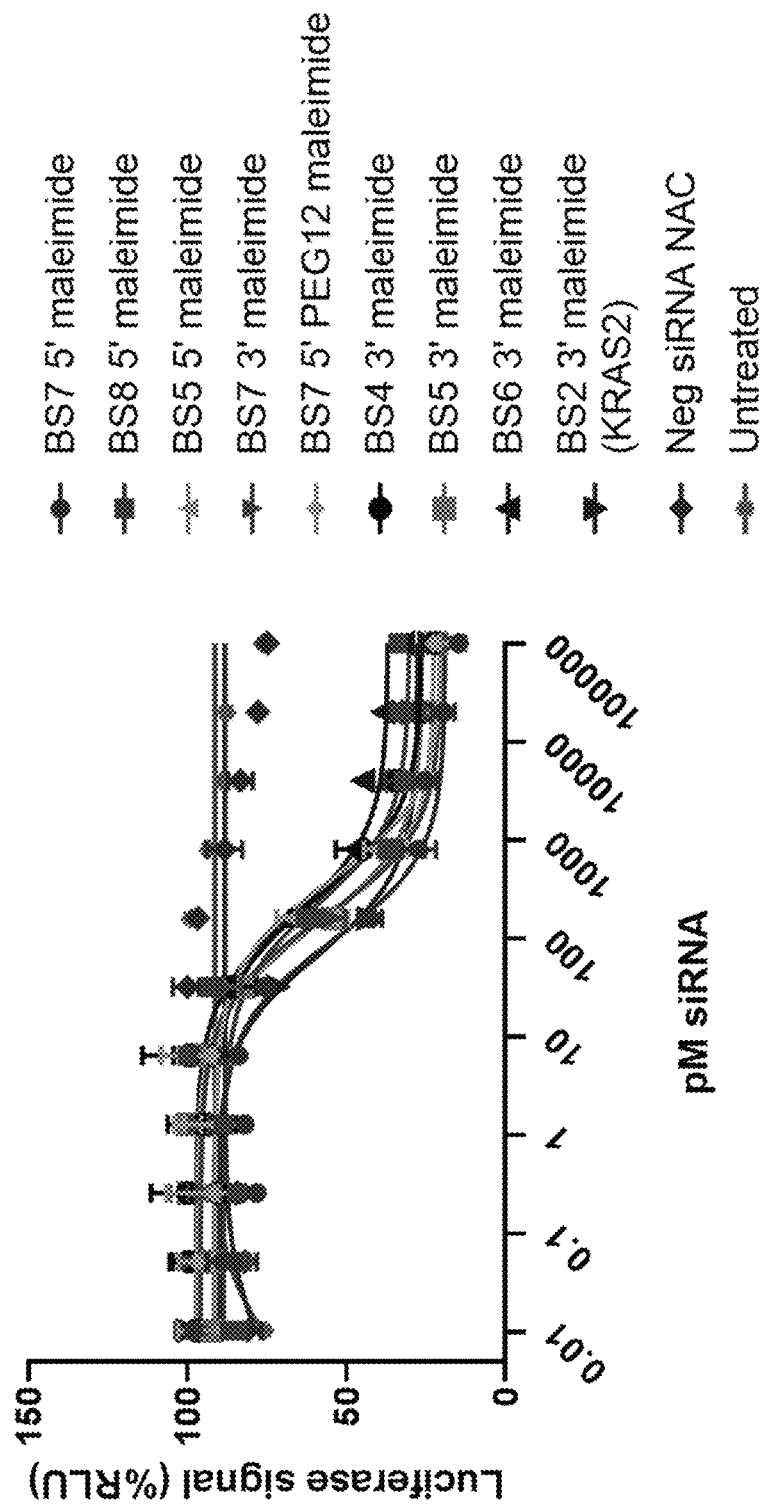
FIG. 3 illustrates various embodiments provided herein.

These examples demonstrate the surprising and unexpected ability of FN3-siRNA conjugates to reduce a target gene and also inhibit cellular proliferation. The results also demonstrate that it can be done with a composition comprising more than one FN3 domain and still effectively deliver a siRNA molecule, which has not previously been demonstrated. Furthermore, the examples and embodiments provided herein demonstrate FN3 Domain-siRNA conjugates enable receptor specific delivery of siRNA to extra-hepatic cell types; intracellular trafficking and an endosomal depot for FN3 contributes to an extended duration of activity of FN3-siRNA conjugates; FN3-siRNA conjugates have demonstrated potent reduction of mRNA and protein and inhibition of proliferation in epithelial tumor cell lines; and bispecific binding of FN3 domains to tumor cells expressing high levels of targeted receptors improves avidity and activity and can improve selectivity Example 4. siRNA sequences directed against KRAS conjugated with malemide were found to inhibit KRAS expression. Various linker site and linkage chemistry of KRAS siRNAs were evaluated by transfection using a HEK293 luciferase cell line. Each of the molecules were found to inhibit KRAS expression by this assay, which are illustrated in FIG. 3.

Figure 4:
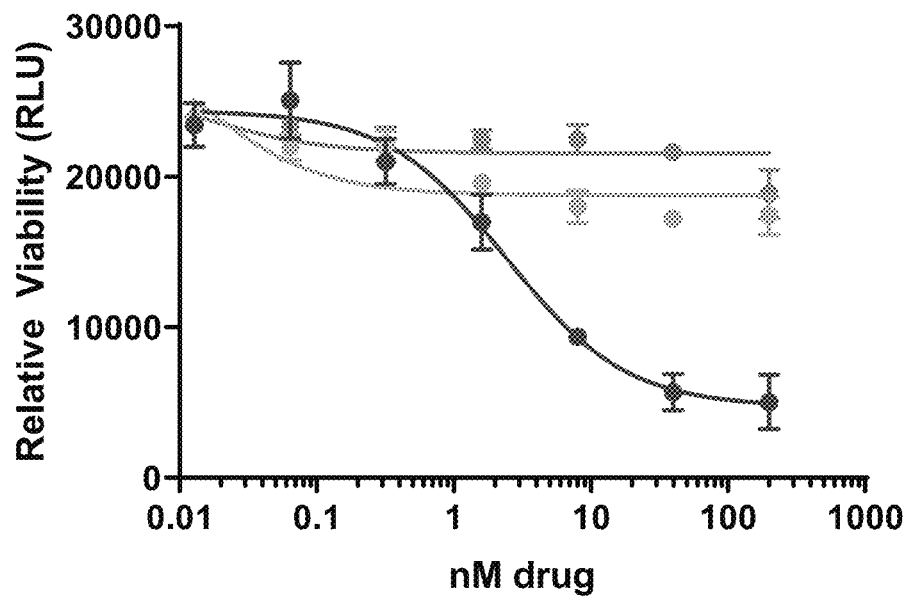
FIG. 4, panels A and B, illustrates various embodiments provided herein.
Figure 4:
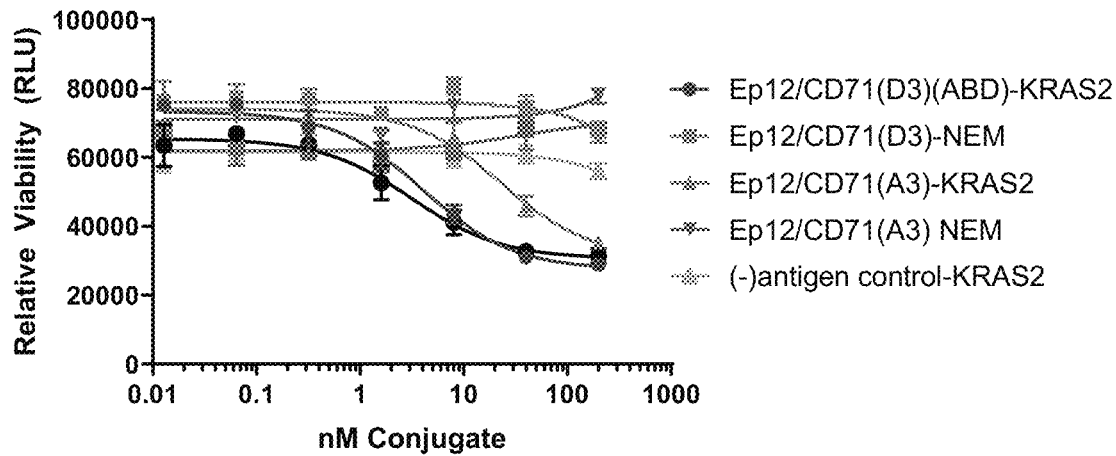

Example 5. KRAS-FN3 domain conjugates inhibit cancer cell growth. H358, NSCLC, cell line in 3D spheroid culture was treated with KRAS FN3 conjugates for 15 days (FIG. 4, Panel A). The siRNA-FN3 domain conjugate was conjugated to either a CD71 or EPCAM FN3 binding domain. Cells were subsequently treated with CellTiter-Glo to assess proliferation MIA-PaCa, pancreatic cancer, cell line in 3D spheroid culture was treated with KRAS FN3 conjugates for 7 days CellTiter-Glo to assess proliferation (FIG. 4, Panel B). The conjugates were found to be effective in inhibit cell growth. The results are illustrated in FIG. 4.

Figure 5:
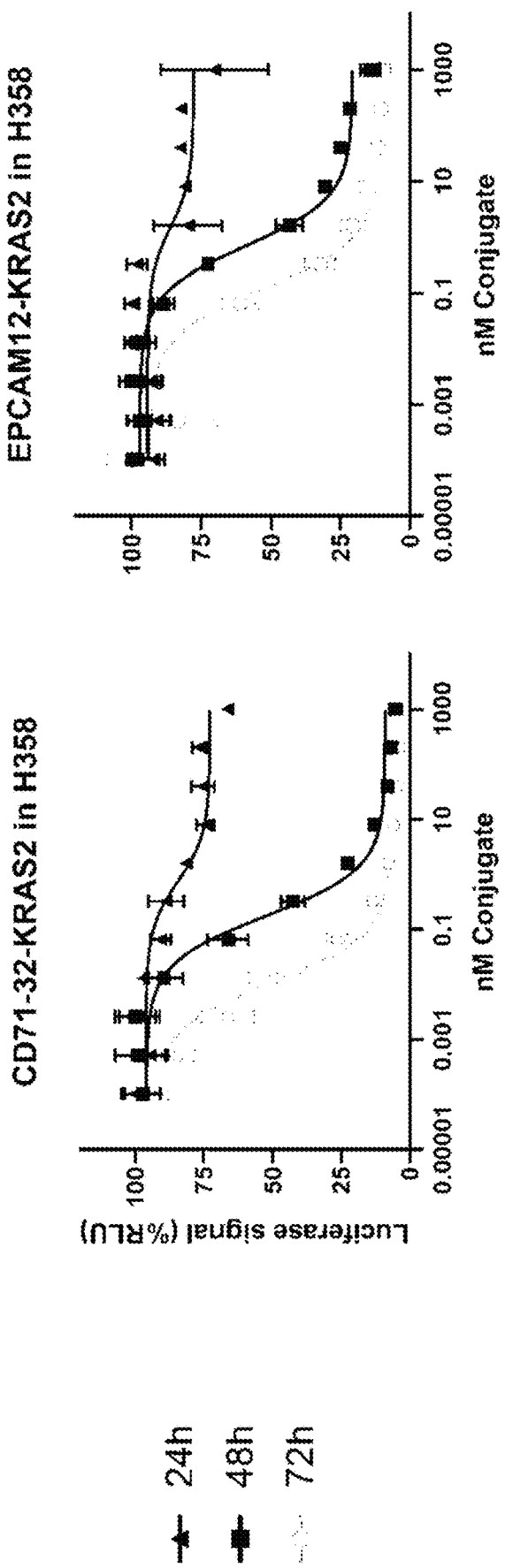
FIG. 5 illustrates various embodiments provided herein.

Example 6. A H358 luciferase line that can be used measure KRAS expression was treated with a monomeric CD71 FN3 binding, EpCam FN3 binding KRAS siRNA conjugates. The plates were read at 24 h, 48 h, and 72 h. A time dependent effect was observed consistent with receptor mediated uptake and accumulation of the conjugate in the cell. These results are illustrated in FIG. 5. These results demonstrate that the FN3-siRNA conjugates can be internalized into the cell.

Figure 6:
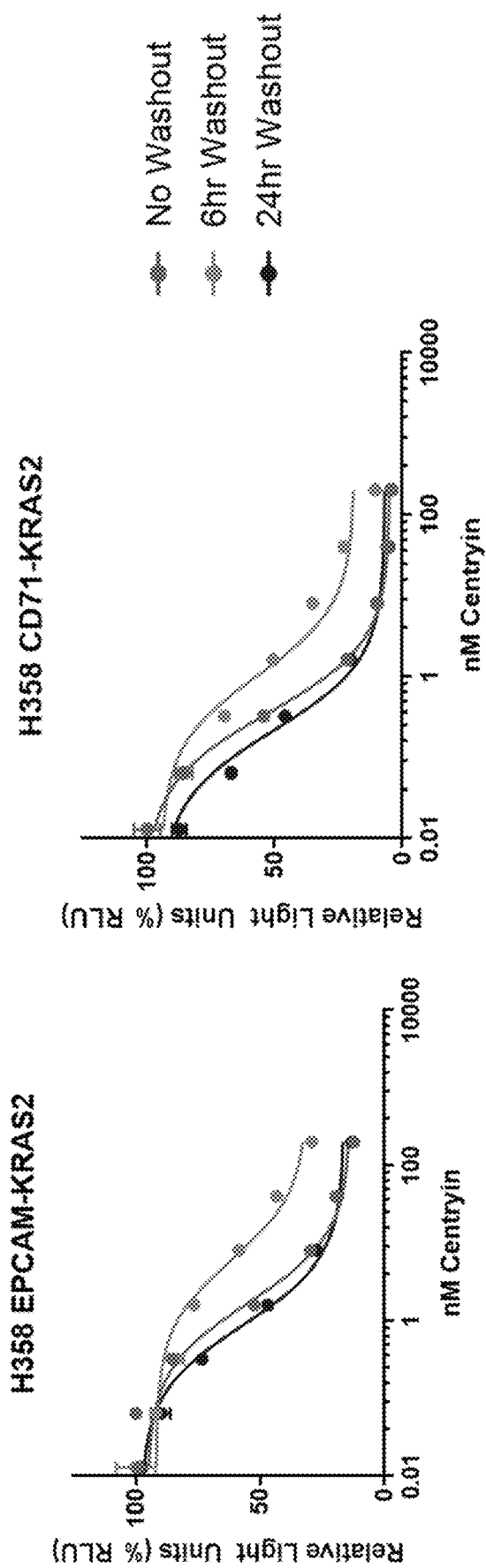
FIG. 6 illustrates various embodiments provided herein.

Example 7. A H358 3D spheroids were treated with FN3 domain KRAS siRNA conjugates for 72 h. The cells were washed after 6 h and 24 h and then measured for fluorescent signal. The 6 h and 24 h washout experiment demonstrates a lasting effects for the FN3 accumulation in the early endosome and siRNA silencing on KRAS mRNA. These results are illustrated in FIG. 6. These results demonstrate the persistence of the effect.

Figure 7:
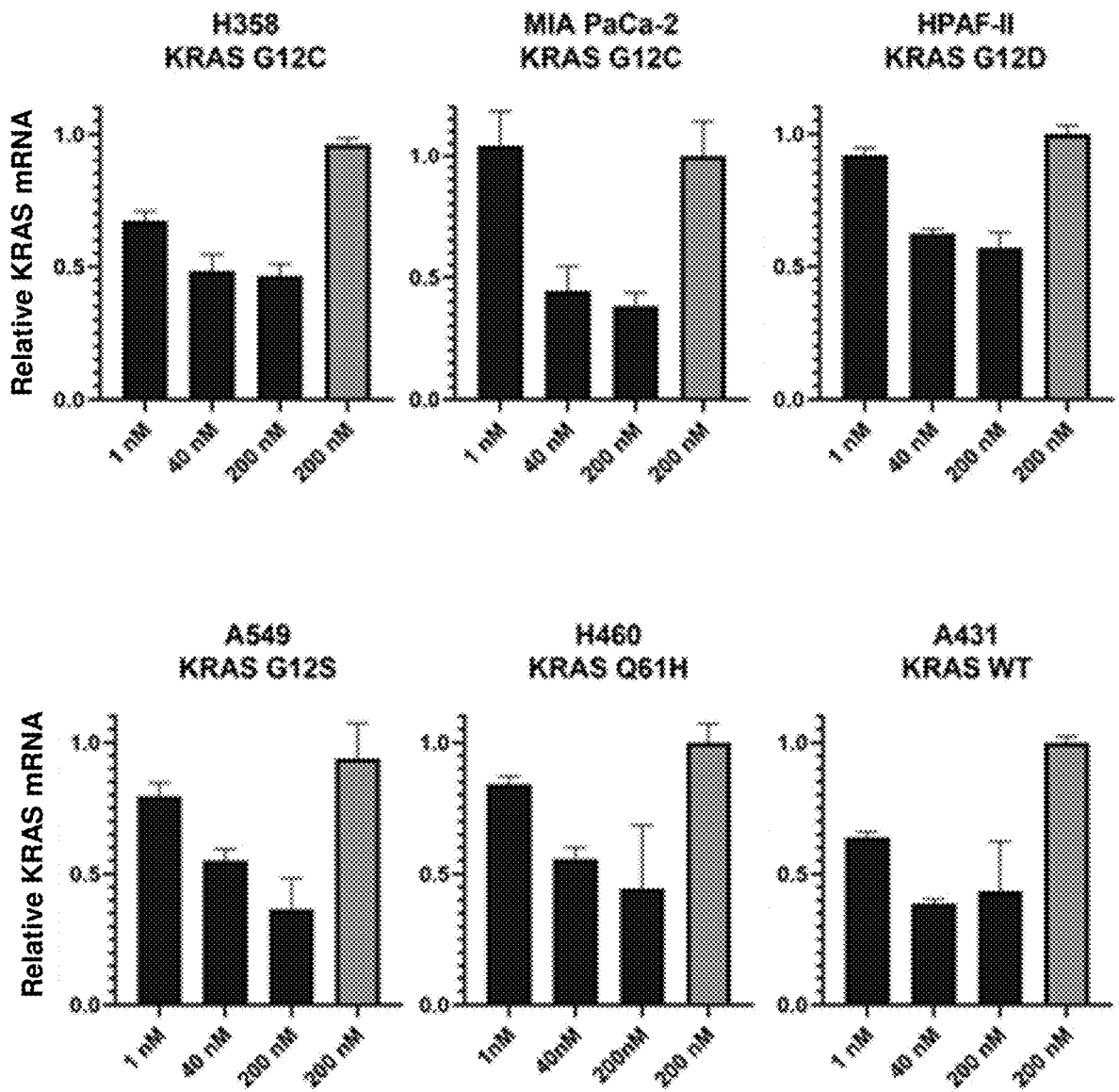
FIG. 7 illustrates various embodiments provided herein.

Example 8. FN3 Binding Domains-siRNA conjugates can inhibit the expression of more than one KRAS mutant. H358-NSCLC (G12C), MIA PaCa-2-pancreatic (G12C), HPAF II-pancreatic (G12D), A549-NSCLC (G12S), H460-NSCLC (Q61H) and A431-skin (KRAS WT) cancer lines were treated with KRAS2 EPCAM/CD71 FN3 conjugates for 72 h. The cells from each experiment were measured for residual KRAS mRNA using qPCR. The conjugates were found to decrease the expression of each variant. These results are illustrated in FIG. 7.

Figure 8:
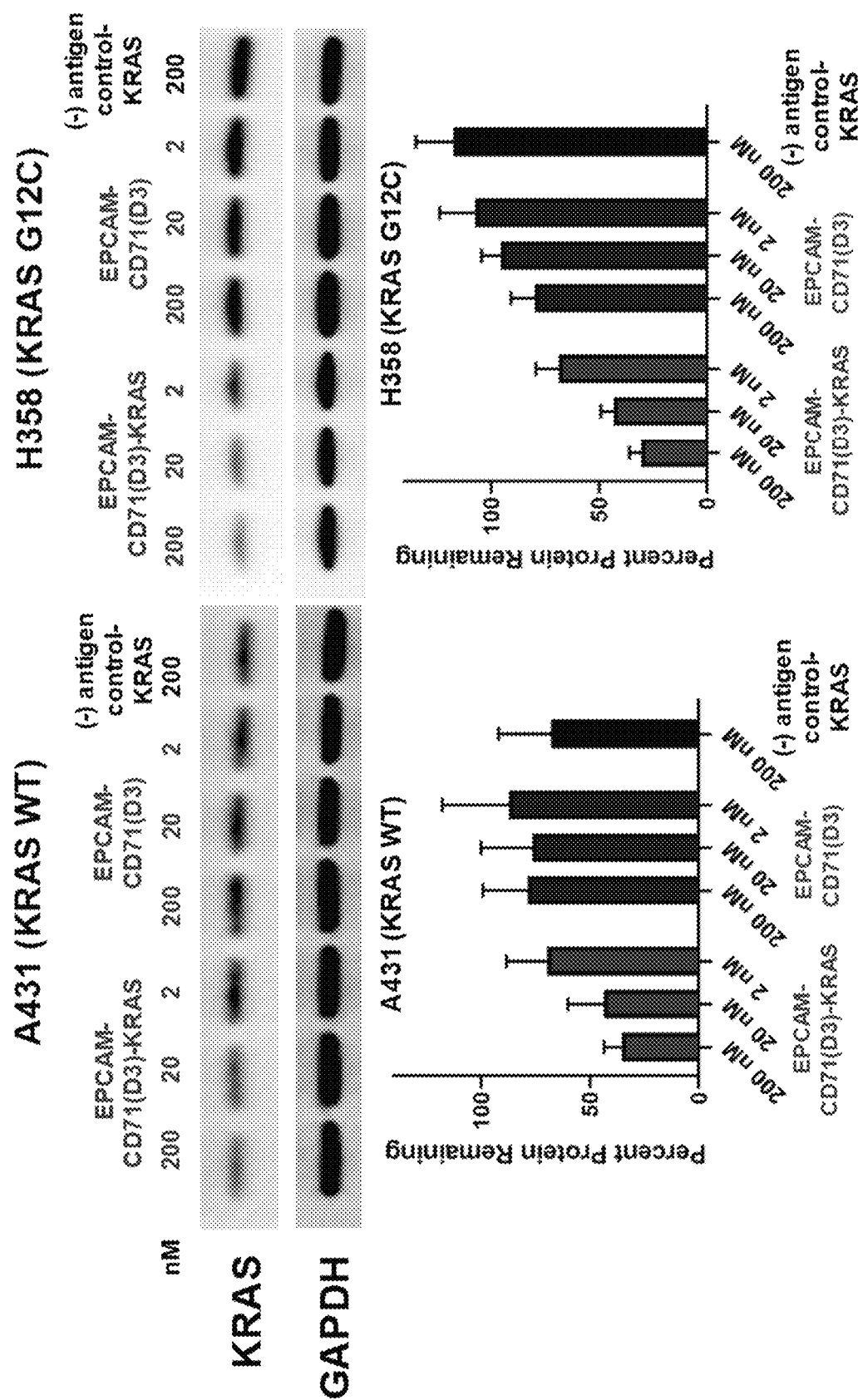
FIG. 8 illustrates various embodiments provided herein.

Example 9. EPCAM/CD71-FN3 Bispecific Binding Domain siRNA conjugates decreases KRAS protein levels. A431 and H358 cells were treated with bispecific FN3 domains conjugated to KRAS siRNA at 2, 20 and 200 nM concentrations. After 72 h the cells were compared by Western blot and for the presence of KRAS protein. A good correlation between mRNA silencing and protein was observed. These results are illustrated in FIG. 8.

Figure 9:
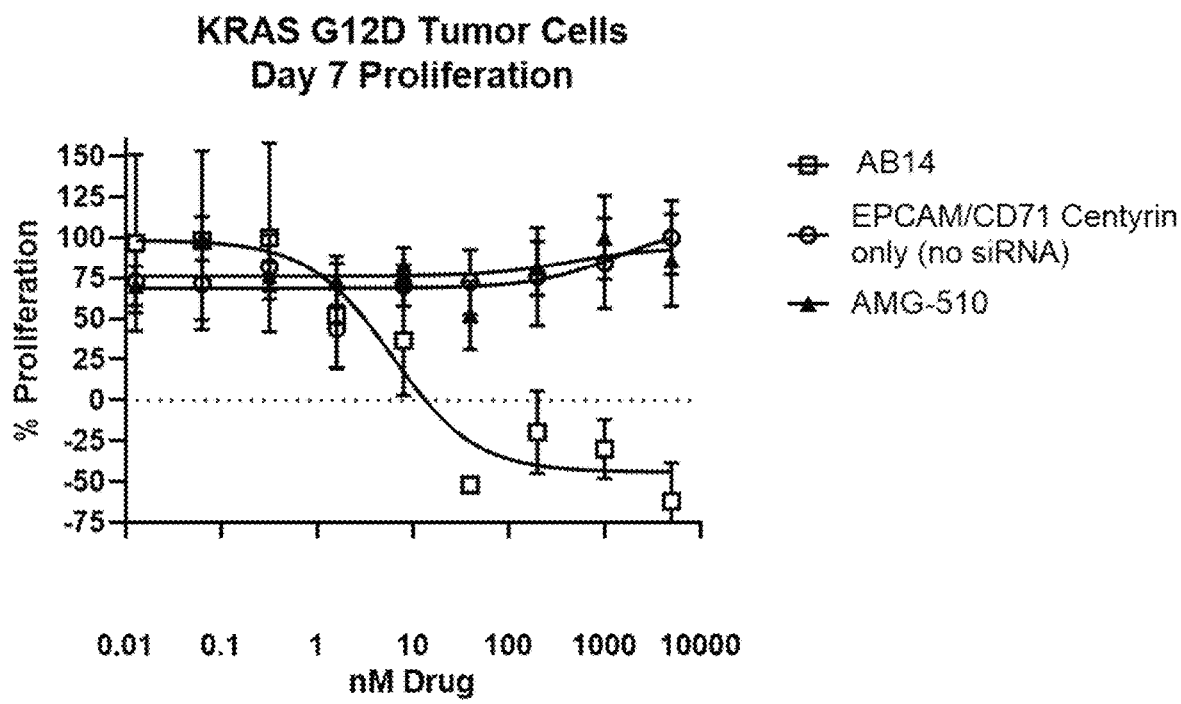
FIG. 9 illustrates various embodiments provided herein.
Figure 9:
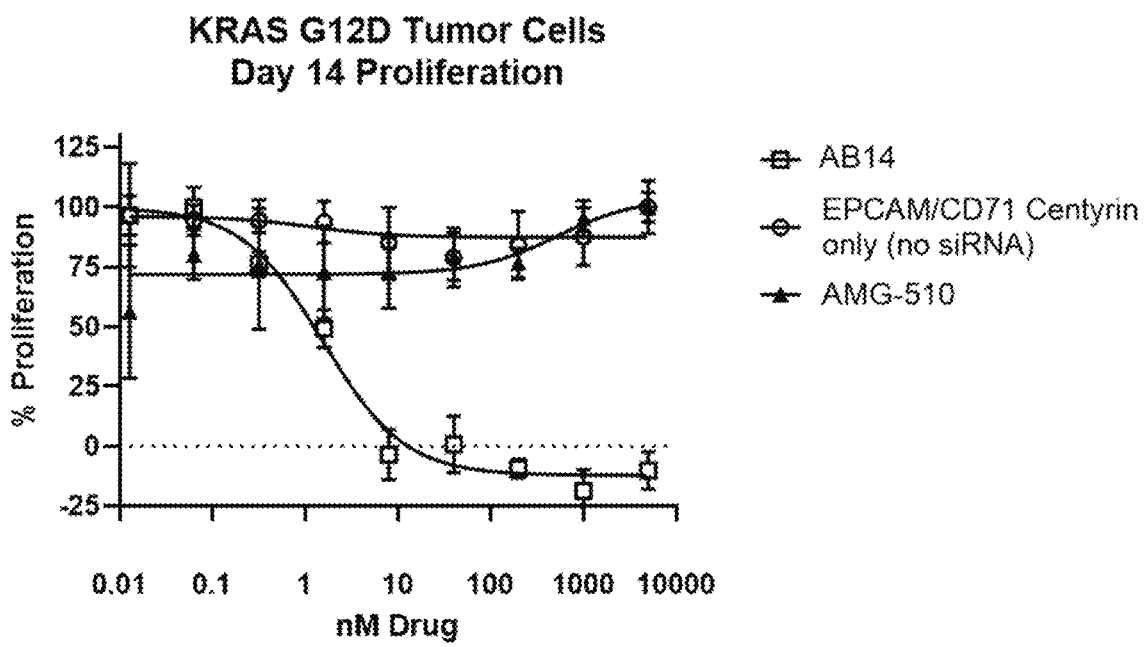

Example 10. FN3-siRNA conjugates reduce proliferation of KRAS dependent cells. SEQ ID 393 conjugated to (AB03) reduce proliferation in KRAS-G12D dependent cells in vitro. The cells grown in 3D spheroid conditions were treated with the constructs with or without a conjugated KRAS siRNA as described in Example 3. A control, AMG-510, that targets G12C was used as a negative control. The FN3-KRAS conjugate inhibited proliferation up to 100%, which was significantly more than the control without the siRNA or AMG-510, which is G12C RAS inhibitor. The data is illustrated in FIG. 9. SEQ ID NO: 393 is illustrated as a polypeptide that comprises 3 FN3 domains that bind to CD71 (SEQ ID NO: 312), EpCAM (SEQ ID NO: 330-without the initial methionine) and an albumin binding domain comprising the sequence of: (LPAPKNLVASRVTEDSARLSWTAPDAAFDSFNIAY-WEPGIGGEAIWLRVPGSERSYDLT GLKPGTEYKVWIHGVKGGASSPPLIARFTTGG (SEQ ID NO: 394). Each of these domains are exemplary only and linked by various peptide linkers. The domains can be swapped with other CD71, EpCAM and albumin binding domains, such as those provided herein or referenced herein.

Example 11. FN3 Domain Conjugation, PEG Modifier and siRNA

Figure 10:
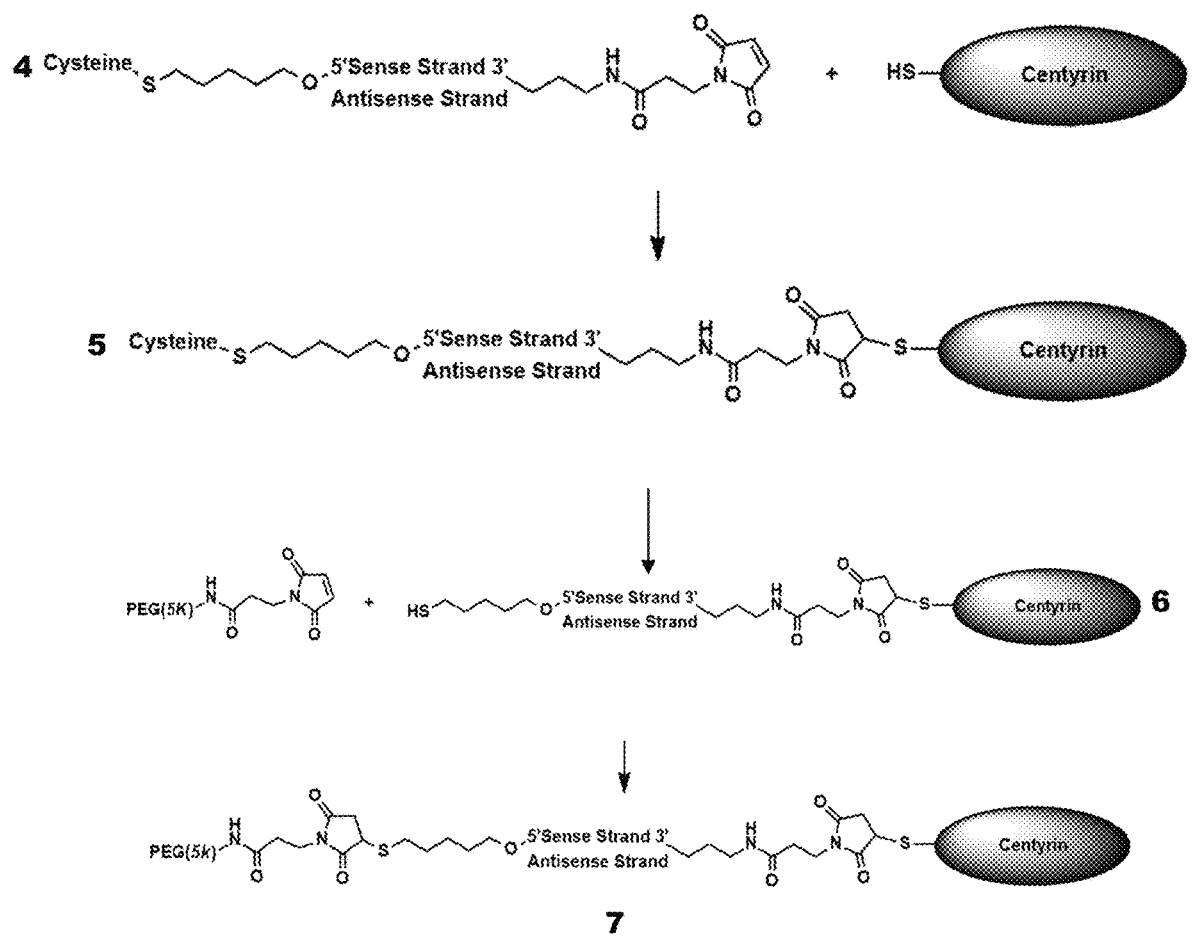
FIG. 10 illustrates various embodiments provided herein.

FIG. 10 illustrates a non-limiting example of how a FN3 domain was linked to a siRNA and PEG molecule. Briefly, a polypeptide as provided herein was conjugated to a siRNA linker with the distal 5' disulfide 4 through cysteine maleimide chemistry. The reaction was passed through a desalting column (7 kD molecular weight cutoff-MCWO) to afford product 5. The conjugate was purified in two steps. Step I affinity chromatography; to remove un-reacted siRNA linker using a Ni-NTA column. Step II-Ion exchange chromatography (CaptoQ or DEAE); to remove un-reacted Centyrin. Fractions containing pure conjugate (determined by SDS gel) were pooled, exchanged into PBS by desalting using Zeba desalting columns (Thermo), and concentrated if necessary.

The cysteine group was removed using 10 mM TCEP. The reaction was monitored by LC-MS. After completion of the reduction TCEP was removed by desalting (7 kD MWCO)

to yield 6. Intermediate 6 with was then stirred with the maleimide-PEG moiety (10 equivalents with respect to 6) in PBS. The reaction was incubated at room temperature (~20-25 C) for 6-12 hrs. The reaction was monitored by LC/MS. After completion of reaction the product 7 was purified by passing the reaction mixture through desalting column (7 kD MCWO) to remove excess maleimide-PEG.

Analytical Characterization of CENTYRIN Domain-siRNA Conjugates

FN3-siRNA conjugates were characterized by a combination of analytical techniques. SDS-PAGE was used to compare amounts of conjugate to free protein. For SDS-PAGE, 4-20% Mini-PROTEAN® TGX Stain-Free™ Protein Gels (BioRad) were run in SDS buffer for one hour at 100 V. Gels were visualized under UV light. Analytical SEC (Superdex-75 5/150 GL column-GE) was used to analyze purity and aggregation state of Centyrin-siRNA conjugates. Liquid chromatography/mass spectrometry (LC/MS) was used to confirm identity and purity of the conjugates. Samples were analyzed using a Waters Acuity UPLC/Xevo G2-XS TOF mass spectrometer system. The instrument was operated in negative electro-spray ionization mode and scanned from m/z 200 to 3000. Conjugate was seen as two fragments; Antisense and Sense-FN3 polypeptide.

Figure 11:
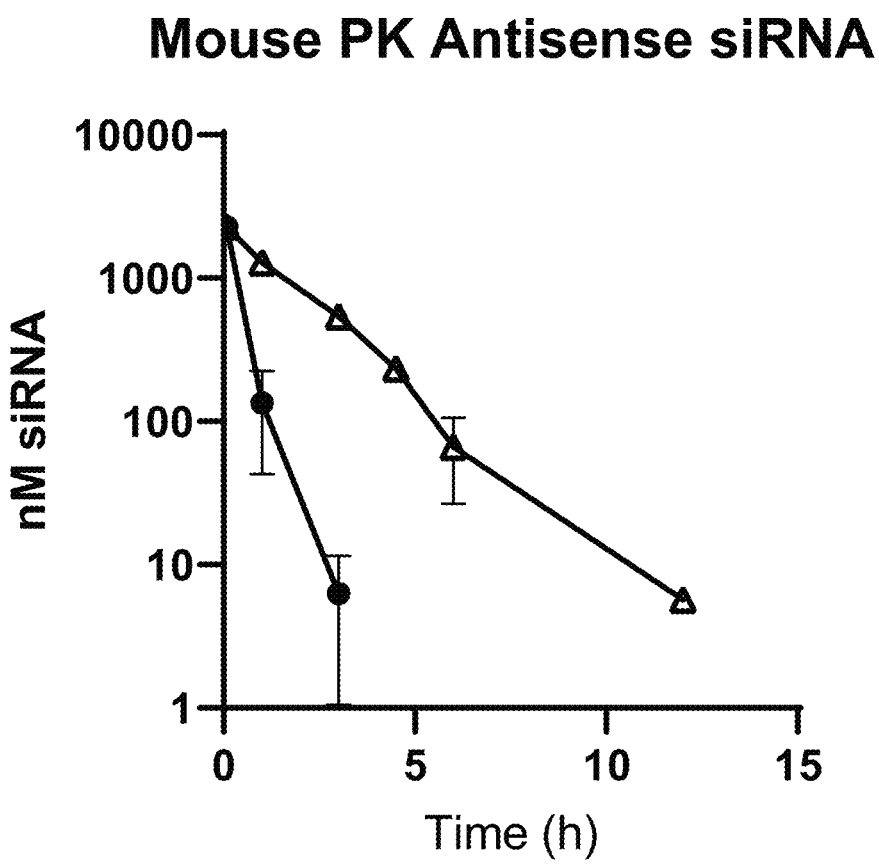
FIG. 11 illustrates various embodiments provided herein.

Example 12. Mice were dosed via intravenous administration of a FN3 domain conjugated according to Example 11 at 5 mg/kg. Serum was collected and analyzed via stem-loop PCR to quantify antisense RNA strand of the siRNA molecule. LLOQ for assay determined to be 1 nM. Two FN3-siRNA conjugates were tested in pK studies and in vitro luciferase assays. The pK of the antisense RNA of the siRNA molecules were found to have adequate stability in the blood of the mice. This is illustrated in FIG. 11. The open triangles were SEQ ID NO: 393 linked to siRNA AB03 and found to have an AUC (1 nm baseline) of 1251. The closed circles were SEQ ID NO: 393 linked to siRNA AB15 and found to have an AUC (1 nm baseline) of 4470. This data demonstrates that the siRNA molecule was stable and detectable.

Luciferase assays of the same molecules were performed as described herein and were read using EnduRen substrate 72 hours following administration of the FN3-siRNA conjugates. Proliferation assays were read using CellTiterGlo 14 days following administration of FN3-siRNA conjugates. The activities in various assays is shown in the table below.

| FN3-siRNA Conjugate# | H358-LUC EC50 (nM) | SW620-LUC EC50 (nM) | A549-LUC EC50 (nM) | H358 Proliferation (nM) |
|---|---|---|---|---|
| SEQ ID NO: 393 linked to siRNA AB03 | 0.55 | 1.28 | 11.35 | 6.44 |
| SEQ ID NO: 393 linked to siRNA AB15 | 0.95 | 2.07 | 17.27 | 37.35 |

These data demonstrate that the FN3-siRNA conjugates were active.

These examples demonstrate the surprising and unexpected ability of the FN3-siRNA conjugates to reduce different mutant forms of a target gene and also inhibit cellular proliferation. The results also demonstrate that it can be done with a composition comprising more than one FN3 domain and still effectively deliver a siRNA molecule, which has not previously been demonstrated. Furthermore, the examples and embodiments provided herein demonstrate FN3 Domain-siRNA conjugates enable receptor specific delivery of siRNA to extra-hepatic cell types; intracellular trafficking and an endosomal depot for FN3 contributes to an extended duration of activity of FN3-siRNA conjugates; FN3-siRNA conjugates have demonstrated potent reduction of mRNA and protein and inhibition of proliferation in epithelial tumor cell lines; and bispecific binding of FN3 domains to tumor cells expressing high levels of targeted receptors improves avidity and activity and can improve selectivity EXAMPLE 12. Knockdown of mRNA in muscle cells using CD71 FN3 domain-oligonucleotide conjugates. muCD71 binding FN3 domains are conjugated to siRNA oligonucleotides or antisense oligonucleotides (ASOs) using maleimide chemistry via a cysteine that is uniquely engineered into the FN3 domain. The cysteine substitutions can be one such as those provided for herein and also as provided for in U.S. Patent Application Publication No. 20150104808, which is hereby incorporated by reference in its entirety. siRNAs or ASOs are modified with standard chemical modifications and confirmed to enable knockdown of the targeted mRNA in vitro. FN3 domain-oligonucleotide conjugates are dosed intravenously in mice at doses up to 10 mg/kg oligonucleotide payload. At various time points following dosing, mice are sacrificed; skeletal muscle, heart muscle and various other tissues will be recovered and stored in RNAlater™ (Sigma Aldrich) until needed. Target gene knockdown is assessed using standard qPCR ΔΔCT methods and primers specific for the target gene and a control gene. The target gene is found to be knock downed in the muscles and such knockdown is enhanced by conjugating the siRNA or ASO to the CD71 FN3 binding domain.

The results and embodiments provided herein demonstrate that the FN3-siRNA conjugates can provide receptor specific delivery of KRAS siRNA. They provide high potency against tumor cell lines and provide FN3 domain conjugates demonstrate differentiated trafficking vs. antibodies facilitating siRNA delivery. These results also demonstrate that the FN3 domains can be used for delivery of any siRNA payloads or other payloads into tumor cells or other cells that have internalizing receptor positive cells.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$* ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for*

*Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol. 1*, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol. 4*, John Wiley, Inc., New York).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications of the embodiments in addition to those described herein will become apparent to those skilled in the art from the foregoing description. Such modifications are intended to fall within the scope of the appended claims.

The foregoing written specification is considered to be sufficient to enable one skilled in the art to practice the embodiments. Various modifications of the embodiments in addition to those shown and described herein will become apparent to those skilled in the art from the foregoing description and fall within the scope of the appended claims.

What is claimed is:

1. A composition comprising a siRNA molecule comprising a sense strand and antisense strand, wherein:
the sense strand comprises a sequence of SEQ ID NO: 12, 18, 24, 30, 34, 152, 154, 164, 170, 182, 212, 214, or 216; and
the anti-sense strand comprises a sequence of SEQ ID NO: 13, 19, 25, 31, 35, 153, 155, 165, 171, 183, 213, 215, or 217.

2. The composition of claim 1, wherein the siRNA further comprises a linker, wherein the linker is covalently attached to the sense strand or the anti-sense strand of the siRNA.

3. The composition of claim 2, wherein the siRNA is linked to one or more FN3 domains.

4. The composition of claim 2, wherein the linker is covalently attached to the 3' end of the sense strand.

5. The composition of claim 4, wherein the siRNA is linked to one or more FN3 domains.

6. The composition of claim 2, wherein the linker comprises a compound having the formula of:

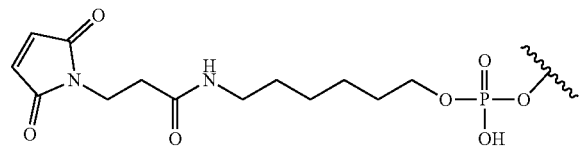 [SMILES: *OP(=O)(O)OCCCCCCNC(=O)CCN1C(=O)C=CC1=O]

7. The composition of claim 6, wherein the siRNA is linked to one or more FN3 domains.

8. The composition of claim 1, wherein the siRNA further comprises a vinyl phosphonate, wherein the vinyl phosphonate is covalently attached to the sense strand or the antisense strand of the siRNA.

9. The composition of claim 8, wherein the siRNA is linked to one or more FN3 domains.

10. The composition of claim 8, wherein the vinyl phosphonate is covalently attached to the 5' end of the antisense strand.

11. The composition of claim 10, wherein the siRNA is linked to one or more FN3 domains.

12. The composition of claim 1, wherein the siRNA further comprises a linker covalently attached to the 3' end of the sense strand and a vinyl phosphonate covalently attached to the 5' end of the antisense strand.

13. The composition of claim 12, wherein the siRNA is linked to one or more FN3 domains.

14. The composition of claim 12, wherein the siRNA molecule comprises:
a sense strand of SEQ ID NO: 188 and an antisense strand of SEQ ID NO: 189;
a sense strand of SEQ ID NO: 190 and an antisense strand of SEQ ID NO: 191;
a sense strand of SEQ ID NO: 192 and an antisense strand of SEQ ID NO: 193;
a sense strand of SEQ ID NO: 196 and an antisense strand of SEQ ID NO: 197;
a sense strand of SEQ ID NO: 206 and an antisense strand of SEQ ID NO: 207; or
a sense strand of SEQ ID NO: 210 and an antisense strand of SEQ ID NO: 211.

15. The composition of claim 12, wherein
the sense strand comprises a sequence of SEQ ID NO: 188, 190, 192, 196, 206, or 210; and
the anti-sense strand comprises a sequence of SEQ ID NO: 189, 191, 193, 197, 207, or 211.

16. The composition of claim 15, wherein the siRNA is linked to one or more FN3 domains.

17. The composition of claim 1, wherein the siRNA molecule comprises:
a sense strand of SEQ ID NO: 12 and an antisense strand of SEQ ID NO: 13;
a sense strand of SEQ ID NO: 18 and an antisense strand of SEQ ID NO: 19;
a sense strand of SEQ ID NO: 24 and an antisense strand of SEQ ID NO: 25;
a sense strand of SEQ ID NO: 30 and an antisense strand of SEQ ID NO: 31;
a sense strand of SEQ ID NO: 34 and an antisense strand of SEQ ID NO: 35;
a sense strand of SEQ ID NO: 152 and an antisense strand of SEQ ID NO: 153;

a sense strand of SEQ ID NO: 154 and an antisense strand of SEQ ID NO: 155;

a sense strand of SEQ ID NO: 164 and an antisense strand of SEQ ID NO: 165;

a sense strand of SEQ ID NO: 170 and an antisense strand of SEQ ID NO: 171;

a sense strand of SEQ ID NO: 182 and an antisense strand of SEQ ID NO: 183;

a sense strand of SEQ ID NO: 212 and an antisense strand of SEQ ID NO: 213;

a sense strand of SEQ ID NO: 214 and an antisense strand of SEQ ID NO: 215; or a sense strand of SEQ ID NO: 216 and an antisense strand of SEQ ID NO: 217.

18. The composition of claim 17, wherein the siRNA is linked to one or more FN3 domains.

19. The composition of claim 1, wherein the siRNA is linked to one or more FN3 domains.

20. A pharmaceutical composition comprising a composition of claim 19.

21. A method of treating cancer in a subject in need thereof, the method comprising administering to the subject the composition of claim 19.

22. A method of reducing the expression of KRAS in a cell, the method comprising contacting the cell with the composition of claim 19.

23. A method of delivering a siRNA that targets KRAS to a cell in a subject, the method comprising administering to the subject a pharmaceutical composition comprising the composition of claim 19.

24. A composition having a formula of (X1)n-(X2)q-(X3)y-L-X4, wherein:
   X1 is a first FN3 domain;
   X2 is second FN3 domain;
   X3 is a third FN3 domain or half-life extender molecule;
   L is a linker; and
   X4 is a nucleic acid molecule,
   wherein n, q, and y are each independently 0 or 1, and
   wherein the nucleic acid molecule comprises a siRNA molecule having:
      a sense strand comprising a sequence of SEQ ID NO: 12, 18, 24, 30, 34, 152, 154, 164, 170, 182, 188, 190, 192, 196, 206, 210, 212, 214, or 216; and
      an anti-sense strand comprising a sequence of SEQ ID NO: 13, 19, 25, 31, 35, 153, 155, 165, 171, 183, 189, 191, 193, 197, 207, 211, 213, 215, or 217.

25. The composition of claim 24, wherein L comprises a compound having the formula of:

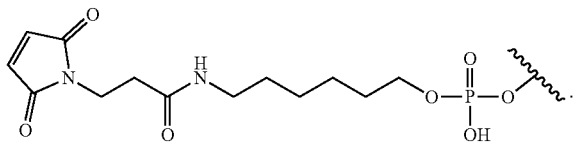 [SMILES: *OP(=O)(O)OCCCCCCNC(=O)CCN1C(=O)C=CC1=O]

26. The composition of claim 24, wherein each of X1, X2, or X3 is linked by a linker, wherein the linker comprises a sequences of SEQ ID NO: 369, 370, 371, 372, 373, 374, 375, or 376.

27. The composition of claim 24, wherein X1 comprises a sequence of SEQ ID NO: 300-335, 337-368, 377-392, or 395-623.

28. The composition of claim 24, wherein X2 comprises a sequence of SEQ ID NO: 300-335, 337-368, 377-392, or 395-623.

29. The composition of claim 24, wherein X3 comprises a sequence of SEQ ID NO: 300-335, 337-368, 377-392, or 395-623.

30. A composition having a formula A1-B1, wherein A1 has a formula of C1-L1-XS and B1 has a formula of XAS-L2-F1, wherein:
   C1 is a polymer;
   L1 and L2 are each, independently, a linker;
   XS is a 5' to 3' oligonucleotide sense strand of a double stranded siRNA molecule comprising a sequence of SEQ ID NO: 12, 18, 24, 30, 34, 152, 154, 164, 170, 182, 188, 190, 192, 196, 206, 210, 212, 214, or 216;
   XAS is a 3' to 5' oligonucleotide antisense strand of a double stranded siRNA molecule comprising a sequence of SEQ ID NO: 13, 19, 25, 31, 35, 153, 155, 165, 171, 183, 189, 191, 193, 197, 207, 211, 213, 215, or 217; and
   F1 is a polypeptide comprising at least one FN3 domain.

31. The composition of claim 30, wherein A1-B1 has a formula of:

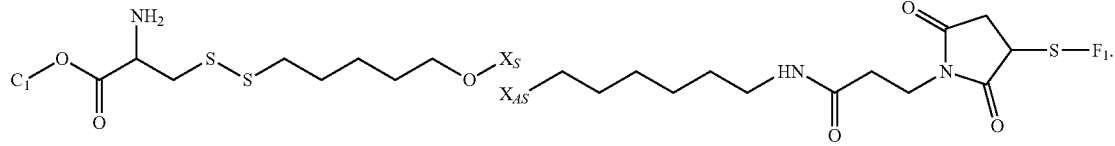

32. The composition of claim 30, wherein F1 comprises a polypeptide having a formula of (X1)n-(X2)q-(X3)y,
   wherein X1 is a first FN3 domain; X2 is second FN3 domain; X3 is a third FN3 domain or half-life extender molecule; and
   wherein n, q, and y are each independently 0 or 1, provided that at least one of n, q, and y is 1.

33. The composition of claim 32, wherein X1 comprises a sequence of SEQ ID NO: 300-335, 337-368, 377-392, or 395-623.

34. The composition of claim 32, wherein X2 comprises a sequence of SEQ ID NO: 300-335, 337-368, 377-392, or 395-623.

35. The composition of claim 32, wherein X3 comprises a sequence of SEQ ID NO: 300-335, 337-368, 377-392, or 395-623.

36. The composition of claim 30, wherein the linker comprises a sequence of SEQ ID NO: 369, 370, 371, 372, 373, 374, 375, or 376.

* * * * *

SEQUENCE LISTING

```
<160> NUMBER OF SEQ ID NOS: 624

<210> SEQ ID NO 1
<211> LENGTH: 87
<212> TYPE: PRT
<213> ORGANISM: Homo sapiens

<400> SEQUENCE: 1

Ser Pro Pro Lys Asp Leu Val Val Thr Glu Val Thr Glu Glu Thr Val
1               5                   10                  15

Asn Leu Ala Trp Asp Asn Glu Met Arg Val Thr Glu Tyr Leu Val Val
            20                  25                  30

Tyr Thr Pro Thr His Glu Gly Gly Leu Glu Met Gln Phe Arg Val Pro
        35                  40                  45

Gly Asp Gln Thr Ser Thr Ile Ile Gln Glu Leu Glu Pro Gly Val Glu
    50                  55                  60

Tyr Phe Ile Arg Val Phe Ala Ile Leu Glu Asn Lys Lys Ser Ile Pro
65                  70                  75                  80

Val Ser Ala Arg Val Ala Thr
                85

<210> SEQ ID NO 2
<211> LENGTH: 291
<212> TYPE: PRT
<213> ORGANISM: Homo sapiens

<400> SEQUENCE: 2

Met Thr Lys Glu Tyr Gln Asp Leu Gln His Leu Asp Asn Glu Glu Ser
1               5                   10                  15

Asp His His Gln Leu Arg Lys Gly Pro Pro Pro Gln Pro Leu Leu
            20                  25                  30

Gln Arg Leu Cys Ser Gly Pro Arg Leu Leu Leu Leu Ser Leu Gly Leu
        35                  40                  45

Ser Leu Leu Leu Leu Val Val Val Cys Val Ile Gly Ser Gln Asn Ser
    50                  55                  60

Gln Leu Gln Glu Glu Leu Arg Gly Leu Arg Glu Thr Phe Ser Asn Phe
65                  70                  75                  80
```

```
Thr Ala Ser Thr Glu Ala Gln Val Lys Gly Leu Ser Thr Gln Gly Gly
                85                  90                  95

Asn Val Gly Arg Lys Met Lys Ser Leu Glu Ser Gln Leu Glu Lys Gln
            100                 105                 110

Gln Lys Asp Leu Ser Glu Asp His Ser Ser Leu Leu His Val Lys
        115                 120                 125

Gln Phe Val Ser Asp Leu Arg Ser Leu Ser Cys Gln Met Ala Ala Leu
    130                 135                 140

Gln Gly Asn Gly Ser Glu Arg Thr Cys Cys Pro Val Asn Trp Val Glu
145                 150                 155                 160

His Glu Arg Ser Cys Tyr Trp Phe Ser Arg Ser Gly Lys Ala Trp Ala
                165                 170                 175

Asp Ala Asp Asn Tyr Cys Arg Leu Glu Asp Ala His Leu Val Val Val
            180                 185                 190

Thr Ser Trp Glu Glu Gln Lys Phe Val Gln His His Ile Gly Pro Val
        195                 200                 205

Asn Thr Trp Met Gly Leu His Asp Gln Asn Gly Pro Trp Lys Trp Val
    210                 215                 220

Asp Gly Thr Asp Tyr Glu Thr Gly Phe Lys Asn Trp Arg Pro Glu Gln
225                 230                 235                 240

Pro Asp Asp Trp Tyr Gly His Gly Leu Gly Gly Gly Glu Asp Cys Ala
                245                 250                 255

His Phe Thr Asp Asp Gly Arg Trp Asn Asp Val Cys Gln Arg Pro
            260                 265                 270

Tyr Arg Trp Val Cys Gly Thr Glu Leu Asp Lys Ala Ser Gln Glu Pro
        275                 280                 285

Pro Leu Leu
    290

<210> SEQ ID NO 3
<211> LENGTH: 92
<212> TYPE: PRT
<213> ORGANISM: Artificial Sequence
<220> FEATURE:
<223> OTHER INFORMATION: synthetic sequence

<400> SEQUENCE: 3

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Leu Tyr Leu Glu Leu Asn His Gly Glu Glu Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Tyr Ile Phe Gly Val Lys Gly Gly Met Tyr
65                  70                  75                  80

Ser Ala Pro Leu Ser Ala Ile Phe Thr Thr Gly Gly
                85                  90

<210> SEQ ID NO 4
<211> LENGTH: 89
<212> TYPE: PRT
<213> ORGANISM: Artificial Sequence
<220> FEATURE:
<223> OTHER INFORMATION: synthetic sequence

<400> SEQUENCE: 4
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
                20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85

<210> SEQ ID NO 5
<211> LENGTH: 230
<212> TYPE: PRT
<213> ORGANISM: Homo sapiens

<400> SEQUENCE: 5

Gln Asn Ser Gln Leu Gln Glu Glu Leu Arg Gly Leu Arg Glu Thr Phe
1               5                   10                  15

Ser Asn Phe Thr Ala Ser Thr Glu Ala Gln Val Lys Gly Leu Ser Thr
                20                  25                  30

Gln Gly Gly Asn Val Gly Arg Lys Met Lys Ser Leu Glu Ser Gln Leu
                35                  40                  45

Glu Lys Gln Gln Lys Asp Leu Ser Glu Asp His Ser Ser Leu Leu Leu
50                  55                  60

His Val Lys Gln Phe Val Ser Asp Leu Arg Ser Leu Ser Cys Gln Met
65                  70                  75                  80

Ala Ala Leu Gln Gly Asn Gly Ser Glu Arg Thr Cys Cys Pro Val Asn
                85                  90                  95

Trp Val Glu His Glu Arg Ser Cys Tyr Trp Phe Ser Arg Ser Gly Lys
                100                 105                 110

Ala Trp Ala Asp Ala Asp Asn Tyr Cys Arg Leu Glu Asp Ala His Leu
                115                 120                 125

Val Val Val Thr Ser Trp Glu Glu Gln Lys Phe Val Gln His His Ile
130                 135                 140

Gly Pro Val Asn Thr Trp Met Gly Leu His Asp Gln Asn Gly Pro Trp
145                 150                 155                 160

Lys Trp Val Asp Gly Thr Asp Tyr Glu Thr Gly Phe Lys Asn Trp Arg
                165                 170                 175

Pro Glu Gln Pro Asp Asp Trp Tyr Gly His Gly Leu Gly Gly Gly Glu
                180                 185                 190

Asp Cys Ala His Phe Thr Asp Asp Gly Arg Trp Asn Asp Asp Val Cys
                195                 200                 205

Gln Arg Pro Tyr Arg Trp Val Cys Glu Thr Glu Leu Asp Lys Ala Ser
                210                 215                 220

Gln Glu Pro Pro Leu Leu
225                 230

<210> SEQ ID NO 6

<400> SEQUENCE: 6

000

-continued

```
<210> SEQ ID NO 7
<400> SEQUENCE: 7

000

<210> SEQ ID NO 8
<400> SEQUENCE: 8

000

<210> SEQ ID NO 9
<400> SEQUENCE: 9

000

<210> SEQ ID NO 10
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residue
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residue
<220> FEATURE:
<221> NAME/KEY: misc_feature
<222> LOCATION: (17)..(17)
<223> OTHER INFORMATION: 2'-F residue
<220> FEATURE:
<221> NAME/KEY: misc_feature
<222> LOCATION: (19)..(19)
<223> OTHER INFORMATION: inverted Dt

<400> SEQUENCE: 10
ccugucucuu ggauauuca                                                  19

<210> SEQ ID NO 11
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
```

```
<223> OTHER INFORMATION: phosphorothioate
<220> FEATURE:
<221> NAME/KEY: misc_feature
<222> LOCATION: (14)..(14)
<223> OTHER INFORMATION: 2'-F residue
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 11 ugaauauccaagagacaggu u                                                   21

<210> SEQ ID NO 12
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residue
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residue
<220> FEATURE:
<221> NAME/KEY: misc_feature
<222> LOCATION: (17)..(17)
<223> OTHER INFORMATION: 2'-F residue
<220> FEATURE:
<221> NAME/KEY: misc_feature
<222> LOCATION: (19)..(19)
<223> OTHER INFORMATION: inverted Dt

<400> SEQUENCE: 12
cagcuaauuc agaaucaua                                                     19

<210> SEQ ID NO 13
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
```

```
<222> LOCATION: (14)..(14)
<223> OTHER INFORMATION: 2'-F residue
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 13
uaugauucug aauuagcugu u                                      21

<210> SEQ ID NO 14
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residue
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residue
<220> FEATURE:
<221> NAME/KEY: misc_feature
<222> LOCATION: (17)..(17)
<223> OTHER INFORMATION: 2'-F residue
<220> FEATURE:
<221> NAME/KEY: misc_feature
<222> LOCATION: (19)..(19)
<223> OTHER INFORMATION: 2'-F residue
<220> FEATURE:
<221> NAME/KEY: misc_feature
<222> LOCATION: (19)..(19)
<223> OTHER INFORMATION: inverted Dt

<400> SEQUENCE: 14
gaauuagcug uaucgucaa                                         19

<210> SEQ ID NO 15
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
```

```
<221> NAME/KEY: misc_feature
<222> LOCATION: (14)..(14)
<223> OTHER INFORMATION: 2'-F residue
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 15
uugacgauac agcuaauucu u                                          21

<210> SEQ ID NO 16
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residue
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residue
<220> FEATURE:
<221> NAME/KEY: misc_feature
<222> LOCATION: (5)..(5)
<223> OTHER INFORMATION: 2'-F residue
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residue
<220> FEATURE:
<221> NAME/KEY: misc_feature
<222> LOCATION: (15)..(15)
<223> OTHER INFORMATION: 2'-F residue
<220> FEATURE:
<221> NAME/KEY: misc_feature
<222> LOCATION: (17)..(17)
<223> OTHER INFORMATION: 2'-F residue
<220> FEATURE:
<221> NAME/KEY: misc_feature
<222> LOCATION: (19)..(19)
<223> OTHER INFORMATION: 2'-F residue
<220> FEATURE:
<221> NAME/KEY: misc_feature
<222> LOCATION: (19)..(19)
<223> OTHER INFORMATION: inverted Dt

<400> SEQUENCE: 16
ccugucucuu ggauauuca                                             19

<210> SEQ ID NO 17
<211> LENGTH: 21
<212> TYPE: RNA
<213> ORGANISM: Artificial Sequence
<220> FEATURE:
<223> OTHER INFORMATION: synthetic sequence
```

```
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residue
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residue
<220> FEATURE:
<221> NAME/KEY: misc_feature
<222> LOCATION: (6)..(8)
<223> OTHER INFORMATION: 2'-F residue
<220> FEATURE:
<221> NAME/KEY: misc_feature
<222> LOCATION: (10)..(10)
<223> OTHER INFORMATION: 2'-F residue
<220> FEATURE:
<221> NAME/KEY: misc_feature
<222> LOCATION: (14)..(14)
<223> OTHER INFORMATION: 2'-F residue
<220> FEATURE:
<221> NAME/KEY: misc_feature
<222> LOCATION: (16)..(16)
<223> OTHER INFORMATION: 2'-F residue
<220> FEATURE:
<221> NAME/KEY: misc_feature
<222> LOCATION: (18)..(18)
<223> OTHER INFORMATION: 2'-F residue
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate
<220> FEATURE:
<221> NAME/KEY: misc_feature
<222> LOCATION: (20)..(20)
<223> OTHER INFORMATION: 2'-F residue

<400> SEQUENCE: 17
ugaauaucca agagacaggu u                                               21

<210> SEQ ID NO 18
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residue
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residue
<220> FEATURE:
<221> NAME/KEY: misc_feature
<222> LOCATION: (6)..(6)
```

```
<223> OTHER INFORMATION: 2'-F residue
<220> FEATURE:
<221> NAME/KEY: misc_feature
<222> LOCATION: (8)..(10)
<223> OTHER INFORMATION: 2'-F residue
<220> FEATURE:
<221> NAME/KEY: misc_feature
<222> LOCATION: (12)..(12)
<223> OTHER INFORMATION: 2'-F residue
<220> FEATURE:
<221> NAME/KEY: misc_feature
<222> LOCATION: (16)..(16)
<223> OTHER INFORMATION: 2'-F residue
<220> FEATURE:
<221> NAME/KEY: misc_feature
<222> LOCATION: (18)..(18)
<223> OTHER INFORMATION: 2'-F residue
<220> FEATURE:
<221> NAME/KEY: misc_feature
<222> LOCATION: (20)..(20)
<223> OTHER INFORMATION: 2'-F residue
<220> FEATURE:
<221> NAME/KEY: misc_feature
<222> LOCATION: (20)..(20)
<223> OTHER INFORMATION: inverted Dt

<400> SEQUENCE: 18
cagcuaauuc agaaucuaua                                              20

<210> SEQ ID NO 19
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residue
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residue
<220> FEATURE:
<221> NAME/KEY: misc_feature
<222> LOCATION: (6)..(8)
<223> OTHER INFORMATION: 2'-F residue
<220> FEATURE:
<221> NAME/KEY: misc_feature
<222> LOCATION: (10)..(10)
<223> OTHER INFORMATION: 2'-F residue
<220> FEATURE:
<221> NAME/KEY: misc_feature
<222> LOCATION: (14)..(14)
<223> OTHER INFORMATION: 2'-F residue
<220> FEATURE:
<221> NAME/KEY: misc_feature
<222> LOCATION: (16)..(16)
<223> OTHER INFORMATION: 2'-F residue
<220> FEATURE:
<221> NAME/KEY: misc_feature
<222> LOCATION: (18)..(18)
<223> OTHER INFORMATION: 2'-F residue
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
```

```
<222> LOCATION: (20)..(20)
<223> OTHER INFORMATION: 2'-F residue
<220> FEATURE:
<221> NAME/KEY: misc_feature
<222> LOCATION: (20)..(21)
<223> OTHER INFORMATION: phosphorothioate

<400> SEQUENCE: 19
uaugauucug aauuagcugu u                                          21

<210> SEQ ID NO 20
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residue
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residue
<220> FEATURE:
<221> NAME/KEY: misc_feature
<222> LOCATION: (5)..(5)
<223> OTHER INFORMATION: 2'-F residue
<220> FEATURE:
<221> NAME/KEY: misc_feature
<222> LOCATION: (7)..(9)
<223> OTHER INFORMATION: 2'-F residue
<220> FEATURE:
<221> NAME/KEY: misc_feature
<222> LOCATION: (11)..(11)
<223> OTHER INFORMATION: 2'-F residue
<220> FEATURE:
<221> NAME/KEY: misc_feature
<222> LOCATION: (15)..(15)
<223> OTHER INFORMATION: 2'-F residue
<220> FEATURE:
<221> NAME/KEY: misc_feature
<222> LOCATION: (17)..(17)
<223> OTHER INFORMATION: 2'-F residue
<220> FEATURE:
<221> NAME/KEY: misc_feature
<222> LOCATION: (19)..(19)
<223> OTHER INFORMATION: 2'-F residue
<220> FEATURE:
<221> NAME/KEY: misc_feature
<222> LOCATION: (20)..(20)
<223> OTHER INFORMATION: inverted Dt

<400> SEQUENCE: 20
gaauuagcug uaucgucaa                                             19

<210> SEQ ID NO 21
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
```

-continued

```
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(8)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 21
uugacgauac agcuaauucu u                                              21

<210> SEQ ID NO 22
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
```

```
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 22
ccugucucuu ggauauuca                                              19

<210> SEQ ID NO 23
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (8)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
```

```
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 23
ugaauaucca agagacaggu u                                          21

<210> SEQ ID NO 24
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (8)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 24
```
cagcuaauuc agaaucaua                                            19

<210> SEQ ID NO 25
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate

<400> SEQUENCE: 25
uaugauucug aauuagcguu                                           20

<210> SEQ ID NO 26
<211> LENGTH: 19
<212> TYPE: RNA
<213> ORGANISM: Artificial Sequence
<220> FEATURE:
<223> OTHER INFORMATION: synthetic sequence
<220> FEATURE:

```
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (8)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 26
gaauuagcug uaucgucaa                                              19

<210> SEQ ID NO 27
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
```

```
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate

<400> SEQUENCE: 27
uugacauaca gcuaauucuu                                                    20

<210> SEQ ID NO 28
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 28
```
ccugucucuu ggauauuca                                                    19

<210> SEQ ID NO 29
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 29
ugaauaucca agagacaggu u                                                 21

<210> SEQ ID NO 30
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 30
cagcuaauuc agaaucaua                                                    19

```
<210> SEQ ID NO 31
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 31
uaugauucug aauuagcugu u                                              21

<210> SEQ ID NO 32
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 32
gaauuagcug uaucgucaa                                                 19

<210> SEQ ID NO 33
<211> LENGTH: 21
<212> TYPE: RNA
```

```
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 33
uugacgauac agcuaauucu u                                              21

<210> SEQ ID NO 34
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 34
cagcuaauuc agaaucaua                                                 19

<210> SEQ ID NO 35
<211> LENGTH: 21
<212> TYPE: RNA
<213> ORGANISM: Artificial Sequence
<220> FEATURE:
<223> OTHER INFORMATION: synthetic sequence
```

```
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 35
uaugauucug aauuagcugu u                                                    21

<210> SEQ ID NO 36
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 36
auauaaacuu gugguagua                                                       19

<210> SEQ ID NO 37
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
```

```
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 37
uacuaccaca aguuuauauu u                                           21

<210> SEQ ID NO 38
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 38
uaaacuugug guaguugga                                              19

<210> SEQ ID NO 39
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
```

```
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 39
uccaacuacc acaaguuuau u                                              21

<210> SEQ ID NO 40
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 40
caagagugcc uugacgaua                                                 19

<210> SEQ ID NO 41
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
```

```
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 41
uaucgucaag gcacucuugu u                                              21

<210> SEQ ID NO 42
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: inverted Dt
<220> FEATURE:
<221> NAME/KEY: misc_feature
<222> LOCATION: (2)..(3)
<223> OTHER INFORMATION: inverted Dt
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 42
gccuugacga uacagcuaa                                                 19

<210> SEQ ID NO 43
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
```

```
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 43
uuagcuguau cgucaaggcu u                                        21

<210> SEQ ID NO 44
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 44
ugacgauaca gcuaauuca                                           19

<210> SEQ ID NO 45
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
```

```
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 45
ugaauuagcu guaucgucau u                                              21

<210> SEQ ID NO 46
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 46
cgauacagcu aauucagaa                                                 19

<210> SEQ ID NO 47
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
```

```
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 47
uucugaauua gcuguaucgu u                                              21

<210> SEQ ID NO 48
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 48
guggacgaau augauccaa                                                 19

<210> SEQ ID NO 49
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
```

```
<221> NAME/KEY: misc_feature
<222> LOCATION: (20)..(21)
<223> OTHER INFORMATION: phosphorothioate

<400> SEQUENCE: 49
uuggaucaua uucguccacu u                                              21

<210> SEQ ID NO 50
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 50
ggacgaauau gauccaaca                                                 19

<210> SEQ ID NO 51
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (2)..(3)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: 2'-F residues
<220> FEATURE:
<221> NAME/KEY: misc_feature
<222> LOCATION: (20)..(21)
<223> OTHER INFORMATION: 2'-F residues
```

-continued

<400> SEQUENCE: 51
uguuggauca uauucguccu u                                              21

<210> SEQ ID NO 52
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 52
gacgaauaug auccaacaa                                                 19

<210> SEQ ID NO 53
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (2)..(3)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: 2'-F residues
<220> FEATURE:
<221> NAME/KEY: misc_feature
<222> LOCATION: (20)..(21)
<223> OTHER INFORMATION: 2'-F residues

<400> SEQUENCE: 53
uuguuggauc auauucgucu u                                         21

<210> SEQ ID NO 54
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 54
acgaauauga uccaacaaa                                            19

<210> SEQ ID NO 55
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 55
uuuguuggau cauauucguu u                                         21

```
<210> SEQ ID NO 56
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 56
cgaauaugau ccaacaaua                                               19

<210> SEQ ID NO 57
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 57
uauuguugga ucauauucgu u                                            21

<210> SEQ ID NO 58
<211> LENGTH: 19
<212> TYPE: RNA
```

```
-continued

<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 58
aauaugaucc aacaauaga                                                    19

<210> SEQ ID NO 59
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 59
ucuauuguug gaucauauuu u                                                 21

<210> SEQ ID NO 60
<211> LENGTH: 19
<212> TYPE: RNA
<213> ORGANISM: Artificial Sequence
<220> FEATURE:
<223> OTHER INFORMATION: synthetic sequence
```

```
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 60
gauccaacaa uagaggaua                                                   19

<210> SEQ ID NO 61
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 61
uauccucuau uguuggaucu u                                                21

<210> SEQ ID NO 62
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
```

```
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 62
ccaacaauag aggauucca                                               19

<210> SEQ ID NO 63
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 63
uggaauccuc uauuguuggu u                                            21

<210> SEQ ID NO 64
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
```

```
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 64
cuacaggaag caaguagua                                                    19

<210> SEQ ID NO 65
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 65
uacuacuugc uuccuguagu u                                                 21

<210> SEQ ID NO 66
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
```

```
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 66
acaggaagca aguaguaaa                                                   19

<210> SEQ ID NO 67
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 67
uuuacuacuu gcuuccuguu u                                                21

<210> SEQ ID NO 68
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
```

```
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 68
guaauugaug gagaaacca                                                      19

<210> SEQ ID NO 69
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 69
ugguuucucc aucaauuacu u                                                   21

<210> SEQ ID NO 70
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
```

```
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 70
cuuggauauu cucgacaca                                               19

<210> SEQ ID NO 71
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 71
ugugucgaga auauccaagu u                                            21

<210> SEQ ID NO 72
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
```

<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 72
cagcagguca agaggagua                                                19

<210> SEQ ID NO 73
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 73
uacuccucuu gaccugcugu u                                             21

<210> SEQ ID NO 74
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:

```
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 74
gcaaugaggg accaguaca                                                        19

<210> SEQ ID NO 75
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 75
uguacugguc ccucauugcu u                                                     21

<210> SEQ ID NO 76
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
```

-continued

```
<220> FEATURE:
<221> NAME/KEY: misc_feature
<222> LOCATION: (19)..(19)
<223> OTHER INFORMATION: inverted Dt

<400> SEQUENCE: 76
caaugaggga ccaguacaa                                                    19

<210> SEQ ID NO 77
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 77
uuguacuggu cccucauugu u                                                 21

<210> SEQ ID NO 78
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
```

<223> OTHER INFORMATION: inverted Dt

<400> SEQUENCE: 78
uuuguguauu ugccauaaa                                                        19

<210> SEQ ID NO 79
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 79
uuuauggcaa auacacaaau u                                                     21

<210> SEQ ID NO 80
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 80

```
uugccauaaa uaauacuaa                                           19
```

<210> SEQ ID NO 81
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 81

```
uuaguauuau uuauggcaau u                                        21
```

<210> SEQ ID NO 82
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 82

```
ugccauaaau aauacuaaa                                           19
```

```
<210> SEQ ID NO 83
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 83
uuuaguauua uuuauggcau u                                            21

<210> SEQ ID NO 84
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 84
ccauaaauaa uacuaaaua                                               19

<210> SEQ ID NO 85
<211> LENGTH: 21
```

```
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 85
uauuuaguau uauuuauggu u                                          21

<210> SEQ ID NO 86
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 86
cauaaauaau acuaaauca                                             19

<210> SEQ ID NO 87
<211> LENGTH: 21
<212> TYPE: RNA
<213> ORGANISM: Artificial Sequence
<220> FEATURE:
```

```
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 87
ugauuuagua uuauuuaugu u                                              21

<210> SEQ ID NO 88
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 88
auaaauaaua cuaaaucaa                                                 19

<210> SEQ ID NO 89
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
```

<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 89
uugauuuagu auuauuuauu u                                        21

<210> SEQ ID NO 90
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 90
gaagauauuc accauuaua                                           19

<210> SEQ ID NO 91
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:

```
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 91
uauaauggug aauaucuucu u                                             21

<210> SEQ ID NO 92
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 92
agauauucac cauuauaga                                                19

<210> SEQ ID NO 93
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
```

```
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 93
ucuauaaugg ugaauaucuu u                                              21

<210> SEQ ID NO 94
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 94
auauucacca uuauagaga                                                 19

<210> SEQ ID NO 95
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
```

```
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 95
ucucuauaau ggugaauauu u                                              21

<210> SEQ ID NO 96
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 96
agaacaaauu aaaagagua                                                 19

<210> SEQ ID NO 97
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
```

```
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 97
uacucuuuua auuuguucuu u                                              21

<210> SEQ ID NO 98
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 98
gacucugaag auguaccua                                                 19

<210> SEQ ID NO 99
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
```

```
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 99
uagguacauc uucagagucu u                                              21

<210> SEQ ID NO 100
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 100
cugaagaugu accuaugga                                                 19

<210> SEQ ID NO 101
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
```

```
<220> FEATURE:
<221> NAME/KEY: misc_feature
<222> LOCATION: (20)..(21)
<223> OTHER INFORMATION: phosphorothioate

<400> SEQUENCE: 101
uccauaggua caucuucagu u                                              21

<210> SEQ ID NO 102
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 102
agaacaguag acacaaaaa                                                 19

<210> SEQ ID NO 103
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
```

<223> OTHER INFORMATION: phosphorothioate

<400> SEQUENCE: 103
uuuuuguguc uacuguucuu u                                              21

<210> SEQ ID NO 104
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 104
caggacuuag caagaagua                                                 19

<210> SEQ ID NO 105
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 105
uacuucuugc uaaguccugu u                                                  21

<210> SEQ ID NO 106
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 106
guugaugaug ccuucuaua                                                     19

<210> SEQ ID NO 107
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 107
uauagaaggc aucaucaacu u                                                  21

```
<210> SEQ ID NO 108
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: inverted Dt
<220> FEATURE:
<221> NAME/KEY: misc_feature
<222> LOCATION: (2)..(3)
<223> OTHER INFORMATION: inverted Dt
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 108
augaugccuu cuauacaua                                              19

<210> SEQ ID NO 109
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 109
uauguauaga aggcaucauu u                                           21

<210> SEQ ID NO 110
<211> LENGTH: 19
```

```
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 110
ugaugccuuc uauacauua                                          19

<210> SEQ ID NO 111
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 111
uaauguauag aaggcaucau u                                       21

<210> SEQ ID NO 112
<211> LENGTH: 19
<212> TYPE: RNA
<213> ORGANISM: Artificial Sequence
<220> FEATURE:
```

<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 112
gaugccuucu auacauuaa                                             19

<210> SEQ ID NO 113
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 113
uuaauguaua gaaggcaucu u                                          21

<210> SEQ ID NO 114
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature

```
<222> LOCATION: (1)..(2)
<223> OTHER INFORMATION: inverted Dt
<220> FEATURE:
<221> NAME/KEY: misc_feature
<222> LOCATION: (2)..(3)
<223> OTHER INFORMATION: inverted Dt
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt
<220> FEATURE:
<221> NAME/KEY: misc_feature
<222> LOCATION: (19)..(20)
<223> OTHER INFORMATION: inverted Dt
<220> FEATURE:
<221> NAME/KEY: misc_feature
<222> LOCATION: (20)..(21)
<223> OTHER INFORMATION: inverted Dt

<400> SEQUENCE: 114
augccuucua uacauuaga                                              19

<210> SEQ ID NO 115
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 115
ucuaauguau agaaggcauu u                                           21

<210> SEQ ID NO 116
<211> LENGTH: 19
<212> TYPE: RNA
```

```
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 116
cuucuauaca uuaguucga                                              19

<210> SEQ ID NO 117
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 117
ucgaacuaau guauagaagu u                                           21

<210> SEQ ID NO 118
<211> LENGTH: 19
<212> TYPE: RNA
<213> ORGANISM: Artificial Sequence
<220> FEATURE:
<223> OTHER INFORMATION: synthetic sequence
```

```
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 118
ucuauacauu aguucgaga                                              19

<210> SEQ ID NO 119
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 119
ucucgaacua auguauagau u                                           21

<210> SEQ ID NO 120
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
```

-continued

```
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 120
uauacauuag uucgagaaa                                                 19

<210> SEQ ID NO 121
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 121
uuucucgaac uaauguauau u                                              21

<210> SEQ ID NO 122
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
```

```
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 122
auacauuagu ucgagaaaa                                            19

<210> SEQ ID NO 123
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 123
uuuucucgaa cuaauguauu u                                         21

<210> SEQ ID NO 124
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
```

```
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 124
uacauuaguu cgagaaaua                                                    19

<210> SEQ ID NO 125
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 125
uauuucucga acuaauguau u                                                 21

<210> SEQ ID NO 126
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
```

```
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 126
uuaguucgag aaauucgaa                                                  19

<210> SEQ ID NO 127
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 127
uucgaauuuc ucgaacuaau u                                               21

<210> SEQ ID NO 128
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
```

```
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 128
aguucgagaa auucgaaaa                                                    19

<210> SEQ ID NO 129
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 129
uuuucgaauu ucucgaacuu u                                                 21

<210> SEQ ID NO 130
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
```

```
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 130
agaaauucga aaacauaaa                                                    19

<210> SEQ ID NO 131
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 131
uuuauguuuu cgaauuucuu u                                                 21

<210> SEQ ID NO 132
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
```

```
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 132
gaaauucgaa aacauaaaa                                                         19

<210> SEQ ID NO 133
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 133
uuuuauguuu ucgaauuucu u                                                      21

<210> SEQ ID NO 134
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
```

```
<220> FEATURE:
<221> NAME/KEY: misc_feature
<222> LOCATION: (19)..(19)
<223> OTHER INFORMATION: inverted Dt

<400> SEQUENCE: 134
aaauucgaaa acauaaaga                                                          19

<210> SEQ ID NO 135
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 135
ucuuuauguu uucgaauuuu u                                                       21

<210> SEQ ID NO 136
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
```

<223> OTHER INFORMATION: inverted Dt

<400> SEQUENCE: 136
aauucgaaaa cauaaagaa                                                     19

<210> SEQ ID NO 137
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 137
uucuuuaugu uuucgaauuu u                                                  21

<210> SEQ ID NO 138
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 138

```
augagcaaag augguaaaa                                              19

<210> SEQ ID NO 139
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 139
uuuuaccauc uuugcucauu u                                           21

<210> SEQ ID NO 140
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 140
agcaaagaug guaaaaaga                                              19
```

```
<210> SEQ ID NO 141
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 141
ucuuuuuacc aucuuugcuu u                                       21

<210> SEQ ID NO 142
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 142
auuucugucu ugggguuua                                          19

<210> SEQ ID NO 143
<211> LENGTH: 21
```

```
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 143
uaaaccccaa gacagaaauu u                                             21

<210> SEQ ID NO 144
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 144
ggguuuuugg ugcaugcaa                                                19

<210> SEQ ID NO 145
<211> LENGTH: 21
<212> TYPE: RNA
<213> ORGANISM: Artificial Sequence
<220> FEATURE:
```

```
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 145
uugcaugcac caaaaacccu u                                               21

<210> SEQ ID NO 146
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 146
cgcacaaggc acuggguaa                                                  19

<210> SEQ ID NO 147
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
```

```
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 147
uuacccagug ccuugugcgu u                                           21

<210> SEQ ID NO 148
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 148
gcacaaggca cuggguaua                                              19

<210> SEQ ID NO 149
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
```

```
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 149
uauacccagu gccuugugcu u                                           21

<210> SEQ ID NO 150
<211> LENGTH: 14
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(4)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (14)..(14)
<223> OTHER INFORMATION: inverted Dt

<400> SEQUENCE: 150
cucuuggaua uuca                                                   14

<210> SEQ ID NO 151
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
```

```
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(4)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (4)..(5)
<223> OTHER INFORMATION: phosphorothioate
<220> FEATURE:
<221> NAME/KEY: misc_feature
<222> LOCATION: (5)..(6)
<223> OTHER INFORMATION: phosphorothioate
<220> FEATURE:
<221> NAME/KEY: misc_feature
<222> LOCATION: (6)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 151
ugaauaucca agagacaggu u                                          21

<210> SEQ ID NO 152
<211> LENGTH: 15
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(5)
```

```
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (15)..(15)
<223> OTHER INFORMATION: inverted Dt

<400> SEQUENCE: 152
aauucagaau cuaua                                                15

<210> SEQ ID NO 153
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(4)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (4)..(5)
<223> OTHER INFORMATION: phosphorothioate
<220> FEATURE:
<221> NAME/KEY: misc_feature
<222> LOCATION: (5)..(6)
<223> OTHER INFORMATION: phosphorothioate
<220> FEATURE:
<221> NAME/KEY: misc_feature
<222> LOCATION: (6)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
```

-continued

```
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 153
uaugauucug aauuagcugu u                                              21

<210> SEQ ID NO 154
<211> LENGTH: 15
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (15)..(15)
<223> OTHER INFORMATION: inverted Dt

<400> SEQUENCE: 154
aauucagaau cuaua                                                     15

<210> SEQ ID NO 155
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
```

```
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(4)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (4)..(5)
<223> OTHER INFORMATION: phosphorothioate
<220> FEATURE:
<221> NAME/KEY: misc_feature
<222> LOCATION: (5)..(6)
<223> OTHER INFORMATION: phosphorothioate
<220> FEATURE:
<221> NAME/KEY: misc_feature
<222> LOCATION: (6)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 155
uaugauucug aauuagcugu u                                      21

<210> SEQ ID NO 156
<211> LENGTH: 14
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
```

```
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (8)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (14)..(14)
<223> OTHER INFORMATION: inverted Dt

<400> SEQUENCE: 156
cucuuggaua uuca                                                         14

<210> SEQ ID NO 157
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (4)..(5)
<223> OTHER INFORMATION: phosphorothioate
<220> FEATURE:
<221> NAME/KEY: misc_feature
<222> LOCATION: (5)..(6)
<223> OTHER INFORMATION: phosphorothioate
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (6)..(7)
<223> OTHER INFORMATION: phosphorothioate
<220> FEATURE:
<221> NAME/KEY: misc_feature
<222> LOCATION: (8)..(8)
<223> OTHER INFORMATION: 2'-F residues
<220> FEATURE:
<221> NAME/KEY: misc_feature
<222> LOCATION: (10)..(10)
```

```
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 157
ugaauaucca agagacaggu u                                              21

<210> SEQ ID NO 158
<211> LENGTH: 14
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
```

```
<222> LOCATION: (14)..(14)
<223> OTHER INFORMATION: inverted Dt

<400> SEQUENCE: 158
aauucagaau caua                                                        14

<210> SEQ ID NO 159
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (3)..(4)
<223> OTHER INFORMATION: phosphorothioate
<220> FEATURE:
<221> NAME/KEY: misc_feature
<222> LOCATION: (4)..(5)
<223> OTHER INFORMATION: phosphorothioate
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (5)..(6)
<223> OTHER INFORMATION: phosphorothioate
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(20)
<223> OTHER INFORMATION: phosphorothioate
<220> FEATURE:
```

```
<221> NAME/KEY: misc_feature
<222> LOCATION: (20)..(20)
<223> OTHER INFORMATION: 2'-F residues

<400> SEQUENCE: 159
uaugauucug aauuagcguu                                               20

<210> SEQ ID NO 160
<211> LENGTH: 14
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (14)..(14)
<223> OTHER INFORMATION: inverted Dt

<400> SEQUENCE: 160
agcuguaucg ucaa                                                     14

<210> SEQ ID NO 161
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
```

```
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (3)..(4)
<223> OTHER INFORMATION: phosphorothioate
<220> FEATURE:
<221> NAME/KEY: misc_feature
<222> LOCATION: (4)..(5)
<223> OTHER INFORMATION: phosphorothioate
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (5)..(6)
<223> OTHER INFORMATION: phosphorothioate
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate

<400> SEQUENCE: 161
uugacauaca gcuaauucuu                                               20

<210> SEQ ID NO 162
<211> LENGTH: 14
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(4)
<223> OTHER INFORMATION: 2'-F residues
<220> FEATURE:
<221> NAME/KEY: misc_feature
<222> LOCATION: (2)..(3)
```

```
<223> OTHER INFORMATION: phosphorothioate
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: inverted Dt

<400> SEQUENCE: 162
cucuuggaua uuca                                                    14

<210> SEQ ID NO 163
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (2)..(3)
<223> OTHER INFORMATION: 2'-F residues
<220> FEATURE:
<221> NAME/KEY: misc_feature
<222> LOCATION: (3)..(4)
<223> OTHER INFORMATION: 2'-F residues
<220> FEATURE:
<221> NAME/KEY: misc_feature
<222> LOCATION: (4)..(5)
<223> OTHER INFORMATION: 2'-F residues
<220> FEATURE:
<221> NAME/KEY: misc_feature
<222> LOCATION: (5)..(6)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: 2'-F residues
<220> FEATURE:
<221> NAME/KEY: misc_feature
<222> LOCATION: (20)..(21)
<223> OTHER INFORMATION: 2'-F residues

<400> SEQUENCE: 163
ugaauaucca agagacaggu u                                            21

<210> SEQ ID NO 164
<211> LENGTH: 14
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
```

```
<222> LOCATION: (2)..(4)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: inverted Dt

<400> SEQUENCE: 164
aauucagaau caua                                                      14

<210> SEQ ID NO 165
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(4)
<223> OTHER INFORMATION: phosphorothioate
<220> FEATURE:
<221> NAME/KEY: misc_feature
<222> LOCATION: (4)..(5)
<223> OTHER INFORMATION: phosphorothioate
<220> FEATURE:
<221> NAME/KEY: misc_feature
<222> LOCATION: (5)..(6)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 165
uaugauucug aauuagcugu u                                              21

<210> SEQ ID NO 166
<211> LENGTH: 14
<212> TYPE: RNA
<213> ORGANISM: Artificial Sequence
<220> FEATURE:
<223> OTHER INFORMATION: synthetic sequence
<220> FEATURE:
```

```
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(4)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: inverted Dt

<400> SEQUENCE: 166
agcuguaucg ucaa                                                       14

<210> SEQ ID NO 167
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(4)
<223> OTHER INFORMATION: phosphorothioate
<220> FEATURE:
<221> NAME/KEY: misc_feature
<222> LOCATION: (4)..(5)
<223> OTHER INFORMATION: phosphorothioate
<220> FEATURE:
<221> NAME/KEY: misc_feature
<222> LOCATION: (5)..(6)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 167
uugacgauac agcuaauucu u                                               21

<210> SEQ ID NO 168
<211> LENGTH: 19
```

```
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 168
ccugucucuu ggauaguca                                              19

<210> SEQ ID NO 169
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(8)
```

```
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 169
ugaauaucca agagacaggu u                                              21

<210> SEQ ID NO 170
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (8)..(10)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
```

```
<222> LOCATION: (20)..(20)
<223> OTHER INFORMATION: 2'-F residues
<220> FEATURE:
<221> NAME/KEY: misc_feature
<222> LOCATION: (20)..(20)
<223> OTHER INFORMATION: inverted Dt

<400> SEQUENCE: 170
cagcuaauuc agaaucgaua                                                    20

<210> SEQ ID NO 171
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 171
uaugauucug aauuagcugu u                                                  21

<210> SEQ ID NO 172
<211> LENGTH: 18
<212> TYPE: RNA
<213> ORGANISM: Artificial Sequence
<220> FEATURE:
<223> OTHER INFORMATION: synthetic sequence
<220> FEATURE:
```

```
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (18)..(18)
<223> OTHER INFORMATION: inverted Dt

<400> SEQUENCE: 172
gaauuagugu aucggcaa                                              18

<210> SEQ ID NO 173
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(8)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
```

```
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 173
uugacgauac agcuaauucu u                                              21

<210> SEQ ID NO 174
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
```

```
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 174
ccugucucuu ggauaguca                                                   19

<210> SEQ ID NO 175
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (8)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 175
``` ugaauauucca agagacaggu u									21

<210> SEQ ID NO 176
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (8)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 176
cagcuaauuc agaagcaua									19

<210> SEQ ID NO 177
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:

```
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate

<400> SEQUENCE: 177
uaugauucug aauuagcguu                                             20

<210> SEQ ID NO 178
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(6)
<223> OTHER INFORMATION: 2'-F residues
```

```
<220> FEATURE:
<221> NAME/KEY: misc_feature
<222> LOCATION: (8)..(8)
<223> OTHER INFORMATION: 2'-F residues
<220> FEATURE:
<221> NAME/KEY: misc_feature
<222> LOCATION: (10)..(10)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 178
gaauuagcug uaucgucaa                                                 19

<210> SEQ ID NO 179
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
```

```
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate

<400> SEQUENCE: 179
uugacauaca gcuaauucuu                                                    20

<210> SEQ ID NO 180
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: inverted Dt
<220> FEATURE:
<221> NAME/KEY: misc_feature
<222> LOCATION: (2)..(3)
<223> OTHER INFORMATION: inverted Dt
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 180
ccugucucuu ggauaguca                                                     19

<210> SEQ ID NO 181
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
```

```
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 181
ugaauaucca agagacaggu u                                              21

<210> SEQ ID NO 182
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 182
cagcuaauuc agaagcaua                                                 19

<210> SEQ ID NO 183
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (2)..(3)
<223> OTHER INFORMATION: 2'-F residues
<220> FEATURE:
```

```
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: 2'-F residues
<220> FEATURE:
<221> NAME/KEY: misc_feature
<222> LOCATION: (20)..(21)
<223> OTHER INFORMATION: 2'-F residues

<400> SEQUENCE: 183
uaugauucug aauuagcugu u                                              21

<210> SEQ ID NO 184
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 184
gaauuagcug uaucggcaa                                                 19

<210> SEQ ID NO 185
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
```

```
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 185
uugacgauac agcuaauucu u                                                   21

<210> SEQ ID NO 186
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: linker
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 186
ccugucucuu ggauauuca                                                      19

<210> SEQ ID NO 187
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
```

```
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 187
ugaauaucca agagacaggu u                                              21

<210> SEQ ID NO 188
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: linker
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 188
cagcuaauuc agaaucaua                                                 19

<210> SEQ ID NO 189
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
```

```
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate

<400> SEQUENCE: 189
uaugauucug aauuagcugu u                                              21

<210> SEQ ID NO 190
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: linker

<400> SEQUENCE: 190
cagcuaauuc agaaucaua                                                 19

<210> SEQ ID NO 191
<211> LENGTH: 21
<212> TYPE: RNA
<213> ORGANISM: Artificial Sequence
<220> FEATURE:
<223> OTHER INFORMATION: synthetic sequence
<220> FEATURE:
```

```
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (20)..(21)
<223> OTHER INFORMATION: phosphorothioate
<220> FEATURE:
<221> NAME/KEY: misc_feature
<222> LOCATION: (21)..(21)
<223> OTHER INFORMATION: 2'-F residues

<400> SEQUENCE: 191
augauucuga auuagcugua u                                            21

<210> SEQ ID NO 192
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
```

```
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: linker

<400> SEQUENCE: 192
cagcuaauuc agaaucaua                                                    19

<210> SEQ ID NO 193
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
```

```
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (20)..(21)
<223> OTHER INFORMATION: phosphorothioate

<400> SEQUENCE: 193
augauucuga auuagcugua u                                        21

<210> SEQ ID NO 194
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: linker
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 194
ccugucucuu ggauauuca                                           19
```

```
<210> SEQ ID NO 195
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: vinylphosphonate
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(20)
<223> OTHER INFORMATION: phosphorothioate

<400> SEQUENCE: 195
gaauauccaa gagacagguu                                            20

<210> SEQ ID NO 196
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: linker
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues

<400> SEQUENCE: 196
cagcuaauuc agaaucaua                                             19
```

```
<210> SEQ ID NO 197
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: vinylphosphonate
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(20)
<223> OTHER INFORMATION: phosphorothioate

<400> SEQUENCE: 197
augauucuga auuagcuguu                                                   20

<210> SEQ ID NO 198
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: linker
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
```

```
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 198
ccugucucuu ggauauuca                                                    19

<210> SEQ ID NO 199
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: 2'-F residues
<220> FEATURE:
<221> NAME/KEY: misc_feature
<222> LOCATION: (1)..(1)
<223> OTHER INFORMATION: vinylphosphonate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (18)..(19)
```

```
<223> OTHER INFORMATION: 2'-F residues
<220> FEATURE:
<221> NAME/KEY: misc_feature
<222> LOCATION: (19)..(20)
<223> OTHER INFORMATION: 2'-F residues

<400> SEQUENCE: 199
gaauauccaa gagacagguu                                                    20

<210> SEQ ID NO 200
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: linker

<400> SEQUENCE: 200
ccugucucuu ggauauuca                                                     19

<210> SEQ ID NO 201
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: vinylphosphonate
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
```

```
<222> LOCATION: (13)..(13)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(20)
<223> OTHER INFORMATION: phosphorothioate

<400> SEQUENCE: 201
gaauauccaa gagacagguu                                              20

<210> SEQ ID NO 202
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: linker
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: inverted Dt

<400> SEQUENCE: 202
ccugucucuu ggauauuca                                               19

<210> SEQ ID NO 203
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
```

```
<221> NAME/KEY: misc_feature
<222> LOCATION: (1)..(1)
<223> OTHER INFORMATION: vinylphosphonate
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(20)
<223> OTHER INFORMATION: phosphorothioate

<400> SEQUENCE: 203
gaauauccaa gagacagguu                                              20

<210> SEQ ID NO 204
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(19)
<223> OTHER INFORMATION: linker

<400> SEQUENCE: 204
ccugucucuu ggauauuca                                               19

<210> SEQ ID NO 205
<211> LENGTH: 20
```

```
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: vinylphosphonate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate

<400> SEQUENCE: 205
gaauauccaa gagacagguu                                               20

<210> SEQ ID NO 206
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
```

```
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(19)
<223> OTHER INFORMATION: linker

<400> SEQUENCE: 206
cagcuaauuc agaaucaua                                                  19

<210> SEQ ID NO 207
<211> LENGTH: 18
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: vinylphosphonate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
```

```
<222> LOCATION: (14)..(15)
<223> OTHER INFORMATION: 2'-F residues
<220> FEATURE:
<221> NAME/KEY: misc_feature
<222> LOCATION: (16)..(17)
<223> OTHER INFORMATION: phosphorothioate
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (17)..(18)
<223> OTHER INFORMATION: phosphorothioate

<400> SEQUENCE: 207
augauucuga auagcguu                                                    18

<210> SEQ ID NO 208
<211> LENGTH: 22
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(2)
<223> OTHER INFORMATION: 2'-F residues
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (4)..(4)
<223> OTHER INFORMATION: 2'-F residues
<220> FEATURE:
<221> NAME/KEY: misc_feature
<222> LOCATION: (6)..(6)
<223> OTHER INFORMATION: 2'-F residues
<220> FEATURE:
<221> NAME/KEY: misc_feature
<222> LOCATION: (8)..(8)
<223> OTHER INFORMATION: 2'-F residues
<220> FEATURE:
<221> NAME/KEY: misc_feature
<222> LOCATION: (10)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (20)..(20)
<223> OTHER INFORMATION: 2'-F residues
<220> FEATURE:
<221> NAME/KEY: misc_feature
<222> LOCATION: (22)..(22)
<223> OTHER INFORMATION: 2'-F residues
<220> FEATURE:
<221> NAME/KEY: misc_feature
<222> LOCATION: (22)..(22)
<223> OTHER INFORMATION: linker

<400> SEQUENCE: 208
uugacgauac agcuaauuca ua                                               22
```

```
<210> SEQ ID NO 209
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: vinylphosphonate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(8)
<223> OTHER INFORMATION: 2'-F residues
<220> FEATURE:
<221> NAME/KEY: misc_feature
<222> LOCATION: (12)..(12)
<223> OTHER INFORMATION: 2'-F residues
<220> FEATURE:
<221> NAME/KEY: misc_feature
<222> LOCATION: (14)..(14)
<223> OTHER INFORMATION: 2'-F residues
<220> FEATURE:
<221> NAME/KEY: misc_feature
<222> LOCATION: (16)..(16)
<223> OTHER INFORMATION: 2'-F residues
<220> FEATURE:
<221> NAME/KEY: misc_feature
<222> LOCATION: (18)..(18)
<223> OTHER INFORMATION: 2'-F residues
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(20)
<223> OTHER INFORMATION: 2'-F residues

<400> SEQUENCE: 209
gaauuagcgu aucgucaagg                                          20

<210> SEQ ID NO 210
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
```

```
<220> FEATURE:
<221> NAME/KEY: misc_feature
<222> LOCATION: (1)..(1)
<223> OTHER INFORMATION: vinylphosphonate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues

<400> SEQUENCE: 210
cagcuaauuc agaaucaua                                                  19

<210> SEQ ID NO 211
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
```

```
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate
<220> FEATURE:
<221> NAME/KEY: misc_feature
<222> LOCATION: (21)..(21)
<223> OTHER INFORMATION: 2'-F residues
<220> FEATURE:
<221> NAME/KEY: misc_feature
<222> LOCATION: (21)..(21)
<223> OTHER INFORMATION: linker

<400> SEQUENCE: 211
augauucuga auuagcugua u                                              21

<210> SEQ ID NO 212
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2',4'-BNANC (2'-O,4'-C-aminomethylene bridged
      nucleic acid)
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (2)..(2)
<223> OTHER INFORMATION: 2',4'-BNANC (2'-O,4'-C-aminomethylene bridged
      nucleic acid)
<220> FEATURE:
<221> NAME/KEY: misc_feature
<222> LOCATION: (3)..(17)
<223> OTHER INFORMATION: unmodified residue
<220> FEATURE:
<221> NAME/KEY: misc_feature
<222> LOCATION: (17)..(18)
<223> OTHER INFORMATION: phosphorothioate
<220> FEATURE:
<221> NAME/KEY: misc_feature
<222> LOCATION: (18)..(19)
<223> OTHER INFORMATION: phosphorothioate
<220> FEATURE:
<221> NAME/KEY: misc_feature
<222> LOCATION: (18)..(18)
<223> OTHER INFORMATION: 2',4'-BNANC (2'-O,4'-C-aminomethylene bridged
      nucleic acid)
<220> FEATURE:
<221> NAME/KEY: misc_feature
<222> LOCATION: (19)..(19)
<223> OTHER INFORMATION: 2',4'-BNANC (2'-O,4'-C-aminomethylene bridged
      nucleic acid)

<400> SEQUENCE: 212
cagcuaauuc agaaucata                                                 19

<210> SEQ ID NO 213
<211> LENGTH: 21
<212> TYPE: RNA
<213> ORGANISM: Artificial Sequence
```

```
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate
<220> FEATURE:
<221> NAME/KEY: misc_feature
<222> LOCATION: (21)..(21)
<223> OTHER INFORMATION: 2'-F residues

<400> SEQUENCE: 213
augauucuga auuagcugua u                                           21

<210> SEQ ID NO 214
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
```

```
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues

<400> SEQUENCE: 214
cagcuaauuc agaaucaua                                                    19

<210> SEQ ID NO 215
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
```

```
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate
<220> FEATURE:
<221> NAME/KEY: misc_feature
<222> LOCATION: (21)..(21)
<223> OTHER INFORMATION: 2'-F residues

<400> SEQUENCE: 215
augauucuga auuagcugua u                                              21

<210> SEQ ID NO 216
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(17)
<223> OTHER INFORMATION: unmodified residue
<220> FEATURE:
<221> NAME/KEY: misc_feature
<222> LOCATION: (17)..(18)
<223> OTHER INFORMATION: phosphorothioate
<220> FEATURE:
<221> NAME/KEY: misc_feature
<222> LOCATION: (18)..(19)
<223> OTHER INFORMATION: phosphorothioate

<400> SEQUENCE: 216
cagcuaauuc agaaucaua                                                 19

<210> SEQ ID NO 217
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (3)..(3)
```

```
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate
<220> FEATURE:
<221> NAME/KEY: misc_feature
<222> LOCATION: (21)..(21)
<223> OTHER INFORMATION: 2'-F residues

<400> SEQUENCE: 217
augauucuga auuagcugua u                                              21

<210> SEQ ID NO 218
<211> LENGTH: 19
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2',4'-BNANC (2'-O,4'-C-aminomethylene bridged
      nucleic acid)
<220> FEATURE:
<221> NAME/KEY: misc_feature
<222> LOCATION: (1)..(2)
<223> OTHER INFORMATION: unmodified residue
<220> FEATURE:
<221> NAME/KEY: misc_feature
<222> LOCATION: (2)..(2)
<223> OTHER INFORMATION: 2',4'-BNANC (2'-O,4'-C-aminomethylene bridged
      nucleic acid)
<220> FEATURE:
<221> NAME/KEY: misc_feature
<222> LOCATION: (2)..(3)
<223> OTHER INFORMATION: unmodified residue
<220> FEATURE:
<221> NAME/KEY: misc_feature
<222> LOCATION: (3)..(17)
<223> OTHER INFORMATION: unmodified residue
<220> FEATURE:
<221> NAME/KEY: misc_feature
<222> LOCATION: (17)..(18)
<223> OTHER INFORMATION: unmodified residue
<220> FEATURE:
<221> NAME/KEY: misc_feature
<222> LOCATION: (18)..(18)
<223> OTHER INFORMATION: 2',4'-BNANC (2'-O,4'-C-aminomethylene bridged
```

```
          nucleic acid)
<220> FEATURE:
<221> NAME/KEY: misc_feature
<222> LOCATION: (18)..(19)
<223> OTHER INFORMATION: unmodified residue
<220> FEATURE:
<221> NAME/KEY: misc_feature
<222> LOCATION: (19)..(19)
<223> OTHER INFORMATION: 2',4'-BNANC (2'-O,4'-C-aminomethylene bridged
      nucleic acid)

<400> SEQUENCE: 218
cagcuaauuc agaaucata                                                  19

<210> SEQ ID NO 219
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate
<220> FEATURE:
<221> NAME/KEY: misc_feature
<222> LOCATION: (21)..(21)
<223> OTHER INFORMATION: 2'-F residues
```

-continued

<400> SEQUENCE: 219
augauucuga auuagcugua u                                              21

<210> SEQ ID NO 220
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: molecule
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(5)
<223> OTHER INFORMATION: 2'-F residues
<220> FEATURE:
<221> NAME/KEY: misc_feature
<222> LOCATION: (7)..(9)
<223> OTHER INFORMATION: 2'-F residues
<220> FEATURE:
<221> NAME/KEY: misc_feature
<222> LOCATION: (11)..(11)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: linker

<400> SEQUENCE: 220
cagcuaauuc agaaucaua                                                 19

<210> SEQ ID NO 221
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate

```
<220> FEATURE:
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate
<220> FEATURE:
<221> NAME/KEY: misc_feature
<222> LOCATION: (21)..(21)
<223> OTHER INFORMATION: 2'-F residues

<400> SEQUENCE: 221
augauucuga auuagcugua u                                              21

<210> SEQ ID NO 222
<211> LENGTH: 19
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(17)
<223> OTHER INFORMATION: unmodified residue
<220> FEATURE:
<221> NAME/KEY: misc_feature
<222> LOCATION: (17)..(18)
<223> OTHER INFORMATION: phosphorothioate
<220> FEATURE:
<221> NAME/KEY: misc_feature
<222> LOCATION: (18)..(19)
<223> OTHER INFORMATION: phosphorothioate

<400> SEQUENCE: 222
```
cagcuaauuc agaaucaua                    19

<210> SEQ ID NO 223
<211> LENGTH: 21
<212> TYPE: RNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 2'-F residues
<220> FEATURE:
<221> NAME/KEY: misc_feature
<222> LOCATION: (1)..(1)
<223> OTHER INFORMATION: phosphorothioate
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (1)..(1)
<223> OTHER INFORMATION: (E)-vinylphosphonate
<220> FEATURE:
<221> NAME/KEY: misc_feature
<222> LOCATION: (3)..(3)
<223> OTHER INFORMATION: 2'-F residues
<220> FEATURE:
<221> NAME/KEY: misc_feature
<222> LOCATION: (5)..(7)
<223> OTHER INFORMATION: 2'-F residues
<220> FEATURE:
<221> NAME/KEY: misc_feature
<222> LOCATION: (9)..(9)
<223> OTHER INFORMATION: 2'-F residues
<220> FEATURE:
<221> NAME/KEY: misc_feature
<222> LOCATION: (13)..(13)
<223> OTHER INFORMATION: 2'-F residues
<220> FEATURE:
<221> NAME/KEY: misc_feature
<222> LOCATION: (15)..(15)
<223> OTHER INFORMATION: 2'-F residues
<220> FEATURE:
<221> NAME/KEY: misc_feature
<222> LOCATION: (17)..(17)
<223> OTHER INFORMATION: 2'-F residues
<220> FEATURE:
<221> NAME/KEY: misc_feature
<222> LOCATION: (19)..(19)
<223> OTHER INFORMATION: 2'-F residues
<220> FEATURE:
<221> NAME/KEY: misc_feature
<222> LOCATION: (19)..(20)
<223> OTHER INFORMATION: phosphorothioate
<220> FEATURE:
<221> NAME/KEY: misc_feature
<222> LOCATION: (20)..(21)
<223> OTHER INFORMATION: phosphorothioate
<220> FEATURE:
<221> NAME/KEY: misc_feature
<222> LOCATION: (21)..(21)
<223> OTHER INFORMATION: 2'-F residues

<400> SEQUENCE: 223
augauucuga auuagcugua u                    21

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237
<400> SEQUENCE: 237
000

<210> SEQ ID NO 238
<400> SEQUENCE: 238
000

<210> SEQ ID NO 239
<400> SEQUENCE: 239
000

<210> SEQ ID NO 240
<400> SEQUENCE: 240
000

<210> SEQ ID NO 241
<400> SEQUENCE: 241
000

<210> SEQ ID NO 242
<400> SEQUENCE: 242
000

<210> SEQ ID NO 243
<400> SEQUENCE: 243
000

<210> SEQ ID NO 244
<400> SEQUENCE: 244
000

<210> SEQ ID NO 245
<400> SEQUENCE: 245
000

<210> SEQ ID NO 246
<400> SEQUENCE: 246
000

<210> SEQ ID NO 247
<400> SEQUENCE: 247
000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259
<400> SEQUENCE: 259
000

<210> SEQ ID NO 260
<400> SEQUENCE: 260
000

<210> SEQ ID NO 261
<400> SEQUENCE: 261
000

<210> SEQ ID NO 262
<400> SEQUENCE: 262
000

<210> SEQ ID NO 263
<400> SEQUENCE: 263
000

<210> SEQ ID NO 264
<400> SEQUENCE: 264
000

<210> SEQ ID NO 265
<400> SEQUENCE: 265
000

<210> SEQ ID NO 266
<400> SEQUENCE: 266
000

<210> SEQ ID NO 267
<400> SEQUENCE: 267
000

<210> SEQ ID NO 268
<400> SEQUENCE: 268
000

<210> SEQ ID NO 269
<400> SEQUENCE: 269
000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290
<400> SEQUENCE: 290
000

<210> SEQ ID NO 291
<400> SEQUENCE: 291
000

<210> SEQ ID NO 292
<400> SEQUENCE: 292
000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 90
<212> TYPE: PRT
<213> ORGANISM: Artificial Sequence
<220> FEATURE:
<223> OTHER INFORMATION: synthetic sequence

<400> SEQUENCE: 300

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Gln Tyr Glu Glu Leu Thr Thr Val Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Val Val Trp Ile Glu Gly Val Lys Gly Gly Leu Arg
65                  70                  75                  80

Ser Asn Pro Leu Gly Ala Ala Phe Thr Thr
                85                  90

<210> SEQ ID NO 301

```
<211> LENGTH: 90
<212> TYPE: PRT
<213> ORGANISM: Artificial Sequence
<220> FEATURE:
<223> OTHER INFORMATION: synthetic sequence

<400> SEQUENCE: 301

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Thr Tyr Ile Glu Trp Trp Asp Val Gly Glu Ala Ile Gly Leu
        35                  40                  45

Lys Val Pro Gly Ser Glu Arg Ser Tyr Asp Leu Thr Gly Leu Lys Pro
    50                  55                  60

Gly Thr Glu Tyr Arg Val His Ile Gln Gly Val Lys Gly Gly Asn Asn
65                  70                  75                  80

Ser Tyr Pro Leu Asp Ala Leu Phe Thr Thr
                85                  90

<210> SEQ ID NO 302
<211> LENGTH: 90
<212> TYPE: PRT
<213> ORGANISM: Artificial Sequence
<220> FEATURE:
<223> OTHER INFORMATION: synthetic sequence

<400> SEQUENCE: 302

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Ala Tyr Phe Glu Ala Ile Trp Asn Gly Glu Ala Ile Tyr Leu
        35                  40                  45

Thr Val Pro Gly Ser Glu Arg Ser Tyr Asp Leu Thr Gly Leu Lys Pro
    50                  55                  60

Gly Thr Glu Tyr Gln Val Glu Ile Arg Gly Val Lys Gly Gly Pro Thr
65                  70                  75                  80

Ser Arg Pro Leu Phe Ala Trp Phe Thr Thr
                85                  90

<210> SEQ ID NO 303
<211> LENGTH: 90
<212> TYPE: PRT
<213> ORGANISM: Artificial Sequence
<220> FEATURE:
<223> OTHER INFORMATION: synthetic sequence

<400> SEQUENCE: 303

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Thr Tyr Ile Glu Trp Trp Glu Asn Gly Glu Ala Ile Ala Leu
        35                  40                  45

Ser Val Pro Gly Ser Glu Arg Ser Tyr Asp Leu Thr Gly Leu Lys Pro
    50                  55                  60

Gly Thr Glu Tyr Gln Val Gly Ile Ala Gly Val Lys Gly Gly Tyr Lys
65                  70                  75                  80
```

Ser Tyr Pro Leu Trp Ala Leu Phe Thr Thr
              85                    90

<210> SEQ ID NO 304
<211> LENGTH: 90
<212> TYPE: PRT
<213> ORGANISM: Artificial Sequence
<220> FEATURE:
<223> OTHER INFORMATION: synthetic sequence

<400> SEQUENCE: 304

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ile Tyr Thr Glu Glu Lys Glu Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Leu Val Glu Ile Glu Gly Val Lys Gly Gly Lys Arg
65                  70                  75                  80

Ser Val Pro Leu Asn Ala Ser Phe Thr Thr
                85                  90

<210> SEQ ID NO 305
<211> LENGTH: 90
<212> TYPE: PRT
<213> ORGANISM: Artificial Sequence
<220> FEATURE:
<223> OTHER INFORMATION: synthetic sequence

<400> SEQUENCE: 305

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ala Tyr Glu Glu Ser His Thr Thr Gly Glu Ala Ile Phe Leu
        35                  40                  45

Arg Val Pro Gly Ser Glu Arg Ser Tyr Asp Leu Thr Gly Leu Lys Pro
    50                  55                  60

Gly Thr Glu Tyr Ser Val Ser Ile Glu Gly Val Lys Gly Gly His Tyr
65                  70                  75                  80

Ser Pro Pro Leu Thr Ala Lys Phe Thr Thr
                85                  90

<210> SEQ ID NO 306
<211> LENGTH: 90
<212> TYPE: PRT
<213> ORGANISM: Artificial Sequence
<220> FEATURE:
<223> OTHER INFORMATION: synthetic sequence

<400> SEQUENCE: 306

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Asp Tyr Arg Glu Trp Trp Thr Leu Gly Glu Ala Ile Val Leu
        35                  40                  45

Thr Val Pro Gly Ser Glu Arg Ser Tyr Asp Leu Thr Gly Leu Lys Pro

```
                    50                  55                  60
Gly Thr Glu Tyr Tyr Val Asn Ile Gln Gly Val Lys Gly Gly Leu Arg
 65                  70                  75                  80

Ser Tyr Pro Leu Ser Ala Ile Phe Thr Thr
                     85                  90
```

<210> SEQ ID NO 307
<211> LENGTH: 90
<212> TYPE: PRT
<213> ORGANISM: Artificial Sequence
<220> FEATURE:
<223> OTHER INFORMATION: synthetic sequence

<400> SEQUENCE: 307

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Val Ile Glu Tyr Trp Glu Tyr Val Gly His Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Ser Val Gly Ile Tyr Gly Val Lys Gly Gly Ser Leu
 65                  70                  75                  80

Ser Arg Pro Leu Ser Ala Ile Phe Thr Thr
                     85                  90
```

<210> SEQ ID NO 308
<211> LENGTH: 90
<212> TYPE: PRT
<213> ORGANISM: Artificial Sequence
<220> FEATURE:
<223> OTHER INFORMATION: synthetic sequence

<400> SEQUENCE: 308

```
Met Leu Pro Ala Pro Lys Asn Leu Val Ile Ser Arg Val Thr Glu Asp
 1               5                  10                  15

Ser Ala Arg Leu Ser Trp Thr Ala Pro Asp Ala Ala Phe Asp Ser Phe
                20                  25                  30

Phe Ile Tyr Tyr Ile Glu Ser Tyr Pro Ala Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Trp Val Gly Ile Asp Gly Val Lys Gly Gly Arg Trp
 65                  70                  75                  80

Ser Thr Pro Leu Ser Ala Ile Phe Thr Thr
                     85                  90
```

<210> SEQ ID NO 309
<211> LENGTH: 90
<212> TYPE: PRT
<213> ORGANISM: Artificial Sequence
<220> FEATURE:
<223> OTHER INFORMATION: synthetic sequence

<400> SEQUENCE: 309

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30
```

```
Thr Ile Glu Tyr Tyr Glu Ser Phe Tyr Gly Gly Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Tyr Val Ser Ile Tyr Gly Val Lys Gly Gly Trp Leu
 65                  70                  75                  80

Ser Arg Pro Leu Ser Ala Ile Phe Thr Thr
                85                  90

<210> SEQ ID NO 310
<211> LENGTH: 90
<212> TYPE: PRT
<213> ORGANISM: Artificial Sequence
<220> FEATURE:
<223> OTHER INFORMATION: synthetic sequence

<400> SEQUENCE: 310

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Tyr Ile Glu Tyr Tyr Glu Ser Tyr Pro Gly Gly Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Asp Val Tyr Ile Tyr Gly Val Lys Gly Gly Tyr Trp
 65                  70                  75                  80

Ser Arg Pro Leu Ser Ala Ile Phe Thr Thr
                85                  90

<210> SEQ ID NO 311
<211> LENGTH: 90
<212> TYPE: PRT
<213> ORGANISM: Artificial Sequence
<220> FEATURE:
<223> OTHER INFORMATION: synthetic sequence

<400> SEQUENCE: 311

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Tyr Ile Glu Tyr Tyr Glu Ser Leu Pro Asp Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Ala Val Tyr Ile Tyr Gly Val Lys Gly Gly Tyr Tyr
 65                  70                  75                  80

Ser Arg Pro Leu Ser Ala Ile Phe Thr Thr
                85                  90

<210> SEQ ID NO 312
<211> LENGTH: 90
<212> TYPE: PRT
<213> ORGANISM: Artificial Sequence
<220> FEATURE:
<223> OTHER INFORMATION: synthetic sequence

<400> SEQUENCE: 312
```

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Tyr Tyr Leu Glu Ser Tyr Pro Glu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Gly Ile Asp Gly Val Lys Gly Gly Thr Trp
65                  70                  75                  80

Ser Ser Pro Leu Ser Ala Ile Phe Thr Thr
                85                  90

<210> SEQ ID NO 313
<211> LENGTH: 90
<212> TYPE: PRT
<213> ORGANISM: Artificial Sequence
<220> FEATURE:
<223> OTHER INFORMATION: synthetic sequence

<400> SEQUENCE: 313

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Glu Tyr Phe Glu Phe Thr Gly Thr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Tyr Val Ser Ile Tyr Gly Val Lys Gly Gly Leu Leu
65                  70                  75                  80

Ser Ala Pro Leu Ser Ala Ile Phe Thr Thr
                85                  90

<210> SEQ ID NO 314
<211> LENGTH: 90
<212> TYPE: PRT
<213> ORGANISM: Artificial Sequence
<220> FEATURE:
<223> OTHER INFORMATION: synthetic sequence

<400> SEQUENCE: 314

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Trp Tyr Ala Glu Ala Leu Gly Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Asp Ile Tyr Gly Val Lys Gly Gly Phe Trp
65                  70                  75                  80

Ser Leu Pro Leu Ser Ala Ile Phe Thr Thr
                85                  90

<210> SEQ ID NO 315
<211> LENGTH: 90
<212> TYPE: PRT
<213> ORGANISM: Artificial Sequence
<220> FEATURE:
<223> OTHER INFORMATION: synthetic sequence

<400> SEQUENCE: 315

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Phe Glu Gln Phe Asn Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Gly Ile Tyr Gly Val Lys Gly Gly Trp Leu
65                  70                  75                  80

Ser His Pro Leu Ser Ala Ile Phe Thr Thr
                85                  90

<210> SEQ ID NO 316
<211> LENGTH: 90
<212> TYPE: PRT
<213> ORGANISM: Artificial Sequence
<220> FEATURE:
<223> OTHER INFORMATION: synthetic sequence

<400> SEQUENCE: 316

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Ser Tyr Leu Glu Trp Trp Glu Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Ser Ile Ala Gly Val Lys Gly Gly Lys Arg
65                  70                  75                  80

Ser Tyr Pro Leu Ser Ala Ile Phe Thr Thr
                85                  90

<210> SEQ ID NO 317
<211> LENGTH: 90
<212> TYPE: PRT
<213> ORGANISM: Artificial Sequence
<220> FEATURE:
<223> OTHER INFORMATION: synthetic sequence

<400> SEQUENCE: 317

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Arg Glu Gly Ala Trp Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Asp Ile Thr Gly Val Lys Gly Gly Trp Trp
65                  70                  75                  80

Ser Asp Pro Leu Ser Ala Ile Phe Thr Thr
                85                  90

```
<210> SEQ ID NO 318
<211> LENGTH: 90
<212> TYPE: PRT
<213> ORGANISM: Artificial Sequence
<220> FEATURE:
<223> OTHER INFORMATION: synthetic sequence

<400> SEQUENCE: 318

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Lys Tyr Ile Glu Trp Trp Ala Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Val Glu Ile Tyr Gly Val Lys Gly Lys Trp
65                  70                  75                  80

Ser Trp Pro Leu Ser Ala Ile Phe Thr Thr
            85                  90

<210> SEQ ID NO 319
<211> LENGTH: 90
<212> TYPE: PRT
<213> ORGANISM: Artificial Sequence
<220> FEATURE:
<223> OTHER INFORMATION: synthetic sequence

<400> SEQUENCE: 319

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Lys Ile Ser Tyr Gln Glu Trp Trp Glu Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Asn Ile Ser Gly Val Lys Gly Gly Val Gln
65                  70                  75                  80

Ser Tyr Pro Leu Ser Ala Ile Phe Thr Thr
            85                  90

<210> SEQ ID NO 320
<211> LENGTH: 90
<212> TYPE: PRT
<213> ORGANISM: Artificial Sequence
<220> FEATURE:
<223> OTHER INFORMATION: synthetic sequence

<400> SEQUENCE: 320

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Ser Tyr Ile Glu Trp Trp Asp Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr His Val Glu Ile Phe Gly Val Lys Gly Gly Thr Gln
```

```
                65                  70                  75                  80
Ser Tyr Pro Leu Ser Ala Ile Phe Thr Thr
                85                  90

<210> SEQ ID NO 321
<211> LENGTH: 90
<212> TYPE: PRT
<213> ORGANISM: Artificial Sequence
<220> FEATURE:
<223> OTHER INFORMATION: synthetic sequence

<400> SEQUENCE: 321

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Gln Ile Leu Tyr Gln Glu Asn Ala Phe Glu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Tyr Ile Tyr Gly Val Lys Gly Gly Tyr Pro
65                  70                  75                  80

Ser Val Pro Leu Ser Ala Ile Phe Thr Thr
                85                  90

<210> SEQ ID NO 322
<211> LENGTH: 90
<212> TYPE: PRT
<213> ORGANISM: Artificial Sequence
<220> FEATURE:
<223> OTHER INFORMATION: synthetic sequence

<400> SEQUENCE: 322

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ile Ile Glu Tyr Trp Glu Phe Val Gly Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Ala Ile Tyr Gly Val Lys Gly Gly Asp Leu
65                  70                  75                  80

Ser Lys Pro Leu Ser Ala Ile Phe Thr Thr
                85                  90

<210> SEQ ID NO 323
<211> LENGTH: 90
<212> TYPE: PRT
<213> ORGANISM: Artificial Sequence
<220> FEATURE:
<223> OTHER INFORMATION: synthetic sequence

<400> SEQUENCE: 323

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Val Ile Glu Tyr Phe Glu Ala Leu Glu Gly Gly Glu Ala Ile Val Leu
            35                  40                  45
```

Thr Val Pro Gly Ser Glu Arg Ser Tyr Asp Leu Thr Gly Leu Lys Pro
            50                  55                  60

Gly Thr Glu Tyr Phe Val Gly Ile Tyr Gly Val Lys Gly Gly Pro Leu
 65                  70                  75                  80

Ser Lys Pro Leu Ser Ala Ile Phe Thr Thr
                85                  90

<210> SEQ ID NO 324
<211> LENGTH: 90
<212> TYPE: PRT
<213> ORGANISM: Artificial Sequence
<220> FEATURE:
<223> OTHER INFORMATION: synthetic sequence

<400> SEQUENCE: 324

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Ser Ile Lys Tyr Leu Glu Trp Trp Gln Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Tyr Val His Ile Ala Gly Val Lys Gly Gly Tyr Arg
 65                  70                  75                  80

Ser Tyr Pro Leu Ser Ala Ile Phe Thr Thr
                85                  90

<210> SEQ ID NO 325
<211> LENGTH: 90
<212> TYPE: PRT
<213> ORGANISM: Artificial Sequence
<220> FEATURE:
<223> OTHER INFORMATION: synthetic sequence

<400> SEQUENCE: 325

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Thr Ile Trp Tyr Ala Glu Ala Asp Gly Trp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Asp Ile Tyr Gly Val Lys Gly Gly Tyr Leu
 65                  70                  75                  80

Ser Val Pro Leu Ser Ala Ile Phe Thr Thr
                85                  90

<210> SEQ ID NO 326
<211> LENGTH: 90
<212> TYPE: PRT
<213> ORGANISM: Artificial Sequence
<220> FEATURE:
<223> OTHER INFORMATION: synthetic sequence

<400> SEQUENCE: 326

Met Leu Pro Ala Pro Lys Asn Leu Val Val Ser Arg Val Thr Glu Asp
  1               5                  10                  15

```
Ser Ala Arg Leu Ser Trp Thr Ala Pro Asp Ala Ala Phe Asp Ser Phe
            20                  25                  30

Thr Ile Trp Tyr Ala Glu Trp Glu Asp Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Glu Ile Tyr Gly Val Lys Gly Gly Tyr Pro
65                  70                  75                  80

Ser Lys Pro Leu Ser Ala Ile Phe Thr Thr
                85                  90

<210> SEQ ID NO 327
<211> LENGTH: 90
<212> TYPE: PRT
<213> ORGANISM: Artificial Sequence
<220> FEATURE:
<223> OTHER INFORMATION: synthetic sequence

<400> SEQUENCE: 327

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Trp Tyr Ala Glu Ala Ile Gly His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Asp Ile Trp Gly Val Lys Gly Gly Gln Gln
65                  70                  75                  80

Ser Lys Pro Leu Ser Ala Ile Phe Thr Thr
                85                  90

<210> SEQ ID NO 328
<211> LENGTH: 94
<212> TYPE: PRT
<213> ORGANISM: Artificial Sequence
<220> FEATURE:
<223> OTHER INFORMATION: synthetic sequence

<400> SEQUENCE: 328

Met Leu Pro Ala Pro Lys Asn Leu Val Val Ser Arg Val Thr Glu Asp
1               5                   10                  15

Ser Ala Arg Leu Ser Trp Arg Val Glu Ser Arg Thr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Val Trp Asp Thr Arg
65                  70                  75                  80

Asp Asn Pro Ile Ser Asn Pro Leu Ser Ala Ile Phe Thr Thr
                85                  90

<210> SEQ ID NO 329
<211> LENGTH: 90
<212> TYPE: PRT
<213> ORGANISM: Artificial Sequence
<220> FEATURE:
<223> OTHER INFORMATION: synthetic sequence
```

```
<400> SEQUENCE: 329

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Ser Tyr Arg Glu Arg Ser Ala Trp Gly Glu Ala Ile Ala Leu
        35                  40                  45

Val Val Pro Gly Ser Glu Arg Ser Tyr Asp Leu Thr Gly Leu Lys Pro
    50                  55                  60

Gly Ile Glu Tyr Ile Val Gly Ile Ile Gly Val Lys Gly Gly Leu Arg
65                  70                  75                  80

Ser Asn Pro Leu Arg Ala Asp Phe Thr Thr
                85                  90

<210> SEQ ID NO 330
<211> LENGTH: 90
<212> TYPE: PRT
<213> ORGANISM: Artificial Sequence
<220> FEATURE:
<223> OTHER INFORMATION: synthetic sequence

<400> SEQUENCE: 330

Met Leu Pro Ala Pro Lys Asn Leu Val Val Ser Arg Val Thr Glu Asp
1               5                   10                  15

Ser Ala Arg Leu Ser Trp Thr Ala Pro Tyr Ala Ala Phe Asp Ser Phe
            20                  25                  30

Ala Ile Ser Tyr Arg Glu Arg Ser Arg Glu Gly Glu Val Ile Ala Leu
        35                  40                  45

Thr Val Pro Gly Ser Glu Arg Ser Tyr Asp Leu Thr Gly Leu Lys Pro
    50                  55                  60

Gly Thr Glu Tyr Ile Val Gly Ile Leu Gly Val Lys Gly Gly Arg Arg
65                  70                  75                  80

Ser Lys Pro Leu Arg Ala Gln Phe Thr Thr
                85                  90

<210> SEQ ID NO 331
<211> LENGTH: 96
<212> TYPE: PRT
<213> ORGANISM: Artificial Sequence
<220> FEATURE:
<223> OTHER INFORMATION: synthetic sequence

<400> SEQUENCE: 331

Met Leu Pro Ala Pro Lys Asn Leu Val Val Ser Arg Val Thr Glu Asp
1               5                   10                  15

Ser Ala Arg Leu Ser Trp Glu Gly Tyr Arg Asn Asn Ala His Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Val Ala Ala
65                  70                  75                  80

Val Pro Arg Asn Tyr Tyr Ser Asn Pro Leu Ser Ala Ile Phe Thr Thr
                85                  90                  95

<210> SEQ ID NO 332
<211> LENGTH: 91
```

```
<212> TYPE: PRT
<213> ORGANISM: Artificial Sequence
<220> FEATURE:
<223> OTHER INFORMATION: synthetic sequence

<400> SEQUENCE: 332

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Arg Tyr Tyr Glu Gly Ser Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Tyr Ile Gly Gly Val Lys Gly Gly Ser Pro
65                  70                  75                  80

Ser Ser Pro Leu Ser Ala Ile Phe Thr Thr Gly
                85                  90

<210> SEQ ID NO 333
<211> LENGTH: 90
<212> TYPE: PRT
<213> ORGANISM: Artificial Sequence
<220> FEATURE:
<223> OTHER INFORMATION: synthetic sequence

<400> SEQUENCE: 333

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Lys Ile Gly Tyr Trp Glu Trp Arg Lys Tyr Gly Glu Ala Ile Glu Leu
        35                  40                  45

Asn Val Pro Gly Ser Glu Arg Ser Tyr Asp Leu Thr Gly Leu Lys Pro
    50                  55                  60

Gly Thr Glu Tyr Arg Val Leu Ile Tyr Gly Val Lys Gly Gly Ala Gly
65                  70                  75                  80

Ser His Pro Leu Arg Ala Leu Phe Thr Thr
                85                  90

<210> SEQ ID NO 334
<211> LENGTH: 199
<212> TYPE: PRT
<213> ORGANISM: Artificial Sequence
<220> FEATURE:
<223> OTHER INFORMATION: synthetic sequence

<400> SEQUENCE: 334

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Ser Tyr Arg Glu Arg Ser Ala Trp Gly Glu Ala Ile Ala Leu
        35                  40                  45

Val Val Pro Gly Ser Glu Arg Ser Tyr Asp Leu Thr Gly Leu Lys Pro
    50                  55                  60

Gly Ile Glu Tyr Ile Val Gly Ile Ile Gly Val Lys Gly Gly Leu Arg
65                  70                  75                  80

Ser Asn Pro Leu Arg Ala Asp Phe Thr Thr Gly Gly Gly Gly Ser Gly
```

```
                85                  90                  95
Gly Gly Gly Ser Gly Gly Gly Ser Gly Gly Gly Ser Leu Pro
            100                 105                 110

Ala Pro Lys Asn Leu Val Val Ser Arg Val Thr Glu Asp Ser Ala Arg
            115                 120                 125

Leu Ser Trp Thr Ala Pro Asp Ala Ala Phe Asp Ser Phe His Ile Glu
            130                 135                 140

Tyr Trp Glu Gln Ser Ile Val Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Arg Val Trp Ile Tyr Gly Val Lys Gly Gly Asn Asp Ser Trp Pro
                180                 185                 190

Leu Ser Ala Ile Phe Thr Thr
            195
```

<210> SEQ ID NO 335
<211> LENGTH: 199
<212> TYPE: PRT
<213> ORGANISM: Artificial Sequence
<220> FEATURE:
<223> OTHER INFORMATION: synthetic sequence

<400> SEQUENCE: 335

```
Met Leu Pro Ala Pro Lys Asn Leu Val Val Ser Arg Val Thr Glu Asp
1               5                   10                  15

Ser Ala Arg Leu Ser Trp Thr Ala Pro Tyr Ala Ala Phe Asp Ser Phe
                20                  25                  30

Ala Ile Ser Tyr Arg Glu Arg Ser Arg Glu Gly Glu Val Ile Ala Leu
            35                  40                  45

Thr Val Pro Gly Ser Glu Arg Ser Tyr Asp Leu Thr Gly Leu Lys Pro
50                  55                  60

Gly Thr Glu Tyr Ile Val Gly Ile Leu Gly Val Lys Gly Gly Arg Arg
65                  70                  75                  80

Ser Lys Pro Leu Arg Ala Gln Phe Thr Thr Gly Gly Gly Gly Ser Gly
                85                  90                  95

Gly Gly Gly Ser Gly Gly Gly Ser Gly Gly Gly Ser Leu Pro
            100                 105                 110

Ala Pro Lys Asn Leu Val Val Ser Arg Val Thr Glu Asp Ser Ala Arg
            115                 120                 125

Leu Ser Trp Thr Ala Pro Asp Ala Ala Phe Asp Ser Phe His Ile Glu
            130                 135                 140

Tyr Trp Glu Gln Ser Ile Val Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Arg Val Trp Ile Tyr Gly Val Lys Gly Gly Asn Asp Ser Trp Pro
                180                 185                 190

Leu Ser Ala Ile Phe Thr Thr
            195
```

<210> SEQ ID NO 336
<211> LENGTH: 242
<212> TYPE: PRT
<213> ORGANISM: Artificial Sequence
<220> FEATURE:
<223> OTHER INFORMATION: synthetic sequence

<400> SEQUENCE: 336

Gln Glu Glu Cys Val Cys Glu Asn Tyr Lys Leu Ala Val Asn Cys Phe
1               5                   10                  15

Val Asn Asn Arg Gln Cys Gln Cys Thr Ser Val Gly Ala Gln Asn
            20                  25                  30

Thr Val Ile Cys Ser Lys Leu Ala Ala Lys Cys Leu Val Met Lys Ala
            35                  40                  45

Glu Met Asn Gly Ser Lys Leu Gly Arg Arg Ala Lys Pro Glu Gly Ala
50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Met Cys Trp Cys Val
                85                  90                  95

Asn Thr Ala Gly Val Arg Arg Thr Asp Lys Asp Thr Glu Ile Thr Cys
                100                 105                 110

Ser Glu Arg Val Arg Thr Tyr Trp Ile Ile Glu Leu Lys His Lys
            115                 120                 125

Ala Arg Glu Lys Pro Tyr Asp Ser Lys Ser Leu Arg Thr Ala Leu Gln
130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
            195                 200                 205

Asp Leu Thr Val Asn Gly Glu Gln Leu Asp Leu Asp Pro Gly Gln Thr
        210                 215                 220

Leu Ile Tyr Tyr Val Asp Glu Lys Ala Pro Glu Phe Ser Met Gln Gly
225                 230                 235                 240

Leu Lys

<210> SEQ ID NO 337
<211> LENGTH: 94
<212> TYPE: PRT
<213> ORGANISM: Artificial Sequence
<220> FEATURE:
<223> OTHER INFORMATION: synthetic sequence

<400> SEQUENCE: 337

Leu Pro Ala Pro Lys Asn Leu Val Val Ser Glu Val Thr Glu Asp Ser
1               5                   10                  15

Leu Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

```
<210> SEQ ID NO 338
<211> LENGTH: 94
<212> TYPE: PRT
<213> ORGANISM: Artificial Sequence
<220> FEATURE:
<223> OTHER INFORMATION: synthetic sequence

<400> SEQUENCE: 338

Leu Pro Ala Pro Lys Asn Leu Val Val Ser Glu Val Thr Glu Asp Ser
1               5                   10                  15

Leu Arg Leu Ser Trp Thr Tyr Asp Arg Asp Gly Tyr Asp Ser Phe Leu
                20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 339
<211> LENGTH: 94
<212> TYPE: PRT
<213> ORGANISM: Artificial Sequence
<220> FEATURE:
<223> OTHER INFORMATION: synthetic sequence

<400> SEQUENCE: 339

Leu Pro Ala Pro Lys Asn Leu Ala Ala Ser Glu Val Thr Glu Asp Ser
1               5                   10                  15

Leu Arg Leu Ser Trp Gly Tyr Asn Gly Asp His Phe Asp Ser Phe Leu
                20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 340
<211> LENGTH: 94
<212> TYPE: PRT
<213> ORGANISM: Artificial Sequence
<220> FEATURE:
<223> OTHER INFORMATION: synthetic sequence

<400> SEQUENCE: 340

Leu Pro Ala Pro Lys Asn Leu Val Val Ser Glu Val Thr Glu Asp Ser
1               5                   10                  15

Leu Arg Leu Ser Trp Asp Asp Pro Arg Gly Phe Tyr Glu Ser Phe Leu
                20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80
```

```
Thr Asn Met Arg Gly Leu Pro Leu Ser Ala Glu Phe Thr Thr
                85                  90
```

<210> SEQ ID NO 341
<211> LENGTH: 94
<212> TYPE: PRT
<213> ORGANISM: Artificial Sequence
<220> FEATURE:
<223> OTHER INFORMATION: synthetic sequence

<400> SEQUENCE: 341

```
Leu Pro Ala Pro Lys Asn Leu Val Val Ser Glu Val Thr Glu Asp Ser
1               5                   10                  15

Leu Arg Leu Ser Trp Thr Trp Pro Tyr Ala Asp Leu Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90
```

<210> SEQ ID NO 342
<211> LENGTH: 94
<212> TYPE: PRT
<213> ORGANISM: Artificial Sequence
<220> FEATURE:
<223> OTHER INFORMATION: synthetic sequence

<400> SEQUENCE: 342

```
Leu Pro Ala Pro Lys Asn Leu Val Val Ser Glu Val Thr Glu Asp Ser
1               5                   10                  15

Leu Arg Leu Ser Trp Gly Tyr Asn Gly Asp His Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90
```

<210> SEQ ID NO 343
<211> LENGTH: 95
<212> TYPE: PRT
<213> ORGANISM: Artificial Sequence
<220> FEATURE:
<223> OTHER INFORMATION: synthetic sequence

<400> SEQUENCE: 343

```
Leu Pro Ala Pro Lys Asn Leu Val Val Ser Glu Val Thr Glu Asp Ser
1               5                   10                  15

Leu Arg Leu Ser Trp Asp Tyr Asp Leu Gly Val Tyr Phe Asp Ser Phe
            20                  25                  30

Leu Ile Gln Tyr Gln Glu Ser Glu Lys Val Gly Glu Ala Ile Asn Leu
        35                  40                  45
```

```
Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Glu Phe Thr Thr
                 85                  90                  95
```

<210> SEQ ID NO 344
<211> LENGTH: 94
<212> TYPE: PRT
<213> ORGANISM: Artificial Sequence
<220> FEATURE:
<223> OTHER INFORMATION: synthetic sequence

<400> SEQUENCE: 344

```
Leu Pro Ala Pro Lys Asn Leu Val Val Ser Glu Val Thr Glu Asp Ser
 1               5                  10                  15

Leu Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Glu Phe Thr Thr
                 85                  90
```

<210> SEQ ID NO 345
<211> LENGTH: 94
<212> TYPE: PRT
<213> ORGANISM: Artificial Sequence
<220> FEATURE:
<223> OTHER INFORMATION: synthetic sequence

<400> SEQUENCE: 345

```
Leu Pro Ala Pro Lys Asn Leu Val Val Ser Glu Val Thr Glu Asp Ser
 1               5                  10                  15

Leu Arg Leu Ser Trp Thr Ala Pro Ala Ala Phe Asp Ser Phe Leu
                20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Leu Gly Ser Tyr Val Phe
 65                  70                  75                  80

Glu His Asp Val Met Leu Pro Leu Ser Ala Glu Phe Thr Thr
                 85                  90
```

<210> SEQ ID NO 346
<211> LENGTH: 94
<212> TYPE: PRT
<213> ORGANISM: Artificial Sequence
<220> FEATURE:
<223> OTHER INFORMATION: synthetic sequence

<400> SEQUENCE: 346

```
Leu Pro Ala Pro Lys Asn Leu Val Val Ser Glu Val Thr Glu Asp Ser
 1               5                  10                  15

Ala Arg Leu Ser Trp Asp Asp Pro Trp Ala Phe Tyr Glu Ser Phe Leu
```

```
                    20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 347
<211> LENGTH: 94
<212> TYPE: PRT
<213> ORGANISM: Artificial Sequence
<220> FEATURE:
<223> OTHER INFORMATION: synthetic sequence

<400> SEQUENCE: 347

Leu Pro Ala Pro Lys Asn Leu Val Val Ser Glu Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Leu Gly Ser Tyr Val Phe
65                  70                  75                  80

Glu His Asp Val Met Leu Pro Leu Ser Ala Ile Phe Thr Thr
                85                  90

<210> SEQ ID NO 348
<211> LENGTH: 94
<212> TYPE: PRT
<213> ORGANISM: Artificial Sequence
<220> FEATURE:
<223> OTHER INFORMATION: synthetic sequence

<400> SEQUENCE: 348

Leu Pro Ala Pro Lys Asn Leu Val Val Ser Glu Val Thr Glu Asp Ser
1               5                   10                  15

Leu Arg Leu Ser Trp Thr Trp Pro Tyr Ala Asp Leu Asp Ser Phe Leu
            20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 349
<211> LENGTH: 94
<212> TYPE: PRT
<213> ORGANISM: Artificial Sequence
<220> FEATURE:
<223> OTHER INFORMATION: synthetic sequence

<400> SEQUENCE: 349
```

```
Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Ala Ile Val Leu Thr
                35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 350
<211> LENGTH: 94
<212> TYPE: PRT
<213> ORGANISM: Artificial Sequence
<220> FEATURE:
<223> OTHER INFORMATION: synthetic sequence

<400> SEQUENCE: 350

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 351
<211> LENGTH: 94
<212> TYPE: PRT
<213> ORGANISM: Artificial Sequence
<220> FEATURE:
<223> OTHER INFORMATION: synthetic sequence

<400> SEQUENCE: 351

Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 352
<211> LENGTH: 94
<212> TYPE: PRT
```

<213> ORGANISM: Artificial Sequence
<220> FEATURE:
<223> OTHER INFORMATION: synthetic sequence

<400> SEQUENCE: 352

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 353
<211> LENGTH: 95
<212> TYPE: PRT
<213> ORGANISM: Artificial Sequence
<220> FEATURE:
<223> OTHER INFORMATION: synthetic sequence

<400> SEQUENCE: 353

Met Leu Pro Ala Pro Lys Asn Leu Val Val Ser Glu Val Thr Glu Asp
1               5                   10                  15

Ser Leu Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 354
<211> LENGTH: 95
<212> TYPE: PRT
<213> ORGANISM: Artificial Sequence
<220> FEATURE:
<223> OTHER INFORMATION: synthetic sequence

<400> SEQUENCE: 354

Met Leu Pro Ala Pro Lys Asn Leu Val Val Ser Glu Val Thr Glu Asp
1               5                   10                  15

Ser Leu Arg Leu Ser Trp Thr Tyr Asp Arg Asp Gly Tyr Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 355
<211> LENGTH: 95
<212> TYPE: PRT
<213> ORGANISM: Artificial Sequence
<220> FEATURE:
<223> OTHER INFORMATION: synthetic sequence

<400> SEQUENCE: 355

Met Leu Pro Ala Pro Lys Asn Leu Val Val Ser Glu Val Thr Glu Asp
1               5                   10                  15

Ser Leu Arg Leu Ser Trp Gly Tyr Asn Gly Asp His Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 356
<211> LENGTH: 95
<212> TYPE: PRT
<213> ORGANISM: Artificial Sequence
<220> FEATURE:
<223> OTHER INFORMATION: synthetic sequence

<400> SEQUENCE: 356

Met Leu Pro Ala Pro Lys Asn Leu Val Val Ser Glu Val Thr Glu Asp
1               5                   10                  15

Ser Leu Arg Leu Ser Trp Asp Asp Pro Arg Gly Phe Tyr Glu Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 357
<211> LENGTH: 95
<212> TYPE: PRT
<213> ORGANISM: Artificial Sequence
<220> FEATURE:
<223> OTHER INFORMATION: synthetic sequence

<400> SEQUENCE: 357

Met Leu Pro Ala Pro Lys Asn Leu Val Val Ser Glu Val Thr Glu Asp
1               5                   10                  15

Ser Leu Arg Leu Ser Trp Thr Trp Pro Tyr Ala Asp Leu Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 358
<211> LENGTH: 95
<212> TYPE: PRT
<213> ORGANISM: Artificial Sequence
<220> FEATURE:
<223> OTHER INFORMATION: synthetic sequence

<400> SEQUENCE: 358

Met Leu Pro Ala Pro Lys Asn Leu Val Val Ser Glu Val Thr Glu Asp
1               5                   10                  15

Ser Leu Arg Leu Ser Trp Gly Tyr Asn Gly Asp His Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 359
<211> LENGTH: 96
<212> TYPE: PRT
<213> ORGANISM: Artificial Sequence
<220> FEATURE:
<223> OTHER INFORMATION: synthetic sequence

<400> SEQUENCE: 359

Met Leu Pro Ala Pro Lys Asn Leu Val Val Ser Glu Val Thr Glu Asp
1               5                   10                  15

Ser Leu Arg Leu Ser Trp Asp Tyr Asp Leu Gly Val Tyr Phe Asp Ser
            20                  25                  30

Phe Leu Ile Gln Tyr Gln Glu Ser Glu Lys Val Gly Glu Ala Ile Asn
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val His Asn Val Tyr
65                  70                  75                  80

Lys Asp Thr Asn Met Arg Gly Leu Pro Leu Ser Ala Glu Phe Thr Thr
                85                  90                  95

<210> SEQ ID NO 360
<211> LENGTH: 95
<212> TYPE: PRT
<213> ORGANISM: Artificial Sequence
<220> FEATURE:
<223> OTHER INFORMATION: synthetic sequence

<400> SEQUENCE: 360

Met Leu Pro Ala Pro Lys Asn Leu Val Val Ser Glu Val Thr Glu Asp
1               5                   10                  15

Ser Leu Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Asn Leu

```
                35                  40                  45
Thr Val Pro Gly Ser Glu Arg Ser Tyr Asp Leu Thr Gly Leu Lys Pro
        50                  55                  60
Gly Thr Glu Tyr Thr Val Ser Ile Tyr Gly Val His Asn Val Tyr Lys
65                  70                  75                  80
Asp Thr Asn Met Arg Gly Leu Pro Leu Ser Ala Glu Phe Thr Thr
                85                  90                  95

<210> SEQ ID NO 361
<211> LENGTH: 95
<212> TYPE: PRT
<213> ORGANISM: Artificial Sequence
<220> FEATURE:
<223> OTHER INFORMATION: synthetic sequence

<400> SEQUENCE: 361

Met Leu Pro Ala Pro Lys Asn Leu Val Val Ser Glu Val Thr Glu Asp
1               5                   10                  15
Ser Leu Arg Leu Ser Trp Thr Ala Pro Asp Ala Ala Phe Asp Ser Phe
                20                  25                  30
Leu Ile Gln Tyr Gln Glu Ser Glu Lys Val Gly Glu Ala Ile Asn Leu
            35                  40                  45
Thr Val Pro Gly Ser Glu Arg Ser Tyr Asp Leu Thr Gly Leu Lys Pro
        50                  55                  60
Gly Thr Glu Tyr Thr Val Ser Ile Tyr Gly Val Leu Gly Ser Tyr Val
65                  70                  75                  80
Phe Glu His Asp Val Met Leu Pro Leu Ser Ala Glu Phe Thr Thr
                85                  90                  95

<210> SEQ ID NO 362
<211> LENGTH: 95
<212> TYPE: PRT
<213> ORGANISM: Artificial Sequence
<220> FEATURE:
<223> OTHER INFORMATION: synthetic sequence

<400> SEQUENCE: 362

Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
                20                  25                  30
Leu Ile Gln Tyr Gln Glu Ser Glu Lys Val Gly Glu Ala Ile Val Leu
            35                  40                  45
Thr Val Pro Gly Ser Glu Arg Ser Tyr Asp Leu Thr Gly Leu Lys Pro
        50                  55                  60
Gly Thr Glu Tyr Thr Val Ser Ile Tyr Gly Val His Asn Val Tyr Lys
65                  70                  75                  80
Asp Thr Asn Met Arg Gly Leu Pro Leu Ser Ala Ile Phe Thr Thr
                85                  90                  95

<210> SEQ ID NO 363
<211> LENGTH: 95
<212> TYPE: PRT
<213> ORGANISM: Artificial Sequence
<220> FEATURE:
<223> OTHER INFORMATION: synthetic sequence

<400> SEQUENCE: 363

Met Leu Pro Ala Pro Lys Asn Leu Val Val Ser Glu Val Thr Glu Asp
1               5                   10                  15
```

Ser Ala Arg Leu Ser Trp Thr Ala Pro Asp Ala Ala Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Leu Gly Ser Tyr Val
65                  70                  75                  80

Phe Glu His Asp Val Met Leu Pro Leu Ser Ala Ile Phe Thr Thr
                85                  90                  95

<210> SEQ ID NO 364
<211> LENGTH: 95
<212> TYPE: PRT
<213> ORGANISM: Artificial Sequence
<220> FEATURE:
<223> OTHER INFORMATION: synthetic sequence

<400> SEQUENCE: 364

Met Leu Pro Ala Pro Lys Asn Leu Val Val Ser Glu Val Thr Glu Asp
1               5                   10                  15

Ser Leu Arg Leu Ser Trp Thr Trp Pro Tyr Ala Asp Leu Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 365
<211> LENGTH: 95
<212> TYPE: PRT
<213> ORGANISM: Artificial Sequence
<220> FEATURE:
<223> OTHER INFORMATION: synthetic sequence

<400> SEQUENCE: 365

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 366
<211> LENGTH: 95
<212> TYPE: PRT
<213> ORGANISM: Artificial Sequence
<220> FEATURE:
<223> OTHER INFORMATION: synthetic sequence

<400> SEQUENCE: 366

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 367
<211> LENGTH: 95
<212> TYPE: PRT
<213> ORGANISM: Artificial Sequence
<220> FEATURE:
<223> OTHER INFORMATION: synthetic sequence

<400> SEQUENCE: 367

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 368
<211> LENGTH: 95
<212> TYPE: PRT
<213> ORGANISM: Artificial Sequence
<220> FEATURE:
<223> OTHER INFORMATION: synthetic sequence

<400> SEQUENCE: 368

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 369

```
<211> LENGTH: 4
<212> TYPE: PRT
<213> ORGANISM: Artificial Sequence
<220> FEATURE:
<223> OTHER INFORMATION: synthetic sequence

<400> SEQUENCE: 369

Gly Ser Gly Ser
1

<210> SEQ ID NO 370
<211> LENGTH: 8
<212> TYPE: PRT
<213> ORGANISM: Artificial Sequence
<220> FEATURE:
<223> OTHER INFORMATION: synthetic sequence

<400> SEQUENCE: 370

Gly Gly Gly Ser Gly Gly Gly Ser
1               5

<210> SEQ ID NO 371
<211> LENGTH: 25
<212> TYPE: PRT
<213> ORGANISM: Artificial Sequence
<220> FEATURE:
<223> OTHER INFORMATION: synthetic sequence

<400> SEQUENCE: 371

Gly Gly Gly Gly Ser Gly Gly Gly Ser Gly Gly Gly Ser Gly
1               5                   10                  15

Gly Gly Ser Gly Gly Gly Gly Ser
            20                  25

<210> SEQ ID NO 372
<211> LENGTH: 4
<212> TYPE: PRT
<213> ORGANISM: Artificial Sequence
<220> FEATURE:
<223> OTHER INFORMATION: synthetic sequence

<400> SEQUENCE: 372

Ala Pro Ala Pro
1

<210> SEQ ID NO 373
<211> LENGTH: 10
<212> TYPE: PRT
<213> ORGANISM: Artificial Sequence
<220> FEATURE:
<223> OTHER INFORMATION: synthetic sequence

<400> SEQUENCE: 373

Ala Pro Ala Pro Ala Pro Ala Pro Ala Pro
1               5                   10

<210> SEQ ID NO 374
<211> LENGTH: 20
<212> TYPE: PRT
<213> ORGANISM: Artificial Sequence
<220> FEATURE:
<223> OTHER INFORMATION: synthetic sequence

<400> SEQUENCE: 374

Ala Pro Ala Pro Ala Pro Ala Pro Ala Pro Ala Pro Ala Pro Ala Pro
1               5                   10                  15
```

-continued

Ala Pro Ala Pro
        20

<210> SEQ ID NO 375
<211> LENGTH: 40
<212> TYPE: PRT
<213> ORGANISM: Artificial Sequence
<220> FEATURE:
<223> OTHER INFORMATION: synthetic sequence

<400> SEQUENCE: 375

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 376
<211> LENGTH: 29
<212> TYPE: PRT
<213> ORGANISM: Artificial Sequence
<220> FEATURE:
<223> OTHER INFORMATION: synthetic sequence

<400> SEQUENCE: 376

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
            20                  25

<210> SEQ ID NO 377
<211> LENGTH: 95
<212> TYPE: PRT
<213> ORGANISM: Artificial Sequence
<220> FEATURE:
<223> OTHER INFORMATION: synthetic sequence

<400> SEQUENCE: 377

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 378
<211> LENGTH: 90
<212> TYPE: PRT
<213> ORGANISM: Artificial Sequence
<220> FEATURE:
<223> OTHER INFORMATION: synthetic sequence

<400> SEQUENCE: 378

Met Leu Pro Ala Pro Lys Asn Leu Val Val Ser Arg Val Thr Glu Asp
1               5                   10                  15

-continued

Ser Ala Arg Leu Ser Trp Thr Ala Pro Asp Ala Ala Phe Asp Ser Phe
            20                  25                  30

Thr Ile Trp Tyr Ala Glu Ala Ile Gly His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Asp Ile Trp Gly Val Lys Gly Gln Gln
65                  70                  75                  80

Ser Lys Pro Leu Ser Ala Ile Phe Thr Thr
            85                  90

<210> SEQ ID NO 379
<211> LENGTH: 199
<212> TYPE: PRT
<213> ORGANISM: Artificial Sequence
<220> FEATURE:
<223> OTHER INFORMATION: synthetic sequence

<400> SEQUENCE: 379

Met Leu Pro Ala Pro Lys Asn Leu Val Val Ser Arg Val Thr Glu Asp
1               5                   10                  15

Ser Ala Arg Leu Ser Trp Thr Ala Pro Tyr Ala Ala Phe Asp Ser Phe
            20                  25                  30

Ala Ile Ser Tyr Arg Glu Arg Ser Arg Glu Gly Glu Val Ile Ala Leu
        35                  40                  45

Thr Val Pro Gly Ser Glu Arg Ser Tyr Asp Leu Thr Gly Leu Lys Pro
    50                  55                  60

Gly Thr Glu Tyr Ile Val Gly Ile Leu Gly Val Lys Gly Gly Arg Arg
65                  70                  75                  80

Ser Lys Pro Leu Arg Ala Gln Phe Thr Thr Gly Gly Gly Ser Gly
            85                  90                  95

Gly Gly Gly Ser Gly Gly Gly Ser Gly Gly Gly Ser Leu Pro
                100                 105                 110

Ala Pro Lys Asn Leu Val Val Ser Arg Val Thr Glu Asp Ser Ala Arg
            115                 120                 125

Leu Ser Trp Thr Ala Pro Asp Ala Ala Phe Asp Ser Phe His Ile Glu
        130                 135                 140

Tyr Trp Glu Gln Ser Ile Val Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Arg Val Trp Ile Tyr Gly Val Lys Gly Gly Asn Asp Ser Trp Pro
            180                 185                 190

Leu Ser Ala Ile Phe Thr Thr
            195

<210> SEQ ID NO 380
<211> LENGTH: 90
<212> TYPE: PRT
<213> ORGANISM: Artificial Sequence
<220> FEATURE:
<223> OTHER INFORMATION: synthetic sequence

<400> SEQUENCE: 380

Met Leu Pro Ala Pro Lys Asn Leu Val Val Ser Glu Val Thr Glu Asp
1               5                   10                  15

Ser Ala Arg Leu Ser Trp Thr Ala Pro Asp Ala Ala Phe Asp Ser Phe
            20                  25                  30

```
Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val Lys Gly Gly His Arg
 65                  70                  75                  80

Ser Asn Pro Leu Ser Ala Ile Phe Thr Thr
                85                  90

<210> SEQ ID NO 381
<211> LENGTH: 199
<212> TYPE: PRT
<213> ORGANISM: Artificial Sequence
<220> FEATURE:
<223> OTHER INFORMATION: synthetic sequence

<400> SEQUENCE: 381

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Thr Ile Trp Tyr Ala Glu Ala Ile Gly His Gly Glu Ala Ile Val Leu
        35                  40                  45

Thr Val Pro Gly Ser Glu Arg Ser Tyr Asp Leu Thr Gly Leu Lys Pro
 50                  55                  60

Gly Thr Glu Tyr Trp Val Asp Ile Trp Gly Val Lys Gly Gly Gln Gln
 65                  70                  75                  80

Ser Lys Pro Leu Ser Ala Ile Phe Thr Thr Gly Gly Gly Ser Gly
                85                  90                  95

Gly Gly Gly Ser Gly Gly Gly Ser Gly Gly Gly Gly Ser Leu Pro
                100                 105                 110

Ala Pro Lys Asn Leu Val Val Ser Arg Val Thr Glu Asp Ser Ala Arg
        115                 120                 125

Leu Ser Trp Thr Ala Pro Asp Ala Ala Phe Asp Ser Phe Thr Ile Trp
        130                 135                 140

Tyr Ala Glu Ala Ile Gly His Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Trp Val Asp Ile Trp Gly Val Lys Gly Gly Gln Gln Ser Lys Pro
                180                 185                 190

Leu Ser Ala Ile Phe Thr Thr
        195

<210> SEQ ID NO 382
<211> LENGTH: 260
<212> TYPE: PRT
<213> ORGANISM: Artificial Sequence
<220> FEATURE:
<223> OTHER INFORMATION: synthetic sequence

<400> SEQUENCE: 382

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Thr Ile Trp Tyr Ala Glu Ala Ile Gly His Gly Glu Ala Ile Val Leu
```

```
            35                  40                  45
Thr Val Pro Gly Ser Glu Arg Ser Tyr Asp Leu Thr Gly Leu Lys Pro
         50                  55                  60
Gly Thr Glu Tyr Trp Val Asp Ile Trp Gly Val Lys Gly Gly Gln Gln
 65                  70                  75                  80
Ser Lys Pro Leu Ser Ala Ile Phe Thr Thr Gly Gly Gly Ser Gly
                 85                  90                  95
Gly Gly Gly Ser Gly Gly Gly Ser Gly Gly Gly Ser Leu Pro
                100                 105                 110
Ala Pro Lys Asn Leu Val Val Ser Arg Val Thr Glu Asp Ser Ala Arg
                115                 120                 125
Leu Ser Trp Thr Ala Pro Asp Ala Ala Phe Asp Ser Phe Thr Ile Trp
        130                 135                 140
Tyr Ala Glu Ala Ile Gly His Gly Glu Ala Ile Val Leu Thr Val Pro
145                 150                 155                 160
Gly Ser Glu Arg Ser Tyr Asp Leu Thr Gly Leu Lys Pro Gly Thr Glu
                165                 170                 175
Tyr Trp Val Asp Ile Trp Gly Val Lys Gly Gly Gln Gln Ser Lys Pro
                180                 185                 190
Leu Ser Ala Ile Phe Thr Thr Ala Pro Ala Pro Ala Pro Ala
        195                 200                 205
Pro Thr Ile Asp Glu Trp Leu Leu Lys Glu Ala Lys Glu Lys Ala Ile
        210                 215                 220
Glu Glu Leu Lys Lys Ala Gly Ile Thr Ser Asp Tyr Tyr Phe Asp Leu
225                 230                 235                 240
Ile Asn Lys Ala Lys Thr Val Glu Gly Val Asn Ala Leu Lys Asp Glu
                245                 250                 255
Ile Leu Lys Ala
        260

<210> SEQ ID NO 383
<211> LENGTH: 260
<212> TYPE: PRT
<213> ORGANISM: Artificial Sequence
<220> FEATURE:
<223> OTHER INFORMATION: synthetic sequence

<400> SEQUENCE: 383

Met Leu Pro Ala Pro Lys Asn Leu Val Val Ser Arg Val Thr Glu Asp
 1               5                  10                  15
Ser Ala Arg Leu Ser Trp Thr Ala Pro Tyr Ala Ala Phe Asp Ser Phe
                20                  25                  30
Ala Ile Ser Tyr Arg Glu Arg Ser Arg Glu Gly Glu Val Ile Ala Leu
        35                  40                  45
Thr Val Pro Gly Ser Glu Arg Ser Tyr Asp Leu Thr Gly Leu Lys Pro
     50                  55                  60
Gly Thr Glu Tyr Ile Val Gly Ile Leu Gly Val Lys Gly Gly Arg Arg
 65                  70                  75                  80
Ser Lys Pro Leu Arg Ala Gln Phe Thr Thr Gly Gly Gly Ser Gly
                 85                  90                  95
Gly Gly Gly Ser Gly Gly Gly Ser Gly Gly Gly Ser Leu Pro
                100                 105                 110
Ala Pro Lys Asn Leu Val Val Ser Arg Val Thr Glu Asp Ser Ala Arg
                115                 120                 125
Leu Ser Trp Thr Ala Pro Tyr Ala Ala Phe Asp Ser Phe Ala Ile Ser
```

```
             130                 135                 140
Tyr Arg Glu Arg Ser Arg Glu Gly Glu Val Ile Ala Leu Thr Val Pro
145                 150                 155                 160

Gly Ser Glu Arg Ser Tyr Asp Leu Thr Gly Leu Lys Pro Gly Thr Glu
                165                 170                 175

Tyr Ile Val Gly Ile Leu Gly Val Lys Gly Gly Arg Arg Ser Lys Pro
            180                 185                 190

Leu Arg Ala Gln Phe Thr Thr Ala Pro Ala Pro Ala Pro Ala Pro Ala
        195                 200                 205

Pro Thr Ile Asp Glu Trp Leu Leu Lys Glu Ala Lys Glu Lys Ala Ile
    210                 215                 220

Glu Glu Leu Lys Lys Ala Gly Ile Thr Ser Asp Tyr Tyr Phe Asp Leu
225                 230                 235                 240

Ile Asn Lys Ala Lys Thr Val Glu Gly Val Asn Ala Leu Lys Asp Glu
                245                 250                 255

Ile Leu Lys Ala
            260

<210> SEQ ID NO 384
<211> LENGTH: 260
<212> TYPE: PRT
<213> ORGANISM: Artificial Sequence
<220> FEATURE:
<223> OTHER INFORMATION: synthetic sequence

<400> SEQUENCE: 384

Met Leu Pro Ala Pro Lys Asn Leu Val Val Ser Arg Val Thr Glu Asp
1               5                   10                  15

Ser Ala Arg Leu Ser Trp Thr Ala Pro Tyr Ala Ala Phe Asp Ser Phe
            20                  25                  30

Ala Ile Ser Tyr Arg Glu Arg Ser Arg Glu Gly Glu Val Ile Ala Leu
        35                  40                  45

Thr Val Pro Gly Ser Glu Arg Ser Tyr Asp Leu Thr Gly Leu Lys Pro
    50                  55                  60

Gly Thr Glu Tyr Ile Val Gly Ile Leu Gly Val Lys Gly Gly Arg Arg
65                  70                  75                  80

Ser Lys Pro Leu Arg Ala Gln Phe Thr Thr Gly Gly Gly Ser Gly
            85                  90                  95

Gly Gly Gly Ser Gly Gly Gly Gly Ser Gly Gly Gly Gly Ser Leu Pro
                100                 105                 110

Ala Pro Lys Asn Leu Val Val Ser Arg Val Thr Glu Asp Ser Ala Arg
            115                 120                 125

Leu Ser Trp Thr Ala Pro Asp Ala Ala Phe Asp Ser Phe Thr Ile Trp
        130                 135                 140

Tyr Ala Glu Ala Ile Gly His Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Trp Val Asp Ile Trp Gly Val Lys Gly Gly Gln Gln Ser Lys Pro
            180                 185                 190

Leu Ser Ala Ile Phe Thr Thr Ala Pro Ala Pro Ala Pro Ala Pro Ala
        195                 200                 205

Pro Thr Ile Asp Glu Trp Leu Leu Lys Glu Ala Lys Glu Lys Ala Ile
    210                 215                 220

Glu Glu Leu Lys Lys Ala Gly Ile Thr Ser Asp Tyr Tyr Phe Asp Leu
```

```
                  225                 230                 235                 240

Ile Asn Lys Ala Lys Thr Val Glu Gly Val Asn Ala Leu Lys Asp Glu
                245                 250                 255

Ile Leu Lys Ala
            260

<210> SEQ ID NO 385
<211> LENGTH: 250
<212> TYPE: PRT
<213> ORGANISM: Artificial Sequence
<220> FEATURE:
<223> OTHER INFORMATION: synthetic sequence

<400> SEQUENCE: 385

Met Leu Pro Ala Pro Lys Asn Leu Val Val Ser Arg Val Thr Glu Asp
1               5                   10                  15

Ser Ala Arg Leu Ser Trp Thr Ala Pro Tyr Ala Ala Phe Asp Ser Phe
                20                  25                  30

Ala Ile Ser Tyr Arg Glu Arg Ser Arg Glu Gly Glu Val Ile Ala Leu
            35                  40                  45

Thr Val Pro Gly Ser Glu Arg Ser Tyr Asp Leu Thr Gly Leu Lys Pro
        50                  55                  60

Gly Thr Glu Tyr Ile Val Gly Ile Leu Gly Val Lys Gly Gly Arg Arg
65                  70                  75                  80

Ser Lys Pro Leu Arg Ala Gln Phe Thr Thr Ala Pro Ala Pro Ala Pro
                85                  90                  95

Ala Pro Ala Pro Leu Pro Ala Pro Lys Asn Leu Val Val Ser Arg Val
            100                 105                 110

Thr Glu Asp Ser Ala Arg Leu Ser Trp Thr Ala Pro Asp Ala Ala Phe
        115                 120                 125

Asp Ser Phe Thr Ile Trp Tyr Ala Glu Ala Ile Gly His Gly Glu Ala
    130                 135                 140

Ile Val Leu Thr Val Pro Gly Ser Glu Arg Ser Tyr Asp Leu Thr Gly
145                 150                 155                 160

Leu Lys Pro Gly Thr Glu Tyr Trp Val Asp Ile Trp Gly Val Lys Gly
                165                 170                 175

Gly Gln Gln Ser Lys Pro Leu Ser Ala Ile Phe Thr Thr Ala Pro Ala
            180                 185                 190

Pro Ala Pro Ala Pro Thr Ile Asp Glu Trp Leu Leu Lys Glu
        195                 200                 205

Ala Lys Glu Lys Ala Ile Glu Glu Leu Lys Lys Ala Gly Ile Thr Ser
    210                 215                 220

Asp Tyr Tyr Phe Asp Leu Ile Asn Lys Ala Lys Thr Val Glu Gly Val
225                 230                 235                 240

Asn Ala Leu Lys Asp Glu Ile Leu Lys Ala
                245                 250

<210> SEQ ID NO 386
<211> LENGTH: 260
<212> TYPE: PRT
<213> ORGANISM: Artificial Sequence
<220> FEATURE:
<223> OTHER INFORMATION: synthetic sequence

<400> SEQUENCE: 386

Met Leu Pro Ala Pro Lys Asn Leu Val Val Ser Arg Val Thr Glu Asp
1               5                   10                  15
```

Ser Ala Arg Leu Ser Trp Thr Ala Pro Tyr Ala Ala Phe Asp Ser Phe
            20                  25                  30

Ala Ile Ser Tyr Arg Glu Arg Ser Arg Glu Gly Glu Val Ile Ala Leu
            35                  40                  45

Thr Val Pro Gly Ser Glu Arg Ser Tyr Asp Leu Thr Gly Leu Lys Pro
        50                  55                  60

Gly Thr Glu Tyr Ile Val Gly Ile Leu Gly Val Lys Gly Gly Arg Arg
65                  70                  75                  80

Ser Lys Pro Leu Arg Ala Gln Phe Thr Thr Gly Gly Gly Ser Gly
            85                  90                  95

Gly Gly Gly Ser Gly Gly Gly Ser Gly Gly Gly Gly Ser Leu Pro
            100                 105                 110

Ala Pro Lys Asn Leu Val Val Ser Arg Val Thr Glu Asp Ser Ala Arg
            115                 120                 125

Leu Ser Trp Thr Ala Pro Asp Ala Ala Phe Asp Ser Phe Ser Ile Ser
            130                 135                 140

Tyr Arg Glu Arg Ser Ala Trp Gly Glu Ala Ile Ala Leu Val Val Pro
145                 150                 155                 160

Gly Ser Glu Arg Ser Tyr Asp Leu Thr Gly Leu Lys Pro Gly Ile Glu
            165                 170                 175

Tyr Ile Val Gly Ile Ile Gly Val Lys Gly Gly Leu Arg Ser Asn Pro
            180                 185                 190

Leu Arg Ala Asp Phe Thr Thr Ala Pro Ala Pro Ala Pro Ala Pro Ala
            195                 200                 205

Pro Thr Ile Asp Glu Trp Leu Leu Lys Glu Ala Lys Glu Lys Ala Ile
            210                 215                 220

Glu Glu Leu Lys Lys Ala Gly Ile Thr Ser Asp Tyr Tyr Phe Asp Leu
225                 230                 235                 240

Ile Asn Lys Ala Lys Thr Val Glu Gly Val Asn Ala Leu Lys Asp Glu
            245                 250                 255

Ile Leu Lys Ala
            260

<210> SEQ ID NO 387
<211> LENGTH: 260
<212> TYPE: PRT
<213> ORGANISM: Artificial Sequence
<220> FEATURE:
<223> OTHER INFORMATION: synthetic sequence

<400> SEQUENCE: 387

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Ser Tyr Arg Glu Arg Ser Ala Trp Gly Glu Ala Ile Ala Leu
            35                  40                  45

Val Val Pro Gly Ser Glu Arg Ser Tyr Asp Leu Thr Gly Leu Lys Pro
        50                  55                  60

Gly Ile Glu Tyr Ile Val Gly Ile Ile Gly Val Lys Gly Gly Leu Arg
65                  70                  75                  80

Ser Asn Pro Leu Arg Ala Asp Phe Thr Thr Gly Gly Gly Ser Gly
            85                  90                  95

Gly Gly Gly Ser Gly Gly Gly Ser Gly Gly Gly Gly Ser Leu Pro
            100                 105                 110

```
Ala Pro Lys Asn Leu Val Val Ser Arg Val Thr Glu Asp Ser Ala Arg
            115                 120                 125

Leu Ser Trp Thr Ala Pro Tyr Ala Ala Phe Asp Ser Phe Ala Ile Ser
    130                 135                 140

Tyr Arg Glu Arg Ser Arg Glu Gly Glu Val Ile Ala Leu Thr Val Pro
145                 150                 155                 160

Gly Ser Glu Arg Ser Tyr Asp Leu Thr Gly Leu Lys Pro Gly Thr Glu
                165                 170                 175

Tyr Ile Val Gly Ile Leu Gly Val Lys Gly Gly Arg Arg Ser Lys Pro
                180                 185                 190

Leu Arg Ala Gln Phe Thr Thr Ala Pro Ala Pro Ala Pro Ala Pro Ala
            195                 200                 205

Pro Thr Ile Asp Glu Trp Leu Leu Lys Glu Ala Lys Glu Lys Ala Ile
    210                 215                 220

Glu Glu Leu Lys Lys Ala Gly Ile Thr Ser Asp Tyr Tyr Phe Asp Leu
225                 230                 235                 240

Ile Asn Lys Ala Lys Thr Val Glu Gly Val Asn Ala Leu Lys Asp Glu
                245                 250                 255

Ile Leu Lys Ala
            260

<210> SEQ ID NO 388
<211> LENGTH: 260
<212> TYPE: PRT
<213> ORGANISM: Artificial Sequence
<220> FEATURE:
<223> OTHER INFORMATION: synthetic sequence

<400> SEQUENCE: 388

Met Leu Pro Ala Pro Lys Asn Leu Val Val Ser Arg Val Thr Glu Asp
1               5                   10                  15

Ser Ala Arg Leu Ser Trp Thr Ala Pro Tyr Ala Ala Phe Asp Ser Phe
                20                  25                  30

Ala Ile Ser Tyr Arg Glu Arg Ser Arg Glu Gly Glu Val Ile Ala Leu
            35                  40                  45

Thr Val Pro Gly Ser Glu Arg Ser Tyr Asp Leu Thr Gly Leu Lys Pro
    50                  55                  60

Gly Thr Glu Tyr Ile Val Gly Ile Leu Gly Val Lys Gly Gly Arg Arg
65                  70                  75                  80

Ser Lys Pro Leu Arg Ala Gln Phe Thr Thr Gly Gly Gly Gly Ser Gly
                85                  90                  95

Gly Gly Gly Ser Gly Gly Gly Gly Ser Gly Gly Gly Gly Ser Leu Pro
                100                 105                 110

Ala Pro Lys Asn Leu Val Ile Ser Arg Val Thr Glu Asp Ser Ala Arg
            115                 120                 125

Leu Ser Trp Thr Ala Pro Asp Ala Ala Phe Asp Ser Phe Phe Ile Tyr
    130                 135                 140

Tyr Ile Glu Ser Tyr Pro Ala Gly Glu Ala Ile Val Leu Thr Val Pro
145                 150                 155                 160

Gly Ser Glu Arg Ser Tyr Asp Leu Thr Gly Leu Lys Pro Gly Thr Glu
                165                 170                 175

Tyr Trp Val Gly Ile Asp Gly Val Lys Gly Gly Arg Trp Ser Thr Pro
                180                 185                 190

Leu Ser Ala Ile Phe Thr Thr Ala Pro Ala Pro Ala Pro Ala Pro Ala
            195                 200                 205
```

```
Pro Thr Ile Asp Glu Trp Leu Leu Lys Glu Ala Lys Glu Lys Ala Ile
    210                 215                 220

Glu Glu Leu Lys Lys Ala Gly Ile Thr Ser Asp Tyr Tyr Phe Asp Leu
225                 230                 235                 240

Ile Asn Lys Ala Lys Thr Val Glu Gly Val Asn Ala Leu Lys Asp Glu
                245                 250                 255

Ile Leu Lys Ala
        260

<210> SEQ ID NO 389
<211> LENGTH: 260
<212> TYPE: PRT
<213> ORGANISM: Artificial Sequence
<220> FEATURE:
<223> OTHER INFORMATION: synthetic sequence

<400> SEQUENCE: 389

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Tyr Tyr Leu Glu Ser Tyr Pro Glu Gly Glu Ala Ile Val Leu
            35                  40                  45

Thr Val Pro Gly Ser Glu Arg Ser Tyr Asp Leu Thr Gly Leu Lys Pro
50                  55                  60

Gly Thr Glu Tyr Trp Val Gly Ile Asp Gly Val Lys Gly Gly Thr Trp
65                  70                  75                  80

Ser Ser Pro Leu Ser Ala Ile Phe Thr Thr Gly Gly Gly Gly Ser Gly
                85                  90                  95

Gly Gly Gly Ser Gly Gly Gly Gly Ser Gly Gly Gly Gly Ser Leu Pro
            100                 105                 110

Ala Pro Lys Asn Leu Val Val Ser Arg Val Thr Glu Asp Ser Ala Arg
            115                 120                 125

Leu Ser Trp Thr Ala Pro Tyr Ala Ala Phe Asp Ser Phe Ala Ile Ser
            130                 135                 140

Tyr Arg Glu Arg Ser Arg Glu Gly Glu Val Ile Ala Leu Thr Val Pro
145                 150                 155                 160

Gly Ser Glu Arg Ser Tyr Asp Leu Thr Gly Leu Lys Pro Gly Thr Glu
                165                 170                 175

Tyr Ile Val Gly Ile Leu Gly Val Lys Gly Gly Arg Arg Ser Lys Pro
            180                 185                 190

Leu Arg Ala Gln Phe Thr Thr Ala Pro Ala Pro Ala Pro Ala Pro Ala
            195                 200                 205

Pro Thr Ile Asp Glu Trp Leu Leu Lys Glu Ala Lys Glu Lys Ala Ile
    210                 215                 220

Glu Glu Leu Lys Lys Ala Gly Ile Thr Ser Asp Tyr Tyr Phe Asp Leu
225                 230                 235                 240

Ile Asn Lys Ala Lys Thr Val Glu Gly Val Asn Ala Leu Lys Asp Glu
                245                 250                 255

Ile Leu Lys Ala
        260

<210> SEQ ID NO 390
<211> LENGTH: 260
<212> TYPE: PRT
<213> ORGANISM: Artificial Sequence
<220> FEATURE:
```

<223> OTHER INFORMATION: synthetic sequence

<400> SEQUENCE: 390

```
Met Leu Pro Ala Pro Lys Asn Leu Val Val Ser Arg Val Thr Glu Asp
1               5                   10                  15
Ser Ala Arg Leu Ser Trp Thr Ala Pro Tyr Ala Ala Phe Asp Ser Phe
            20                  25                  30
Ala Ile Ser Tyr Arg Glu Arg Ser Arg Glu Gly Glu Val Ile Ala Leu
        35                  40                  45
Thr Val Pro Gly Ser Glu Arg Ser Tyr Asp Leu Thr Gly Leu Lys Pro
    50                  55                  60
Gly Thr Glu Tyr Ile Val Gly Ile Leu Gly Val Lys Gly Gly Arg Arg
65                  70                  75                  80
Ser Lys Pro Leu Arg Ala Gln Phe Thr Thr Gly Gly Gly Ser Gly
            85                  90                  95
Gly Gly Gly Ser Gly Gly Gly Ser Gly Gly Gly Ser Leu Pro
            100                 105                 110
Ala Pro Lys Asn Leu Val Val Ser Arg Val Thr Glu Asp Ser Ala Arg
            115                 120                 125
Leu Ser Trp Thr Ala Pro Asp Ala Ala Phe Asp Ser Phe Ala Ile Tyr
    130                 135                 140
Tyr Leu Glu Ser Tyr Pro Glu Gly Glu Ala Ile Val Leu Thr Val Pro
145                 150                 155                 160
Gly Ser Glu Arg Ser Tyr Asp Leu Thr Gly Leu Lys Pro Gly Thr Glu
                165                 170                 175
Tyr Trp Val Gly Ile Asp Gly Val Lys Gly Gly Thr Trp Ser Ser Pro
            180                 185                 190
Leu Ser Ala Ile Phe Thr Thr Ala Pro Ala Pro Ala Pro Ala Pro Ala
            195                 200                 205
Pro Thr Ile Asp Glu Trp Leu Leu Lys Glu Ala Lys Glu Lys Ala Ile
    210                 215                 220
Glu Glu Leu Lys Lys Ala Gly Ile Thr Ser Asp Tyr Tyr Phe Asp Leu
225                 230                 235                 240
Ile Asn Lys Ala Lys Thr Val Glu Gly Val Asn Ala Leu Lys Asp Glu
                245                 250                 255
Ile Leu Lys Ala
            260
```

<210> SEQ ID NO 391
<211> LENGTH: 369
<212> TYPE: PRT
<213> ORGANISM: Artificial Sequence
<220> FEATURE:
<223> OTHER INFORMATION: synthetic sequence

<400> SEQUENCE: 391

```
Met Leu Pro Ala Pro Lys Asn Leu Val Val Ser Arg Val Thr Glu Asp
1               5                   10                  15
Ser Ala Arg Leu Ser Trp Thr Ala Pro Tyr Ala Ala Phe Asp Ser Phe
            20                  25                  30
Ala Ile Ser Tyr Arg Glu Arg Ser Arg Glu Gly Glu Val Ile Ala Leu
        35                  40                  45
Thr Val Pro Gly Ser Glu Arg Ser Tyr Asp Leu Thr Gly Leu Lys Pro
    50                  55                  60
Gly Thr Glu Tyr Ile Val Gly Ile Leu Gly Val Lys Gly Gly Arg Arg
65                  70                  75                  80
```

```
Ser Lys Pro Leu Arg Ala Gln Phe Thr Thr Gly Gly Gly Ser Gly
                85                  90                  95

Gly Gly Gly Ser Gly Gly Gly Ser Gly Gly Gly Ser Leu Pro
           100                 105                 110

Ala Pro Lys Asn Leu Val Val Ser Arg Val Thr Glu Asp Ser Ala Arg
           115                 120                 125

Leu Ser Trp Thr Ala Pro Asp Ala Ala Phe Asp Ser Phe Ser Ile Ser
       130                 135                 140

Tyr Arg Glu Arg Ser Ala Trp Gly Glu Ala Ile Ala Leu Val Val Pro
145                 150                 155                 160

Gly Ser Glu Arg Ser Tyr Asp Leu Thr Gly Leu Lys Pro Gly Ile Glu
               165                 170                 175

Tyr Ile Val Gly Ile Ile Gly Val Lys Gly Gly Leu Arg Ser Asn Pro
               180                 185                 190

Leu Arg Ala Asp Phe Thr Thr Gly Gly Gly Ser Gly Gly Gly Gly
               195                 200                 205

Ser Gly Gly Gly Gly Ser Gly Gly Gly Ser Leu Pro Ala Pro Lys
       210                 215                 220

Asn Leu Val Ile Ser Arg Val Thr Glu Asp Ser Ala Arg Leu Ser Trp
225                 230                 235                 240

Thr Ala Pro Asp Ala Ala Phe Asp Ser Phe Phe Ile Tyr Tyr Ile Glu
               245                 250                 255

Ser Tyr Pro Ala Gly Glu Ala Ile Val Leu Thr Val Pro Gly Ser Glu
               260                 265                 270

Arg Ser Tyr Asp Leu Thr Gly Leu Lys Pro Gly Thr Glu Tyr Trp Val
               275                 280                 285

Gly Ile Asp Gly Val Lys Gly Gly Arg Trp Ser Thr Pro Leu Ser Ala
               290                 295                 300

Ile Phe Thr Thr Ala Pro Ala Pro Ala Pro Ala Pro Thr Ile
305                 310                 315                 320

Asp Glu Trp Leu Leu Lys Glu Ala Lys Glu Lys Ala Ile Glu Glu Leu
               325                 330                 335

Lys Lys Ala Gly Ile Thr Ser Asp Tyr Tyr Phe Asp Leu Ile Asn Lys
               340                 345                 350

Ala Lys Thr Val Glu Gly Val Asn Ala Leu Lys Asp Glu Ile Leu Lys
               355                 360                 365

Ala

<210> SEQ ID NO 392
<211> LENGTH: 288
<212> TYPE: PRT
<213> ORGANISM: Artificial Sequence
<220> FEATURE:
<223> OTHER INFORMATION: synthetic sequence

<400> SEQUENCE: 392

Met Leu Pro Ala Pro Lys Asn Leu Val Val Ser Arg Val Thr Glu Asp
1               5                   10                  15

Ser Ala Arg Leu Ser Trp Thr Ala Pro Tyr Ala Ala Phe Asp Ser Phe
               20                  25                  30

Ala Ile Ser Tyr Arg Glu Arg Ser Arg Glu Gly Glu Val Ile Ala Leu
               35                  40                  45

Thr Val Pro Gly Ser Glu Arg Ser Tyr Asp Leu Thr Gly Leu Lys Pro
       50                  55                  60
```

```
Gly Thr Glu Tyr Ile Val Gly Ile Leu Gly Val Lys Gly Gly Arg Arg
65                  70                  75                  80

Ser Lys Pro Leu Arg Ala Gln Phe Thr Thr Ala Pro Ala Pro Ala Pro
                85                  90                  95

Ala Pro Ala Pro Leu Pro Ala Pro Lys Asn Leu Val Val Ser Arg Val
            100                 105                 110

Thr Glu Asp Ser Ala Arg Leu Ser Trp Thr Ala Pro Asp Ala Ala Phe
            115                 120                 125

Asp Ser Phe Thr Ile Trp Tyr Ala Glu Ala Ile Gly His Gly Glu Ala
            130                 135                 140

Ile Val Leu Thr Val Pro Gly Ser Glu Arg Ser Tyr Asp Leu Thr Gly
145                 150                 155                 160

Leu Lys Pro Gly Thr Glu Tyr Trp Val Asp Ile Trp Gly Val Lys Gly
                165                 170                 175

Gly Gln Gln Ser Lys Pro Leu Ser Ala Ile Phe Thr Thr Ala Pro Ala
            180                 185                 190

Pro Ala Pro Ala Pro Ala Pro Leu Pro Ala Pro Lys Asn Leu Val Val
            195                 200                 205

Ser Arg Val Thr Glu Asp Ser Ala Arg Leu Ser Trp Thr Ala Pro Tyr
210                 215                 220

Ala Ala Phe Asp Ser Phe Ala Ile Ser Tyr Arg Glu Arg Ser Arg Glu
225                 230                 235                 240

Gly Glu Val Ile Ala Leu Thr Val Pro Gly Ser Glu Arg Ser Tyr Asp
                245                 250                 255

Leu Thr Gly Leu Lys Pro Gly Thr Glu Tyr Ile Val Gly Ile Leu Gly
            260                 265                 270

Val Lys Gly Gly Arg Arg Ser Lys Pro Leu Arg Ala Gln Phe Thr Thr
            275                 280                 285

<210> SEQ ID NO 393
<211> LENGTH: 317
<212> TYPE: PRT
<213> ORGANISM: Artificial Sequence
<220> FEATURE:
<223> OTHER INFORMATION: synthetic sequence

<400> SEQUENCE: 393

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Tyr Tyr Leu Glu Ser Tyr Pro Glu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Gly Ile Asp Gly Val Lys Gly Gly Thr Trp
65                  70                  75                  80

Ser Ser Pro Leu Ser Ala Ile Phe Thr Thr Gly Gly Gly Ser Gly
                85                  90                  95

Gly Gly Gly Ser Gly Gly Gly Ser Gly Gly Gly Ser Leu Pro
            100                 105                 110

Ala Pro Lys Asn Leu Val Val Ser Arg Val Thr Glu Asp Ser Ala Arg
            115                 120                 125

Leu Ser Trp Thr Ala Pro Tyr Ala Ala Phe Asp Ser Phe Ala Ile Ser
            130                 135                 140
```

Tyr Arg Glu Arg Ser Arg Glu Gly Glu Val Ile Ala Leu Thr Val Pro
145                 150                 155                 160

Gly Ser Glu Arg Ser Tyr Asp Leu Thr Gly Leu Lys Pro Gly Thr Glu
            165                 170                 175

Tyr Ile Val Gly Ile Leu Gly Val Lys Gly Arg Arg Ser Lys Pro
            180                 185                 190

Leu Arg Ala Gln Phe Thr Thr Gly Gly Ser Gly Gly Gly
        195                 200                 205

Ser Gly Gly Gly Ser Gly Gly Gly Ser Leu Pro Ala Pro Lys
    210                 215                 220

Asn Leu Val Ala Ser Arg Val Thr Glu Asp Ser Ala Arg Leu Ser Trp
225                 230                 235                 240

Thr Ala Pro Asp Ala Ala Phe Asp Ser Phe Asn Ile Ala Tyr Trp Glu
            245                 250                 255

Pro Gly Ile Gly Gly Glu Ala Ile Trp Leu Arg Val Pro Gly Ser Glu
            260                 265                 270

Arg Ser Tyr Asp Leu Thr Gly Leu Lys Pro Gly Thr Glu Tyr Lys Val
            275                 280                 285

Trp Ile His Gly Val Lys Gly Ala Ser Ser Pro Pro Leu Ile Ala
290                 295                 300

Arg Phe Thr Thr Gly Gly His His His His His Cys
305                 310                 315

<210> SEQ ID NO 394
<211> LENGTH: 91
<212> TYPE: PRT
<213> ORGANISM: Artificial Sequence
<220> FEATURE:
<223> OTHER INFORMATION: synthetic sequence

<400> SEQUENCE: 394

Leu Pro Ala Pro Lys Asn Leu Val Ala Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Ala Tyr Trp Glu Pro Gly Ile Gly Gly Glu Ala Ile Trp Leu Arg
        35                  40                  45

Val Pro Gly Ser Glu Arg Ser Tyr Asp Leu Thr Gly Leu Lys Pro Gly
    50                  55                  60

Thr Glu Tyr Lys Val Trp Ile His Gly Val Lys Gly Ala Ser Ser
65                  70                  75                  80

Pro Pro Leu Ile Ala Arg Phe Thr Thr Gly Gly
            85                  90

<210> SEQ ID NO 395
<211> LENGTH: 90
<212> TYPE: PRT
<213> ORGANISM: Artificial Sequence
<220> FEATURE:
<223> OTHER INFORMATION: synthetic sequence

<400> SEQUENCE: 395

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Arg Glu Gly Ala Trp Tyr Gly Glu Ala Ile Val Leu
        35                  40                  45

```
Thr Val Pro Gly Ser Glu Arg Ser Tyr Asp Leu Thr Gly Leu Lys Pro
    50                  55                  60

Gly Thr Glu Tyr Ala Val Tyr Ile Pro Gly Val Lys Gly Gly Pro Arg
65                  70                  75                  80

Ser Phe Pro Leu Ser Ala Ile Phe Thr Thr
                85                  90

<210> SEQ ID NO 396
<211> LENGTH: 90
<212> TYPE: PRT
<213> ORGANISM: Artificial Sequence
<220> FEATURE:
<223> OTHER INFORMATION: synthetic sequence

<400> SEQUENCE: 396

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Ala Tyr Val Glu Trp Trp Lys Leu Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Val Val Pro Ile Pro Gly Val Lys Gly Gly Gly His
65                  70                  75                  80

Ser Ser Pro Leu Ser Ala Ile Phe Thr Thr
                85                  90

<210> SEQ ID NO 397
<211> LENGTH: 90
<212> TYPE: PRT
<213> ORGANISM: Artificial Sequence
<220> FEATURE:
<223> OTHER INFORMATION: synthetic sequence

<400> SEQUENCE: 397

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Tyr Tyr Tyr Glu Ser Ser Gly Thr Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Phe Val Asp Ile Gly Gly Val Lys Gly Gly Ser Tyr
65                  70                  75                  80

Ser Leu Pro Leu Ser Ala Ile Phe Thr Thr
                85                  90

<210> SEQ ID NO 398
<211> LENGTH: 90
<212> TYPE: PRT
<213> ORGANISM: Artificial Sequence
<220> FEATURE:
<223> OTHER INFORMATION: synthetic sequence

<400> SEQUENCE: 398

Met Leu Pro Ala Pro Lys Asn Leu Val Val Ser Arg Val Thr Glu Asp
1               5                   10                  15
```

Ser Ala Arg Leu Ser Trp Thr Ala Pro Asp Ala Ala Phe Asp Ser Phe
            20                  25                  30

Pro Ile Tyr Tyr Trp Glu Val Phe Pro Ala Gly Glu Ala Ile Glu Leu
        35                  40                  45

Asp Val Pro Gly Ser Glu Arg Ser Tyr Asp Leu Thr Gly Leu Lys Pro
 50                  55                  60

Gly Thr Glu Tyr Phe Val Arg Ile Glu Gly Val Lys Gly Gly Ala Ser
 65                  70                  75                  80

Ser Tyr Pro Leu Arg Ala Glu Phe Thr Thr
                85                  90

<210> SEQ ID NO 399
<211> LENGTH: 90
<212> TYPE: PRT
<213> ORGANISM: Artificial Sequence
<220> FEATURE:
<223> OTHER INFORMATION: synthetic sequence

<400> SEQUENCE: 399

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
            20                  25                  30

Phe Ile Trp Tyr Trp Glu Lys Ser Val Asp Gly Glu Ala Ile Val Leu
        35                  40                  45

Thr Val Pro Gly Ser Glu Arg Ser Tyr Asp Leu Thr Gly Leu Lys Pro
 50                  55                  60

Gly Thr Glu Tyr Asn Val Gly Ile Gln Gly Val Lys Gly Gly Thr Pro
 65                  70                  75                  80

Ser Asp Pro Leu Ser Ala Ile Phe Thr Thr
                85                  90

<210> SEQ ID NO 400
<211> LENGTH: 90
<212> TYPE: PRT
<213> ORGANISM: Artificial Sequence
<220> FEATURE:
<223> OTHER INFORMATION: synthetic sequence

<400> SEQUENCE: 400

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
            20                  25                  30

Ile Ile Trp Tyr Ala Glu Trp Val Asn Asp Gly Glu Ala Ile Val Leu
        35                  40                  45

Thr Val Pro Gly Ser Glu Arg Ser Tyr Asp Leu Thr Gly Leu Lys Pro
 50                  55                  60

Gly Thr Glu Tyr Arg Val Glu Ile Thr Gly Val Lys Gly Gly Thr Trp
 65                  70                  75                  80

Ser Arg Pro Leu Ser Ala Ile Phe Thr Thr
                85                  90

<210> SEQ ID NO 401
<211> LENGTH: 90
<212> TYPE: PRT
<213> ORGANISM: Artificial Sequence
<220> FEATURE:
<223> OTHER INFORMATION: synthetic sequence

<400> SEQUENCE: 401

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Tyr Glu Pro Val Pro Ala Gly Glu Ala Ile Tyr Leu
        35                  40                  45

Asp Val Pro Gly Ser Glu Arg Ser Tyr Asp Leu Thr Gly Leu Lys Pro
    50                  55                  60

Gly Thr Glu Tyr Asp Val Thr Ile Tyr Gly Val Lys Gly Gly Tyr Tyr
65                  70                  75                  80

Ser His Pro Leu Phe Ala Ser Phe Thr Thr
                85                  90

<210> SEQ ID NO 402
<211> LENGTH: 90
<212> TYPE: PRT
<213> ORGANISM: Artificial Sequence
<220> FEATURE:
<223> OTHER INFORMATION: synthetic sequence

<400> SEQUENCE: 402

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Glu Tyr Phe Glu Trp Thr Val Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Ser Ile Tyr Gly Val Lys Gly Gly Trp Leu
65                  70                  75                  80

Ser Pro Pro Leu Ser Ala Ile Phe Thr Thr
                85                  90

<210> SEQ ID NO 403
<211> LENGTH: 90
<212> TYPE: PRT
<213> ORGANISM: Artificial Sequence
<220> FEATURE:
<223> OTHER INFORMATION: synthetic sequence

<400> SEQUENCE: 403

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ser Tyr Glu Glu Thr Pro Val Val Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Thr Val Ala Ile His Gly Val Lys Gly Gly Arg Glu
65                  70                  75                  80

Ser Thr Pro Leu Ile Ala Pro Phe Thr Thr
                85                  90

<210> SEQ ID NO 404
<211> LENGTH: 90

-continued

```
<212> TYPE: PRT
<213> ORGANISM: Artificial Sequence
<220> FEATURE:
<223> OTHER INFORMATION: synthetic sequence

<400> SEQUENCE: 404

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile His Tyr Trp Glu Phe Asp Pro Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Tyr Ile Glu Gly Val Lys Gly Gly Trp Trp
65                  70                  75                  80

Ser Lys Pro Leu Ser Ala Ile Phe Thr Thr
                85                  90

<210> SEQ ID NO 405
<211> LENGTH: 90
<212> TYPE: PRT
<213> ORGANISM: Artificial Sequence
<220> FEATURE:
<223> OTHER INFORMATION: synthetic sequence

<400> SEQUENCE: 405

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Trp Glu Arg Thr Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Ser Gly Val Lys Gly Gly Lys Trp
65                  70                  75                  80

Ser Glu Pro Leu Ser Ala Ile Phe Thr Thr
                85                  90

<210> SEQ ID NO 406
<211> LENGTH: 90
<212> TYPE: PRT
<213> ORGANISM: Artificial Sequence
<220> FEATURE:
<223> OTHER INFORMATION: synthetic sequence

<400> SEQUENCE: 406

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Arg Tyr Trp Glu Trp Tyr Val Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Glu Ile Ser Gly Val Lys Gly Gly Trp Gln
65                  70                  75                  80

Ser Trp Pro Leu Ser Ala Ile Phe Thr Thr
```

```
                85                  90

<210> SEQ ID NO 407
<211> LENGTH: 90
<212> TYPE: PRT
<213> ORGANISM: Artificial Sequence
<220> FEATURE:
<223> OTHER INFORMATION: synthetic sequence

<400> SEQUENCE: 407

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Gly Tyr Leu Glu Pro Gly Asp Asn Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Ser Ile Gly Gly Val Lys Gly Gly Leu Gly
65                  70                  75                  80

Ser Tyr Pro Leu Ser Ala Ile Phe Thr Thr
                85                  90

<210> SEQ ID NO 408
<211> LENGTH: 90
<212> TYPE: PRT
<213> ORGANISM: Artificial Sequence
<220> FEATURE:
<223> OTHER INFORMATION: synthetic sequence

<400> SEQUENCE: 408

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Gly Ile Tyr Tyr Tyr Glu Trp Trp Ser Thr Gly Glu Ala Ile Val Leu
        35                  40                  45

Thr Val Pro Gly Ser Glu Arg Ser Tyr Asp Leu Thr Gly Pro Lys Pro
    50                  55                  60

Gly Thr Glu Tyr Tyr Val Lys Ile Ser Gly Val Lys Gly Gly Tyr Arg
65                  70                  75                  80

Ser Tyr Pro Leu Ser Ala Ile Phe Thr Thr
                85                  90

<210> SEQ ID NO 409
<211> LENGTH: 90
<212> TYPE: PRT
<213> ORGANISM: Artificial Sequence
<220> FEATURE:
<223> OTHER INFORMATION: synthetic sequence

<400> SEQUENCE: 409

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Ser Tyr Tyr Glu Trp Tyr Asp Leu Gly Glu Ala Ile Val Leu
        35                  40                  45

Thr Val Pro Gly Ser Glu Arg Ser Tyr Asp Leu Thr Gly Leu Lys Pro
    50                  55                  60
```

```
Gly Thr Glu Tyr Trp Val Asp Ile Ala Gly Val Lys Gly Gly Tyr Tyr
65                  70                  75                  80

Ser Tyr Pro Leu Ser Ala Ile Phe Thr Thr
                85                  90

<210> SEQ ID NO 410
<211> LENGTH: 90
<212> TYPE: PRT
<213> ORGANISM: Artificial Sequence
<220> FEATURE:
<223> OTHER INFORMATION: synthetic sequence

<400> SEQUENCE: 410

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 411
<211> LENGTH: 90
<212> TYPE: PRT
<213> ORGANISM: Artificial Sequence
<220> FEATURE:
<223> OTHER INFORMATION: synthetic sequence

<400> SEQUENCE: 411

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Ser Tyr Phe Glu Gly Trp Ala Ser Gly Glu Ala Ile His Leu
            35                  40                  45

Tyr Val Pro Gly Ser Glu Arg Ser Tyr Asp Leu Thr Gly Leu Lys Pro
        50                  55                  60

Gly Thr Glu Tyr Ser Val His Ile Gln Gly Val Lys Gly Gly Gln Pro
65                  70                  75                  80

Ser Thr Pro Leu Ser Ala Ile Phe Thr Thr
                85                  90

<210> SEQ ID NO 412
<211> LENGTH: 90
<212> TYPE: PRT
<213> ORGANISM: Artificial Sequence
<220> FEATURE:
<223> OTHER INFORMATION: synthetic sequence

<400> SEQUENCE: 412

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
                20                  25                  30
```

-continued

Asp Ile Pro Tyr Gly Glu Phe Asp Thr Ile Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Asp Val Tyr Ile Glu Gly Val Lys Gly Gly His Leu
 65                  70                  75                  80

Ser Trp Pro Leu Ser Ala Ile Phe Thr Thr
                85                  90

<210> SEQ ID NO 413
<211> LENGTH: 90
<212> TYPE: PRT
<213> ORGANISM: Artificial Sequence
<220> FEATURE:
<223> OTHER INFORMATION: synthetic sequence

<400> SEQUENCE: 413

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Gly Ile Gln Tyr Asn Glu Phe Val Phe Arg Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Phe Val Pro Ile Ser Gly Val Lys Gly Gly Asp Asp
 65                  70                  75                  80

Ser Arg Pro Leu Ser Ala Ile Phe Thr Thr
                85                  90

<210> SEQ ID NO 414
<211> LENGTH: 90
<212> TYPE: PRT
<213> ORGANISM: Artificial Sequence
<220> FEATURE:
<223> OTHER INFORMATION: synthetic sequence

<400> SEQUENCE: 414

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Trp Ile Glu Tyr Trp Glu Val Val Gly Phe Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Trp Val Gly Ile Tyr Gly Val Lys Gly Gly Asn Pro
 65                  70                  75                  80

Ser Val Pro Leu Ser Ala Ile Phe Thr Thr
                85                  90

<210> SEQ ID NO 415
<211> LENGTH: 90
<212> TYPE: PRT
<213> ORGANISM: Artificial Sequence
<220> FEATURE:
<223> OTHER INFORMATION: synthetic sequence

<400> SEQUENCE: 415

Met Leu Pro Ala Pro Lys Asn Leu Val Val Ser Arg Val Thr Glu Asp

```
                1               5                   10                  15
Ser Ala Arg Leu Ser Trp Thr Ala Pro Asp Ala Ala Phe Asp Ser Phe
                20                  25                  30

Ala Ile Asp Tyr Asp Glu Pro Ile Asn Ser Gly Glu Ala Ile Val Leu
                35                  40                  45

Thr Val Pro Gly Ser Glu Arg Ser Tyr Asp Leu Thr Gly Pro Lys Pro
                50                  55                  60

Gly Thr Glu Tyr Glu Val Glu Ile Tyr Gly Val Lys Gly Gly Tyr Leu
65                  70                  75                  80

Ser Arg Pro Leu Ser Ala Ile Phe Thr Thr
                85                  90

<210> SEQ ID NO 416
<211> LENGTH: 90
<212> TYPE: PRT
<213> ORGANISM: Artificial Sequence
<220> FEATURE:
<223> OTHER INFORMATION: synthetic sequence

<400> SEQUENCE: 416

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ser Ile Asp Tyr Asp Glu Pro Gln Pro Val Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Arg Val Asp Ile Trp Gly Val Lys Gly Gly Pro Thr
65                  70                  75                  80

Ser Gly Pro Leu Arg Ala Thr Phe Thr Thr
                85                  90

<210> SEQ ID NO 417
<211> LENGTH: 90
<212> TYPE: PRT
<213> ORGANISM: Artificial Sequence
<220> FEATURE:
<223> OTHER INFORMATION: synthetic sequence

<400> SEQUENCE: 417

Met Leu Leu Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Glu Tyr Phe Glu Tyr Thr Gly Glu Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Tyr Val Gly Ile Tyr Gly Val Lys Gly Gly Tyr Leu
65                  70                  75                  80

Ser Arg Pro Leu Ser Ala Ile Phe Thr Thr
                85                  90

<210> SEQ ID NO 418
<211> LENGTH: 90
<212> TYPE: PRT
<213> ORGANISM: Artificial Sequence
<220> FEATURE:
```

<223> OTHER INFORMATION: synthetic sequence

<400> SEQUENCE: 418

Met Leu Pro Ala Pro Lys Asn Leu Val Val Ser His Val Thr Glu Asp
1               5                   10                  15

Ser Ala Arg Leu Ser Trp Thr Ala Pro Asp Ala Ala Phe Asp Ser Phe
            20                  25                  30

Asp Ile Glu Tyr Tyr Glu Leu Val Gly Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Ala Ile Tyr Gly Val Lys Gly Gly Tyr Leu
65                  70                  75                  80

Ser Arg Pro Leu Ser Ala Ile Phe Thr Thr
                85                  90

<210> SEQ ID NO 419
<211> LENGTH: 90
<212> TYPE: PRT
<213> ORGANISM: Artificial Sequence
<220> FEATURE:
<223> OTHER INFORMATION: synthetic sequence

<400> SEQUENCE: 419

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Ala Tyr Tyr Glu Arg Ser Gly Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Met Val Tyr Ile Asn Gly Val Lys Gly Gly Phe Val
65                  70                  75                  80

Ser Ser Pro Leu Ser Ala Ile Phe Thr Thr
                85                  90

<210> SEQ ID NO 420
<211> LENGTH: 90
<212> TYPE: PRT
<213> ORGANISM: Artificial Sequence
<220> FEATURE:
<223> OTHER INFORMATION: synthetic sequence

<400> SEQUENCE: 420

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Ala Tyr Glu Glu His Gly Leu Val Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr His Val Gly Ile Met Gly Val Lys Gly Gly Val Phe
65                  70                  75                  80

Ser Ser Pro Leu Ser Ala Ile Phe Thr Thr
                85                  90

```
<210> SEQ ID NO 421
<211> LENGTH: 90
<212> TYPE: PRT
<213> ORGANISM: Artificial Sequence
<220> FEATURE:
<223> OTHER INFORMATION: synthetic sequence

<400> SEQUENCE: 421

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gln Tyr Thr Glu Ser His Trp Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ala Val Pro Ile Glu Gly Val Lys Gly Gly Asp Ser
65                  70                  75                  80

Ser Thr Pro Leu Ser Ala Ile Phe Thr Thr
                85                  90

<210> SEQ ID NO 422
<211> LENGTH: 90
<212> TYPE: PRT
<213> ORGANISM: Artificial Sequence
<220> FEATURE:
<223> OTHER INFORMATION: synthetic sequence

<400> SEQUENCE: 422

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Ile Tyr Gly Glu Val Asn Pro Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Phe Ile Glu Gly Val Lys Gly Gly His Leu
65                  70                  75                  80

Ser Trp Pro Leu Ser Ala Ile Phe Thr Thr
                85                  90

<210> SEQ ID NO 423
<211> LENGTH: 90
<212> TYPE: PRT
<213> ORGANISM: Artificial Sequence
<220> FEATURE:
<223> OTHER INFORMATION: synthetic sequence

<400> SEQUENCE: 423

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ala Tyr Glu Glu Leu Val Thr Glu Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Leu Val Asp Ile Glu Gly Val Lys Gly Gly His Leu
65                  70                  75                  80
```

Ser Ser Pro Leu Ser Ala Ile Phe Thr Thr
            85                  90

<210> SEQ ID NO 424
<211> LENGTH: 90
<212> TYPE: PRT
<213> ORGANISM: Artificial Sequence
<220> FEATURE:
<223> OTHER INFORMATION: synthetic sequence

<400> SEQUENCE: 424

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile His Tyr His Glu Trp Trp Ala Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Leu Val Asp Ile Pro Gly Val Lys Gly Gly Asp Leu
65              70                  75                  80

Ser Val Pro Leu Ser Ala Ile Phe Thr Thr
            85                  90

<210> SEQ ID NO 425
<211> LENGTH: 90
<212> TYPE: PRT
<213> ORGANISM: Artificial Sequence
<220> FEATURE:
<223> OTHER INFORMATION: synthetic sequence

<400> SEQUENCE: 425

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Tyr Tyr Tyr Glu Ser Val Gly Thr Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Phe Val Asp Ile Ser Gly Val Lys Val Gly Thr Tyr
65              70                  75                  80

Ser Leu Pro Leu Ser Ala Ile Phe Thr Thr
            85                  90

<210> SEQ ID NO 426
<211> LENGTH: 90
<212> TYPE: PRT
<213> ORGANISM: Artificial Sequence
<220> FEATURE:
<223> OTHER INFORMATION: synthetic sequence

<400> SEQUENCE: 426

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Ala Tyr Phe Glu Phe Ala Asn Pro Gly Glu Ala Ile Val Leu
            35                  40                  45

```
Thr Val Pro Gly Ser Glu Arg Ser Tyr Asp Leu Thr Gly Leu Lys Pro
 50                  55                  60

Gly Thr Glu Tyr Lys Val Val Ile Gln Gly Val Lys Gly Gly Thr Pro
 65                  70                  75                  80

Ser Glu Pro Leu Ser Ala Ile Ser Thr Thr
                 85                  90

<210> SEQ ID NO 427
<211> LENGTH: 90
<212> TYPE: PRT
<213> ORGANISM: Artificial Sequence
<220> FEATURE:
<223> OTHER INFORMATION: synthetic sequence

<400> SEQUENCE: 427

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Asp Ile His Tyr Lys Glu His Ser Trp Trp Gly Glu Ala Ile Val Leu
                 35                  40                  45

Thr Val Pro Gly Ser Glu Arg Ser Tyr Asp Leu Thr Gly Leu Lys Pro
 50                  55                  60

Gly Thr Glu Tyr Ile Val Pro Ile Pro Gly Val Lys Gly Gly Gly Ile
 65                  70                  75                  80

Ser Arg Pro Leu Ser Ala Ile Phe Thr Thr
                 85                  90

<210> SEQ ID NO 428
<211> LENGTH: 90
<212> TYPE: PRT
<213> ORGANISM: Artificial Sequence
<220> FEATURE:
<223> OTHER INFORMATION: synthetic sequence

<400> SEQUENCE: 428

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Ala Ile Glu Tyr Trp Glu Ala Val Gly Ser Gly Glu Ala Ile Val Leu
                 35                  40                  45

Thr Val Pro Gly Ser Glu Arg Ser Tyr Asp Leu Thr Gly Leu Lys Pro
 50                  55                  60

Gly Thr Glu Tyr His Val Tyr Ile Tyr Gly Val Lys Gly Gly Tyr Leu
 65                  70                  75                  80

Ser Leu Pro Leu Ser Ala Ile Phe Thr Thr
                 85                  90

<210> SEQ ID NO 429
<211> LENGTH: 91
<212> TYPE: PRT
<213> ORGANISM: Artificial Sequence
<220> FEATURE:
<223> OTHER INFORMATION: synthetic sequence

<400> SEQUENCE: 429

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
```

```
                    20                  25                  30

Phe Ile Gly Tyr Leu Glu Pro Gln Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr Thr
                85                  90

<210> SEQ ID NO 430
<211> LENGTH: 90
<212> TYPE: PRT
<213> ORGANISM: Artificial Sequence
<220> FEATURE:
<223> OTHER INFORMATION: synthetic sequence

<400> SEQUENCE: 430

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Ala Tyr Ser Glu Val Arg Tyr Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Val Val Pro Ile Gly Gly Val Lys Gly Gly Gly Ser
65                  70                  75                  80

Ser Ser Pro Leu Ser Ala Ile Phe Thr Thr
                85                  90

<210> SEQ ID NO 431
<211> LENGTH: 90
<212> TYPE: PRT
<213> ORGANISM: Artificial Sequence
<220> FEATURE:
<223> OTHER INFORMATION: synthetic sequence

<400> SEQUENCE: 431

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Pro Tyr Gly Glu Ala Phe Asn Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Phe Ile Glu Gly Val Lys Gly Gly Thr Leu
65                  70                  75                  80

Ser Trp Pro Leu Ser Ala Ile Phe Thr Thr
                85                  90

<210> SEQ ID NO 432
<211> LENGTH: 90
<212> TYPE: PRT
<213> ORGANISM: Artificial Sequence
<220> FEATURE:
<223> OTHER INFORMATION: synthetic sequence

<400> SEQUENCE: 432
```

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Leu Tyr Gly Glu Val Asp Pro Trp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Lys Leu
65                  70                  75                  80

Ser Trp Pro Leu Ser Ala Ile Phe Thr Thr
                85                  90

<210> SEQ ID NO 433
<211> LENGTH: 90
<212> TYPE: PRT
<213> ORGANISM: Artificial Sequence
<220> FEATURE:
<223> OTHER INFORMATION: synthetic sequence

<400> SEQUENCE: 433

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Glu Tyr Glu Glu Thr Pro Gln Lys Gly Glu Ala Ile Phe Leu
        35                  40                  45

Arg Val Pro Gly Ser Glu Arg Ser Tyr Asp Leu Thr Gly Leu Lys Pro
    50                  55                  60

Gly Thr Glu Tyr Val Val Asn Ile Arg Gly Val Lys Gly Gly Asp Leu
65                  70                  75                  80

Ser Ser Pro Leu Gly Ala Leu Phe Thr Thr
                85                  90

<210> SEQ ID NO 434
<211> LENGTH: 90
<212> TYPE: PRT
<213> ORGANISM: Artificial Sequence
<220> FEATURE:
<223> OTHER INFORMATION: synthetic sequence

<400> SEQUENCE: 434

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Glu Tyr Ile Glu Trp Trp Val Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Asp Ile Lys Gly Val Lys Gly Gly Lys Arg
65                  70                  75                  80

Ser Tyr Pro Leu Ser Ala Ile Phe Thr Thr
                85                  90

<210> SEQ ID NO 435
<211> LENGTH: 90
<212> TYPE: PRT
```

<213> ORGANISM: Artificial Sequence
<220> FEATURE:
<223> OTHER INFORMATION: synthetic sequence

<400> SEQUENCE: 435

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asp Tyr Pro Glu Phe Pro Val Arg Gly Glu Ala Ile Val Leu
        35                  40                  45

Thr Val Pro Gly Ser Glu Arg Ser Tyr Asp Leu Thr Gly Pro Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 436
<211> LENGTH: 90
<212> TYPE: PRT
<213> ORGANISM: Artificial Sequence
<220> FEATURE:
<223> OTHER INFORMATION: synthetic sequence

<400> SEQUENCE: 436

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gln Ile Pro Tyr Trp Glu Gln Ser Leu Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Glu Val Trp Ile Glu Gly Val Lys Gly Gly Asp Leu
65                  70                  75                  80

Ser Phe Pro Leu Ser Ala Ile Ser Thr Thr
                85                  90

<210> SEQ ID NO 437
<211> LENGTH: 90
<212> TYPE: PRT
<213> ORGANISM: Artificial Sequence
<220> FEATURE:
<223> OTHER INFORMATION: synthetic sequence

<400> SEQUENCE: 437

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Pro Tyr Glu Glu Tyr Leu Tyr Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Leu Thr
65                  70                  75                  80

Ser Trp Pro Leu Ser Ala Ile Phe Thr Thr
                85                  90

<210> SEQ ID NO 438
<211> LENGTH: 90
<212> TYPE: PRT
<213> ORGANISM: Artificial Sequence
<220> FEATURE:
<223> OTHER INFORMATION: synthetic sequence

<400> SEQUENCE: 438

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asp Tyr Pro Glu Phe Pro Val Arg Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ala Val Thr Ile Trp Gly Val Lys Gly Gly Phe Thr
65                  70                  75                  80

Ser Gln Pro Leu Ser Ala Ile Phe Thr Thr
                85                  90

<210> SEQ ID NO 439
<211> LENGTH: 90
<212> TYPE: PRT
<213> ORGANISM: Artificial Sequence
<220> FEATURE:
<223> OTHER INFORMATION: synthetic sequence

<400> SEQUENCE: 439

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Phe Glu Phe Val Gly Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Gly Ile Tyr Gly Val Lys Gly Gly Ser Leu
65                  70                  75                  80

Ser Ser Pro Leu Ser Ala Ile Phe Thr Thr
                85                  90

<210> SEQ ID NO 440
<211> LENGTH: 90
<212> TYPE: PRT
<213> ORGANISM: Artificial Sequence
<220> FEATURE:
<223> OTHER INFORMATION: synthetic sequence

<400> SEQUENCE: 440

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asp Tyr Leu Glu Leu Gly Glu Ser Gly Glu Ala Ile Val Leu
        35                  40                  45

Thr Val Pro Gly Ser Glu Arg Ser Tyr Asp Leu Thr Gly Leu Lys Pro
    50                  55                  60

```
Gly Thr Glu Tyr Trp Val Tyr Ile Phe Gly Val Lys Gly Gly Tyr Pro
65                  70                  75                  80

Ser Ala Pro Leu Ser Ala Ile Phe Thr Thr
                85                  90

<210> SEQ ID NO 441
<211> LENGTH: 90
<212> TYPE: PRT
<213> ORGANISM: Artificial Sequence
<220> FEATURE:
<223> OTHER INFORMATION: synthetic sequence

<400> SEQUENCE: 441

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Pro Tyr Gly Glu Ser Pro Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Ile Ile Arg Gly Val Lys Gly Gly Gly Arg
65                  70                  75                  80

Ser Gly Pro Leu Ser Ala Ile Ser Thr Thr
                85                  90

<210> SEQ ID NO 442
<211> LENGTH: 90
<212> TYPE: PRT
<213> ORGANISM: Artificial Sequence
<220> FEATURE:
<223> OTHER INFORMATION: synthetic sequence

<400> SEQUENCE: 442

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ile Ile Asn Tyr Ile Glu Ile Val Gln Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Glu Ser Ile Trp Gly Val Lys Gly Gly Gly Ala
65                  70                  75                  80

Ser Ser Pro Leu Ser Ala Ile Phe Thr Thr
                85                  90

<210> SEQ ID NO 443
<211> LENGTH: 90
<212> TYPE: PRT
<213> ORGANISM: Artificial Sequence
<220> FEATURE:
<223> OTHER INFORMATION: synthetic sequence

<400> SEQUENCE: 443

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asp Ile Glu Tyr Tyr Glu Ala Val Gly Ala Gly Glu Ala Ile Val Leu
```

```
                35                  40                  45

Thr Val Pro Gly Ser Glu Arg Ser Tyr Asp Leu Thr Gly Leu Lys Pro
            50                  55                  60

Gly Thr Glu Tyr Thr Val Gly Ile Tyr Gly Val Lys Gly Gly Trp Leu
65                  70                  75                  80

Ser Lys Pro Leu Ser Val Ile Phe Thr Thr
                85                  90

<210> SEQ ID NO 444
<211> LENGTH: 90
<212> TYPE: PRT
<213> ORGANISM: Artificial Sequence
<220> FEATURE:
<223> OTHER INFORMATION: synthetic sequence

<400> SEQUENCE: 444

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Pro Tyr Val Glu Ala Glu Val Pro Gly Glu Ala Ile Gln Leu
        35                  40                  45

His Val Pro Gly Ser Glu Arg Ser Tyr Asp Leu Thr Gly Leu Lys Pro
    50                  55                  60

Gly Thr Glu Tyr Tyr Val Glu Ile Trp Gly Val Lys Gly Gly Phe Tyr
65                  70                  75                  80

Ser Pro Pro Leu Ile Ala Glu Phe Thr Thr
                85                  90

<210> SEQ ID NO 445
<211> LENGTH: 90
<212> TYPE: PRT
<213> ORGANISM: Artificial Sequence
<220> FEATURE:
<223> OTHER INFORMATION: synthetic sequence

<400> SEQUENCE: 445

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asp Tyr Tyr Glu Gly Lys Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gln Val Leu Ile Ser Gly Val Lys Gly Gly Lys Tyr
65                  70                  75                  80

Ser Leu Pro Leu Ser Ala Ile Phe Thr Thr
                85                  90

<210> SEQ ID NO 446
<211> LENGTH: 90
<212> TYPE: PRT
<213> ORGANISM: Artificial Sequence
<220> FEATURE:
<223> OTHER INFORMATION: synthetic sequence

<400> SEQUENCE: 446

Met Leu Pro Ala Pro Lys Asn Leu Val Val Ser Arg Val Thr Glu Asp
1               5                   10                  15
```

```
Ser Ala Arg Leu Ser Trp Thr Ala Pro Asp Ala Ala Phe Asp Ser Phe
            20                  25                  30

Thr Ile Val Tyr Ala Glu Val Thr Tyr Asp Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Asp Val Phe Ile Glu Gly Val Lys Gly Gly Glu Leu
 65                  70                  75                  80

Ser Trp Pro Leu Ser Ala Ile Phe Thr Thr
            85                  90

<210> SEQ ID NO 447
<211> LENGTH: 90
<212> TYPE: PRT
<213> ORGANISM: Artificial Sequence
<220> FEATURE:
<223> OTHER INFORMATION: synthetic sequence

<400> SEQUENCE: 447

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
            20                  25                  30

Pro Ile Val Tyr Gly Glu Ala Trp Val Thr Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Asp Val Trp Ile Glu Gly Val Lys Gly Gly Glu Leu
 65                  70                  75                  80

Ser Trp Pro Leu Ser Ala Ile Phe Thr Thr
            85                  90

<210> SEQ ID NO 448
<211> LENGTH: 90
<212> TYPE: PRT
<213> ORGANISM: Artificial Sequence
<220> FEATURE:
<223> OTHER INFORMATION: synthetic sequence

<400> SEQUENCE: 448

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
            20                  25                  30

Trp Ile Asp Tyr Tyr Glu Arg Lys Tyr Val Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Glu Val Thr Ile Tyr Gly Val Lys Gly Gly Trp Tyr
 65                  70                  75                  80

Ser Asp Pro Leu Ser Ala Ile Phe Thr Thr
            85                  90

<210> SEQ ID NO 449
<211> LENGTH: 90
<212> TYPE: PRT
<213> ORGANISM: Artificial Sequence
<220> FEATURE:
<223> OTHER INFORMATION: synthetic sequence
```

<400> SEQUENCE: 449

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Ser Tyr Tyr Glu Met Ser Gly Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Met Val Tyr Ile Phe Gly Val Lys Gly Gly Leu Asn
65                  70                  75                  80

Ser Leu Pro Leu Ser Ala Ile Phe Thr Thr
            85                  90

<210> SEQ ID NO 450
<211> LENGTH: 90
<212> TYPE: PRT
<213> ORGANISM: Artificial Sequence
<220> FEATURE:
<223> OTHER INFORMATION: synthetic sequence

<400> SEQUENCE: 450

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Tyr Tyr Ile Glu Ser Tyr Pro Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Met Gly Ile Asp Gly Val Lys Gly Gly Arg Trp
65                  70                  75                  80

Ser Thr Pro Leu Ser Ala Ile Phe Thr Thr
            85                  90

<210> SEQ ID NO 451
<211> LENGTH: 90
<212> TYPE: PRT
<213> ORGANISM: Artificial Sequence
<220> FEATURE:
<223> OTHER INFORMATION: synthetic sequence

<400> SEQUENCE: 451

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Glu Tyr Asp Glu Pro Ser Val Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Phe Ile Trp Gly Val Lys Gly Gly Asn Gln
65                  70                  75                  80

Ser Trp Pro Leu Ser Ala Ile Phe Thr Thr
            85                  90

<210> SEQ ID NO 452

```
<211> LENGTH: 90
<212> TYPE: PRT
<213> ORGANISM: Artificial Sequence
<220> FEATURE:
<223> OTHER INFORMATION: synthetic sequence

<400> SEQUENCE: 452

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Lys Tyr Ile Glu Trp Trp Ala Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Leu Val Glu Ile Tyr Gly Val Lys Gly Gly Arg Gln
65                  70                  75                  80

Ser Tyr Pro Leu Ser Ala Ile Phe Thr Thr
                85                  90

<210> SEQ ID NO 453
<211> LENGTH: 90
<212> TYPE: PRT
<213> ORGANISM: Artificial Sequence
<220> FEATURE:
<223> OTHER INFORMATION: synthetic sequence

<400> SEQUENCE: 453

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asp Ile Ser Tyr Trp Glu Ser Gly Lys Tyr Gly Glu Ala Ile Val Leu
            35                  40                  45

Thr Val Pro Gly Ser Glu Ser Ser Tyr Asp Leu Thr Gly Leu Lys Pro
        50                  55                  60

Gly Thr Glu Tyr Leu Val Asp Ile Phe Gly Val Lys Gly Gly Tyr Pro
65                  70                  75                  80

Ser Glu Pro Leu Ser Ala Ile Phe Thr Thr
                85                  90

<210> SEQ ID NO 454
<211> LENGTH: 90
<212> TYPE: PRT
<213> ORGANISM: Artificial Sequence
<220> FEATURE:
<223> OTHER INFORMATION: synthetic sequence

<400> SEQUENCE: 454

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Trp Ile Ser Tyr Glu Glu Ser Asp Thr Glu Gly Glu Ala Ile Tyr Leu
            35                  40                  45

Arg Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
65                  70                  75                  80
```

-continued

Ser Met Pro Leu Ser Ala Ile Phe Thr Thr
            85                  90

<210> SEQ ID NO 455
<211> LENGTH: 90
<212> TYPE: PRT
<213> ORGANISM: Artificial Sequence
<220> FEATURE:
<223> OTHER INFORMATION: synthetic sequence

<400> SEQUENCE: 455

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Phe Glu Gln Phe Asn Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Val Gly Ile Tyr Gly Val Lys Gly Gly Trp Leu
65                  70                  75                  80

Ser His Pro Leu Ser Ala Ile Phe Thr Thr
            85                  90

<210> SEQ ID NO 456
<211> LENGTH: 90
<212> TYPE: PRT
<213> ORGANISM: Artificial Sequence
<220> FEATURE:
<223> OTHER INFORMATION: synthetic sequence

<400> SEQUENCE: 456

Met Leu Pro Ala Pro Lys Asn Leu Val Val Ser Arg Val Thr Lys Asp
1               5                   10                  15

Ser Ala Arg Leu Ser Trp Thr Ala Pro Asp Ala Ala Phe Asp Ser Phe
            20                  25                  30

His Ile Ala Tyr Glu Glu Ala Thr Thr Tyr Gly Glu Ala Ile Phe Leu
        35                  40                  45

Arg Val Pro Gly Ser Glu Arg Ser Tyr Asp Leu Thr Gly Leu Lys Pro
    50                  55                  60

Gly Thr Glu Tyr Glu Val Lys Ile His Gly Val Lys Gly Gly Ala Asp
65                  70                  75                  80

Ser Lys Pro Leu Val Ala Pro Phe Thr Thr
            85                  90

<210> SEQ ID NO 457
<211> LENGTH: 90
<212> TYPE: PRT
<213> ORGANISM: Artificial Sequence
<220> FEATURE:
<223> OTHER INFORMATION: synthetic sequence

<400> SEQUENCE: 457

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ala Tyr Glu Glu Ala Asp Ser Glu Gly Glu Ala Ile Tyr Leu
        35                  40                  45

Arg Val Pro Gly Ser Glu Arg Ser Tyr Asp Leu Thr Gly Leu Lys Pro

```
                    50                  55                  60

Gly Thr Glu Tyr Ser Val Asn Ile Gln Gly Val Lys Gly Gly Ile Val
 65                  70                  75                  80

Ser Phe Pro Leu His Ala Glu Phe Thr Thr
                 85                  90

<210> SEQ ID NO 458
<211> LENGTH: 90
<212> TYPE: PRT
<213> ORGANISM: Artificial Sequence
<220> FEATURE:
<223> OTHER INFORMATION: synthetic sequence

<400> SEQUENCE: 458

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Ile Ile Pro Tyr Ala Glu Val Arg Pro Asp Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Lys Leu
 65                  70                  75                  80

Ser Leu Pro Leu Ser Ala Ile Phe Thr Thr
                 85                  90

<210> SEQ ID NO 459
<211> LENGTH: 90
<212> TYPE: PRT
<213> ORGANISM: Artificial Sequence
<220> FEATURE:
<223> OTHER INFORMATION: synthetic sequence

<400> SEQUENCE: 459

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Phe Ile Pro Tyr Ala Glu Pro Ser Pro Thr Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Asp Val Trp Ile Glu Gly Val Lys Gly Gly Thr Leu
 65                  70                  75                  80

Ser Trp Pro Leu Ser Ala Ile Phe Thr Thr
                 85                  90

<210> SEQ ID NO 460
<211> LENGTH: 90
<212> TYPE: PRT
<213> ORGANISM: Artificial Sequence
<220> FEATURE:
<223> OTHER INFORMATION: synthetic sequence

<400> SEQUENCE: 460

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30
```

Tyr Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 461
<211> LENGTH: 90
<212> TYPE: PRT
<213> ORGANISM: Artificial Sequence
<220> FEATURE:
<223> OTHER INFORMATION: synthetic sequence

<400> SEQUENCE: 461

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Arg Asn
65                  70                  75                  80

Ser Asp Pro Leu Ser Ala Ile Ser Thr Thr
                85                  90

<210> SEQ ID NO 462
<211> LENGTH: 90
<212> TYPE: PRT
<213> ORGANISM: Artificial Sequence
<220> FEATURE:
<223> OTHER INFORMATION: synthetic sequence

<400> SEQUENCE: 462

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Glu Tyr Glu Glu Gln Tyr Ser Thr Gly Glu Ala Ile Tyr Leu
            35                  40                  45

Arg Val Pro Gly Ser Glu Arg Ser Tyr Asp Leu Thr Gly Leu Lys Pro
        50                  55                  60

Gly Thr Glu Tyr His Val Asp Ile Glu Gly Val Lys Gly Gly Arg Arg
65                  70                  75                  80

Ser Phe Pro Leu Asn Ala Phe Phe Thr Thr
                85                  90

<210> SEQ ID NO 463
<211> LENGTH: 90
<212> TYPE: PRT
<213> ORGANISM: Artificial Sequence
<220> FEATURE:
<223> OTHER INFORMATION: synthetic sequence

<400> SEQUENCE: 463

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ile Ile Pro Tyr Ala Glu Val Arg Pro Asp Gly Glu Ala Ile Val Leu
                35                  40                  45

Thr Val Pro Gly Ser Glu Arg Ser Tyr Asp Leu Thr Gly Leu Lys Pro
            50                  55                  60

Gly Thr Glu Tyr Ser Val Leu Ile His Gly Val Lys Gly Gly Lys Leu
65                  70                  75                  80

Ser Glu Pro Leu Ser Ala Ile Phe Thr Thr
                85                  90

<210> SEQ ID NO 464
<211> LENGTH: 90
<212> TYPE: PRT
<213> ORGANISM: Artificial Sequence
<220> FEATURE:
<223> OTHER INFORMATION: synthetic sequence

<400> SEQUENCE: 464

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ala Tyr Ala Glu Pro Ser Thr Gly Glu Ala Ile Val Leu
                35                  40                  45

Thr Val Pro Gly Ser Glu Arg Ser Tyr Asp Leu Thr Gly Leu Lys Pro
            50                  55                  60

Gly Thr Glu Tyr Ser Val Leu Ile His Gly Val Lys Gly Gly His Leu
65                  70                  75                  80

Ser Asp Pro Leu Ser Ala Ile Phe Thr Thr
                85                  90

<210> SEQ ID NO 465
<211> LENGTH: 90
<212> TYPE: PRT
<213> ORGANISM: Artificial Sequence
<220> FEATURE:
<223> OTHER INFORMATION: synthetic sequence

<400> SEQUENCE: 465

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Pro Tyr Ala Glu Pro Ser Pro Thr Gly Glu Ala Ile Val Leu
                35                  40                  45

Thr Val Pro Gly Ser Glu Arg Ser Tyr Asp Leu Thr Gly Leu Lys Pro
            50                  55                  60

Gly Thr Glu Tyr Gly Val Val Ile Leu Gly Val Lys Gly Gly Tyr Gly
65                  70                  75                  80

Ser Asp Pro Leu Ser Ala Ile Phe Thr Thr
                85                  90

<210> SEQ ID NO 466
<211> LENGTH: 90
<212> TYPE: PRT
<213> ORGANISM: Artificial Sequence
<220> FEATURE:
<223> OTHER INFORMATION: synthetic sequence

<400> SEQUENCE: 466

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Ser Pro Leu Ser Ala Ile Phe Thr Thr
                85                  90

<210> SEQ ID NO 467
<211> LENGTH: 90
<212> TYPE: PRT
<213> ORGANISM: Artificial Sequence
<220> FEATURE:
<223> OTHER INFORMATION: synthetic sequence

<400> SEQUENCE: 467

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Leu Asp Ser Phe
            20                  25                  30

Arg Ile Ala Tyr Thr Glu Tyr Phe Val Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Gly Ile Tyr Gly Val Lys Gly Gly Ala Gly
65                  70                  75                  80

Ser Ser Pro Leu Ser Ala Ile Phe Thr Thr
                85                  90

<210> SEQ ID NO 468
<211> LENGTH: 90
<212> TYPE: PRT
<213> ORGANISM: Artificial Sequence
<220> FEATURE:
<223> OTHER INFORMATION: synthetic sequence

<400> SEQUENCE: 468

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Pro Tyr Ala Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 469
<211> LENGTH: 90
<212> TYPE: PRT
<213> ORGANISM: Artificial Sequence
<220> FEATURE:
<223> OTHER INFORMATION: synthetic sequence

<400> SEQUENCE: 469

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Thr Tyr Arg Glu Arg Ser Gln Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Pro Ile Glu Gly Val Lys Gly Gly Arg Gly
65                  70                  75                  80

Ser Lys Pro Leu Ser Ala Ile Phe Thr Thr
                85                  90
```

<210> SEQ ID NO 470
<211> LENGTH: 90
<212> TYPE: PRT
<213> ORGANISM: Artificial Sequence
<220> FEATURE:
<223> OTHER INFORMATION: synthetic sequence

<400> SEQUENCE: 470

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Glu Tyr Phe Glu Asn Leu Gly Ile Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Asn Ile Tyr Gly Val Lys Gly Gly Trp Leu
65                  70                  75                  80

Ser Ser Pro Leu Ser Ala Ile Phe Thr Thr
                85                  90
```

<210> SEQ ID NO 471
<211> LENGTH: 90
<212> TYPE: PRT
<213> ORGANISM: Artificial Sequence
<220> FEATURE:
<223> OTHER INFORMATION: synthetic sequence

<400> SEQUENCE: 471

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Glu Tyr Tyr Glu Tyr Val Gly Asn Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Gln Val Gly Ile Tyr Gly Val Lys Gly Gly Tyr Tyr
```

```
                65                  70                  75                  80
Ser Arg Pro Leu Ser Ala Ile Phe Thr Thr
                    85                  90
```

<210> SEQ ID NO 472
<211> LENGTH: 90
<212> TYPE: PRT
<213> ORGANISM: Artificial Sequence
<220> FEATURE:
<223> OTHER INFORMATION: synthetic sequence

<400> SEQUENCE: 472

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ile Ile Asp Tyr Leu Glu Leu Asp Asp Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Tyr Ile Tyr Gly Val Lys Gly Gly Leu Pro
65                  70                  75                  80

Ser Thr Pro Leu Ser Ala Ile Phe Thr Thr
                85                  90
```

<210> SEQ ID NO 473
<211> LENGTH: 90
<212> TYPE: PRT
<213> ORGANISM: Artificial Sequence
<220> FEATURE:
<223> OTHER INFORMATION: synthetic sequence

<400> SEQUENCE: 473

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Arg Asn
65                  70                  75                  80

Ser Asp Pro Leu Ser Ala Ile Phe Thr Thr
                85                  90
```

<210> SEQ ID NO 474
<211> LENGTH: 90
<212> TYPE: PRT
<213> ORGANISM: Artificial Sequence
<220> FEATURE:
<223> OTHER INFORMATION: synthetic sequence

<400> SEQUENCE: 474

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Ala Tyr Gly Glu Trp Arg Gln His Gly Glu Ala Ile Val Leu
        35                  40                  45
```

```
Thr Val Pro Gly Ser Glu Arg Ser Tyr Asp Leu Thr Gly Leu Lys Pro
        50                  55                  60

Gly Thr Glu Tyr Asp Val Phe Ile Asp Gly Val Lys Gly Gly Asn Leu
 65                  70                  75                  80

Ser Trp Pro Leu Ser Ala Ile Phe Thr Thr
                85                  90

<210> SEQ ID NO 475
<211> LENGTH: 90
<212> TYPE: PRT
<213> ORGANISM: Artificial Sequence
<220> FEATURE:
<223> OTHER INFORMATION: synthetic sequence

<400> SEQUENCE: 475

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Thr Ile Arg Tyr Trp Glu Glu Leu Pro Thr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Glu Ile Phe Gly Val Lys Gly Gly Tyr Leu
 65                  70                  75                  80

Ser Arg Pro Leu Ser Ala Ile Ser Thr Thr
                85                  90

<210> SEQ ID NO 476
<211> LENGTH: 90
<212> TYPE: PRT
<213> ORGANISM: Artificial Sequence
<220> FEATURE:
<223> OTHER INFORMATION: synthetic sequence

<400> SEQUENCE: 476

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

His Ile Ala Tyr Glu Glu Ala Thr Thr Tyr Gly Glu Ala Ile Phe Leu
            35                  40                  45

Arg Val Pro Gly Ser Glu Arg Ser Tyr Asp Leu Thr Gly Leu Lys Pro
        50                  55                  60

Gly Thr Glu Tyr Asp Val Trp Ile Glu Gly Val Lys Gly Gly Thr Ile
 65                  70                  75                  80

Ser Gly Pro Leu Ser Ala Ile Phe Thr Thr
                85                  90

<210> SEQ ID NO 477
<211> LENGTH: 90
<212> TYPE: PRT
<213> ORGANISM: Artificial Sequence
<220> FEATURE:
<223> OTHER INFORMATION: synthetic sequence

<400> SEQUENCE: 477

Met Leu Pro Ala Pro Lys Asn Leu Val Val Ser Arg Val Thr Glu Asp
 1               5                  10                  15
```

```
Ser Ala Arg Leu Ser Trp Thr Ala Pro Asp Ala Ala Phe Asp Ser Phe
            20                  25                  30

Pro Ile Ala Tyr Ala Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Asp Ile Phe Gly Val Lys Gly Gly Thr Leu
65                  70                  75                  80

Ser Arg Pro Leu Ser Ala Ile Phe Thr Thr
                85                  90

<210> SEQ ID NO 478
<211> LENGTH: 90
<212> TYPE: PRT
<213> ORGANISM: Artificial Sequence
<220> FEATURE:
<223> OTHER INFORMATION: synthetic sequence

<400> SEQUENCE: 478

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
65                  70                  75                  80

Ser Asp Pro Leu Ser Ala Ile Phe Thr Thr
                85                  90

<210> SEQ ID NO 479
<211> LENGTH: 90
<212> TYPE: PRT
<213> ORGANISM: Artificial Sequence
<220> FEATURE:
<223> OTHER INFORMATION: synthetic sequence

<400> SEQUENCE: 479

Met Leu Pro Ala Arg Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Pro Tyr Ala Glu Pro Ser Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
65                  70                  75                  80

Ser Asp Pro Leu Ser Ala Ile Ser Thr Thr
                85                  90

<210> SEQ ID NO 480
<211> LENGTH: 90
<212> TYPE: PRT
<213> ORGANISM: Artificial Sequence
<220> FEATURE:
<223> OTHER INFORMATION: synthetic sequence
```

```
<400> SEQUENCE: 480

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Leu Tyr Asn Glu Ile Gln Asn Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asp Val Trp Ile Glu Gly Val Lys Gly Gly Glu Leu
65                  70                  75                  80

Ser Trp Pro Leu Ser Ala Ile Phe Thr Thr
                85                  90

<210> SEQ ID NO 481
<211> LENGTH: 90
<212> TYPE: PRT
<213> ORGANISM: Artificial Sequence
<220> FEATURE:
<223> OTHER INFORMATION: synthetic sequence

<400> SEQUENCE: 481

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Thr Pro
65                  70                  75                  80

Ser Glu Pro Leu Ser Ala Ile Phe Thr Thr
                85                  90

<210> SEQ ID NO 482
<211> LENGTH: 90
<212> TYPE: PRT
<213> ORGANISM: Artificial Sequence
<220> FEATURE:
<223> OTHER INFORMATION: synthetic sequence

<400> SEQUENCE: 482

Met Leu Pro Ala Pro Lys Asn Leu Val Val Ser Arg Val Thr Glu Asp
1               5                   10                  15

Ser Ala Arg Leu Ser Trp Thr Thr Pro Asp Ala Ala Phe Asp Ser Phe
                20                  25                  30

Phe Ile Gly Tyr Leu Glu Pro Tyr Pro Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Ser Ile Gln Gly Val Lys Gly Gly Lys Pro
65                  70                  75                  80

Ser Asp Pro Leu Ser Ala Ile Phe Thr Thr
                85                  90

<210> SEQ ID NO 483
<211> LENGTH: 90
```

```
<212> TYPE: PRT
<213> ORGANISM: Artificial Sequence
<220> FEATURE:
<223> OTHER INFORMATION: synthetic sequence

<400> SEQUENCE: 483

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Asn Val Thr Ile Gln Gly Val Lys Gly Gly Phe Pro
65                  70                  75                  80

Ser Val Pro Leu Ser Ala Ile Phe Thr Thr
                85                  90

<210> SEQ ID NO 484
<211> LENGTH: 90
<212> TYPE: PRT
<213> ORGANISM: Artificial Sequence
<220> FEATURE:
<223> OTHER INFORMATION: synthetic sequence

<400> SEQUENCE: 484

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Pro Glu Tyr Pro Ala Thr Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Phe Val Asp Ile Asn Gly Val Lys Gly Gly Ser Leu
65                  70                  75                  80

Ser Tyr Pro Leu Ser Ala Ile Phe Thr Thr
                85                  90

<210> SEQ ID NO 485
<211> LENGTH: 90
<212> TYPE: PRT
<213> ORGANISM: Artificial Sequence
<220> FEATURE:
<223> OTHER INFORMATION: synthetic sequence

<400> SEQUENCE: 485

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Arg Tyr Leu Glu Trp Trp Asp Val Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Leu Val Glu Ile Lys Gly Val Lys Gly Gly Lys Phe
65                  70                  75                  80

Ser Tyr Pro Leu Ser Ala Ile Phe Thr Thr
```

```
                  85                  90

<210> SEQ ID NO 486
<211> LENGTH: 90
<212> TYPE: PRT
<213> ORGANISM: Artificial Sequence
<220> FEATURE:
<223> OTHER INFORMATION: synthetic sequence

<400> SEQUENCE: 486

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Glu Tyr Asp Glu Trp Trp Ala Leu Gly Glu Ala Ile Thr Leu
        35                  40                  45

Ile Val Pro Ala Ser Glu Arg Ser Tyr Asp Leu Thr Gly Leu Lys Pro
    50                  55                  60

Gly Thr Glu Tyr Val Val Lys Ile His Gly Val Lys Gly Gly Gln Arg
65                  70                  75                  80

Ser Tyr Pro Leu Ile Ala Phe Phe Thr Thr
                85                  90

<210> SEQ ID NO 487
<211> LENGTH: 88
<212> TYPE: PRT
<213> ORGANISM: Artificial Sequence
<220> FEATURE:
<223> OTHER INFORMATION: synthetic sequence

<400> SEQUENCE: 487

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile His Tyr Arg Glu Leu Tyr Val Gln Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Leu Val Met Ile Pro Gly Val Lys Gly Gly Pro Thr Ser Val
65                  70                  75                  80

Pro Leu Ser Ala Ile Phe Thr Thr
                85

<210> SEQ ID NO 488
<211> LENGTH: 90
<212> TYPE: PRT
<213> ORGANISM: Artificial Sequence
<220> FEATURE:
<223> OTHER INFORMATION: synthetic sequence

<400> SEQUENCE: 488

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60
```

```
Gly Thr Glu Tyr Lys Val Val Ile Gln Gly Val Lys Gly Gly Thr Pro
 65                  70                  75                  80

Ser Glu Pro Leu Ser Ala Ile Phe Thr Thr
                 85                  90

<210> SEQ ID NO 489
<211> LENGTH: 90
<212> TYPE: PRT
<213> ORGANISM: Artificial Sequence
<220> FEATURE:
<223> OTHER INFORMATION: synthetic sequence

<400> SEQUENCE: 489

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Phe Ile Gly Tyr Leu Glu Pro Gln Pro Pro Gly Glu Ala Ile Val Leu
                 35                  40                  45

Thr Val Pro Gly Ser Glu Arg Ser Tyr Asp Leu Thr Gly Leu Lys Pro
 50                  55                  60

Gly Thr Glu Tyr Ser Val Val Ile Gln Gly Val Lys Gly Gly Phe Pro
 65                  70                  75                  80

Ser Asp Pro Leu Ser Ala Ile Phe Thr Thr
                 85                  90

<210> SEQ ID NO 490
<211> LENGTH: 90
<212> TYPE: PRT
<213> ORGANISM: Artificial Sequence
<220> FEATURE:
<223> OTHER INFORMATION: synthetic sequence

<400> SEQUENCE: 490

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Pro Ile Ala Tyr Ala Glu Pro Arg Pro Asp Gly Glu Ala Ile Val Leu
                 35                  40                  45

Thr Val Pro Gly Ser Glu Arg Ser Tyr Asp Leu Thr Gly Leu Lys Pro
 50                  55                  60

Gly Thr Glu Tyr Ser Val Gly Ile His Gly Val Lys Gly Gly His Asp
 65                  70                  75                  80

Ser Ser Pro Leu Ser Ala Ile Phe Thr Thr
                 85                  90

<210> SEQ ID NO 491
<211> LENGTH: 90
<212> TYPE: PRT
<213> ORGANISM: Artificial Sequence
<220> FEATURE:
<223> OTHER INFORMATION: synthetic sequence

<400> SEQUENCE: 491

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30
```

```
Phe Ile Gly Tyr Leu Glu Pro Gln Pro Pro Gly Glu Ala Ile Val Leu
         35                  40                  45

Thr Val Pro Gly Ser Glu Arg Ser Tyr Asp Leu Thr Gly Leu Lys Pro
 50                  55                  60

Gly Thr Glu Tyr Asn Val Thr Ile Gln Gly Val Lys Gly Gly Arg Ala
 65                  70                  75                  80

Ser Gly Pro Leu Ser Ala Ile Phe Thr Thr
                 85                  90

<210> SEQ ID NO 492
<211> LENGTH: 90
<212> TYPE: PRT
<213> ORGANISM: Artificial Sequence
<220> FEATURE:
<223> OTHER INFORMATION: synthetic sequence

<400> SEQUENCE: 492

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Asp Ile Ala Tyr Ala Glu Pro Ile Pro Arg Gly Glu Ala Ile Val Leu
         35                  40                  45

Thr Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Arg Arg
 65                  70                  75                  80

Ser Val Pro Leu Ser Ala Ile Phe Thr Thr
                 85                  90

<210> SEQ ID NO 493
<211> LENGTH: 90
<212> TYPE: PRT
<213> ORGANISM: Artificial Sequence
<220> FEATURE:
<223> OTHER INFORMATION: synthetic sequence

<400> SEQUENCE: 493

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Tyr Ile Ala Tyr Ala Glu Pro Arg Pro Asp Gly Glu Ala Ile Val Leu
         35                  40                  45

Thr Val Pro Gly Ser Glu Arg Ser Tyr Asp Leu Thr Gly Leu Lys Pro
 50                  55                  60

Gly Thr Glu Tyr Pro Val Pro Ile Pro Gly Val Lys Gly Gly Pro Gly
 65                  70                  75                  80

Ser Ser Pro Leu Ser Ala Ile Phe Thr Thr
                 85                  90

<210> SEQ ID NO 494
<211> LENGTH: 90
<212> TYPE: PRT
<213> ORGANISM: Artificial Sequence
<220> FEATURE:
<223> OTHER INFORMATION: synthetic sequence

<400> SEQUENCE: 494

Met Leu Pro Ala Pro Lys Asn Leu Val Val Ser Arg Val Thr Glu Asp
```

-continued

```
                 1               5                  10                  15
            Ser Ala Arg Leu Ser Trp Thr Ala Pro Asp Ala Ala Phe Asp Ser Phe
                            20                  25                  30

Glu Ile Ser Tyr Tyr Glu Met Arg Gly Tyr Gly Glu Ala Ile Val Leu
                            35                  40                  45

Thr Val Pro Gly Ser Glu Arg Ser Tyr Asp Leu Thr Gly Leu Lys Pro
                            50                  55                  60

Gly Thr Glu Tyr Ser Val Leu Ile His Gly Val Glu Gly Gly Asp Tyr
            65                  70                  75                  80

Ser Ser Pro Leu Ser Ala Ile Ser Thr Thr
                            85                  90

<210> SEQ ID NO 495
            <211> LENGTH: 90
            <212> TYPE: PRT
            <213> ORGANISM: Artificial Sequence
            <220> FEATURE:
            <223> OTHER INFORMATION: synthetic sequence

<400> SEQUENCE: 495

Met Leu Pro Ala Pro Lys Asn Leu Val Val Ser His Val Thr Glu Asp
            1               5                  10                  15

Ser Ala Arg Leu Ser Trp Thr Ala Pro Asp Ala Ala Phe Asp Ser Phe
                            20                  25                  30

Pro Ile Ala Tyr Ala Glu Pro Arg Pro Asp Gly Glu Ala Ile Val Leu
                            35                  40                  45

Thr Val Pro Gly Ser Glu Arg Ser Tyr Asp Leu Thr Gly Leu Lys Pro
                            50                  55                  60

Gly Thr Glu Tyr Ser Val Leu Ile His Gly Val Lys Gly Gly Leu Leu
            65                  70                  75                  80

Ser Ser Pro Leu Ser Ala Ile Phe Thr Thr
                            85                  90

<210> SEQ ID NO 496
            <211> LENGTH: 90
            <212> TYPE: PRT
            <213> ORGANISM: Artificial Sequence
            <220> FEATURE:
            <223> OTHER INFORMATION: synthetic sequence

<400> SEQUENCE: 496

Met Leu Pro Ala Pro Lys Asn Leu Val Val Ser Arg Val Thr Glu Asp
            1               5                  10                  15

Ser Ala Arg Leu Ser Trp Thr Ala Pro Asp Ala Ala Phe Asp Ser Phe
                            20                  25                  30

Phe Ile Gly Tyr Leu Glu Pro Tyr Pro Pro Gly Glu Ala Ile Val Leu
                            35                  40                  45

Thr Val Pro Gly Ser Glu Arg Ser Tyr Asp Leu Thr Gly Leu Lys Pro
                            50                  55                  60

Gly Thr Glu Tyr Val Val Ser Ile Gln Gly Val Lys Gly Gly Thr Pro
            65                  70                  75                  80

Ser Gln Pro Leu Ser Ala Ile Phe Thr Thr
                            85                  90

<210> SEQ ID NO 497
            <211> LENGTH: 90
            <212> TYPE: PRT
            <213> ORGANISM: Artificial Sequence
            <220> FEATURE:
```

<223> OTHER INFORMATION: synthetic sequence

<400> SEQUENCE: 497

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Arg Pro
65                  70                  75                  80

Ser Asn Pro Leu Val Ala Ala Phe Thr Thr
                85                  90

<210> SEQ ID NO 498
<211> LENGTH: 90
<212> TYPE: PRT
<213> ORGANISM: Artificial Sequence
<220> FEATURE:
<223> OTHER INFORMATION: synthetic sequence

<400> SEQUENCE: 498

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Gly Ile Gly Tyr Tyr Glu His Lys Arg Phe Gly Glu Ala Ile Gln Leu
        35                  40                  45

Ser Val Pro Gly Ser Glu Arg Ser Tyr Asp Leu Thr Gly Leu Lys Pro
    50                  55                  60

Gly Thr Glu Tyr Glu Val Asp Ile Glu Gly Val Lys Gly Gly Val Leu
65                  70                  75                  80

Ser Trp Pro Leu Phe Ala Glu Phe Thr Thr
                85                  90

<210> SEQ ID NO 499
<211> LENGTH: 90
<212> TYPE: PRT
<213> ORGANISM: Artificial Sequence
<220> FEATURE:
<223> OTHER INFORMATION: synthetic sequence

<400> SEQUENCE: 499

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Asp Tyr Asp Glu Leu Ala Ile Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Met Ile Ile Gly Val Lys Gly Gly Leu Pro
65                  70                  75                  80

Ser Asp Pro Leu Ser Ala Ile Phe Thr Thr
                85                  90

```
<210> SEQ ID NO 500
<211> LENGTH: 87
<212> TYPE: PRT
<213> ORGANISM: Artificial Sequence
<220> FEATURE:
<223> OTHER INFORMATION: synthetic sequence

<400> SEQUENCE: 500

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Ser Ala Glu Ala Ile Val Leu Thr Val Pro
        35                  40                  45

Gly Ser Glu Arg Ser Tyr Asp Leu Thr Gly Leu Lys Pro Gly Thr Glu
50                  55                  60

Tyr Leu Val Thr Ile Gln Gly Val Lys Gly Gly Ile Ala Ser Asp Pro
65                  70                  75                  80

Leu Ser Ala Ile Phe Thr Thr
                85

<210> SEQ ID NO 501
<211> LENGTH: 90
<212> TYPE: PRT
<213> ORGANISM: Artificial Sequence
<220> FEATURE:
<223> OTHER INFORMATION: synthetic sequence

<400> SEQUENCE: 501

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Phe Glu Phe Val Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Gly Ile Tyr Gly Val Lys Gly Gly Lys Leu
65                  70                  75                  80

Ser Pro Pro Leu Ser Ala Ile Phe Thr Thr
                85                  90

<210> SEQ ID NO 502
<211> LENGTH: 90
<212> TYPE: PRT
<213> ORGANISM: Artificial Sequence
<220> FEATURE:
<223> OTHER INFORMATION: synthetic sequence

<400> SEQUENCE: 502

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Lys Leu
65                  70                  75                  80
```

```
Ser Leu Pro Leu Ser Ala Ile Phe Thr Thr
                85                  90

<210> SEQ ID NO 503
<211> LENGTH: 86
<212> TYPE: PRT
<213> ORGANISM: Artificial Sequence
<220> FEATURE:
<223> OTHER INFORMATION: synthetic sequence

<400> SEQUENCE: 503

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

His Glu Trp Val Tyr Phe Gly Glu Ala Ile Val Leu Thr Val Pro Gly
            35                  40                  45

Ser Glu Arg Ser Tyr Asp Leu Thr Gly Leu Lys Pro Gly Thr Glu Tyr
        50                  55                  60

Phe Val Asp Ile Trp Gly Val Lys Gly Gly Thr Val Ser Lys Pro Leu
65                  70                  75                  80

Ser Ala Ile Phe Thr Thr
                85

<210> SEQ ID NO 504
<211> LENGTH: 90
<212> TYPE: PRT
<213> ORGANISM: Artificial Sequence
<220> FEATURE:
<223> OTHER INFORMATION: synthetic sequence

<400> SEQUENCE: 504

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Pro Glu Tyr Pro Ala Thr Gly Glu Ala Ile Thr Leu
            35                  40                  45

Phe Val Pro Gly Ser Glu Arg Ser Tyr Asp Leu Thr Gly Leu Lys Pro
        50                  55                  60

Gly Thr Glu Tyr Asn Val Val Ile Gln Gly Val Lys Gly Gly Arg Pro
65                  70                  75                  80

Ser Asn Pro Leu Val Val Ala Phe Thr Thr
                85                  90

<210> SEQ ID NO 505
<211> LENGTH: 90
<212> TYPE: PRT
<213> ORGANISM: Artificial Sequence
<220> FEATURE:
<223> OTHER INFORMATION: synthetic sequence

<400> SEQUENCE: 505

Met Leu Pro Ala Pro Glu Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Glu Ile Thr Tyr Glu Glu Asn Trp Arg Arg Gly Glu Ala Ile Val Leu
            35                  40                  45
```

```
Thr Val Pro Gly Ser Glu Arg Ser Tyr Asp Leu Thr Gly Pro Lys Pro
    50                  55                  60

Gly Thr Glu Tyr Ile Val Ile Ile Gln Gly Val Lys Gly Gly Ala Glu
 65                  70                  75                  80

Ser Trp Pro Leu Ser Ala Ile Phe Thr Thr
                85                  90

<210> SEQ ID NO 506
<211> LENGTH: 90
<212> TYPE: PRT
<213> ORGANISM: Artificial Sequence
<220> FEATURE:
<223> OTHER INFORMATION: synthetic sequence

<400> SEQUENCE: 506

Met Leu Pro Ala Pro Lys Asn Leu Val Val Ser Arg Val Thr Glu Asp
  1               5                  10                  15

Ser Ala Arg Leu Ser Trp Thr Ala Leu Asp Ala Ala Phe Asp Ser Phe
                 20                  25                  30

Phe Ile Gly Tyr Leu Glu Pro Gln Pro Pro Gly Glu Ala Ile Val Leu
                 35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
 65                  70                  75                  80

Ser Met Pro Leu Ser Ala Ile Phe Thr Thr
                85                  90

<210> SEQ ID NO 507
<211> LENGTH: 90
<212> TYPE: PRT
<213> ORGANISM: Artificial Sequence
<220> FEATURE:
<223> OTHER INFORMATION: synthetic sequence

<400> SEQUENCE: 507

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Thr Ile Trp Tyr Ala Glu Ala Val Gly Asn Gly Glu Ala Ile Val Leu
                 35                  40                  45

Thr Val Pro Gly Ser Glu Arg Ser Tyr Asp Leu Thr Gly Leu Lys Pro
    50                  55                  60

Gly Thr Glu Tyr Trp Val Asp Ile Trp Gly Val Lys Gly Gly Glu Phe
 65                  70                  75                  80

Ser Ser Pro Leu Ser Ala Ile Phe Thr Thr
                85                  90

<210> SEQ ID NO 508
<211> LENGTH: 90
<212> TYPE: PRT
<213> ORGANISM: Artificial Sequence
<220> FEATURE:
<223> OTHER INFORMATION: synthetic sequence

<400> SEQUENCE: 508

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
```

```
                    20                  25                  30

Glu Ile Asp Tyr Asp Glu Leu Ala Ile Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Arg Val Phe Ile Tyr Gly Val Lys Gly Gly Trp Thr
65                  70                  75                  80

Ser Trp Pro Leu Ser Thr Ile Phe Thr Thr
                85                  90

<210> SEQ ID NO 509
<211> LENGTH: 90
<212> TYPE: PRT
<213> ORGANISM: Artificial Sequence
<220> FEATURE:
<223> OTHER INFORMATION: synthetic sequence

<400> SEQUENCE: 509

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Glu Tyr Asp Glu Ile Pro Phe Trp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Arg Val Trp Ile His Gly Val Lys Gly Gly Asn Ser
65                  70                  75                  80

Ser Trp Pro Leu Ser Ala Ile Phe Thr Thr
                85                  90

<210> SEQ ID NO 510
<211> LENGTH: 90
<212> TYPE: PRT
<213> ORGANISM: Artificial Sequence
<220> FEATURE:
<223> OTHER INFORMATION: synthetic sequence

<400> SEQUENCE: 510

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile His Tyr Val Glu Trp Trp Val Leu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Tyr Ile Tyr Gly Val Lys Gly Gly Pro Lys
65                  70                  75                  80

Ser Ile Pro Leu Ser Ala Ile Phe Thr Thr
                85                  90

<210> SEQ ID NO 511
<211> LENGTH: 90
<212> TYPE: PRT
<213> ORGANISM: Artificial Sequence
<220> FEATURE:
<223> OTHER INFORMATION: synthetic sequence

<400> SEQUENCE: 511
```

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Lys Ile Asp Tyr Leu Glu Ile Asn Asp Asn Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Tyr Ile Trp Gly Val Lys Gly Gly Tyr Pro
65                  70                  75                  80

Ser Ser Pro Leu Ser Ala Ile Phe Thr Thr
                85                  90

<210> SEQ ID NO 512
<211> LENGTH: 90
<212> TYPE: PRT
<213> ORGANISM: Artificial Sequence
<220> FEATURE:
<223> OTHER INFORMATION: synthetic sequence

<400> SEQUENCE: 512

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Ala Tyr Asn Glu Asp Arg Lys Phe Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Ser Leu
65                  70                  75                  80

Ser Phe Pro Leu Ser Ala Ile Phe Thr Thr
                85                  90

<210> SEQ ID NO 513
<211> LENGTH: 90
<212> TYPE: PRT
<213> ORGANISM: Artificial Sequence
<220> FEATURE:
<223> OTHER INFORMATION: synthetic sequence

<400> SEQUENCE: 513

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Arg Tyr Phe Glu Trp Trp Asp Leu Gly Glu Ala Ile Val Leu
        35                  40                  45

Thr Val Pro Gly Ser Glu Arg Ser Tyr Asp Pro Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 514
<211> LENGTH: 90
<212> TYPE: PRT

<213> ORGANISM: Artificial Sequence
<220> FEATURE:
<223> OTHER INFORMATION: synthetic sequence

<400> SEQUENCE: 514

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Glu Tyr Tyr Glu Trp Met His Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Tyr Ile Tyr Gly Val Lys Gly Gly Tyr Pro
65                  70                  75                  80

Ser Ser Pro Leu Ser Ala Ile Phe Thr Thr
                85                  90

<210> SEQ ID NO 515
<211> LENGTH: 90
<212> TYPE: PRT
<213> ORGANISM: Artificial Sequence
<220> FEATURE:
<223> OTHER INFORMATION: synthetic sequence

<400> SEQUENCE: 515

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Asp Tyr Trp Glu Thr Trp Val Ile Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Glu Val Ile Ile Pro Gly Val Lys Gly Gly Thr Ile
65                  70                  75                  80

Ser Pro Pro Leu Ser Ala Ile Phe Thr Thr
                85                  90

<210> SEQ ID NO 516
<211> LENGTH: 90
<212> TYPE: PRT
<213> ORGANISM: Artificial Sequence
<220> FEATURE:
<223> OTHER INFORMATION: synthetic sequence

<400> SEQUENCE: 516

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Asp Tyr Leu Glu Leu Thr Tyr Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Tyr Ile Tyr Gly Val Lys Gly Gly Tyr Pro
65                  70                  75                  80

Ser Ser Pro Leu Ser Ala Ile Phe Thr Thr
                85                  90

<210> SEQ ID NO 517
<211> LENGTH: 90
<212> TYPE: PRT
<213> ORGANISM: Artificial Sequence
<220> FEATURE:
<223> OTHER INFORMATION: synthetic sequence

<400> SEQUENCE: 517

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Leu Asp Ser Phe
            20                  25                  30

Arg Ile Glu Tyr Tyr Glu Ser Tyr Gly His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Gly Ile Tyr Gly Val Lys Gly Gly Tyr Tyr
65                  70                  75                  80

Ser Arg Pro Leu Ser Ala Ile Phe Thr Thr
                85                  90

<210> SEQ ID NO 518
<211> LENGTH: 90
<212> TYPE: PRT
<213> ORGANISM: Artificial Sequence
<220> FEATURE:
<223> OTHER INFORMATION: synthetic sequence

<400> SEQUENCE: 518

Met Leu Pro Ala Pro Lys Asn Leu Val Val Ser Arg Val Thr Glu Asp
1               5                   10                  15

Ser Ala Arg Leu Pro Trp Thr Ala Pro Asp Ala Ala Phe Asp Ser Phe
            20                  25                  30

Trp Ile Ser Tyr Tyr Glu Ser Val Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Asp Ile Ser Gly Val Lys Gly Gly Val Tyr
65                  70                  75                  80

Ser Leu Pro Leu Ser Ala Ile Phe Thr Thr
                85                  90

<210> SEQ ID NO 519
<211> LENGTH: 90
<212> TYPE: PRT
<213> ORGANISM: Artificial Sequence
<220> FEATURE:
<223> OTHER INFORMATION: synthetic sequence

<400> SEQUENCE: 519

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Asp Tyr Asp Glu Pro Ala Trp Asn Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Phe Ile Tyr Gly Val Lys Gly Gly Asn Thr
65                  70                  75                  80

Ser Trp Pro Leu Ser Ala Ile Phe Thr Thr
                85                  90

<210> SEQ ID NO 520
<211> LENGTH: 90
<212> TYPE: PRT
<213> ORGANISM: Artificial Sequence
<220> FEATURE:
<223> OTHER INFORMATION: synthetic sequence

<400> SEQUENCE: 520

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asp Ile Glu Tyr Asp Glu Leu Trp Lys Asn Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Arg Val Phe Ile Tyr Gly Val Lys Gly Gly Tyr Gly
65                  70                  75                  80

Ser Phe Pro Leu Ser Ala Ile Phe Thr Thr
                85                  90

<210> SEQ ID NO 521
<211> LENGTH: 90
<212> TYPE: PRT
<213> ORGANISM: Artificial Sequence
<220> FEATURE:
<223> OTHER INFORMATION: synthetic sequence

<400> SEQUENCE: 521

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Thr Pro
65                  70                  75                  80

Ser Glu Pro Leu Ser Ala Ile Ser Thr Thr
                85                  90

<210> SEQ ID NO 522
<211> LENGTH: 90
<212> TYPE: PRT
<213> ORGANISM: Artificial Sequence
<220> FEATURE:
<223> OTHER INFORMATION: synthetic sequence

<400> SEQUENCE: 522

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Gly Ile Val Tyr Arg Glu Pro Tyr Val Gly Gly Glu Ala Ile Val Leu

```
                35                  40                  45

Thr Val Pro Gly Ser Glu Arg Ser Tyr Asp Leu Thr Gly Leu Lys Pro
         50                  55                  60

Gly Thr Glu Tyr Gly Val Pro Ile Pro Gly Val Lys Gly Gly Tyr Asp
 65                  70                  75                  80

Ser Gly Pro Leu Ser Ala Ile Phe Thr Thr
                 85                  90

<210> SEQ ID NO 523
<211> LENGTH: 90
<212> TYPE: PRT
<213> ORGANISM: Artificial Sequence
<220> FEATURE:
<223> OTHER INFORMATION: synthetic sequence

<400> SEQUENCE: 523

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Thr Ile Pro Tyr Ile Glu Tyr Val Trp Trp Gly Glu Ala Ile Val Leu
                35                  40                  45

Thr Val Gln Gly Ser Glu Arg Ser Tyr Asp Leu Thr Gly Leu Lys Pro
         50                  55                  60

Gly Thr Glu Tyr Pro Val Thr Ile Gly Gly Val Lys Gly Gly Ser Arg
 65                  70                  75                  80

Ser His Pro Leu His Ala His Phe Thr Thr
                 85                  90

<210> SEQ ID NO 524
<211> LENGTH: 90
<212> TYPE: PRT
<213> ORGANISM: Artificial Sequence
<220> FEATURE:
<223> OTHER INFORMATION: synthetic sequence

<400> SEQUENCE: 524

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Ser Ile Val Tyr Gly Glu Arg Phe Val Asn Gly Glu Ala Ile Val Leu
                35                  40                  45

Thr Val Pro Gly Ser Glu Arg Ser Tyr Asp Leu Thr Gly Leu Lys Pro
         50                  55                  60

Gly Thr Glu Tyr His Val Tyr Ile Asp Gly Val Lys Gly Gly Asp Leu
 65                  70                  75                  80

Ser Trp Pro Leu Ser Ala Ile Phe Thr Thr
                 85                  90

<210> SEQ ID NO 525
<211> LENGTH: 90
<212> TYPE: PRT
<213> ORGANISM: Artificial Sequence
<220> FEATURE:
<223> OTHER INFORMATION: synthetic sequence

<400> SEQUENCE: 525

Met Leu Pro Ala Pro Lys Asn Leu Val Val Ser Arg Val Thr Glu Asp
 1               5                  10                  15
```

```
Ser Ala Arg Leu Ser Trp Thr Ala Pro Asp Ala Ala Phe Asp Ser Phe
            20                  25                  30

Trp Ile Asn Tyr Tyr Glu Ala Gln Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Glu Ile Ala Gly Val Lys Gly Gly Thr Ala
65                  70                  75                  80

Ser Leu Pro Leu Ser Ala Ile Phe Thr Thr
                85                  90

<210> SEQ ID NO 526
<211> LENGTH: 90
<212> TYPE: PRT
<213> ORGANISM: Artificial Sequence
<220> FEATURE:
<223> OTHER INFORMATION: synthetic sequence

<400> SEQUENCE: 526

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ile Ile Glu Tyr Trp Glu Gln Ile Gly Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Gly Ile Tyr Gly Val Lys Gly Gly Leu Leu
65                  70                  75                  80

Ser Ser Pro Leu Ser Ala Ile Phe Thr Thr
                85                  90

<210> SEQ ID NO 527
<211> LENGTH: 90
<212> TYPE: PRT
<213> ORGANISM: Artificial Sequence
<220> FEATURE:
<223> OTHER INFORMATION: synthetic sequence

<400> SEQUENCE: 527

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Tyr Tyr Trp Glu Ile Glu Arg Ala Gly Glu Ala Ile Arg Leu
        35                  40                  45

Asp Val Pro Gly Ser Glu Arg Ser Tyr Asp Leu Thr Gly Leu Lys Pro
    50                  55                  60

Gly Thr Glu Tyr Arg Val Asp Ile Trp Gly Val Lys Gly Gly Pro Thr
65                  70                  75                  80

Ser Gly Pro Leu Arg Ala Thr Phe Thr Thr
                85                  90

<210> SEQ ID NO 528
<211> LENGTH: 90
<212> TYPE: PRT
<213> ORGANISM: Artificial Sequence
<220> FEATURE:
<223> OTHER INFORMATION: synthetic sequence
```

<400> SEQUENCE: 528

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Pro Tyr Gly Glu Arg Gln Glu Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Val Ile Gln Gly Val Lys Gly Gly Gln Pro
65                  70                  75                  80

Ser Tyr Pro Leu Ser Ala Ile Phe Thr Thr
                85                  90

<210> SEQ ID NO 529
<211> LENGTH: 90
<212> TYPE: PRT
<213> ORGANISM: Artificial Sequence
<220> FEATURE:
<223> OTHER INFORMATION: synthetic sequence

<400> SEQUENCE: 529

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Tyr Pro
65                  70                  75                  80

Ser Ser Pro Leu Ser Ala Ile Phe Thr Thr
                85                  90

<210> SEQ ID NO 530
<211> LENGTH: 90
<212> TYPE: PRT
<213> ORGANISM: Artificial Sequence
<220> FEATURE:
<223> OTHER INFORMATION: synthetic sequence

<400> SEQUENCE: 530

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Ala Tyr Ala Glu Pro Thr Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Gly Leu
65                  70                  75                  80

Ser Leu Pro Leu Ser Ala Ile Phe Thr Thr
                85                  90

<210> SEQ ID NO 531

```
<211> LENGTH: 90
<212> TYPE: PRT
<213> ORGANISM: Artificial Sequence
<220> FEATURE:
<223> OTHER INFORMATION: synthetic sequence

<400> SEQUENCE: 531

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ile Ile Glu Tyr Trp Glu Trp Tyr Phe Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Trp Ile Thr Gly Val Lys Gly Gly Thr Trp
65                  70                  75                  80

Ser Glu Pro Leu Ser Ala Ile Phe Thr Thr
                85                  90

<210> SEQ ID NO 532
<211> LENGTH: 90
<212> TYPE: PRT
<213> ORGANISM: Artificial Sequence
<220> FEATURE:
<223> OTHER INFORMATION: synthetic sequence

<400> SEQUENCE: 532

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Leu Tyr Tyr Glu Met Val Gly Glu Gly Ala Ile Val Leu
        35                  40                  45

Thr Val Pro Gly Ser Glu Arg Ser Tyr Asp Leu Thr Gly Pro Lys Pro
    50                  55                  60

Gly Thr Glu Tyr Trp Val Asp Ile Tyr Gly Val Lys Gly Gly Gly Trp
65                  70                  75                  80

Ser Arg Pro Leu Ser Ala Ile Phe Thr Thr
                85                  90

<210> SEQ ID NO 533
<211> LENGTH: 90
<212> TYPE: PRT
<213> ORGANISM: Artificial Sequence
<220> FEATURE:
<223> OTHER INFORMATION: synthetic sequence

<400> SEQUENCE: 533

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Asp Tyr Leu Glu Leu Thr Tyr Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Thr Ile Tyr Gly Val Lys Gly Gly Tyr Pro
65                  70                  75                  80
```

```
Ser Ser Pro Leu Ser Ala Ile Phe Thr Thr
                85                  90
```

<210> SEQ ID NO 534
<211> LENGTH: 90
<212> TYPE: PRT
<213> ORGANISM: Artificial Sequence
<220> FEATURE:
<223> OTHER INFORMATION: synthetic sequence

<400> SEQUENCE: 534

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ile Tyr Glu Glu Asp Gly Thr Glu Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Glu Val Asp Ile Glu Gly Val Lys Gly Gly Val Leu
65                  70                  75                  80

Ser Trp Pro Leu Phe Ala Glu Phe Thr Thr
                85                  90
```

<210> SEQ ID NO 535
<211> LENGTH: 90
<212> TYPE: PRT
<213> ORGANISM: Artificial Sequence
<220> FEATURE:
<223> OTHER INFORMATION: synthetic sequence

<400> SEQUENCE: 535

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ser Tyr Gln Glu Val Val Ala Glu Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Tyr Val Leu Ile His Gly Val Lys Gly Gly Tyr Glu
65                  70                  75                  80

Ser Lys Pro Leu Asp Ala Ser Phe Thr Thr
                85                  90
```

<210> SEQ ID NO 536
<211> LENGTH: 90
<212> TYPE: PRT
<213> ORGANISM: Artificial Sequence
<220> FEATURE:
<223> OTHER INFORMATION: synthetic sequence

<400> SEQUENCE: 536

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Glu Tyr Phe Glu Trp Thr Gly Ser Gly Glu Ala Ile Val Leu
        35                  40                  45

Thr Val Pro Gly Ser Glu Arg Ser Tyr Asp Leu Thr Gly Leu Lys Pro
```

```
            50                  55                  60
Gly Thr Glu Tyr Asn Val Ala Ile Tyr Gly Val Lys Gly Gly Ala Val
 65                  70                  75                  80

Ser Tyr Pro Leu Ser Ala Ile Phe Thr Thr
                 85                  90

<210> SEQ ID NO 537
<211> LENGTH: 90
<212> TYPE: PRT
<213> ORGANISM: Artificial Sequence
<220> FEATURE:
<223> OTHER INFORMATION: synthetic sequence

<400> SEQUENCE: 537

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Thr Ile Trp Tyr Ala Glu Ala Leu Gly Asp Gly Glu Ala Ile Val Leu
             35                  40                  45

Thr Val Pro Gly Ser Glu Arg Ser Tyr Asp Leu Thr Gly Leu Lys Pro
 50                  55                  60

Gly Thr Glu Tyr Phe Val Asp Ile Pro Gly Val Lys Gly Gly Thr Arg
 65                  70                  75                  80

Ser Ser Pro Leu Ser Ala Ile Ser Thr Thr
                 85                  90

<210> SEQ ID NO 538
<211> LENGTH: 88
<212> TYPE: PRT
<213> ORGANISM: Artificial Sequence
<220> FEATURE:
<223> OTHER INFORMATION: synthetic sequence

<400> SEQUENCE: 538

Met Leu Leu Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Arg Tyr Leu Glu Gln Gly Leu Tyr Gly Glu Ala Ile Val Leu Thr Val
             35                  40                  45

Pro Gly Ser Glu Arg Ser Tyr Asp Leu Thr Gly Leu Lys Pro Gly Thr
 50                  55                  60

Glu Tyr Trp Val Glu Ile Ile Gly Val Lys Gly Glu Tyr Ser Thr
 65                  70                  75                  80

Pro Leu Ser Ala Ile Phe Thr Thr
                 85

<210> SEQ ID NO 539
<211> LENGTH: 90
<212> TYPE: PRT
<213> ORGANISM: Artificial Sequence
<220> FEATURE:
<223> OTHER INFORMATION: synthetic sequence

<400> SEQUENCE: 539

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30
```

Lys Ile Glu Tyr Phe Glu Tyr Val Gly Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Tyr Val Ala Ile Tyr Gly Val Lys Gly Gly Trp Tyr
65                  70                  75                  80

Ser Arg Pro Leu Ser Ala Ile Phe Thr Thr
                85                  90

<210> SEQ ID NO 540
<211> LENGTH: 90
<212> TYPE: PRT
<213> ORGANISM: Artificial Sequence
<220> FEATURE:
<223> OTHER INFORMATION: synthetic sequence

<400> SEQUENCE: 540

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ile Tyr Glu Glu Val Leu Thr Glu Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Gly Val Thr Ile Lys Gly Val Lys Gly Gly Ala Tyr
65                  70                  75                  80

Ser Ile Pro Leu Ile Ala Thr Phe Thr Thr
                85                  90

<210> SEQ ID NO 541
<211> LENGTH: 90
<212> TYPE: PRT
<213> ORGANISM: Artificial Sequence
<220> FEATURE:
<223> OTHER INFORMATION: synthetic sequence

<400> SEQUENCE: 541

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Arg Tyr Leu Glu Trp Trp Asn Ile Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr His Val Asp Ile Trp Gly Val Lys Gly Gly Tyr Ser
65                  70                  75                  80

Ser Tyr Pro Leu Ser Ala Ile Phe Thr Thr
                85                  90

<210> SEQ ID NO 542
<211> LENGTH: 90
<212> TYPE: PRT
<213> ORGANISM: Artificial Sequence
<220> FEATURE:
<223> OTHER INFORMATION: synthetic sequence

<400> SEQUENCE: 542

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Glu Ile Tyr Tyr Val Glu Trp Ser Glu Ala Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Arg Val Glu Ile Arg Gly Val Lys Gly Gly Ser Trp
65                  70                  75                  80

Ser Ser Pro Leu Ser Ala Ile Phe Thr Thr
                85                  90
```

<210> SEQ ID NO 543
<211> LENGTH: 90
<212> TYPE: PRT
<213> ORGANISM: Artificial Sequence
<220> FEATURE:
<223> OTHER INFORMATION: synthetic sequence

<400> SEQUENCE: 543

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ser Ile His Tyr Asp Glu Asp Trp Arg Arg Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Leu Val Glu Ile Pro Gly Val Lys Gly Gly Lys Ala
65                  70                  75                  80

Ser Tyr Pro Leu Ser Ala Ile Phe Thr Thr
                85                  90
```

<210> SEQ ID NO 544
<211> LENGTH: 90
<212> TYPE: PRT
<213> ORGANISM: Artificial Sequence
<220> FEATURE:
<223> OTHER INFORMATION: synthetic sequence

<400> SEQUENCE: 544

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Gln Ile Arg Tyr Pro Lys Arg Trp Ile Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Glu Val Val Ile Arg Gly Val Lys Gly Gly Glu Tyr
65                  70                  75                  80

Ser Trp Pro Leu Ser Ala Ile Phe Thr Thr
                85                  90
```

<210> SEQ ID NO 545
<211> LENGTH: 90
<212> TYPE: PRT
<213> ORGANISM: Artificial Sequence -continued
<220> FEATURE:
<223> OTHER INFORMATION: synthetic sequence

<400> SEQUENCE: 545

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Pro Tyr Ile Glu Thr Val Ala Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Glu Ile Tyr Gly Val Lys Gly Gly Ser Tyr
65                  70                  75                  80

Ser Tyr Pro Leu Ser Ala Ile Ser Thr Thr
                85                  90
```

<210> SEQ ID NO 546
<211> LENGTH: 90
<212> TYPE: PRT
<213> ORGANISM: Artificial Sequence
<220> FEATURE:
<223> OTHER INFORMATION: synthetic sequence

<400> SEQUENCE: 546

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Ala Tyr Asp Glu Thr Leu Asn Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ile Val Gly Ile Phe Gly Val Lys Gly Gly Thr His
65                  70                  75                  80

Ser Trp Pro Leu Ser Ala Ile Phe Thr Thr
                85                  90
```

<210> SEQ ID NO 547
<211> LENGTH: 90
<212> TYPE: PRT
<213> ORGANISM: Artificial Sequence
<220> FEATURE:
<223> OTHER INFORMATION: synthetic sequence

<400> SEQUENCE: 547

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Val Tyr Ala Glu Pro Ile Pro Asn Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Arg Asn
65                  70                  75                  80

Ser Asp Pro Leu Ser Ala Ile Phe Thr Thr
                85                  90
```

<210> SEQ ID NO 548
<211> LENGTH: 90
<212> TYPE: PRT
<213> ORGANISM: Artificial Sequence
<220> FEATURE:
<223> OTHER INFORMATION: synthetic sequence

<400> SEQUENCE: 548

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Thr Tyr Trp Glu Thr Trp Asp Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Lys Val Pro Ile Thr Gly Val Lys Gly Gly Gly Pro
65                  70                  75                  80

Ser Val Pro Leu Ser Ala Ile Phe Thr Thr
                85                  90

<210> SEQ ID NO 549
<211> LENGTH: 90
<212> TYPE: PRT
<213> ORGANISM: Artificial Sequence
<220> FEATURE:
<223> OTHER INFORMATION: synthetic sequence

<400> SEQUENCE: 549

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asn Tyr Arg Glu Trp Trp Ser Asp Gly Glu Ala Ile Tyr Leu
        35                  40                  45

Pro Val Pro Gly Ser Glu Arg Ser Tyr Asp Leu Thr Gly Leu Lys Pro
    50                  55                  60

Gly Thr Glu Tyr Ala Val Tyr Ile Gln Gly Val Lys Gly Gly Ser Arg
65                  70                  75                  80

Ser Phe Pro Leu His Ala Trp Phe Thr Thr
                85                  90

<210> SEQ ID NO 550
<211> LENGTH: 90
<212> TYPE: PRT
<213> ORGANISM: Artificial Sequence
<220> FEATURE:
<223> OTHER INFORMATION: synthetic sequence

<400> SEQUENCE: 550

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Glu Tyr Tyr Glu Glu Leu Gly Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Tyr Ile Tyr Gly Val Lys Gly Gly Tyr Pro

-continued

```
                65                  70                  75                  80
Ser Ser Pro Leu Ser Ala Ile Phe Thr Thr
                85                  90

<210> SEQ ID NO 551
<211> LENGTH: 90
<212> TYPE: PRT
<213> ORGANISM: Artificial Sequence
<220> FEATURE:
<223> OTHER INFORMATION: synthetic sequence

<400> SEQUENCE: 551

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Leu Tyr Gly Glu Met Gly Thr Thr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asp Val Phe Ile Glu Gly Val Lys Gly Gly Glu Leu
65                  70                  75                  80

Ser Trp Pro Leu Ser Ala Ile Phe Thr Thr
                85                  90

<210> SEQ ID NO 552
<211> LENGTH: 88
<212> TYPE: PRT
<213> ORGANISM: Artificial Sequence
<220> FEATURE:
<223> OTHER INFORMATION: synthetic sequence

<400> SEQUENCE: 552

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Lys Ile Phe Tyr Gln Glu Phe Gly Gly Glu Ala Ile Val Leu Thr Val
            35                  40                  45

Pro Gly Ser Glu Arg Ser Tyr Asp Leu Thr Gly Leu Lys Pro Gly Thr
        50                  55                  60

Glu Tyr Trp Val Asp Ile Tyr Gly Val Lys Gly Gly Tyr Thr Ser Ser
65                  70                  75                  80

Pro Leu Ser Ala Ile Phe Thr Thr
                85

<210> SEQ ID NO 553
<211> LENGTH: 90
<212> TYPE: PRT
<213> ORGANISM: Artificial Sequence
<220> FEATURE:
<223> OTHER INFORMATION: synthetic sequence

<400> SEQUENCE: 553

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Thr Tyr Tyr Glu Gly Arg Trp Arg Gly Glu Ala Ile Val Leu
            35                  40                  45
```

```
Thr Val Pro Gly Ser Glu Arg Ser Tyr Asp Leu Thr Gly Leu Lys Pro
            50                  55                  60

Gly Thr Glu Tyr Gly Val Pro Ile Arg Gly Val Lys Gly Gly Thr Gly
 65                  70                  75                  80

Ser Leu Pro Leu Ser Ala Ile Phe Thr Thr
                85                  90

<210> SEQ ID NO 554
<211> LENGTH: 90
<212> TYPE: PRT
<213> ORGANISM: Artificial Sequence
<220> FEATURE:
<223> OTHER INFORMATION: synthetic sequence

<400> SEQUENCE: 554

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Arg Ile Lys Tyr Leu Glu Trp Trp Leu Gly Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Asp Ile Gln Gly Val Lys Gly Gly Val Leu
 65                  70                  75                  80

Ser Trp Pro Leu Ser Ala Ile Phe Thr Thr
                85                  90

<210> SEQ ID NO 555
<211> LENGTH: 90
<212> TYPE: PRT
<213> ORGANISM: Artificial Sequence
<220> FEATURE:
<223> OTHER INFORMATION: synthetic sequence

<400> SEQUENCE: 555

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Asn Ile Tyr Tyr Tyr Glu Trp Phe Val Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Asp Ile Asp Gly Val Lys Gly Gly Tyr Arg
 65                  70                  75                  80

Ser Arg Pro Leu Ser Ala Ile Phe Thr Thr
                85                  90

<210> SEQ ID NO 556
<211> LENGTH: 90
<212> TYPE: PRT
<213> ORGANISM: Artificial Sequence
<220> FEATURE:
<223> OTHER INFORMATION: synthetic sequence

<400> SEQUENCE: 556

Met Leu Pro Ala Pro Lys Asn Leu Val Val Ser Arg Val Thr Glu Asp
 1               5                  10                  15
```

```
Ser Ala Arg Leu Ser Trp Thr Ala Pro Asp Ala Ala Phe Asp Ser Phe
            20                  25                  30

Pro Ile Lys Tyr Leu Glu Trp Trp Ser Trp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Pro Ile Ser Gly Val Lys Gly Gly Gly Met
65                  70                  75                  80

Ser Gly Pro Leu Ser Ala Ile Phe Thr Thr
                85                  90
```

<210> SEQ ID NO 557
<211> LENGTH: 90
<212> TYPE: PRT
<213> ORGANISM: Artificial Sequence
<220> FEATURE:
<223> OTHER INFORMATION: synthetic sequence

<400> SEQUENCE: 557

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Pro Tyr Tyr Glu Trp Val Asn His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Gly Ile Asp Gly Val Lys Gly Gly Gly Pro
65                  70                  75                  80

Ser Trp Pro Leu Ser Ala Ile Phe Thr Thr
                85                  90
```

<210> SEQ ID NO 558
<211> LENGTH: 89
<212> TYPE: PRT
<213> ORGANISM: Artificial Sequence
<220> FEATURE:
<223> OTHER INFORMATION: synthetic sequence

<400> SEQUENCE: 558

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Asp Tyr Ser Glu Phe His Leu Arg Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Gly Ile Phe Gly Val Lys Gly Gly Glu Gln Ser
65                  70                  75                  80

Gly Pro Leu Ser Ala Ile Phe Thr Thr
                85
```

<210> SEQ ID NO 559
<211> LENGTH: 90
<212> TYPE: PRT
<213> ORGANISM: Artificial Sequence
<220> FEATURE:
<223> OTHER INFORMATION: synthetic sequence

<400> SEQUENCE: 559

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Gly Ile Ala Tyr Asn Glu Gly Asp His Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Trp Ile Glu Gly Val Lys Gly Gly Asn Leu
65                  70                  75                  80

Ser Tyr Pro Leu Ser Ala Ile Phe Thr Thr
            85                  90

<210> SEQ ID NO 560
<211> LENGTH: 90
<212> TYPE: PRT
<213> ORGANISM: Artificial Sequence
<220> FEATURE:
<223> OTHER INFORMATION: synthetic sequence

<400> SEQUENCE: 560

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Ala Tyr Asn Glu Gln Asn His Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Trp Ile Glu Gly Val Lys Gly Gly Thr Leu
65                  70                  75                  80

Ser Trp Pro Leu Ser Ala Ile Phe Thr Thr
            85                  90

<210> SEQ ID NO 561
<211> LENGTH: 87
<212> TYPE: PRT
<213> ORGANISM: Artificial Sequence
<220> FEATURE:
<223> OTHER INFORMATION: synthetic sequence

<400> SEQUENCE: 561

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Glu Trp Thr Tyr Lys Gly Glu Ala Ile Val Leu Thr Val Pro
        35                  40                  45

Gly Ser Glu Arg Ser Tyr Asp Leu Thr Gly Leu Lys Pro Gly Thr Glu
    50                  55                  60

Tyr Phe Val Gly Ile Pro Gly Val Lys Gly Gly Lys Ser Ser Tyr Pro
65                  70                  75                  80

Leu Ser Ala Ile Phe Thr Thr
            85

<210> SEQ ID NO 562
<211> LENGTH: 92

```
<212> TYPE: PRT
<213> ORGANISM: Artificial Sequence
<220> FEATURE:
<223> OTHER INFORMATION: synthetic sequence

<400> SEQUENCE: 562

Met Gly Ser Leu Pro Ala Pro Lys Asn Leu Val Val Ser Arg Val Thr
1               5                   10                  15

Glu Asp Ser Ala Arg Leu Ser Trp Thr Ala Pro Asp Ala Ala Phe Asp
            20                  25                  30

Ser Phe Ala Ile Pro Tyr Ala Glu Pro Ser Pro Thr Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Pro Val Trp Ile Gln Gly Val Lys Gly Gly
65                  70                  75                  80

Ser Pro Ser Ala Pro Leu Ser Ala Glu Phe Thr Thr
                85                  90

<210> SEQ ID NO 563
<211> LENGTH: 90
<212> TYPE: PRT
<213> ORGANISM: Artificial Sequence
<220> FEATURE:
<223> OTHER INFORMATION: synthetic sequence

<400> SEQUENCE: 563

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asp Tyr Phe Glu Ser Val Gly Phe Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Gln Ile Thr Gly Val Lys Gly Gly Pro His
65                  70                  75                  80

Ser Leu Pro Leu Ser Ala Ile Phe Thr Thr
                85                  90

<210> SEQ ID NO 564
<211> LENGTH: 90
<212> TYPE: PRT
<213> ORGANISM: Artificial Sequence
<220> FEATURE:
<223> OTHER INFORMATION: synthetic sequence

<400> SEQUENCE: 564

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Tyr Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ala Val Glu Ile Ala Gly Val Lys Gly Gly Leu Leu
65                  70                  75                  80

Ser Ser Pro Leu Ser Ala Ile Ser Thr Thr
```

```
                    85                  90

<210> SEQ ID NO 565
<211> LENGTH: 90
<212> TYPE: PRT
<213> ORGANISM: Artificial Sequence
<220> FEATURE:
<223> OTHER INFORMATION: synthetic sequence

<400> SEQUENCE: 565

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Val Thr Thr
                85                  90

<210> SEQ ID NO 566
<211> LENGTH: 90
<212> TYPE: PRT
<213> ORGANISM: Artificial Sequence
<220> FEATURE:
<223> OTHER INFORMATION: synthetic sequence

<400> SEQUENCE: 566

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Gly Tyr Thr Glu Tyr Gly Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Leu Ile Gln Gly Val Lys Gly Gly Gly Ser
65                  70                  75                  80

Ser Val Pro Leu Ser Ala Ile Phe Thr Thr
                85                  90

<210> SEQ ID NO 567
<211> LENGTH: 90
<212> TYPE: PRT
<213> ORGANISM: Artificial Sequence
<220> FEATURE:
<223> OTHER INFORMATION: synthetic sequence

<400> SEQUENCE: 567

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Glu Tyr Trp Glu Thr Ile Gly Gly Gly Glu Ala Ile Val Leu
        35                  40                  45

Thr Val Pro Gly Ser Glu Arg Ser Tyr Asp Leu Thr Gly Leu Lys Pro
    50                  55                  60
```

Gly Thr Glu Tyr Tyr Val Gly Ile Tyr Gly Val Lys Gly Gly Trp Trp
65                  70                  75                  80

Ser Arg Pro Leu Ser Ala Ile Phe Thr Thr
                85                  90

<210> SEQ ID NO 568
<211> LENGTH: 90
<212> TYPE: PRT
<213> ORGANISM: Artificial Sequence
<220> FEATURE:
<223> OTHER INFORMATION: synthetic sequence

<400> SEQUENCE: 568

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Pro Tyr Ala Glu Pro Ser Pro Thr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly His Leu
65                  70                  75                  80

Ser Asp Pro Leu Ser Ala Ile Ser Thr Thr
                85                  90

<210> SEQ ID NO 569
<211> LENGTH: 90
<212> TYPE: PRT
<213> ORGANISM: Artificial Sequence
<220> FEATURE:
<223> OTHER INFORMATION: synthetic sequence

<400> SEQUENCE: 569

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asp Ile Glu Tyr Tyr Glu Leu Ile Gly Arg Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Gly Ile Tyr Gly Val Lys Gly Gly Trp Leu
65                  70                  75                  80

Ser Arg Pro Leu Ser Ala Ile Phe Thr Thr
                85                  90

<210> SEQ ID NO 570
<211> LENGTH: 90
<212> TYPE: PRT
<213> ORGANISM: Artificial Sequence
<220> FEATURE:
<223> OTHER INFORMATION: synthetic sequence

<400> SEQUENCE: 570

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

His Ile Val Tyr His Glu Pro Arg Pro Ser Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Glu Val Gly Ile Val Gly Val Lys Gly Gly Asp Leu
 65                  70                  75                  80

Ser Val Pro Leu Ser Ala Ile Phe Thr Thr
                 85                  90

<210> SEQ ID NO 571
<211> LENGTH: 90
<212> TYPE: PRT
<213> ORGANISM: Artificial Sequence
<220> FEATURE:
<223> OTHER INFORMATION: synthetic sequence

<400> SEQUENCE: 571

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

His Ile Val Tyr His Glu Pro Arg Pro Ser Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Glu Val Gly Ile Val Ser Val Lys Gly Gly Asp Leu
 65                  70                  75                  80

Ser Val Pro Leu Ser Ala Ile Phe Thr Thr
                 85                  90

<210> SEQ ID NO 572
<211> LENGTH: 90
<212> TYPE: PRT
<213> ORGANISM: Artificial Sequence
<220> FEATURE:
<223> OTHER INFORMATION: synthetic sequence

<400> SEQUENCE: 572

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Phe Ile Pro Tyr Ala Glu Pro Ser Pro Thr Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Asp Val Trp Ile Glu Gly Val Lys Gly Gly Val Leu
 65                  70                  75                  80

Ser Trp Pro Leu Ser Ala Ile Phe Thr Thr
                 85                  90

<210> SEQ ID NO 573
<211> LENGTH: 90
<212> TYPE: PRT
<213> ORGANISM: Artificial Sequence
<220> FEATURE:
<223> OTHER INFORMATION: synthetic sequence

<400> SEQUENCE: 573

Met Leu Pro Ala Pro Lys Asn Leu Val Val Ser Arg Val Thr Glu Asp

```
                1               5                   10                  15
Ser Ala Arg Leu Ser Trp Thr Ala Pro Asp Ala Ala Phe Asp Ser Phe
                20                  25                  30

Thr Ile Glu Tyr Phe Glu Phe Val Asp Ala Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Trp Val Glu Ile Trp Gly Val Lys Gly Gly Ser Trp
65                  70                  75                  80

Ser Lys Pro Leu Ser Ala Ile Phe Thr Thr
                85                  90
```

<210> SEQ ID NO 574
<211> LENGTH: 89
<212> TYPE: PRT
<213> ORGANISM: Artificial Sequence
<220> FEATURE:
<223> OTHER INFORMATION: synthetic sequence

<400> SEQUENCE: 574

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Ser Tyr Tyr Glu Tyr Phe Val His Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Tyr Val Ile Asp Gly Val Lys Gly Gly Asp Pro Ser
65                  70                  75                  80

Glu Pro Leu Ser Ala Ile Phe Thr Thr
                85
```

<210> SEQ ID NO 575
<211> LENGTH: 90
<212> TYPE: PRT
<213> ORGANISM: Artificial Sequence
<220> FEATURE:
<223> OTHER INFORMATION: synthetic sequence

<400> SEQUENCE: 575

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Val Tyr Gly Glu Trp Gly Val Pro Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Asp Val Trp Ile Glu Gly Val Lys Gly Gly Asp Leu
65                  70                  75                  80

Ser Trp Pro Leu Ser Ala Ile Val Thr Thr
                85                  90
```

<210> SEQ ID NO 576
<211> LENGTH: 90
<212> TYPE: PRT
<213> ORGANISM: Artificial Sequence
<220> FEATURE:

<223> OTHER INFORMATION: synthetic sequence

<400> SEQUENCE: 576

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Phe Glu Tyr Thr Gly Glu Gly Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Gly Ile Tyr Gly Val Lys Gly Gly Tyr Leu
65                  70                  75                  80

Ser Arg Pro Leu Ser Ala Ile Phe Thr Thr
            85                  90

<210> SEQ ID NO 577
<211> LENGTH: 90
<212> TYPE: PRT
<213> ORGANISM: Artificial Sequence
<220> FEATURE:
<223> OTHER INFORMATION: synthetic sequence

<400> SEQUENCE: 577

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Ser Thr Thr
            85                  90

<210> SEQ ID NO 578
<211> LENGTH: 90
<212> TYPE: PRT
<213> ORGANISM: Artificial Sequence
<220> FEATURE:
<223> OTHER INFORMATION: synthetic sequence

<400> SEQUENCE: 578

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Lys Tyr Gln Glu Trp Trp Val Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Val Val Gln Ile Ala Gly Val Lys Gly Gly Leu Ser
65                  70                  75                  80

Ser Tyr Pro Leu Ser Ala Ile Phe Thr Thr
            85                  90

-continued

```
<210> SEQ ID NO 579
<211> LENGTH: 90
<212> TYPE: PRT
<213> ORGANISM: Artificial Sequence
<220> FEATURE:
<223> OTHER INFORMATION: synthetic sequence

<400> SEQUENCE: 579

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Tyr Tyr Ile Glu Thr Ser His Gln Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Leu Ile Lys Gly Val Lys Gly Gly Tyr Asp
65                  70                  75                  80

Ser Val Pro Leu Ser Ala Ile Phe Thr Thr
                85                  90

<210> SEQ ID NO 580
<211> LENGTH: 90
<212> TYPE: PRT
<213> ORGANISM: Artificial Sequence
<220> FEATURE:
<223> OTHER INFORMATION: synthetic sequence

<400> SEQUENCE: 580

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Met Ile Arg Tyr Gln Glu Gly Thr Arg Trp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ile Val Met Ile Ala Gly Val Lys Gly Gly Gln Ile
65                  70                  75                  80

Ser Leu Pro Leu Ser Ala Ile Phe Thr Thr
                85                  90

<210> SEQ ID NO 581
<211> LENGTH: 90
<212> TYPE: PRT
<213> ORGANISM: Artificial Sequence
<220> FEATURE:
<223> OTHER INFORMATION: synthetic sequence

<400> SEQUENCE: 581

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Val Tyr Ser Glu Ile His Val Ile Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly His Leu
65                  70                  75                  80
```

```
Ser Glu Pro Leu Ser Ala Ile Phe Thr Thr
                85                  90

<210> SEQ ID NO 582
<211> LENGTH: 90
<212> TYPE: PRT
<213> ORGANISM: Artificial Sequence
<220> FEATURE:
<223> OTHER INFORMATION: synthetic sequence

<400> SEQUENCE: 582

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Val Tyr Gly Glu Ala Gly Ala Phe Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asp Val Leu Ile Glu Gly Val Lys Gly Gly Asn Leu
65                  70                  75                  80

Ser Trp Pro Leu Ser Ala Ile Phe Thr Thr
                85                  90

<210> SEQ ID NO 583
<211> LENGTH: 90
<212> TYPE: PRT
<213> ORGANISM: Artificial Sequence
<220> FEATURE:
<223> OTHER INFORMATION: synthetic sequence

<400> SEQUENCE: 583

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

His Ile Asn Tyr Ala Glu Val Tyr Thr Lys Gly Glu Ala Ile Leu Leu
            35                  40                  45

Thr Val Pro Gly Ser Glu Arg Ser Tyr Asp Leu Thr Gly Leu Lys Pro
        50                  55                  60

Gly Thr Glu Tyr Glu Val Tyr Ile Pro Gly Val Lys Gly Gly Pro Phe
65                  70                  75                  80

Ser Arg Pro Leu Asn Ala Gln Phe Thr Thr
                85                  90

<210> SEQ ID NO 584
<211> LENGTH: 90
<212> TYPE: PRT
<213> ORGANISM: Artificial Sequence
<220> FEATURE:
<223> OTHER INFORMATION: synthetic sequence

<400> SEQUENCE: 584

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Leu Ile Arg Tyr Gln Glu Trp Gln Arg Trp Gly Glu Ala Ile Val Leu
            35                  40                  45
```

```
Thr Val Pro Gly Ser Glu Arg Ser Tyr Asp Leu Thr Gly Leu Lys Pro
         50                  55                  60

Gly Thr Glu Tyr Thr Val His Ile Ala Gly Val Lys Gly Gly Met Leu
 65                  70                  75                  80

Ser Leu Pro Leu Ser Ala Ile Phe Thr Thr
                 85                  90

<210> SEQ ID NO 585
<211> LENGTH: 90
<212> TYPE: PRT
<213> ORGANISM: Artificial Sequence
<220> FEATURE:
<223> OTHER INFORMATION: synthetic sequence

<400> SEQUENCE: 585

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Tyr Ile Pro Tyr Ala Glu Thr Arg Asp Asp Gly Glu Ala Ile Val Leu
                 35                  40                  45

Thr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Asp Leu
 65                  70                  75                  80

Ser Ser Pro Leu Ser Ala Ile Phe Thr Thr
                 85                  90

<210> SEQ ID NO 586
<211> LENGTH: 90
<212> TYPE: PRT
<213> ORGANISM: Artificial Sequence
<220> FEATURE:
<223> OTHER INFORMATION: synthetic sequence

<400> SEQUENCE: 586

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Gly Ile Pro Tyr Ala Glu Ser Thr Pro Thr Gly Glu Ala Ile Val Leu
                 35                  40                  45

Thr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly His Leu
 65                  70                  75                  80

Ser Asp Pro Leu Ser Ala Ile Phe Thr Thr
                 85                  90

<210> SEQ ID NO 587
<211> LENGTH: 85
<212> TYPE: PRT
<213> ORGANISM: Artificial Sequence
<220> FEATURE:
<223> OTHER INFORMATION: synthetic sequence

<400> SEQUENCE: 587

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
```

```
                  20                  25                  30

Thr Ile Phe Lys Asp Gly Glu Ala Ile Val Leu Thr Val Pro Gly Ser
            35                  40                  45

Glu Arg Ser Tyr Asp Leu Thr Gly Leu Lys Pro Gly Thr Glu Tyr Tyr
        50                  55                  60

Val Tyr Ile Tyr Gly Val Lys Gly Gly Tyr Pro Ser Lys Pro Leu Ser
65                  70                  75                  80

Ala Ile Phe Thr Thr
                85

<210> SEQ ID NO 588
<211> LENGTH: 90
<212> TYPE: PRT
<213> ORGANISM: Artificial Sequence
<220> FEATURE:
<223> OTHER INFORMATION: synthetic sequence

<400> SEQUENCE: 588

Met Leu Pro Ala Pro Lys Asn Leu Val Val Ser Arg Val Thr Glu Asp
1               5                   10                  15

Ser Val Arg Leu Ser Trp Thr Ala Pro Asp Ala Ala Phe Asp Ser Phe
            20                  25                  30

Ala Ile Ser Tyr Glu Glu Trp Trp Val His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Val Ile Pro Gly Val Lys Gly Gly Leu Tyr
65                  70                  75                  80

Ser Trp Thr Leu Ser Ala Ile Ser Thr Thr
            85                  90

<210> SEQ ID NO 589
<211> LENGTH: 90
<212> TYPE: PRT
<213> ORGANISM: Artificial Sequence
<220> FEATURE:
<223> OTHER INFORMATION: synthetic sequence

<400> SEQUENCE: 589

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Ala Tyr Ala Glu Val Thr Leu His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Arg Asn
65                  70                  75                  80

Ser Asp Pro Leu Ser Ala Ile Phe Thr Thr
            85                  90

<210> SEQ ID NO 590
<211> LENGTH: 90
<212> TYPE: PRT
<213> ORGANISM: Artificial Sequence
<220> FEATURE:
<223> OTHER INFORMATION: synthetic sequence

<400> SEQUENCE: 590
```

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Arg Ile Asp Tyr Leu Glu Leu Thr Ser Leu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Pro Ile Leu Gly Val Lys Gly Gly Leu Ser
65                  70                  75                  80

Ser Trp Pro Leu Ser Ala Ile Phe Thr Thr
                85                  90
```

<210> SEQ ID NO 591
<211> LENGTH: 90
<212> TYPE: PRT
<213> ORGANISM: Artificial Sequence
<220> FEATURE:
<223> OTHER INFORMATION: synthetic sequence

<400> SEQUENCE: 591

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Trp Ile Asn Tyr Tyr Glu Gly Ile Gly Glu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Tyr Val Asp Ile Ser Gly Val Lys Gly Gly Ser Tyr
65                  70                  75                  80

Ser Leu Pro Leu Ser Ala Ile Phe Thr Thr
                85                  90
```

<210> SEQ ID NO 592
<211> LENGTH: 90
<212> TYPE: PRT
<213> ORGANISM: Artificial Sequence
<220> FEATURE:
<223> OTHER INFORMATION: synthetic sequence

<400> SEQUENCE: 592

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly His Leu
65                  70                  75                  80

Ser Asp Pro Leu Ser Ala Ile Phe Thr Thr
                85                  90
```

<210> SEQ ID NO 593
<211> LENGTH: 90
<212> TYPE: PRT

```
<213> ORGANISM: Artificial Sequence
<220> FEATURE:
<223> OTHER INFORMATION: synthetic sequence

<400> SEQUENCE: 593

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Glu Tyr Tyr Glu Ser Gly Leu Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Asp Val Ser Ile Tyr Gly Val Lys Gly Tyr Leu
65                  70                  75                  80

Ser Arg Pro Leu Ser Ala Ile Phe Thr Thr
                85                  90

<210> SEQ ID NO 594
<211> LENGTH: 90
<212> TYPE: PRT
<213> ORGANISM: Artificial Sequence
<220> FEATURE:
<223> OTHER INFORMATION: synthetic sequence
<220> FEATURE:
<221> NAME/KEY: misc_feature
<222> LOCATION: (12)..(12)
<223> OTHER INFORMATION: Xaa can be any naturally occurring amino acid

<400> SEQUENCE: 594

Met Leu Pro Ala Pro Lys Asn Leu Val Val Arg Xaa Val Thr Glu Asp
1               5                   10                  15

Ser Ala Arg Leu Ser Trp Thr Ala Pro Asp Ala Ala Phe Asp Ser Phe
            20                  25                  30

Glu Ile Glu Tyr Asp Glu Pro Tyr Arg Gly Gly Glu Ala Ile Val Leu
        35                  40                  45

Thr Val Pro Gly Ser Glu Arg Ser Tyr Asp Leu Thr Ser Leu Lys Pro
50                  55                  60

Gly Thr Glu Tyr Pro Val Ser Ile Gly Gly Val Lys Gly Gly Ile Thr
65                  70                  75                  80

Ser Asp Pro Leu Ser Ala Ile Phe Thr Thr
                85                  90

<210> SEQ ID NO 595
<211> LENGTH: 90
<212> TYPE: PRT
<213> ORGANISM: Artificial Sequence
<220> FEATURE:
<223> OTHER INFORMATION: synthetic sequence

<400> SEQUENCE: 595

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Asp Tyr Asp Glu Ile His Asp Trp Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Ala Val Gln Ile Gly Gly Val Lys Gly Gly Ser Phe
```

```
                65                  70                  75                  80

Ser Trp Thr Leu Ser Ala Ile Phe Thr Thr
                85                  90

<210> SEQ ID NO 596
<211> LENGTH: 90
<212> TYPE: PRT
<213> ORGANISM: Artificial Sequence
<220> FEATURE:
<223> OTHER INFORMATION: synthetic sequence

<400> SEQUENCE: 596

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Val Tyr His Glu Pro Arg Pro Asp Gly Glu Ala Ile Val Leu
                35                  40                  45

Thr Val Pro Gly Ser Glu Arg Ser Tyr Asp Leu Thr Gly Leu Lys Pro
        50                  55                  60

Gly Thr Glu Tyr Glu Val Val Ile Leu Gly Val Lys Gly Gly Val His
65                  70                  75                  80

Ser Tyr Pro Leu Ser Ala Ile Phe Thr Thr
                85                  90

<210> SEQ ID NO 597
<211> LENGTH: 90
<212> TYPE: PRT
<213> ORGANISM: Artificial Sequence
<220> FEATURE:
<223> OTHER INFORMATION: synthetic sequence

<400> SEQUENCE: 597

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ala Tyr Ala Glu Pro Arg Pro Asp Gly Glu Ala Ile Val Leu
                35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 598
<211> LENGTH: 90
<212> TYPE: PRT
<213> ORGANISM: Artificial Sequence
<220> FEATURE:
<223> OTHER INFORMATION: synthetic sequence

<400> SEQUENCE: 598

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Pro Gly Glu Ala Ile Val Leu
                35                  40                  45
```

```
Thr Val Pro Gly Ser Glu Arg Ser Tyr Asp Leu Thr Gly Leu Lys Pro
            50                  55                  60

Gly Thr Glu Tyr Asn Val Thr Ile Gln Gly Val Lys Gly Gly Phe Pro
 65                  70                  75                  80

Ser Met Pro Leu Ser Ala Ile Phe Thr Thr
                85                  90

<210> SEQ ID NO 599
<211> LENGTH: 90
<212> TYPE: PRT
<213> ORGANISM: Artificial Sequence
<220> FEATURE:
<223> OTHER INFORMATION: synthetic sequence

<400> SEQUENCE: 599

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Leu Ile Pro Tyr Ala Glu Thr Ser Pro Ser Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Asp Tyr
 65                  70                  75                  80

Ser Ser Pro Leu Ser Ala Ile Phe Thr Thr
                85                  90

<210> SEQ ID NO 600
<211> LENGTH: 90
<212> TYPE: PRT
<213> ORGANISM: Artificial Sequence
<220> FEATURE:
<223> OTHER INFORMATION: synthetic sequence

<400> SEQUENCE: 600

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Asn Ile Tyr Tyr Pro Glu Phe Pro Val Arg Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Val Val Ser Ile Trp Gly Val Lys Gly Gly Thr Gln
 65                  70                  75                  80

Ser Trp Pro Leu Ser Ala Ile Phe Thr Thr
                85                  90

<210> SEQ ID NO 601
<211> LENGTH: 90
<212> TYPE: PRT
<213> ORGANISM: Artificial Sequence
<220> FEATURE:
<223> OTHER INFORMATION: synthetic sequence

<400> SEQUENCE: 601

Met Leu Pro Ala Pro Lys Asn Leu Val Val Ser Arg Val Thr Glu Asp
  1               5                  10                  15
```

```
Ser Ala Arg Leu Ser Trp Thr Ala Pro Asp Ala Ala Phe Asp Ser Phe
            20                  25                  30

Thr Ile Glu Tyr His Glu Ser Gly Pro Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Met Val Trp Ile Phe Gly Val Lys Gly Gly Phe Val
65                  70                  75                  80

Ser Arg Pro Leu Ser Ala Ile Phe Thr Thr
                85                  90
```

<210> SEQ ID NO 602
<211> LENGTH: 90
<212> TYPE: PRT
<213> ORGANISM: Artificial Sequence
<220> FEATURE:
<223> OTHER INFORMATION: synthetic sequence

<400> SEQUENCE: 602

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Asp Tyr
65                  70                  75                  80

Ser Ser Pro Leu Ser Ala Ile Ser Thr Thr
                85                  90
```

<210> SEQ ID NO 603
<211> LENGTH: 90
<212> TYPE: PRT
<213> ORGANISM: Artificial Sequence
<220> FEATURE:
<223> OTHER INFORMATION: synthetic sequence

<400> SEQUENCE: 603

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Pro Tyr Tyr Glu Asp Thr Asn Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Ser Ile Gln Gly Val Lys Gly Gly Thr Val
65                  70                  75                  80

Ser Gly Pro Leu Ser Ala Ile Phe Thr Thr
                85                  90
```

<210> SEQ ID NO 604
<211> LENGTH: 88
<212> TYPE: PRT
<213> ORGANISM: Artificial Sequence
<220> FEATURE:
<223> OTHER INFORMATION: synthetic sequence

<400> SEQUENCE: 604

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Tyr Leu Glu Gln Ala Trp Gly Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Trp Val Glu Ile Thr Gly Val Lys Gly Gly Tyr Ala Ser Ser
65                  70                  75                  80

Pro Leu Ser Ala Ile Phe Thr Thr
                85

<210> SEQ ID NO 605
<211> LENGTH: 90
<212> TYPE: PRT
<213> ORGANISM: Artificial Sequence
<220> FEATURE:
<223> OTHER INFORMATION: synthetic sequence

<400> SEQUENCE: 605

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Glu Tyr Glu Glu Pro Glu Thr Glu Gly Glu Ala Ile Tyr Leu
        35                  40                  45

His Val Pro Gly Ser Glu Arg Ser Tyr Asp Leu Thr Gly Leu Lys Pro
    50                  55                  60

Gly Thr Glu Tyr Lys Val Leu Ile Arg Gly Val Lys Gly Gly Ser Tyr
65                  70                  75                  80

Ser Ile Pro Leu Gln Ala Pro Phe Thr Thr
                85                  90

<210> SEQ ID NO 606
<211> LENGTH: 90
<212> TYPE: PRT
<213> ORGANISM: Artificial Sequence
<220> FEATURE:
<223> OTHER INFORMATION: synthetic sequence

<400> SEQUENCE: 606

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Ala Tyr Trp Glu Leu Thr Pro Ser Gly Glu Ala Ile Glu Leu
        35                  40                  45

Leu Val Pro Gly Ser Glu Arg Ser Tyr Asp Leu Thr Gly Leu Lys Pro
    50                  55                  60

Gly Thr Glu Tyr Arg Val Asp Ile Ile Gly Val Lys Gly Gly Phe Ile
65                  70                  75                  80

Ser Glu Pro Leu Gly Ala Thr Phe Thr Thr
                85                  90

<210> SEQ ID NO 607
<211> LENGTH: 90

```
<212> TYPE: PRT
<213> ORGANISM: Artificial Sequence
<220> FEATURE:
<223> OTHER INFORMATION: synthetic sequence

<400> SEQUENCE: 607

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Glu Tyr Trp Glu Phe Thr Gly Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Ser Ile Tyr Gly Val Lys Gly Gly Trp Leu
65                  70                  75                  80

Ser Tyr Pro Leu Ser Ala Ile Phe Thr Thr
                85                  90

<210> SEQ ID NO 608
<211> LENGTH: 90
<212> TYPE: PRT
<213> ORGANISM: Artificial Sequence
<220> FEATURE:
<223> OTHER INFORMATION: synthetic sequence

<400> SEQUENCE: 608

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Ile Tyr Ser Glu Trp Asn Val Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Gly Met
65                  70                  75                  80

Ser Lys Pro Leu Ser Ala Ile Ser Thr Thr
                85                  90

<210> SEQ ID NO 609
<211> LENGTH: 90
<212> TYPE: PRT
<213> ORGANISM: Artificial Sequence
<220> FEATURE:
<223> OTHER INFORMATION: synthetic sequence

<400> SEQUENCE: 609

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Ile Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Val Ile Gln Gly Val Lys Gly Gly His Pro
65                  70                  75                  80

Ser Gln Pro Leu Ser Ala Ile Phe Thr Thr
```

```
                85                  90

<210> SEQ ID NO 610
<211> LENGTH: 90
<212> TYPE: PRT
<213> ORGANISM: Artificial Sequence
<220> FEATURE:
<223> OTHER INFORMATION: synthetic sequence

<400> SEQUENCE: 610

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Ile Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 611
<211> LENGTH: 90
<212> TYPE: PRT
<213> ORGANISM: Artificial Sequence
<220> FEATURE:
<223> OTHER INFORMATION: synthetic sequence

<400> SEQUENCE: 611

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Thr Leu
        35                  40                  45

Phe Val Pro Gly Ser Glu Arg Ser Tyr Asp Leu Thr Gly Leu Lys Pro
    50                  55                  60

Gly Thr Glu Tyr Asn Val Val Ile Gln Gly Val Lys Gly Gly Arg Pro
65                  70                  75                  80

Ser Asn Pro Leu Val Ala Ala Ser Thr Thr
                85                  90

<210> SEQ ID NO 612
<211> LENGTH: 90
<212> TYPE: PRT
<213> ORGANISM: Artificial Sequence
<220> FEATURE:
<223> OTHER INFORMATION: synthetic sequence

<400> SEQUENCE: 612

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Ala Tyr Ala Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60
```

```
Gly Thr Glu Tyr Ser Val Leu Ile His Gly Val Lys Gly Gly Leu Leu
65                  70                  75                  80

Ser Ser Pro Leu Ser Ala Ile Ser Thr Thr
                85                  90

<210> SEQ ID NO 613
<211> LENGTH: 90
<212> TYPE: PRT
<213> ORGANISM: Artificial Sequence
<220> FEATURE:
<223> OTHER INFORMATION: synthetic sequence

<400> SEQUENCE: 613

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Leu Ile Glu Tyr Trp Glu Ser Val Gly Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Gly Ile Tyr Gly Val Lys Gly Gly Tyr Tyr
65                  70                  75                  80

Ser Arg Pro Leu Ser Ala Ile Phe Thr Thr
                85                  90

<210> SEQ ID NO 614
<211> LENGTH: 90
<212> TYPE: PRT
<213> ORGANISM: Artificial Sequence
<220> FEATURE:
<223> OTHER INFORMATION: synthetic sequence

<400> SEQUENCE: 614

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Thr Ile His Gly Val Lys Gly Gly Thr Pro
65                  70                  75                  80

Ser Met Pro Leu Ser Ala Ile Phe Thr Thr
                85                  90

<210> SEQ ID NO 615
<211> LENGTH: 90
<212> TYPE: PRT
<213> ORGANISM: Artificial Sequence
<220> FEATURE:
<223> OTHER INFORMATION: synthetic sequence

<400> SEQUENCE: 615

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30
```

Glu Ile Glu Tyr Asp Glu Pro Tyr Arg Gly Gly Glu Ala Ile Val Leu
            35                  40                  45

Thr Val Pro Gly Ser Glu Arg Ser Tyr Asp Leu Thr Ser Leu Lys Pro
 50                  55                  60

Gly Thr Glu Tyr Pro Val Ser Ile Gly Gly Val Lys Gly Gly Ile Thr
 65                  70                  75                  80

Ser Asp Pro Leu Ser Ala Ile Phe Thr Thr
                 85                  90

<210> SEQ ID NO 616
<211> LENGTH: 90
<212> TYPE: PRT
<213> ORGANISM: Artificial Sequence
<220> FEATURE:
<223> OTHER INFORMATION: synthetic sequence

<400> SEQUENCE: 616

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Asp Ile Tyr Tyr Pro Glu Tyr Tyr Asp Arg Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Thr Val Tyr Ile Asp Gly Val Lys Gly Gly Gly Val
 65                  70                  75                  80

Ser Gly Pro Leu Ser Ala Ile Phe Thr Thr
                 85                  90

<210> SEQ ID NO 617
<211> LENGTH: 90
<212> TYPE: PRT
<213> ORGANISM: Artificial Sequence
<220> FEATURE:
<223> OTHER INFORMATION: synthetic sequence

<400> SEQUENCE: 617

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Phe Ile Ala Tyr Phe Glu Phe Ala Asn Pro Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Lys Val Val Ile Gln Gly Val Lys Gly Gly Thr Pro
 65                  70                  75                  80

Ser Glu Pro Leu Ser Ala Ile Phe Thr Thr
                 85                  90

<210> SEQ ID NO 618
<211> LENGTH: 90
<212> TYPE: PRT
<213> ORGANISM: Artificial Sequence
<220> FEATURE:
<223> OTHER INFORMATION: synthetic sequence

<400> SEQUENCE: 618

Met Leu Pro Ala Pro Lys Asn Leu Val Val Ser Arg Val Thr Glu Asp

```
1               5                   10                  15
Ser Ala Arg Leu Ser Trp Thr Ala Pro Asp Ala Ala Phe Asp Ser Phe
            20                  25                  30

Ile Ile Thr Tyr Trp Glu His Val Gly Asp Gly Glu Ala Ile Val Leu
            35                  40                  45

Thr Val Pro Gly Ser Glu Arg Ser Tyr Asp Leu Thr Gly Leu Lys Pro
            50                  55                  60

Gly Thr Glu Tyr Phe Val Glu Ile Tyr Gly Val Lys Gly Gly Tyr Leu
65                  70                  75                  80

Ser Lys Pro Leu Ser Ala Ile Phe Thr Thr
            85                  90

<210> SEQ ID NO 619
<211> LENGTH: 90
<212> TYPE: PRT
<213> ORGANISM: Artificial Sequence
<220> FEATURE:
<223> OTHER INFORMATION: synthetic sequence

<400> SEQUENCE: 619

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Asp Tyr Asp Glu Pro Phe Val Tyr Gly Glu Ala Ile Val Leu
            35                  40                  45

Thr Val Pro Gly Ser Glu Arg Ser Tyr Asp Leu Thr Gly Leu Lys Pro
            50                  55                  60

Gly Thr Glu Tyr Arg Val Phe Ile Phe Gly Val Lys Gly Gly Asn Gly
65                  70                  75                  80

Ser Trp Pro Leu Ser Ala Ile Phe Thr Thr
            85                  90

<210> SEQ ID NO 620
<211> LENGTH: 90
<212> TYPE: PRT
<213> ORGANISM: Artificial Sequence
<220> FEATURE:
<223> OTHER INFORMATION: synthetic sequence

<400> SEQUENCE: 620

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Glu Tyr Phe Glu Thr Gln Gly Tyr Gly Glu Ala Ile Val Leu
            35                  40                  45

Thr Val Pro Gly Ser Glu Arg Ser Tyr Asp Leu Thr Gly Leu Lys Pro
            50                  55                  60

Gly Thr Glu Tyr Tyr Val Ala Ile Tyr Gly Val Lys Gly Gly Tyr Leu
65                  70                  75                  80

Ser Arg Pro Leu Ser Ala Ile Phe Thr Thr
            85                  90

<210> SEQ ID NO 621
<211> LENGTH: 90
<212> TYPE: PRT
<213> ORGANISM: Artificial Sequence
<220> FEATURE:
```

<223> OTHER INFORMATION: synthetic sequence

<400> SEQUENCE: 621

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Phe Asp Ser Phe
            20                  25                  30

Pro Ile Thr Tyr Ser Glu Pro Ala His Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr His Val Gly Ile Met Gly Val Lys Gly Gly Val Phe
65                  70                  75                  80

Ser Ser Pro Leu Ser Ala Ile Phe Thr Thr
                85                  90

<210> SEQ ID NO 622
<211> LENGTH: 90
<212> TYPE: PRT
<213> ORGANISM: Artificial Sequence
<220> FEATURE:
<223> OTHER INFORMATION: synthetic sequence

<400> SEQUENCE: 622

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Trp Ile Gln Gly Val Lys Gly Gly Ser Pro
65                  70                  75                  80

Ser Ala Pro Leu Ser Ala Ile Ser Thr Thr
                85                  90

<210> SEQ ID NO 623
<211> LENGTH: 90
<212> TYPE: PRT
<213> ORGANISM: Artificial Sequence
<220> FEATURE:
<223> OTHER INFORMATION: synthetic sequence

<400> SEQUENCE: 623

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Phe Asp Ser Phe
            20                  25                  30

Ile Ile Asp Tyr Leu Glu Leu Asp Gln Glu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ala Val Tyr Ile Phe Gly Val Lys Gly Gly Tyr Pro
65                  70                  75                  80

Ser Thr Pro Leu Ser Ala Ile Phe Thr Thr
                85                  90

```
<210> SEQ ID NO 624
<211> LENGTH: 89
<212> TYPE: PRT
<213> ORGANISM: Artificial Sequence
<220> FEATURE:
<223> OTHER INFORMATION: synthetic sequence

<400> SEQUENCE: 624

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
                20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85
```